US007588671B2

(12) United States Patent
Morita et al.

(10) Patent No.: US 7,588,671 B2
(45) Date of Patent: Sep. 15, 2009

(54) MICROFLUIDIC TREATMENT METHOD AND DEVICE

(75) Inventors: Tomoyuki Morita, Kanagawa-ken (JP); Akiko Miya, Kanagawa-ken (JP); Akira Fukuda, Kanagawa-ken (JP); Motohiko Nomi, Kanagawa-ken (JP); Katsunori Ichiki, Kanagawa-ken (JP); Manabu Tsujimura, Tokyo (JP); Shunsuke Shimizu, Kanagawa-ken (JP)

(73) Assignee: Ebara Corporation, Ohtu-Ku, Tokyo (JP)

( * ) Notice: Subject to any disclaimer, the term of this patent is extended or adjusted under 35 U.S.C. 154(b) by 824 days.

(21) Appl. No.: 10/992,770

(22) Filed: Nov. 22, 2004

(65) Prior Publication Data

US 2005/0161326 A1 Jul. 28, 2005

(30) Foreign Application Priority Data

| Nov. 21, 2003 | (JP) | 2003-392302 |
|---|---|---|
| Feb. 2, 2004 | (JP) | 2004-025266 |
| Feb. 3, 2004 | (JP) | 2004-026391 |
| Feb. 3, 2004 | (JP) | 2004-026877 |
| Feb. 3, 2004 | (JP) | 2004-027111 |
| Feb. 4, 2004 | (JP) | 2004-027907 |
| Feb. 4, 2004 | (JP) | 2004-028108 |
| Feb. 5, 2004 | (JP) | 2004-029815 |
| Feb. 5, 2004 | (JP) | 2004-029874 |
| Feb. 12, 2004 | (JP) | 2004-035392 |

(51) Int. Cl.
*G01N 27/447* (2006.01)
*B01D 57/02* (2006.01)

(52) U.S. Cl. .............. 204/601; 204/600; 204/451; 204/450

(58) Field of Classification Search .......... 204/450, 204/600, 451, 601
See application file for complete search history.

(56) References Cited

U.S. PATENT DOCUMENTS 5,785,831 A 7/1998 Bek (Continued)

FOREIGN PATENT DOCUMENTS

JP 8-261986 10/1996

(Continued)

OTHER PUBLICATIONS

Cremonesi, L., et al. "Validation of Double Gradient Denaturing Gradient Gel Electrophoresis through Multigenic Retrospective Analysis", Clinical Chemistry, vol. 45, No. 1, no month, 1999, pp. 35-40.*

*Primary Examiner*—Alex Noguerola
*Assistant Examiner*—J. Christopher Ball
(74) *Attorney, Agent, or Firm*—Wenderoth, Lind & Ponack, L.L.P.

(57) ABSTRACT

The present invention relates to a microchip apparatus using liquids. More specifically, the invention provides a liquid mixing apparatus comprising at least two microchannels for introducing liquids and a mixing microchannel that connects to the at least two liquid-introducing microchannels, wherein the liquids are transported from the respective liquid-introducing microchannels toward the mixing microchannel, the apparatus further comprising means for enhancing the mixing of the liquids that converge in the mixing microchannel. The invention also provides an electrophoretic apparatus and a microchip electrophoretic apparatus for denaturing gradient gel electrophoresis.

11 Claims, 79 Drawing Sheets

U.S. PATENT DOCUMENTS 6,042,709 A 3/2000 Parce et al.
6,406,893 B1 * 6/2002 Knapp et al. ............... 435/91.2

FOREIGN PATENT DOCUMENTS

| JP | 10-502738 | 3/1998 |
| JP | 10-507516 | 7/1998 |
| JP | 2001-120971 | 5/2001 |
| JP | 2001-252897 | 9/2001 |
| JP | 2001-521622 | 11/2001 |
| JP | 2003-66003 | 3/2003 |
| JP | 2003-210963 | 7/2003 |
| WO | 96/04547 | 2/1996 |
| WO | 96/08715 | 3/1996 |
| WO | 98/45481 | 10/1998 |

* cited by examiner

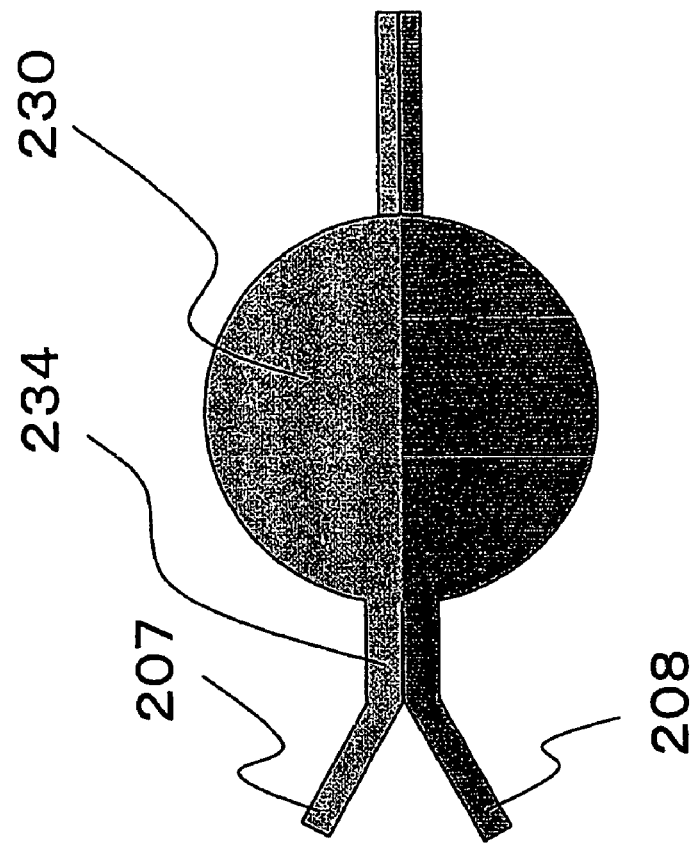
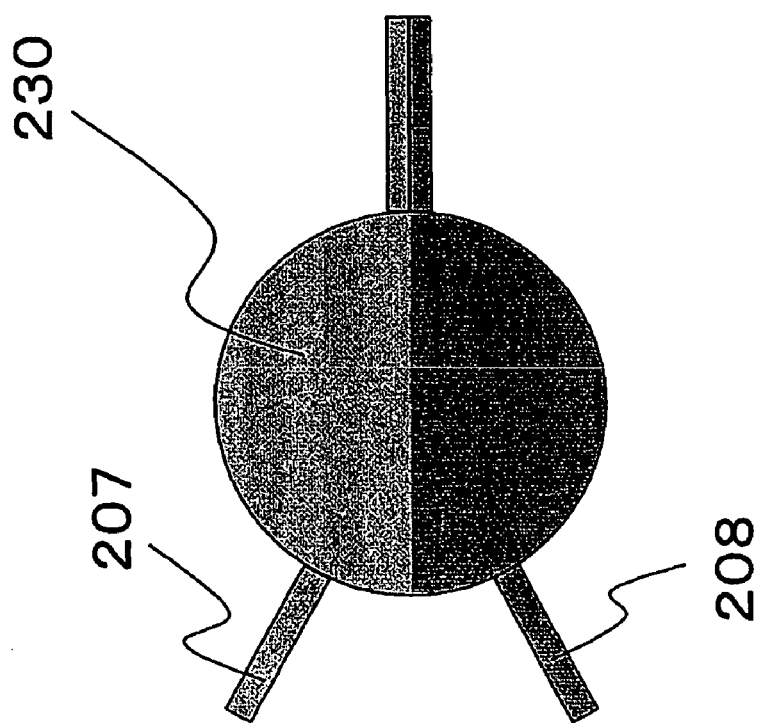
FIG. 32b
FIG. 32a

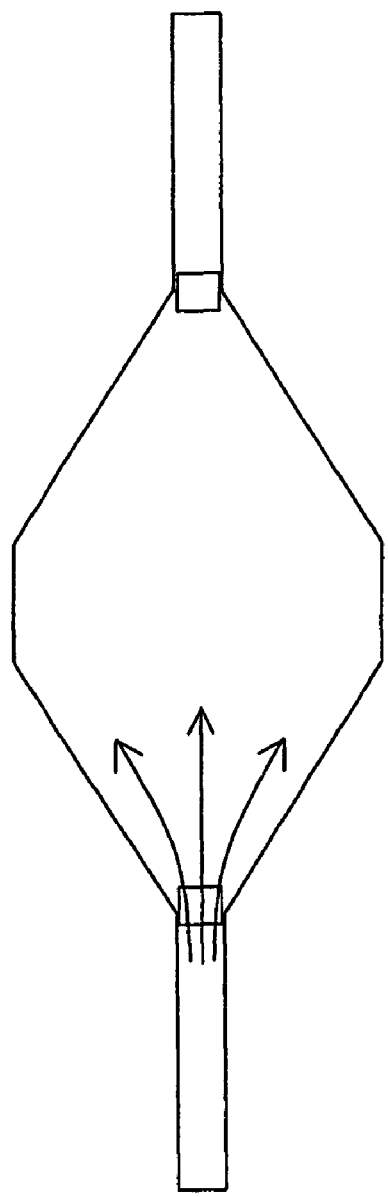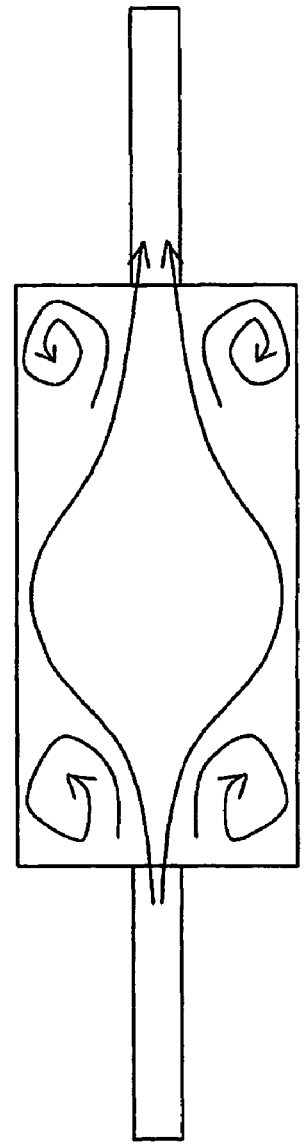
FIG. 34a
FIG. 34b (a)

(b)

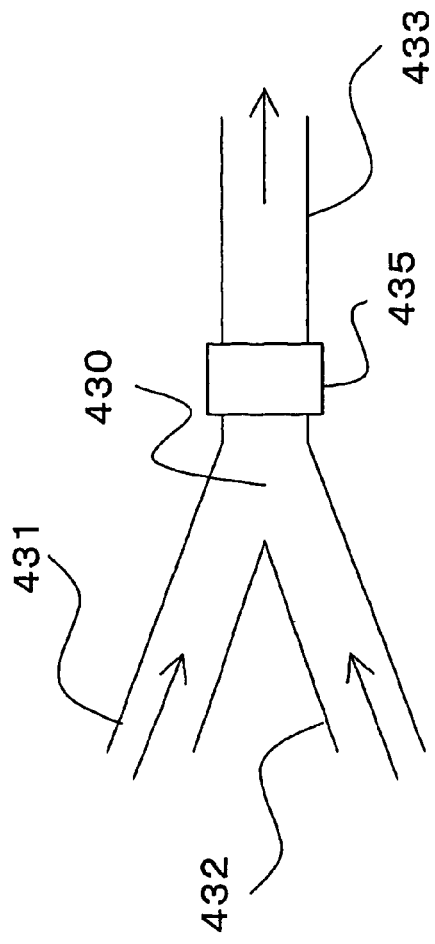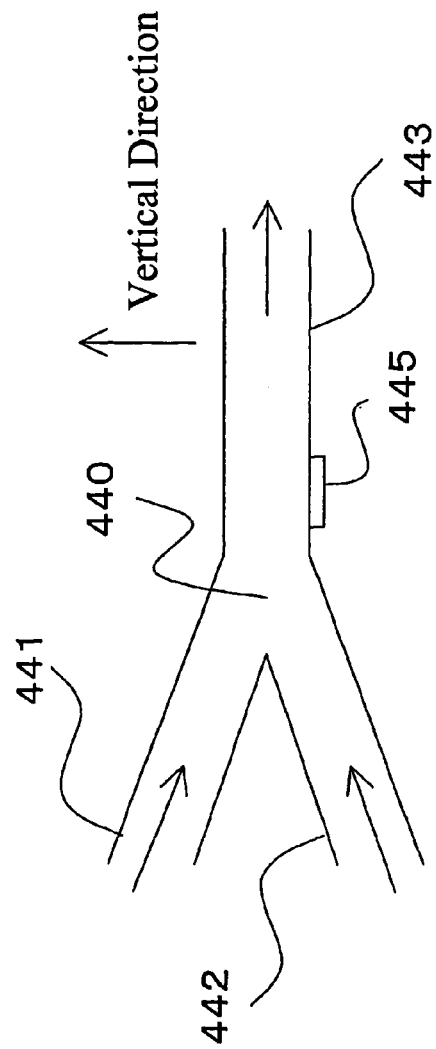
FIG. 44
FIG. 45

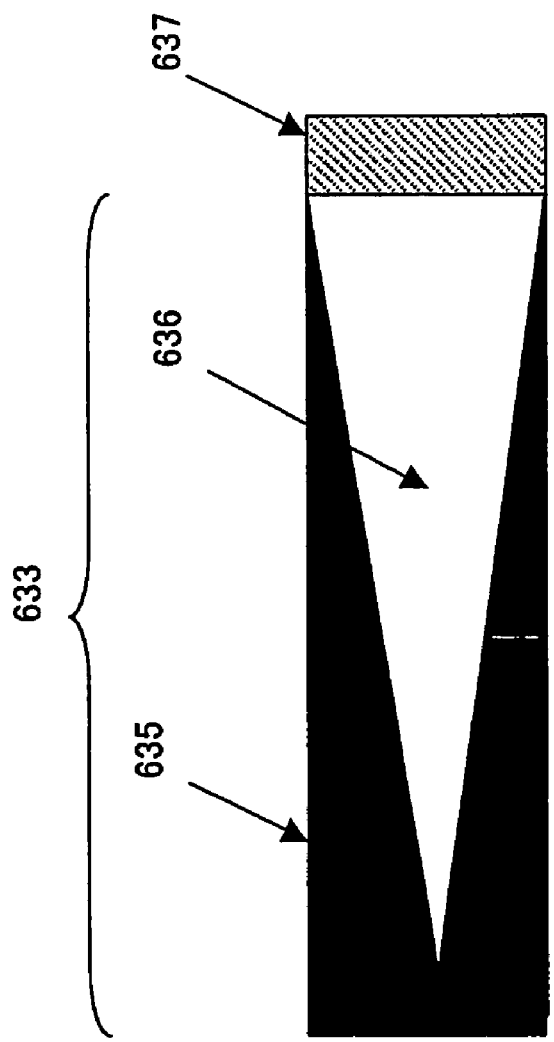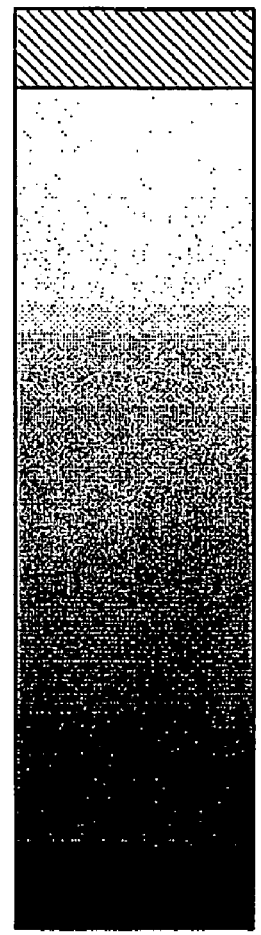
FIG. 53(a)
FIG. 53(b)

(a)

(b)

(a) Substrate having Channel (b) Substrate having Liquid Inlets and Outlets

MICROFLUIDIC TREATMENT METHOD AND DEVICE

BACKGROUND OF THE INVENTION

This invention relates to a microfluid apparatus, and a miniaturized chemical analysis apparatus. More particularly, the present invention relates to a liquid mixing apparatus and a liquid mixing method for causing small amounts of two or more liquids (may be referred to hereinafter as "reagent solutions") to converge in a microchannel, thereby mixing the liquids with high efficiency. The present invention relates, particularly, to a microreactor, etc. for producing, for example, a desired reaction product with high efficiency by a chemical reaction between the liquids mixed in the microchannel.

Further, the present invention relates to a chemical analysis system for separating and analyzing an analyte by utilizing the concentration gradient of a denaturant for the analyte. More particularly, the present invention relates to denaturing gradient gel electrophoresis (DGGE) for separating double-stranded nucleic acids (may hereinafter be referred to simply as "nucleic acids") according to a difference in base sequence with the use of the concentration gradient of a nucleic acid denaturant, a method for forming a denaturing gradient for such a purpose, and a microchip electrophoretic apparatus for performing such DGGE in a microchannel.

Particularly, the present invention relates to a microchip electrophoretic apparatus, etc. which can efficiently mix buffers containing the denaturant in a microchannel and are thus useful for DGGE.

An example of a chemical analysis apparatus having a microchannel structure is a microchip electrophoretic apparatus. Hereinafter, the technical background for the present invention will be described, with a microchip electrophoretic apparatus taken as an example.

Electrophoresis is often used as a means of separating, purifying or analyzing a biopolymer such as a nucleic acid or protein. Electrophoresis is designed to apply a potential to a gel of agarose, polyacrylamide or the like, or a microchannel (capillary), which has been filled with an electrolyte solution, to move charged particles therein and separate particles according to differences in mobility. In electrophoresing double-stranded nucleic acids, the factor that influences mobility is only a molecular weight (the length of a molecule). Thus, they can be separated based on the difference in the molecular weight (length).

As a method for separating double-stranded nucleic acids based on a difference in base sequence, denaturing gradient gel electrophoresis (DGGE) is known. DGGE is used, for example, in detecting the mutation of a nucleic acid, or detecting single nucleotide polymorphism (SNP). In recent years, DGGE has also been used, for example, in the structural analysis of a microbial community which plays an active role in organic waste water and solid waste treatment processes such as the activated sludge process and anaerobic digestion process such as methane fermentation, or in bioremediation which cleans up and restores contaminated soil and groundwater with the use of microorganisms. In the structural analysis of the microbial community, 16S rRNA gene, which is a sequence common to all microorganisms, is often utilized. That is, nucleic acids are extracted from a sample containing a microbial community to be analyzed, and separated by DGGE. The sample to be analyzed by DGGE is an amplification product amplified using primers for PCR which can amplify a sequence portion of the 16S rRNA gene common to microorganisms. With DGGE, nucleic acids originating from main microorganisms constituting the microbial community can be separated on the gel based on differences in the base sequences of the 16S rRNA gene. Among a plurality of lanes on the same gel, nucleic acids located at the same migration distance can be judged to have the same base sequence, so that differences in the constitution of the microbial community to be analyzed can be analyzed. For example, the 16S rRNA gene of a particular microorganism is similarly handled and electrophoresed in a different lane on the same gel. By comparison of the location of its nucleic acid band, it can be determined whether this microorganism is present in the microbial community of interest.

DGGE has the following drawbacks: Since it takes time for gel preparation and electrophoresis, it is not suitable for high throughput (high speed mass treatment) analysis. Since the size of the gel is as large as about 20 cm×about 20 cm×about 1 mm, a large thermostatic chamber is required, making the entire apparatus upsized. Resolution is low compared with microchip electrophoresis.

In preparing a denaturing gradient gel, moreover, a complicated manual procedure is required, and it is difficult to provide a constant denaturing gradient of the gel. Thus, when the structure of the microbial community is analyzed by DGGE, a proper comparison of data between different gels is difficult.

In the early 1990s, Manz proposed the concept of a miniaturized chemical analysis apparatus incorporating all factors necessary for chemical analysis and biochemical analysis onto one chip, so-called micro total analysis system (μTAS). Since then, various types of μTAS's have been developed.

In microchip electrophoresis, which belongs to a field of μTAS, there is used a microchip comprising a substrate having micro-scale channels with a width and a depth of the order of 10 to 100 μm formed thereon by a microfabrication technology, and another substrate bonded onto the substrate. Generally, this microchip is used in measuring the molecular weight of DNA or RNA. In the measurement of the molecular weight of DNA or RNA, the surfaces of the channels are chemically modified to suppress an electroosmotic flow and, in this state, a solution of a polymer matrix such as linear polyacrylamide or hydroxymethylcellulose is filled into the channels to separate DNA or RNA. Conventional agarose gel electrophoresis requires a migration time of 30 minutes to 1 hour. A microchip electrophoretic apparatus, on the other hand, is advantageous in that migration is completed in 10 minutes or less, thus shortening the analysis time, and the amounts of a sample and a reagent consumed are small.

With the aim of further converting a microchip electrophoretic apparatus into μTAS, Ramsey (Domestic Patent Publication (Japanese Translation of PCT application) No. 1998-507516; Patent Document 1) proposes a microchip laboratory apparatus for analyzing or synthesizing a chemical substance. This microchip laboratory apparatus is characterized by simultaneously controlling the potentials of a plurality of reservoirs in order to transport a subject substance from a reservoir filled with the subject substance toward another reservoir. In this apparatus, however, double-stranded nucleic acids are merely separated based on a difference in molecular weight, and double-stranded nucleic acids are not separated based on a difference in base sequence.

Knapp (Domestic Patent Publication No. 2001-521622; Patent Document 2) proposes a method for analysis of nucleic acid and a method for analyzing the melting point of nucleic acid in a microfluidic device. In these methods, a mutation of a nucleic acid sequence is detected with the use of a chemical denaturant concentration gradient and an oligonucleotide probe. However, it is necessary to design, beforehand, an oligonucleotide probe unique to an intended nucleic acid sample. Thus, only a mutation of a known base sequence can be detected, and a mutation of an unknown base sequence cannot be detected.

Bek (Japanese Patent Application Laid-Open No. 1996-261986; Patent Document 3) proposes a liquid mixing method and a liquid mixing apparatus using an electroosmotic flow on a microchip. In this document, only the method and apparatus for liquid mixing on the microchip are provided, there is no mention of a denaturant concentration gradient or separation of double-stranded nucleic acids.

Righetti (Domestic Patent Publication No. 1998-502738; Patent Document 4) provides a method for detecting a point mutation in a double-stranded nucleic acid fragment with the use of a viscous polymer on a microchip. However, a temporal temperature gradient is utilized, and a dedicated computer program for temperature control is required separately.

Baba (Japanese Patent Application Laid-Open No. 2003-66003; Patent Document 5) proposes a microchip electrophoretic apparatus in which a water-soluble polymer solution is filled into microchannels as a running buffer with a concentration gradient. However, what is formed on a microchip is the concentration gradient of the water-soluble polymer. Thus, measurement of the molecular weights of nucleic acids can be made, but double-stranded nucleic acids cannot be separated based on a difference in base sequence. The formation of the polymer concentration gradient, in particular, involves the complicated task of sequentially filling buffer solutions having different polymer concentrations.

As described above, conventional DGGE has drawbacks, such as a complicated experimental procedure, a long time of analysis, unsuitability for high throughput analysis, necessity for a large apparatus, and low resolution compared with capillary electrophoresis. Another drawback is that comparison of data among different gels is difficult in analyzing a microbial community structure by DGGE. Moreover, µTAS's proposed thus far, including microchip electrophoretic apparatuses, concern measurement of the molecular weights of nucleic acids, or separately require a dedicated computer program for temperature control, etc., or necessitate previous designing of an oligonucleotide probe for detection of a particular base sequence and cannot separate unknown double-stranded nucleic acid fragments based on a difference in base sequence.

Patent Document 1: Domestic Patent Publication No. 1998-507516
Patent Document 2: Domestic patent Publication No. 2001-521622
Patent Document 3: Japanese Patent Application Laid-Open No. 1996-261986
Patent Document 4: Domestic Patent Publication No. 1998-502738
Patent Document 5: Japanese Patent Application Laid-Open No. 2003-66003
Patent Document 6: Japanese Patent Application Laid-Open No. 2001-120971

SUMMARY OF THE INVENTION

The problem of difficulty in mixing is a general problem encountered not only in microchip electrophoresis, but also in mixing a plurality of liquids in a microchannel. As discussed earlier, when the width or depth of the channel is small, a Reynolds number relevant to fluidity within the channel is very low. If the Reynolds number is 100 or less, the flow in the channel is prone to become a stable laminar flow, and turbulent diffusion between liquids which have converged tends to occur minimally between liquids which have converged. Thus, the liquids mix substantially only upon molecular diffusion at the interface, and this hinders prompt mixing. Particularly if the flow velocity within the channel is low, this tendency is noticeable. The above problem has been a factor for impeding the simplification of the experimental procedure, the shortening of the analysis and reaction times, high throughput, microchip downsizing, and high accuracy (for example, high resolution) in microchip apparatuses as a whole, such as analytical microchips and microreactors.

Lengthening of channels is a solution to the above-described problem. For example, in a structure in which two microchannels for introducing liquids are connected to a mixing microchannel to mix two liquids simply (FIG. 1 or FIG. 29), it is conceivable to lengthen the mixing microchannel for performing sufficient mixing (FIG. 2 or FIG. 29). In this case, however, the mixing microchannel accounts for a large area, thus posing the defects that downsizing of the apparatus is difficult, and that the liquids take time for passing the channel, thus lengthening the analysis time and the reaction time.

As another solution, Abe et al. propose a liquid mixing apparatus in which a channel from a reservoir is branched, and the branched channels are interconnected to facilitate mixing of liquids (Japanese Patent Application Laid-Open No. 2001-120971; Patent Document 6). According to this method, however, the liquid flowing anteriorly and the liquid flowing posteriorly are mixed. This makes it impossible to exercise quantitative concentration control such that a concentration gradient is formed in the flowing direction.

(1) An object of the present invention is to provide a liquid mixing apparatus and a liquid mixing method which can promptly mix minute amounts of liquids on a microscale, and which permit quantitative concentration control.

(2) Another object of the present invention is to provide an analytical microchip (for example, a microchip electrophoretic apparatus) and a microreactor, to which a series of liquid mixing techniques found by the inventor has been applied in order to accomplish the simplification of an experimental procedure performed on a microscale, the shortening of the analysis and reaction times, high throughput, microchip downsizing, and high accuracy (for example, high resolution).

As stated already, conventional DGGE poses problems, such as a complicated experimental procedure, a long analysis time, unsuitability for high throughput analysis, necessity for a large apparatus, and low resolution compared with analysis made on a microscale.

(3) Yet another object of the present invention is to provide a microchip electrophoretic apparatus and an electrophoretic method for performing DGGE on a microchip.

To carry out DGGE on a microchip, it is necessary to mix a plurality of buffer solutions, which contain a denaturant at different concentrations, on a microscale. For example, it is necessary to introduce a denaturant-containing buffer solution and a denaturant-free buffer solution into a microchannel, while varying the ratio of their mixing continuously, to form a denaturing gradient. To provide a useful microchip for DGGE, it is important to form a precise, highly reproducible denaturing gradient.

However, as stated earlier, the problem exists that liquids mix minimally within a microchannel. Two buffer solution of different concentrations, which have converged in the microchannel, tend to form a laminar flow, without mingling. Thus, it takes time to obtain a concentration gradient uniform in the width direction of the channel, resulting in a hindrance to the shortening of the analysis time. If mixing is performed over a lengthy time with the use of a long channel as shown in FIG.

2, it is difficult to obtain a predetermined concentration gradient promptly. In the mixing method shown in FIG. 3 (the method described in Japanese Patent Application Laid-Open No. 2001-120971), a liquid flowing ahead and a liquid flowing behind are mixed at a plurality of sites, so that an accurate concentration gradient required for DGGE is difficult to form. The conventional mixing method, as noted here, cannot fulfill the requirement that a concentration gradient required on a microscale be formed accurately. With the conventional method, it is also difficult to control the formation of the concentration gradient precisely and freely.

(4) A further object of the present invention is to provide a microchip electrophoretic apparatus and an electrophoretic method which enable a plurality of buffer solutions containing a denaturant at different concentrations to be mixed promptly in a microchannel, particularly uniformly in the width direction of the channel, whereby a denaturing gradient useful for DGGE can be formed.

(5) A still further object of the present invention is to provide a microchip electrophoretic apparatus and an electrophoretic method useful particularly for DGGE by applying a series of techniques for promotion of liquid mixing, which has been found by the inventor, to the mixing of buffer solutions on a microscale.

Means for Solving the Problems

[Liquid Mixing Apparatus and Liquid Mixing Method]

The present invention for attaining the objects (1) and (2) relates to a liquid mixing apparatus comprising at least two microchannels for introducing liquids and a mixing microchannel that connects to the at least two liquid-introducing microchannels, wherein the liquids are transported from the respective liquid-introducing microchannels toward the mixing microchannel, the apparatus further comprising means for enhancing the mixing of the liquids that converge in the mixing microchannel.

Preferred embodiments of the present invention include a first embodiment (embodiment 1-1, embodiment 1-2, embodiment 1-3, and embodiment 1-4) in which the mixing enhancing means is a means for increasing the area of the interface between the liquids, and a second embodiment (embodiment 2-1, embodiment 2-2, and embodiment 2-3) in which the mixing enhancing means is a means for rendering unstable the interface between the liquids.

EMBODIMENT 1-1

Embodiment 1-1 of the present invention has, as the mixing enhancing means, a mechanism for controlling the flow rates (flow velocities) of the liquids so as to increase the interface between the liquids that converge in the mixing microchannel.

The mixing enhancing means of the apparatus according to the embodiment 1-1 comprises one or more liquid-introducing means by which the flow rate of the liquid being introduced into one liquid-introducing microchannel can be controlled independently of the flow rate of the liquid being introduced into another liquid-introducing microchannel.

In an example of the embodiment 1-1, the mixing enhancing means is preferably such that the liquid-introducing means is a pump capable of low rate control, a valve provided on at least one of the liquid-introducing microchannels, or a combination of the pump and the valve.

In another example of the embodiment 1-1, the liquid-introducing means comprises a first electrode provided at each of the inlets of the liquid-introducing microchannels and a second electrode provided at the outlet of the mixing microchannel, and an electroosmotic flow is generated in each of the liquid-introducing microchannels by application of voltage between the first and second electrodes.

An example of the liquid mixing method used in the embodiment 1-1 includes the step of introducing two or more liquids through two or more liquid-introducing microchannels to the liquids in a mixing microchannel where the liquid-introducing microchannels converge at the same point (a common site), the step by which the flow rate of the liquid being introduced from one liquid-introducing microchannel is rendered different from the flow rate of the liquid being introduced from another liquid-introducing microchannel, whereby the area of the interface between the liquids that converge in the mixing microchannel is increased.

Another example of the liquid mixing method used in the embodiment 1-1 includes controlling by pumps the flow rates of the liquids introduced into the liquid-introducing microchannels, controlling the flow rates of the liquids by valves provided on the liquid-introducing microchannels, and controlling the flow rates of the liquids by combinations thereof.

Still another example of the liquid mixing method used in the embodiment 1-1 includes the step of introducing the liquids into the mixing microchannel by an electroosmotic flow generated by applying voltage between a first electrode provided at each of the inlets of the liquid-introducing microchannels and a second electrode provided at the outlet of the mixing microchannel, the step by which the potential applied is varied according to each of the liquid-introducing microchannels, whereby the flow rate of the liquid introduced from each of the liquid-introducing microchannels is controlled independently.

EMBODIMENT 1-2

Embodiment 1-2 of the present invention has, as the mixing enhancing means, a fast operating valve provided on at least any one of a plurality of liquid-introducing microchannels.

In an example of the embodiment 1-2, the driving means of the fast operating valve makes use of a piezoelectric effect. In another example of the embodiment 1-2, the fast operating valve is such that the liquid-introducing microchannel is locally heated to expand the volume of the liquid in the liquid-introducing microchannel, whereby the ejection of a very small amount of liquid into the liquid mixing microchannel can be controlled at a high speed. In still another example of the embodiment 1-2, the fast operating valve is a means for driving a valve element capable of opening and closing a micro-clearance within the liquid-introducing microchannel.

An example of the liquid mixing method used in the embodiment 1-2 includes the step of introducing liquids from two or more liquid-introducing microchannels connected to a mixing microchannel, and allowing two or more liquids to converge in the mixing microchannel, the step by which a fast operating valve provided on at least any one of a plurality of liquid-introducing microchannels is opened and closed at a high speed to vary the flow rate of the liquid introduced.

Another example of the liquid mixing method used in the embodiment 1-2 includes the step of opening and closing the fast operating valve at a high speed to vary the flow rate of the introduced liquid at short time intervals, so that the ratio (volume ratio) of the liquids accounting for the interior of the mixing microchannel is changed continuously or intermittently in the direction of the channel width, whereby the area of the interface between the liquids is increased.

Still another example of the liquid mixing method used in the embodiment 1-2 includes a step by which the opening and closing cycle of the fast operating valve is rendered constant, and the ratio of the valve-opening time to one opening and closing cycle (i.e., duty ratio) is rendered variable. This liquid mixing method includes the step of providing the fast operating valves on at least two of the plurality of liquid-introducing microchannels, and opening and closing the plurality of fast operating valves in synchronism. Another example of this liquid mixing method includes the step of opening and closing the plurality of fast operating valves in synchronism such that the total flow rate of the liquids flowing into the mixing microchannel becomes constant.

The liquid mixing apparatuses of the embodiments 1-1 and 1-2 can be applied to a microchip and, preferably, can be applied to a microchip electrophoretic apparatus further having a sample inlet through which an analyte can be introduced into the mixing microchannel.

In another aspect of the present invention, the flow rate control mechanism used in the microchip electrophoretic apparatus is useful not only for enhancing mixing, but also for forming a denaturing gradient for separating the analyte. By using the above control mechanism (for example, the embodiment 1-1, the embodiment 1-2, or a combination of them can be used) to control the flow rates of a plurality of introduced liquids (for example, liquids containing a denaturant at different concentrations), particular liquids converging in the mixing microchannel, or a concentration distribution of a reagent in the converging liquids (for example, a concentration distribution of the denaturant) can be formed in the flowing direction.

EMBODIMENT 1-3

Embodiment 1-3 of the present invention has a mixing compartment, as the mixing enhancing means, in at least a part of the mixing microchannel, the mixing compartment having a height smaller than its width.

In an example of the embodiment 1-3, a plurality of microchannels for introducing the liquids to be mixed are connected to the mixing compartment such that one microchannel is placed above or below another to converge.

Another example of the embodiment 1-3 has a premixing microchannel formed upstream of the mixing compartment, the plurality of liquid-introducing microchannels converging into the premixing microchannel.

An example of the liquid mixing method used in the embodiment 1-3 includes a step in which liquids to be mixed are introduced through the plurality of microchannels, and the introduced liquids are converged and introduced into the mixing compartment, the step being the step of introducing the convergent liquids into the mixing compartment having a width smaller than its width.

Another example of the liquid mixing method used in the embodiment 1-3 includes a step in which the liquids introduced into the microchannels are caused to converge so as to be placed one below or above another.

Still another example of the liquid mixing method used in the embodiment 1-3 includes a step in which the liquids introduced into the microchannels converge, are then introduced into one premixing microchannel, and then introduced into the mixing compartment.

EMBODIMENT 1-4

Embodiment 1-4 of the present invention has, as the mixing enhancing means, a mixing section where a plurality of branches leading from each of the liquid-introducing microchannels are three-dimensionally connected with the mixing microchannel in such a way that a plurality of branches are alternately allocated to each other.

An example of the embodiment 1-4 has a layered structure formed by a plurality of substrates laminated together, in which the plurality of substrates are stacked nearly in the converging direction or nearly in the branching direction of the branches. Preferably, the mixing section is in a curved shape.

An example of a manufacturing method for the apparatus of the embodiment 1-4 includes the step of fabricating the channels at the mixing section by use of a photolithography technology. Another example of the manufacturing method may be that for processing the sectional shape of the channel at the mixing section into a curved shape.

Another example of the embodiment 1-4 is a liquid mixing apparatus comprising a group of liquid-introducing microchannels having a plurality of liquid inlets for introducing liquids, and a mixing microchannel connecting to these channels, and wherein the plurality of liquid inlets are geometrically arranged (provided in a geometrical arrangement). An example of the geometrical arrangement is a rectilinear form, an arcuate form, or an elliptical form.

In an example of the embodiment 1-4 having the plurality of liquid inlets, the liquid-introducing microchannels, each of which has a width smaller than the width of the mixing microchannel, gather to form the mixing microchannel. Another example of this embodiment is an apparatus for driving at least some of the liquids by an electroosmotic flow, the apparatus having branched drive electrodes detachably mounted thereto in correspondence with the geometrical arrangement of the plurality of liquid inlets. Still another example of this embodiment is an apparatus for driving at least some of the liquids by a pump pressure, the apparatus having branched liquid-introducing channels detachably connected with the plurality of liquid inlets, which are three-dimensionally arranged.

In another example of the embodiment 1-4 having the plurality of liquid inlets, electrodes arranged on nearly the same planes as the plurality of liquid inlets are provided for the plurality of liquid inlets. In still another example of this embodiment, control means capable of independently controlling the pump pressure and/or the electroosmotic flow is present for each of the group of liquid-introducing microchannels. In a further example of this embodiment, the control means controls the number of channels through which liquid feeding is performed, among the liquid-introducing microchannels accepting the same liquid introduced therein, whereby the total inflow amount of the same liquid into the mixing microchannel can be changed. In a still further example of this embodiment, the control means can exercise control of valves for the liquid-introducing microchannels through which the same liquid is introduced. In another example of the embodiment 1-4 having the control means, a smaller number of pressure pumps or electroosmotic flow drive mechanisms than the number of the liquid-introducing microchannels are provided for the liquid-introducing microchannels through which the same liquid is introduced, the pumps or drive mechanisms being provided upstream of these liquid-introducing microchannels.

In an example of the embodiment 1-4 having the drive electrodes provided at the liquid inlets, the control means can independently exercise (exercise) on-off control on the way from the power to the electrodes for the liquid-introducing microchannels. In another example of this embodiment, the electroosmotic flow drive mechanisms include switches or relays for turning on and off the power to the electrodes.

EMBODIMENT 2-1

Embodiment 2-1 of the present invention has, as the mixing enhancing means, a heater for heating the liquids within the liquid-introducing microchannels and/or the mixing microchannel.

In an example of the embodiment 2-1, the mixing enhancing means is a heater for heating the liquids within the mixing microchannel from the underside of the mixing microchannel.

Another example of the embodiment 2-1 includes at least one heater for heating at least one of a plurality of the liquid-introducing microchannels, and the plurality of liquid-introducing microchannels are connected to the mixing microchannel such that the liquid-introducing microchannels are stacked from below in a vertical direction in a sequence in which their temperatures increase upon heating by the heater.

An example of the liquid mixing method used in the embodiment 2-1 includes a step in which a plurality of liquids to be mixed are introduced through a plurality of liquid-introducing microchannels, and the plurality of liquids are converged and introduced into a mixing microchannel, the step being a step of heating the liquids within the liquid-introducing microchannels and/or the mixing microchannel by a heater. Another example of the liquid mixing method includes a step in which a plurality of liquids are converged, one liquid placed above or below another, and introduced into a mixing microchannel. Still another example of the liquid mixing method includes the step of heating the liquids within the mixing microchannel by a heater. Yet another example of the liquid mixing method includes the step of heating the liquids within the mixing microchannel from below by a heater.

Another example of the liquid mixing method used in the embodiment 2-1 includes the step of heating the liquid within at least one of a plurality of the liquid-introducing microchannels, and introducing the liquids within the plurality of liquid-introducing microchannels into the mixing microchannel such that the liquids are stacked and converged from below in a vertical direction in a sequence of decreasing temperature.

EMBODIMENT 2-2

Embodiment 2-2 of the present invention includes, as the mixing enhancing means, a mechanical mixing and/or stirring means for disturbing the interface between the liquids that converge in the mixing microchannel.

In an example of the embodiment 2-2, the mechanical mixing and/or stirring means is a lifting surface, a rotator or an oscillator that is provided in or near the area where the liquids converge in the mixing microchannel.

In another example of the embodiment 2-2, the mechanical mixing and/or stirring means is a vibrator provided on the inner wall surface of the mixing microchannel. In still another example of the embodiment 2-2, the mechanical mixing and/or stirring means is a vibrator provided on the outer wall surface of the mixing microchannel. The lifting surface refers to a surface which, when actuated in the flow, generates a pressure difference between upper surface and lower surface to form vorticity at the behind. Preferably, the lifting surface may be a flap with airfoil cross section, or may be a simple flat surface.

In another example of the embodiment 2-2, the rotator or oscillator is driven by a magnetic force.

An example of the liquid mixing method used in the embodiment 2-2 includes the step of mixing two or more liquids by introducing the liquids through two or more liquid-introducing microchannels into a mixing microchannel where the liquid-introducing microchannels converge at a common site, the step being a step in which the interface between the liquids to converge is disturbed by a mechanical mixing and/or stirring means in or near the area where the liquid-introducing microchannels converge (i.e., upstream of the mixing microchannel). In another example of this liquid mixing method, the mechanical mixing and/or stirring means is a vibrator provided on the outer wall of the mixing microchannel, or a lifting surface, a rotator or an oscillator provided within the mixing microchannel.

Another example of the liquid mixing method used in the embodiment 2-2 includes a step in which liquids to converge are introduced into the mixing microchannel such that the interface between the liquids is retained, and a step in which after completion of the introduction of the liquids, the interface between the liquids is rendered unstable by a vibrator after flowing of the liquids comes to a halt. An example of this liquid mixing method includes the step of rendering the interface between the liquids unstable by a vibrator provided on the inner wall surface of the mixing microchannel. Another example of this liquid mixing method includes the step of transmitting vibrations to the liquids within the mixing microchannel by a vibrator provided on the outer wall surface of the mixing microchannel, thereby rendering the interface between the liquids unstable.

EMBODIMENT 2-3

Embodiment 2-3 of the present invention has, as the mixing enhancing means, a number of nano- to micron-structures allocated within the mixing microchannel. In an example of the embodiment 2-3, the nano- to micron-structures are projections or grooves that are sufficiently smaller than the width of the mixing microchannel.

Combinations of the Embodiments Having the Mixing Enhancing Means

For the liquid mixing apparatus and method of the present invention, the mixing enhancing means shown in the embodiments 1-1 to 2-3 can be used alone, or in any combinations.

An example of the preferred combination is a combination of the first embodiment for increasing the interface between the liquids by flow rate control, and the second embodiment for destroying the interface between the liquids increased by flow rate control. Particularly preferred combinations include a combination of the independent flow rate control of the embodiment 1-1, and the heater of the embodiment 2-1. Mixing is effectively enhanced, if the area of the interface between the liquids formed in the mixing microchannel is increased by the flow rate control of the embodiment 1-1 and, at the same time, the increased interface is rendered unstable by heat convection produced by the heater of the embodiment 2-1.

Similarly, mixing can be effectively enhanced by a combination of at least one aspect of the first embodiment (embodiments 1-1 to 1-4) which can increase the area of the interface between the liquids, and at least one aspect of the second embodiment (embodiments 2-1 to 2-3) which can render the interface between the liquids unstable.

The heater of the embodiment 2-1 can be easily combined with other mixing enhancing means. For example, the use of the heater on the underside of the mixing compartment of the embodiment 1-3, or on the underside of the mixing section of the branches of the embodiment 1-4 is preferred, because it increases the area of the interface between the liquids to be heated. A material with high thermal conductivity may be used for the nano- to micron-structures of the embodiment 2-3, which may be heated by the heater.

Mixing enhancing means of the same type can be together applied onto one microchip, if they are applicable onto the same microchip. For example, the increase in the interface between the convergent liquids by the flow rate control of the embodiment 1-1 or 1-2, and the increase in the interface between the convergent liquids based on the channel shape of the embodiment 1-3 or the embodiment 1-4 may be used simultaneously. Similarly, a plurality of mixing enhancing means can be installed on a single channel, if they can be applied in series on the same channel. In case a temperature sensitive reagent or reactant is used, it is advisable to use a method employing a means other than a heater, for example, the vibrator of the embodiment 2-2.

Application of Liquid Mixing Apparatus and Method to Microchip Electrophoretic Apparatus The liquid mixing apparatuses and methods of the foregoing embodiments 1-1 to 2-3 can be used in a microchip electrophoretic apparatus.

An example of the microchip electrophoretic apparatus using the liquid mixing apparatus and method comprises liquid-introducing microchannels for introducing buffer solutions containing a denaturant at different concentrations, a mixing microchannel for forming a concentration gradient region by the mixing of the buffer solutions introduced from the liquid-introducing microchannels, a sample inlet for introducing a sample containing an analyte into the mixing microchannel, and at least one mixing enhancing means shown in the embodiments 1-1 through 2-3 for convergence of liquids within the mixing microchannel. In this embodiment, the mixing of buffer solutions containing a denaturant at different concentrations can be enhanced by applying the liquid mixing apparatuses and methods of the embodiments 1-1 to 2-3 singly or in any preferred combination.

The liquid mixing means or flow rate control means of the above-mentioned respective embodiments can be used in embodiment A or embodiment B described below. Combinations of them are applicable in any embodiments in accordance with the disclosures offered herein. The disclosures herein teach their preferred combinations and embodiments of the preferred combinations.

[Apparatus and Method for Separating Analyte]

The present invention, which attains the aforementioned objects (3), (4) and (5), relates to an apparatus and method for separating an analyte, which makes use of the concentration gradient of a denaturant for the analyte. Preferred embodiments of this invention are concerned with an apparatus which comprises a microchannel for forming a denaturing gradient region containing a denaturant for an analyte, and wherein the analyte is electrophoresed as it is introduced into the denaturing gradient region. The separating apparatus and method of the present invention include "embodiment A" and "embodiment B" which are different in the form of the denaturing gradient, as stated below. In these embodiments, a typical analyte is a double-stranded nucleic acid. The double-stranded nucleic acid includes double-stranded DNA and double-stranded RNA.

EMBODIMENT A

In embodiment A, a denaturing gradient in which the concentration of a denaturant continuously varies is formed by mixing buffer solutions containing the denaturant at different concentrations.

An example of the embodiment A is a microchip electrophoretic apparatus which comprises at least two liquid-introducing microchannels for introducing buffer solutions containing a denaturant at different concentrations, and a mixing microchannel to which the at least two liquid-introducing microchannels connect, wherein a denaturing gradient region is formed by introducing the buffer solutions from the respective liquid-introducing microchannels at varying ratios and converging the buffer solutions in the mixing microchannel.

In another example of the embodiment A, "two buffer solutions containing the denaturant at different concentrations" are a denaturant-containing buffer solution and a denaturant-free buffer solution (may be hereinafter referred to as a buffer solution).

An example of the microchip electrophoretic apparatus of the embodiment A, preferably, has at least one means for enhancing the mixing of the buffer solutions that converge in the mixing microchannel. The mixing enhancing means used in the embodiment A includes the liquid mixing apparatuses of the embodiments 1-1 to 2-3, and combinations thereof. An example of the mixing enhancing means used in the embodiment A is an independent flow rate control means which does not separately require a special apparatus, but which is advantageous in cost, for example, a means of control over an electroosmotic flow as in the embodiment 1-1, or independent control by the pump of the embodiment 1-1.

Another example of the apparatus of the embodiment A comprises a gradient region channel (mixing microchannel) where a nucleic acid denaturing gradient in an electrophoretic buffer solution is formed; a gradient forming portion having a plurality of reservoirs and channels (liquid-introducing microchannels) provided upstream of the gradient region channel for supplying buffer solutions to the gradient region channel; and a sample introduction portion provided downstream of the gradient region channel for introducing a nucleic acid sample containing double-stranded nucleic acids into the gradient region channel. In this embodiment, the reservoirs are filled with buffer solutions containing the nucleic acid denaturant at different concentrations. For example, potential is given to each of the buffer solutions within the reservoirs, whereby electroosmotic flows produced therein can be controlled. By controlling the electroosmotic flows, the buffer solutions from arbitrary reservoirs can be supplied at appropriate flow rates into the gradient region channel. The supply of the buffer solutions is not limited to driving by electroosmotic flows. The supply of the buffer solutions from the reservoirs can be controlled by providing the reservoirs and channels with a pump and/or a valve as explained in the embodiments 1-1 and 1-2.

By using the above control means for liquid driving, the buffer solutions containing the nucleic acid denaturant at different concentrations can be converged at varying ratios from the reservoirs and channels of the gradient forming portion into the gradient region channel. By continuously changing the incoming ratio of the buffer solutions at different concentrations introduced into the gradient region channel, the nucleic acid denaturing gradient can be formed within the gradient region channel. A nucleic acid sample can be introduced into this gradient region and electrophoresed there.

In an example of the apparatus of the embodiment A, a gradient region channel (9) is provided, a gradient forming portion (2) is provided upstream of the gradient region channel (9), and an electrophoretic portion (4) having a sample introduction portion (3) is provided downstream of the gradient forming portion (2). In this embodiment, moreover, the gradient forming portion (2) includes a first reservoir (5) filled with a denaturant-containing buffer solution, and a first channel (7) leading from the first reservoir (5); and a second reservoir (6) filled with a nucleic acid denaturant-free buffer solution, and a second channel (8) leading from the second reservoir (6). In this embodiment, the gradient region channel (9) is formed by the convergence of the first channel (7) and the second channel (8). This embodiment further includes a first electrode (10) connected to the first reservoir (5) and a first power source (11) connected to the first electrode (10), and a second electrode (12) connected to the second reservoir (6) and a second power source (13) connected to the second electrode (12).

In the above embodiment, the potentials of the first and second power sources (11, 13) are controlled, whereby electroosmotic flows produced in the denaturant-containing buffer solution and the denaturant-free buffer solution are controlled, with the result that the two liquids can be mixed at varying ratios. Because of the mixing of these buffer solution at varying ratios, the liquids can be introduced into the electrophoretic portion (4), with the denaturing gradient region being formed within the gradient region channel (9) (for the reference numerals, see FIGS. 59 to 64).

In another example of the apparatus of the embodiment A, the gradient forming portion further includes a first pump (14) capable of driving the liquid within the first reservoir or first channel, and a second pump (15) capable of driving the liquid within the second reservoir or second channel (for the reference numerals, see FIGS. 59 to 64). In this embodiment, the flow rates of the denaturant-containing buffer solution and the denaturant-free buffer solution can be controlled by controlling the application of the potentials by the first power source and the second power source, and controlling the outputs of the first pump and the second pump.

In another example of the apparatus of the embodiment A, the sample introduction portion provided in the electrophoretic portion includes a third reservoir filled with a nucleic acid sample, and a fourth channel leading from the third reservoir, and a fourth reservoir for a nucleic acid waste liquid, and a fifth channel leading from the fourth reservoir. In this embodiment, the fourth channel and the fifth channel communicate with each other while crossing the gradient region channel, and there are further included a third electrode connected to the third reservoir and a third power source connected to the third electrode, and a fourth electrode connected to the fourth reservoir and a fourth power source connected to the fourth electrode. In this embodiment, the nucleic acid sample can be introduced into the gradient region channel by controlling the potentials of the third and fourth power sources and generating electroosmotic flows and/or electrophoresis. The supply of the nucleic acid sample is not limited to driving by the electroosmotic flow. The supply of the nucleic acid sample from the reservoir can be controlled by providing the reservoir and the channel with a pump and/or valve as described in the embodiment 1-1 and 1-2.

In another example of the apparatus of the embodiment A, the electrophoretic portion (4) includes a fifth reservoir (24) for a waste liquid, which is provided downstream on the gradient region channel (downstream of the sample introduction portion), a fifth electrode (25) connected to the fifth reservoir (24), and a fifth power source (26) connected to the fifth electrode (25) (for the reference numerals, see FIGS. 59 to 64). In this embodiment, the nucleic acid sample introduced from the sample introduction portion (3) can be electrophoresed within the gradient region channel (9).

An example of the analyte separating method used in the embodiment A is a method which comprises mixing a denaturant-containing buffer solution and a buffer solution at varying ratios in a channel within a microchip to form a denaturing gradient, and introducing a nucleic acid sample containing double-stranded nucleic acids into the channel, and moving and separating the introduced nucleic acid sample by electrophoresis.

Another example of the separating method used in the embodiment A is a method performed on a microchip which comprises a gradient region channel for forming the concentration gradient of a nucleic acid denaturant, a plurality of reservoirs and channels provided upstream of the gradient region channel for supplying buffer solutions containing the nucleic acid denaturant at different concentrations, and a sample introduction portion provided downstream of the reservoirs and channels for introducing a nucleic acid sample containing double-stranded nucleic acids. This method includes the step of applying potentials to the buffer solutions within the reservoirs, and controlling electroosmotic flows generated therein, to introduce the buffer solutions into the gradient region channel while mixing the buffer solutions at varying ratios, thereby forming the concentration gradient of the nucleic acid denaturant within the gradient region channel, and the step of introducing a nucleic acid sample into the gradient region channel for electrophoresis.

EMBODIMENT B

The applicant filed the apparatus and method related to the embodiment A as Japanese Patent Application No. 2003-392302. In the present application, the applicant does not cling to the concentration gradient forming method of conventional DGGE, and also provides a separation technology which facilitates mass production and enables analysis with high reproducibility.

Embodiment B relates to an apparatus and method for separation which obviate the need for mixing buffer solutions containing a denaturant at different concentrations. The embodiment B relates to a method for separating an analyte, which makes use of a denaturing gradient as a discontinuous concentration gradient of a denaturant, a method for forming a buffer solution zone arrangement for this purpose, and a microchip electrophoretic apparatus using them.

The embodiment B includes a step in which buffer solution zones containing a denaturant for an analyte at different concentrations are arranged alternately in the direction of electrophoresis, and the analyte is introduced into the arrangement of the buffer solution zones for electrophoresis.

In an example of the embodiment B, buffer solution zones containing the denaturant at zero or low concentration, among the buffer solution zones arranged, are arranged such that their length (width in the direction of electrophoresis) decreases progressively downstream in the direction of electrophoresis. In another example of the embodiment B, buffer solution zones containing the denaturant at high concentration, among the buffer solution zones arranged, are arranged such that their length (width in the direction of electrophoresis) increases progressively downstream in the direction of electrophoresis.

In another example of the embodiment B, an arrangement of buffer solution zones containing a denaturant at different concentrations is formed in a microchannel. In this case, a first buffer solution containing the denaturant at a predetermined concentration, and a second buffer solution containing the denaturant at a concentration different from the predetermined concentration are alternately introduced into the microchannel, whereby buffer solution zones containing the denaturant at different concentrations are alternately arranged in the microchannel. In this embodiment, the means for flow rate control used in the aforementioned embodiments 1-1 and 1-2 are used, whereby buffer solution zones containing the denaturant at different concentrations can be alternately introduced into the microchannel.

In another example of the embodiment B, the step of arranging the buffer solution zones alternately includes the step of introducing a first buffer solution into a first microchannel, and then introducing a second buffer solution into a second microchannel intersecting the first microchannel, thereby dividing the first buffer solution within the first microchannel by the second buffer solution within the second microchannel at their intersection, and the step of feeding the first buffer solution and the second buffer solution alternately according to the above step. These steps form an alternate arrangement of the first buffer solution and the second buffer solution within the first microchannel. This embodiment can include the step of progressively changing the length of the first buffer solution in the direction of electrophoresis by controlling the amount of the first buffer solution fed.

An example of the apparatus using the method of the embodiment B is a microchip electrophoretic apparatus which comprises a first microchannel for performing electrophoresis, a means for introducing a first buffer solution into the first microchannel, a means for introducing into the first microchannel a second buffer solution containing a denaturant at a concentration different from the concentration of the first buffer solution, and a means for introducing a sample containing double-stranded nucleic acids into the first microchannel.

Another example of the embodiment B relates to a method for forming an arrangement of buffer solution zones containing a denaturant for a double-stranded nucleic acid at different concentrations on a substrate for electrophoresis, the method comprising holding the substrate, on which the arrangement of the buffer solution zones is to be formed, on a stage means; providing an ejection means for ejecting buffer solutions containing the denaturant for the double-stranded nucleic acids at different concentrations toward the substrate; and controlling the position of the stage means and/or the ejection means and sequentially driving the ejection means, thereby arranging buffer solution zones containing the denaturant at different concentrations on the substrate.

Another example of the method for forming an arrangement of buffer solution zones according to the embodiment B comprises holding a microchip substrate for electrophoresis as the substrate, and placing an arrangement of buffer solution zones containing a denaturant at different concentrations within a microchannel of the held microchip substrate. Yet another example of the method comprises holding a slab gel for electrophoresis instead of the substrate, and placing an arrangement of buffer solution zones containing a denaturant at different concentrations on the held slab gel.

An example of the apparatus for forming an arrangement of buffer solution zones according to the embodiment B is an apparatus for forming an arrangement of buffer solution zones containing a denaturant for a double-stranded nucleic acid at different concentrations on a substrate or a slab gel for electrophoresis, the apparatus comprising a stage means for holding the substrate or slab gel, on which the arrangement of the buffer solution zones is to be formed; an ejection means for ejecting buffer solutions containing the denaturant for the double-stranded nucleic acid at different concentrations toward the substrate or slab gel; and control means for controlling the position of the stage means and/or the ejection means and sequentially driving the ejection means.

In other examples of the apparatus and method for forming an arrangement of buffer solution zones according to the embodiment B, the ejection means can make use of the liquid mixing apparatus and method of the embodiment 1-1 to the embodiment 2-3 having the mixing enhancing means. In this embodiment, the mixing of buffer solutions containing a denaturant at different concentrations, the buffer solutions being supplied to the ejection means, is enhanced by an appropriate liquid mixing means.

The present invention provides a liquid mixing apparatus or method which can promptly and uniformly mix minute amounts of liquids on a microscale. The liquid mixing apparatus or method, provided by the present invention, can be applied to any μTAS's, for example, microchemical analyzers or micro chemical reactors (microreactors), which are existent currently or will be developed in the future. Consequently, the present invention brings various advantages, such as the simplification of an experimental procedure performed on a microscale, the shortening of the analysis and reaction times, high throughput, microchip downsizing, and high accuracy (for example, high resolution).

In another aspect, the present invention provides an apparatus and method for separating an analyte by making use of the concentration gradient of a denaturant for the analyte, and an apparatus and method for forming a denaturing gradient. Particularly, this invention provides a microchip electrophoretic apparatus and an electrophoretic method for performing DGGE on a microchip. This invention also provides a microchip electrophoretic apparatus and an electrophoretic method useful for DGGE, by applying a series of technologies for enhancing liquid mixing on a microscale to the mixing of buffer solutions within a microchannel.

According to the DGGE microchip electrophoretic apparatus and electrophoretic method of the present invention, the concentration gradient of a nucleic acid denaturant can be formed accurately, and the concentration gradient can be controlled freely. Particularly, it is possible to provide, in large quantities, analytical chips which can reproduce always the same denaturing gradient or denaturant arrangement. As a result, strict comparisons and studies of different data become possible, producing various advantages, for example, such that in analyzing the structure of a microbial community based on a comparison of nucleic acids (typically, comparison of base sequences of rRNA gene) contained in samples being analyzed, collected data can be easily compiled into database.

BRIEF DESCRIPTION OF THE DRAWINGS

[FIG. 32a] A view showing the state of liquids in a mixing compartment when the stacking direction of introducing microchannels and the height direction of the mixing compartment are vertical to each other, and the introducing microchannels and the mixing compartment are directly connected together.

[FIG. 32b] A view showing the state of liquids in the mixing compartment when the stacking direction of the introducing microchannels and the height direction of the mixing compartment are vertical to each other, and the introducing microchannels and the mixing compartment are connected together via a premixing microchannel.

[FIG. 34a] A view showing the flow of liquids when the premixing microchannel and the mixing compartment are connected with a gentle slope.

[FIG. 34b] A view showing the flow of the liquids when the premixing microchannel and the mixing compartment are not connected with a gentle slope.

[FIG. 44] A view showing an example of the liquid mixing apparatus of the embodiment 2-1.

[FIG. 45] A view showing another example of the liquid mixing apparatus of the present embodiment.

[FIGS. 53(a) and 53(b)] Schematic views showing still other examples of the liquid mixing apparatus of the present embodiment. (Embodiment 2-3)

EMBODIMENT B

Figure 69:
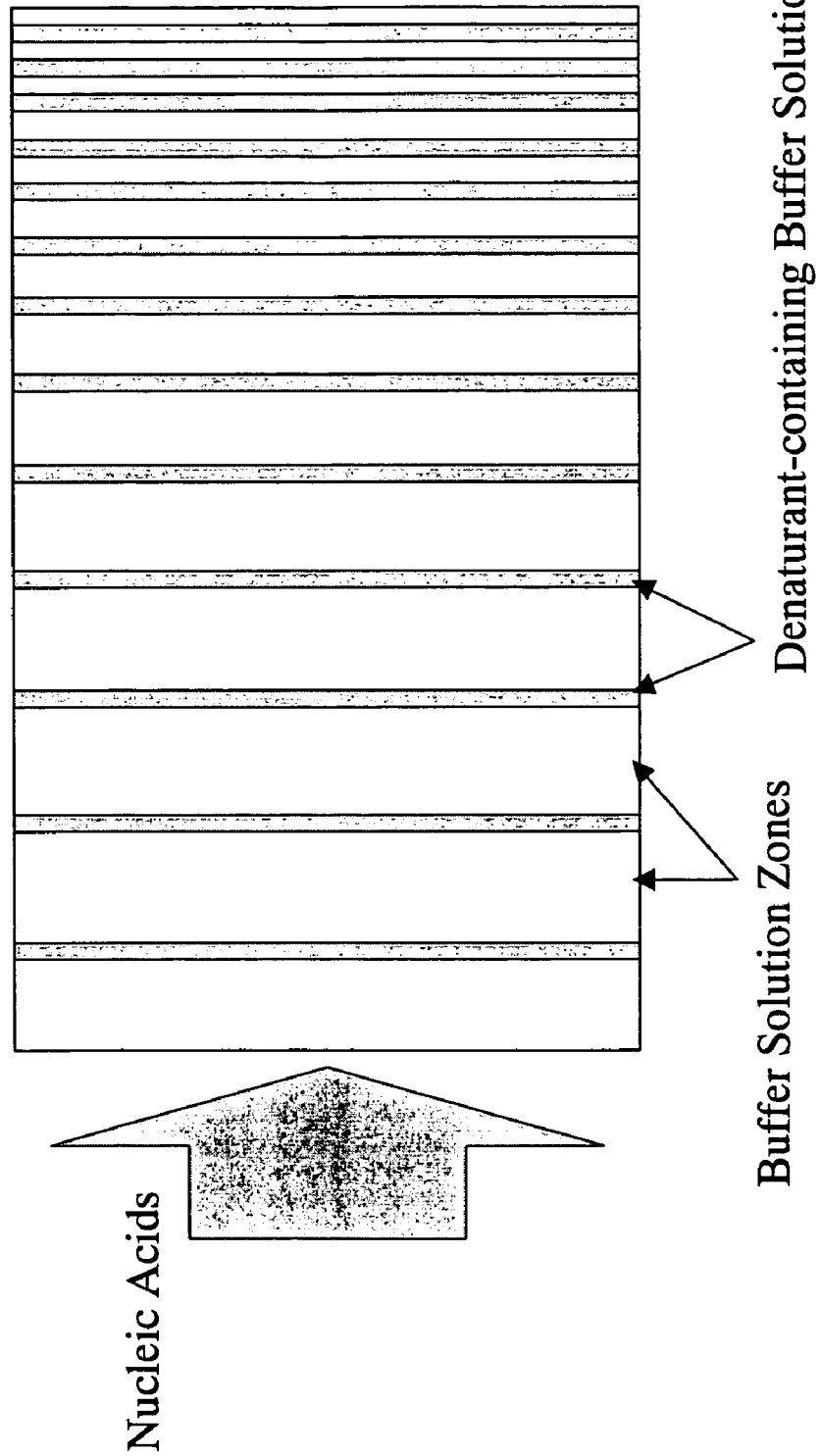

[FIG. 69] A conceptual view showing an intermittent denaturant arrangement of a first form according to the embodiment B.

Figure 70:
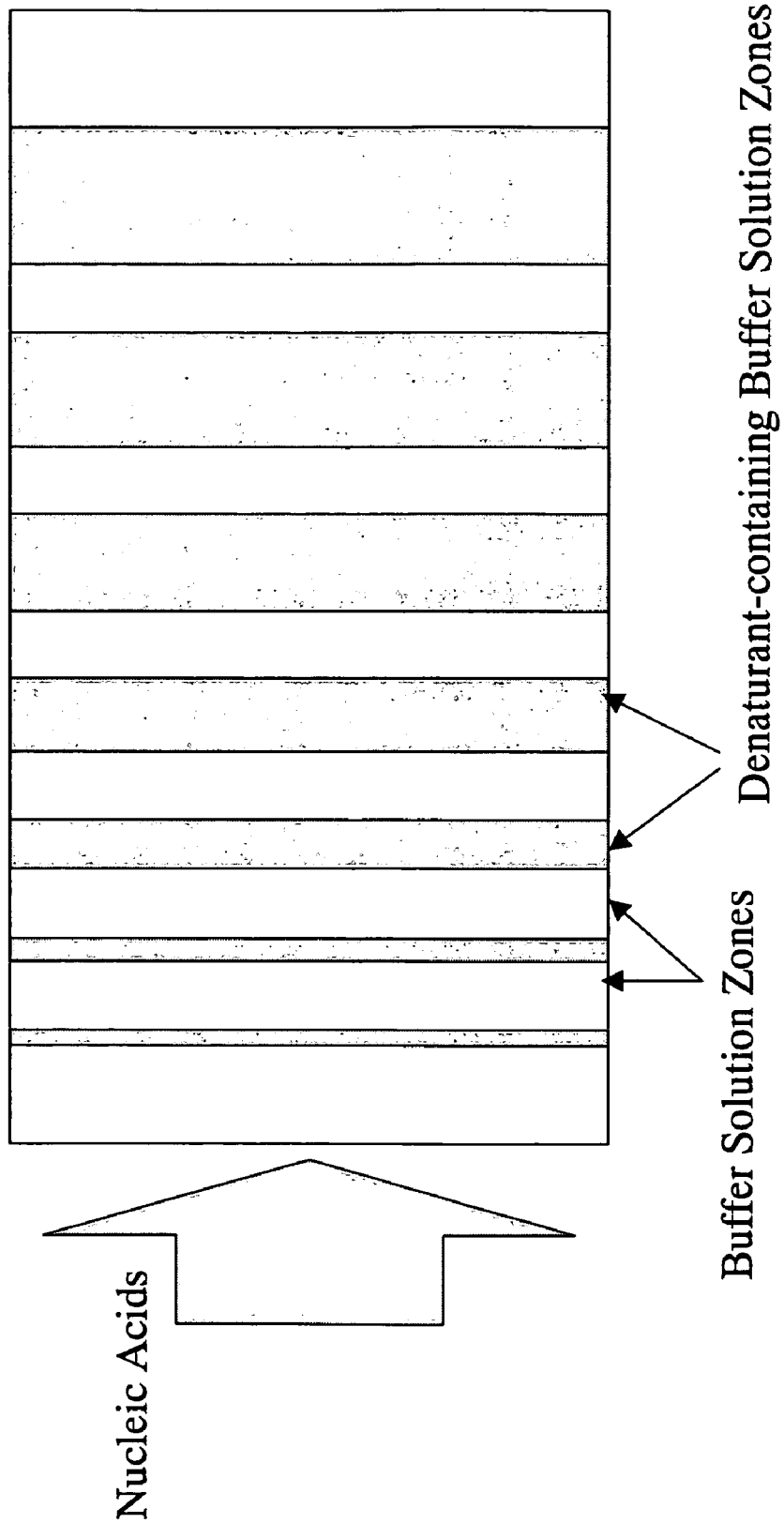

[FIG. 70] A conceptual view showing an intermittent denaturant arrangement of a second form according to the embodiment B.

Figure 71:
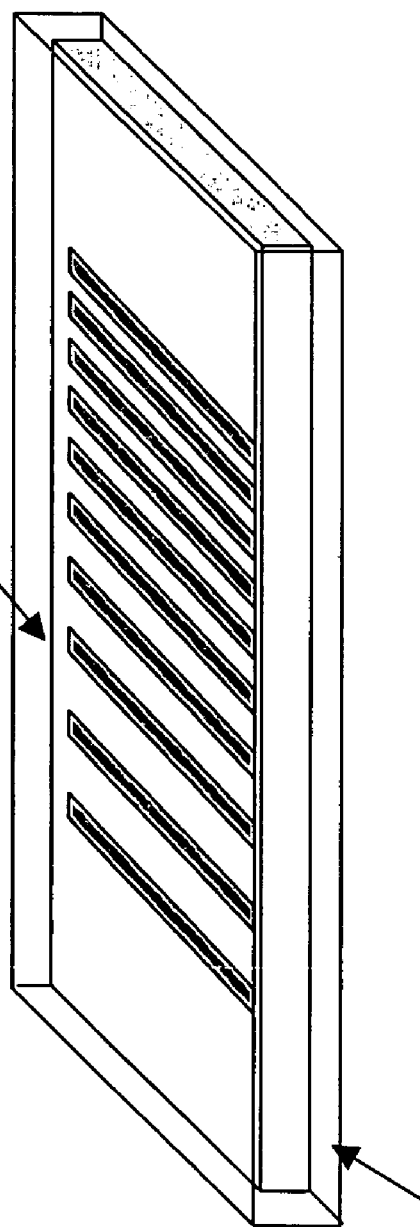

[FIG. 71] A perspective view showing the schematic configuration of an electrophoretic apparatus containing a slab gel having the intermittent denaturant arrangement.

Figure 72:
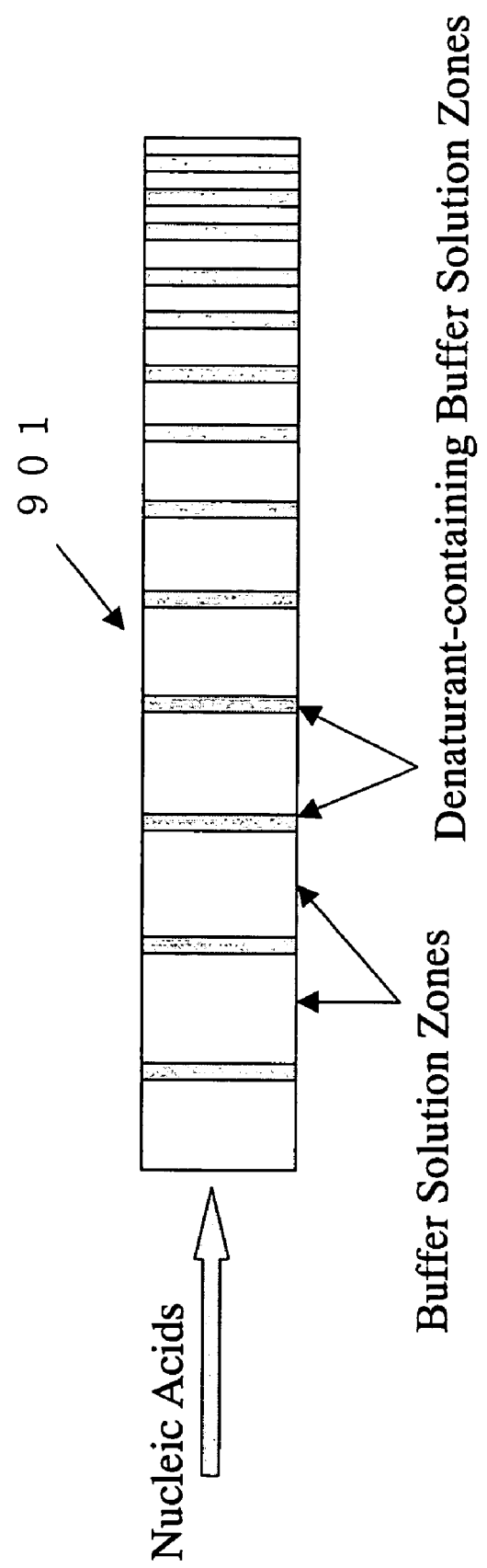

[FIG. 72] A conceptual view showing the intermittent denaturant arrangement formed on a microchannel.

Figure 73:
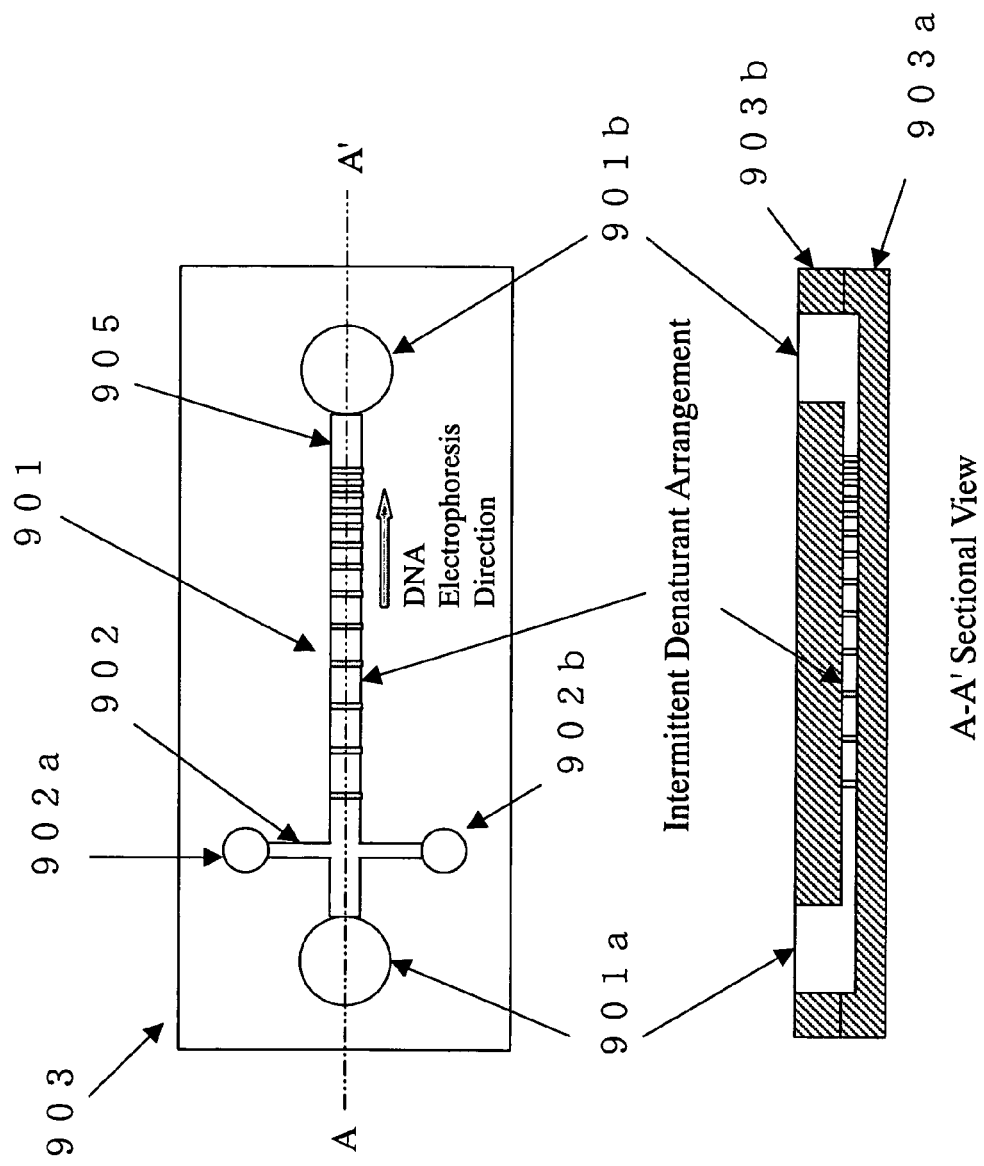

[FIG. 73] A view showing an example of a microchip electrophoretic apparatus according to the embodiment B.

Figure 74:
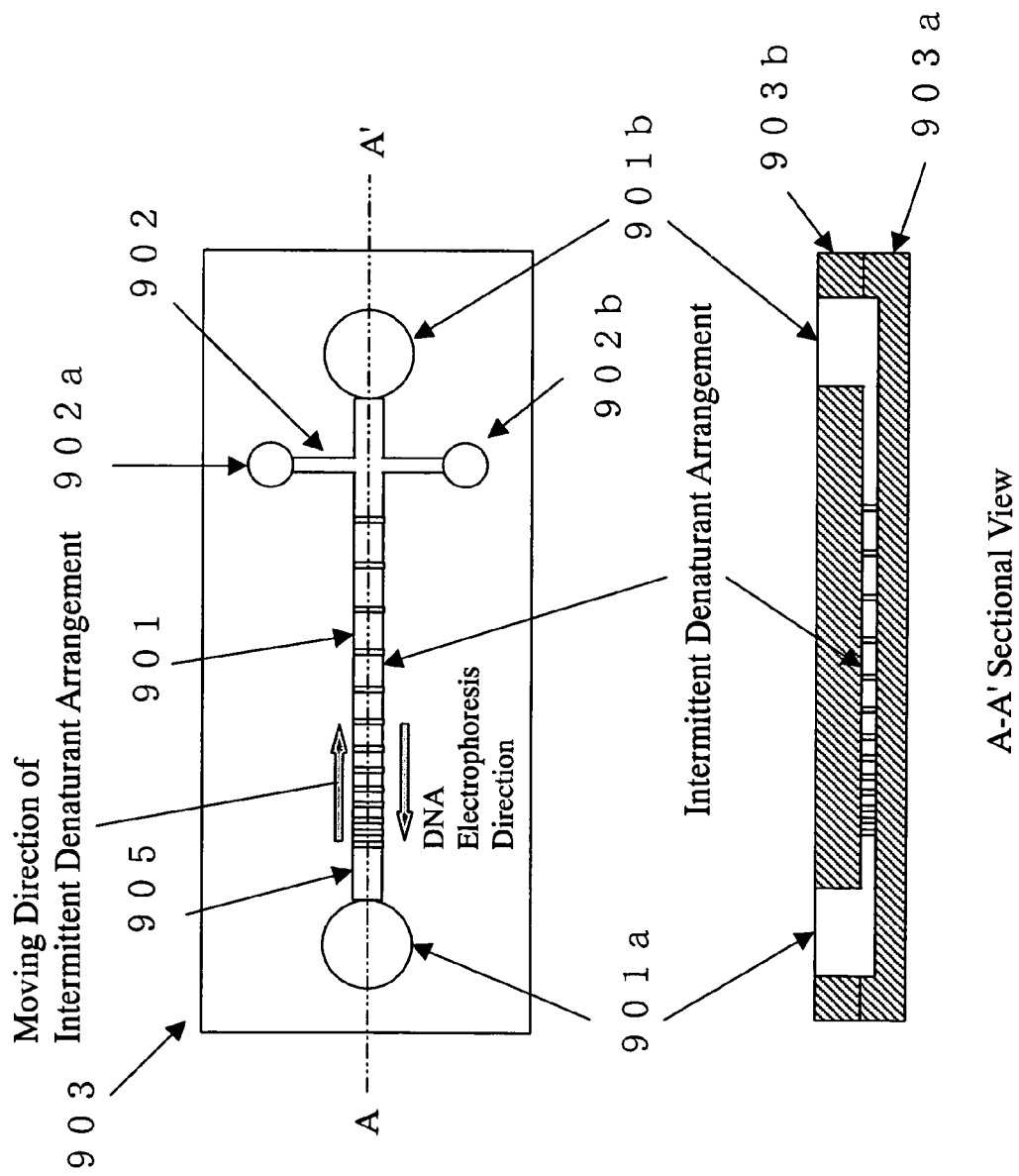

[FIG. 74] A view showing another example of the microchip electrophoretic apparatus according to the embodiment B.

Figure 75:
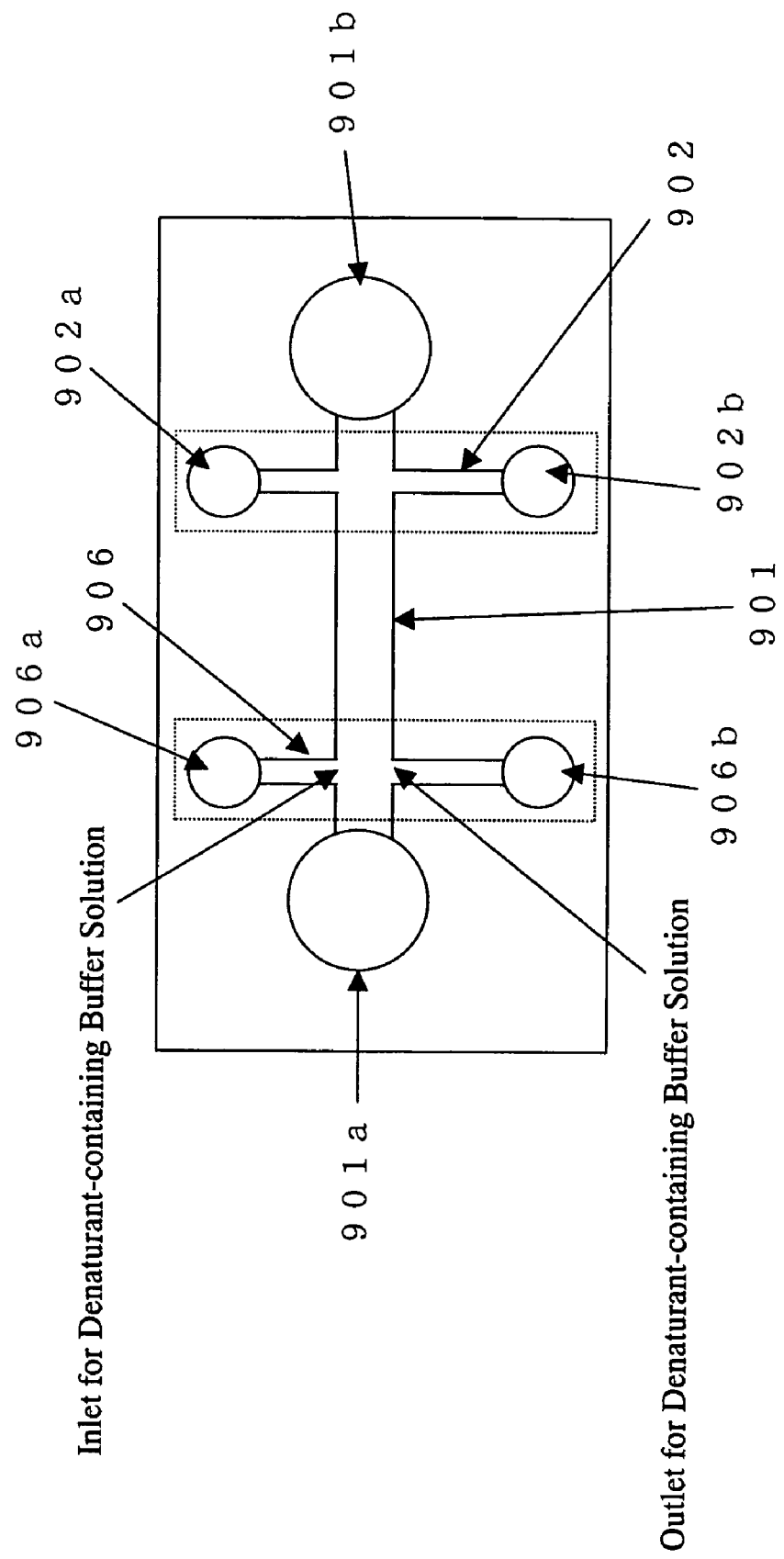

[FIG. 75] A view showing another example of the microchip electrophoretic apparatus according to the embodiment B.

Figure 76:
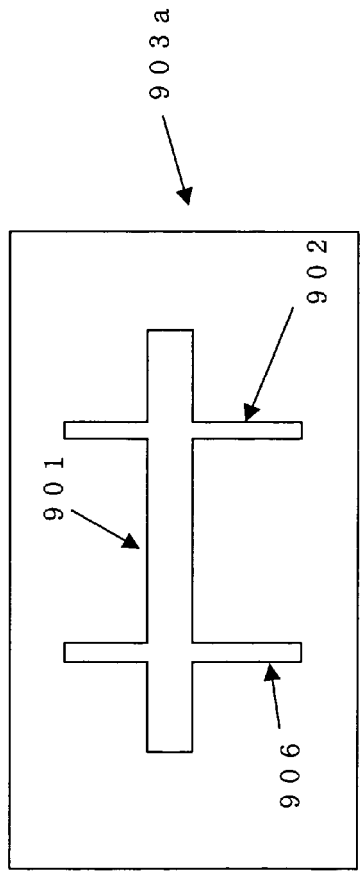
Figure 76:
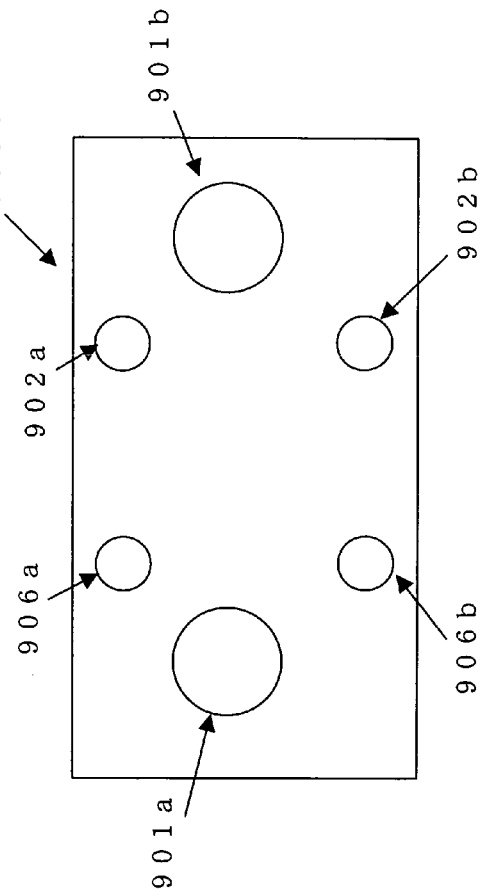

[FIGS. 76(a) and 76(b)] Configurational drawings of respective substrates constituting the apparatus of FIG. 75.

Figure 77:
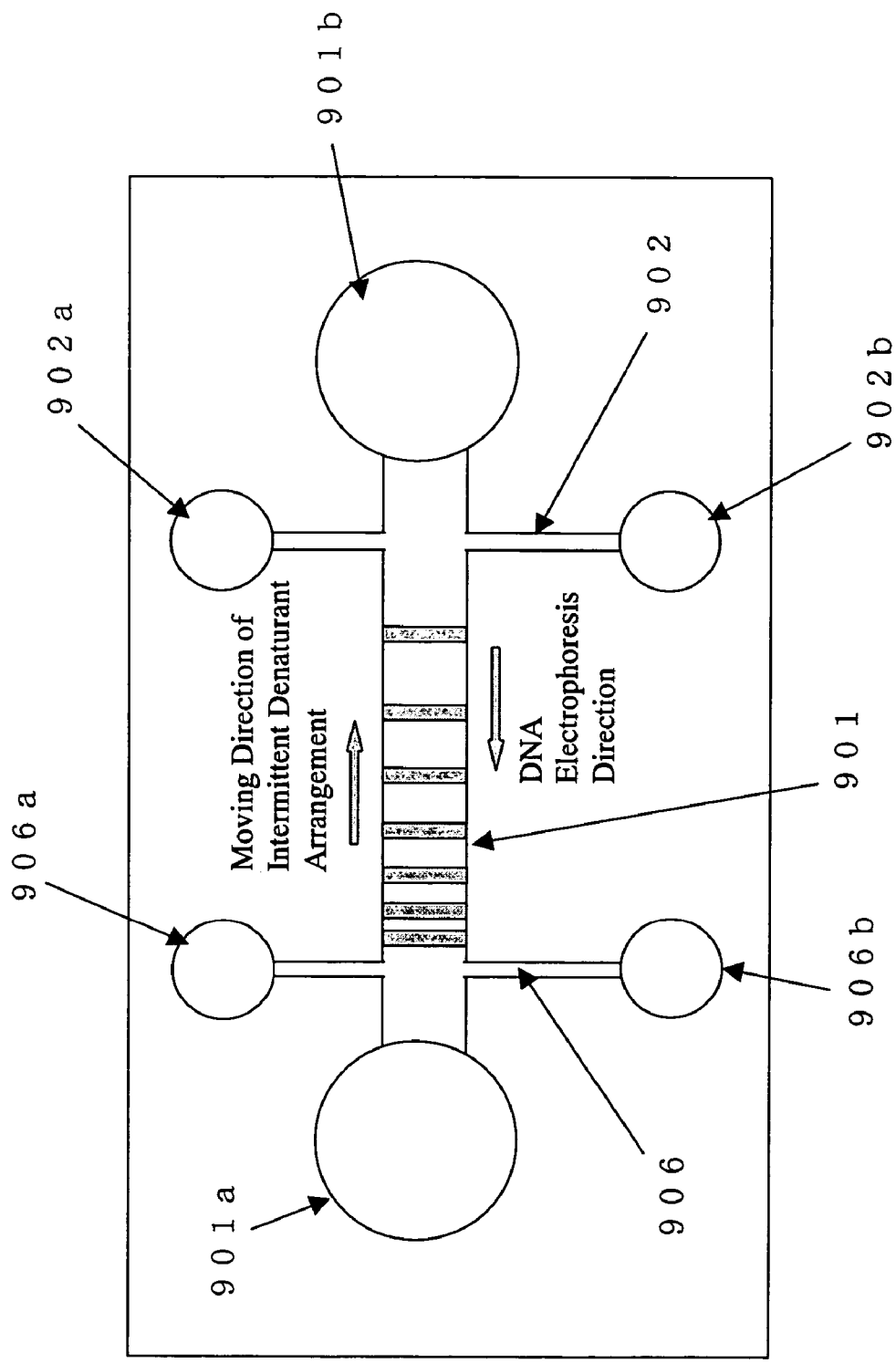

[FIG. 77] A view showing another example of the microchip electrophoretic apparatus according to the embodiment B.

Figure 78:
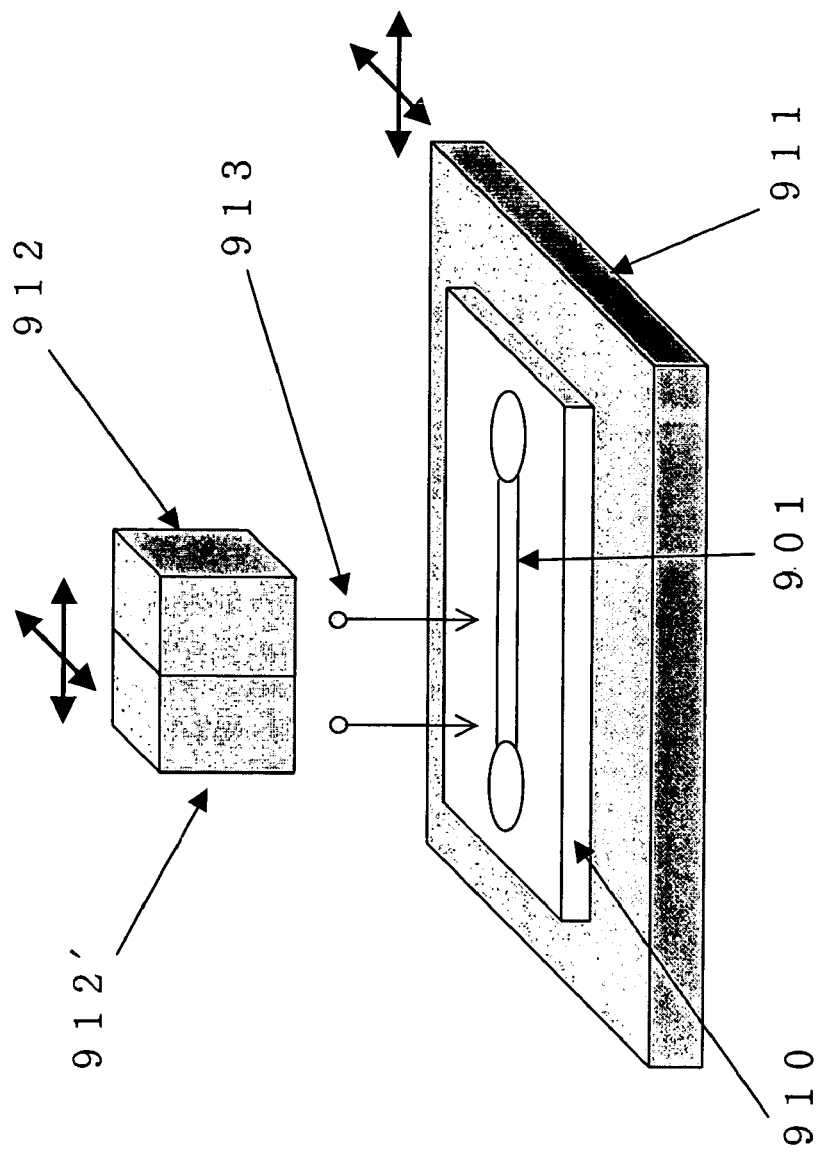

[FIG. 78] A perspective view showing the schematic configuration of an apparatus which forms a buffer solution zone arrangement for the embodiment B.

Figure 79:
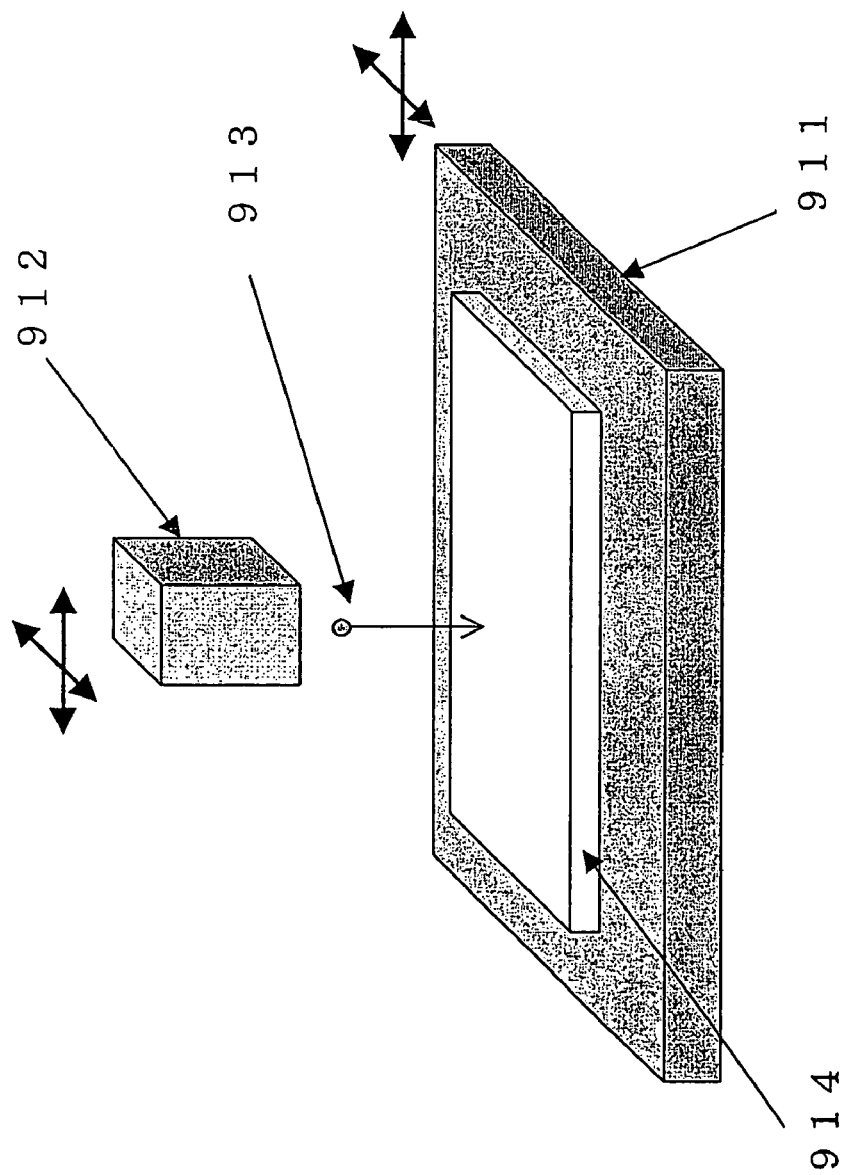

[FIG. 79] A perspective view showing the schematic configuration of an apparatus suitable for forming a buffer solution zone arrangement on a slab gel.

Figure 80:
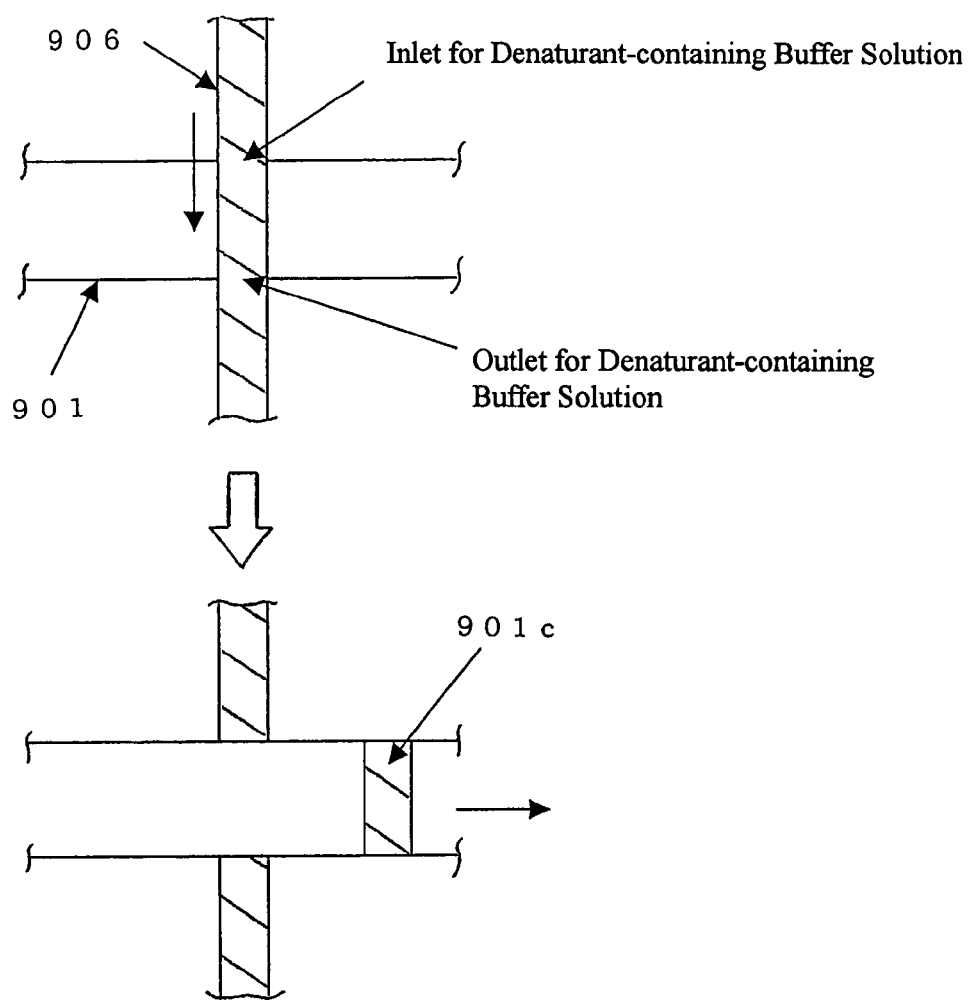

[FIG. 80] A conceptual view showing an example of a method for forming the buffer solution zone arrangement for the embodiment B.

Figure 81:
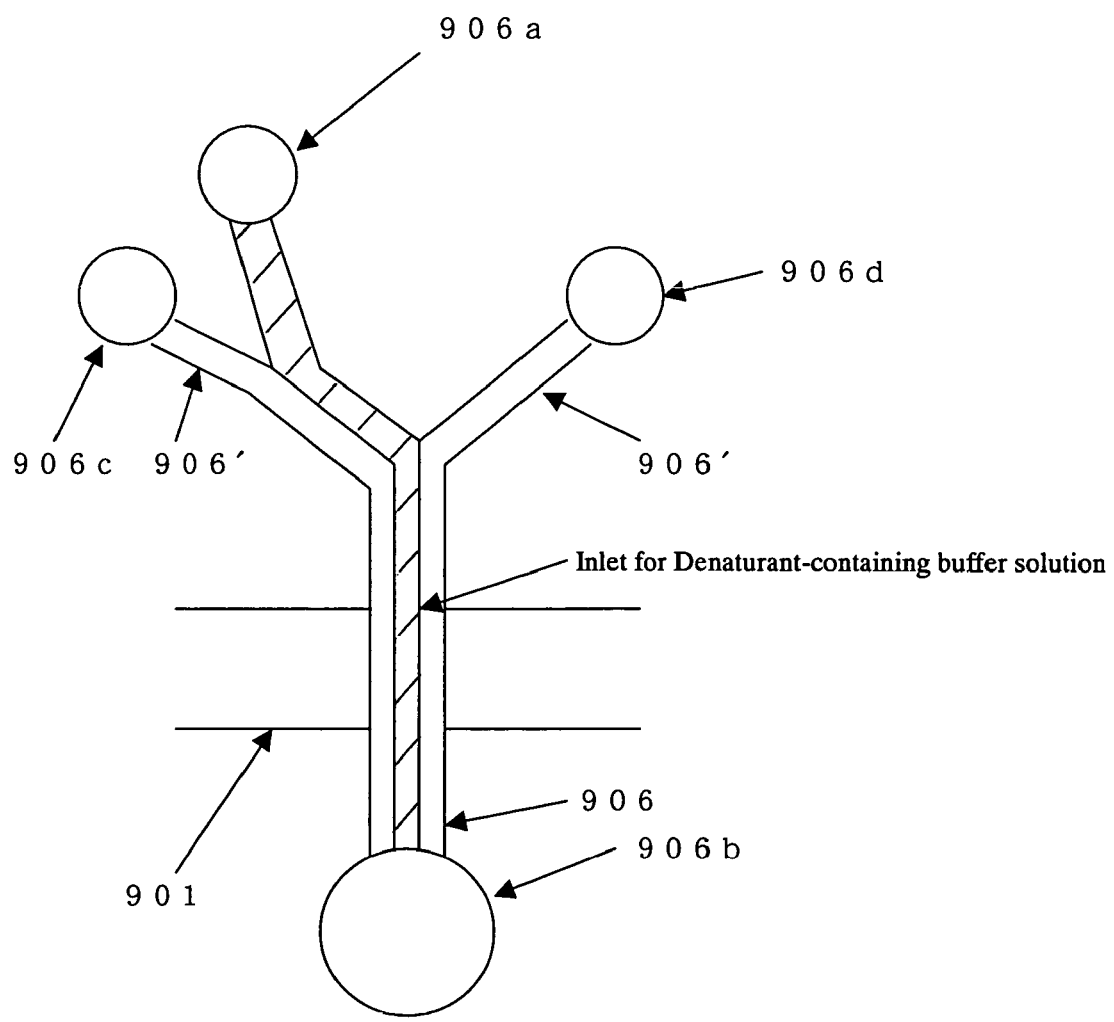

[FIG. 81] A conceptual view showing a method for adjusting the length of a denaturant-containing buffer solution zone for the embodiment B.

Figure 82:
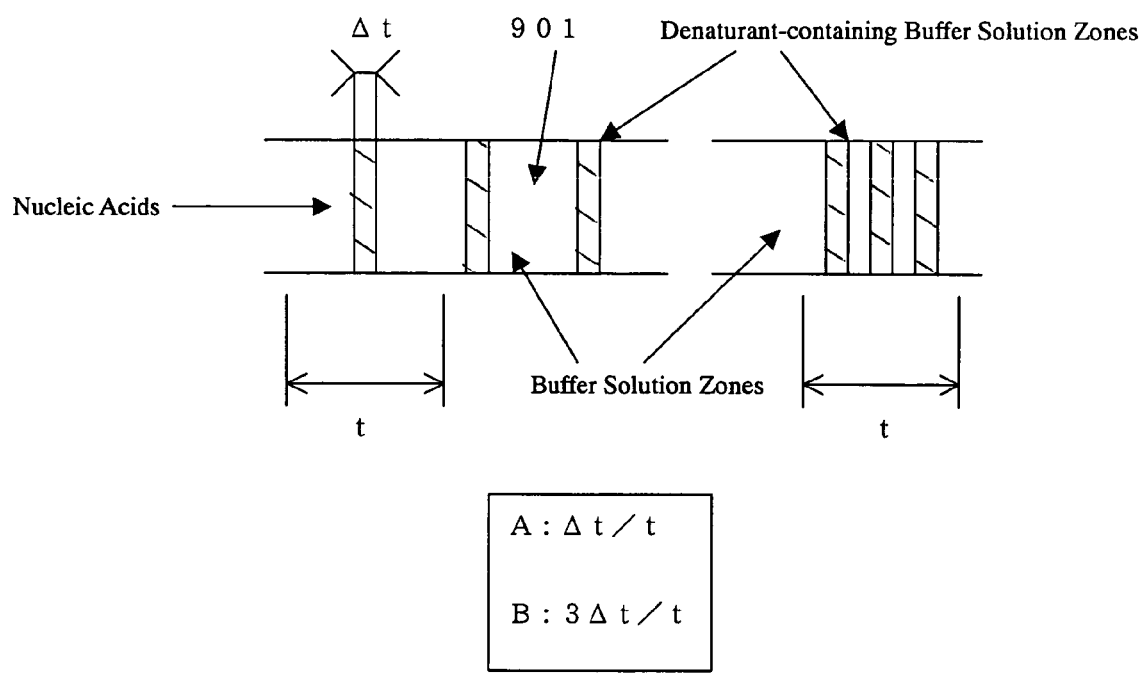

[FIG. 82] A view for explaining the principle of the embodiment B.

Figure 83:
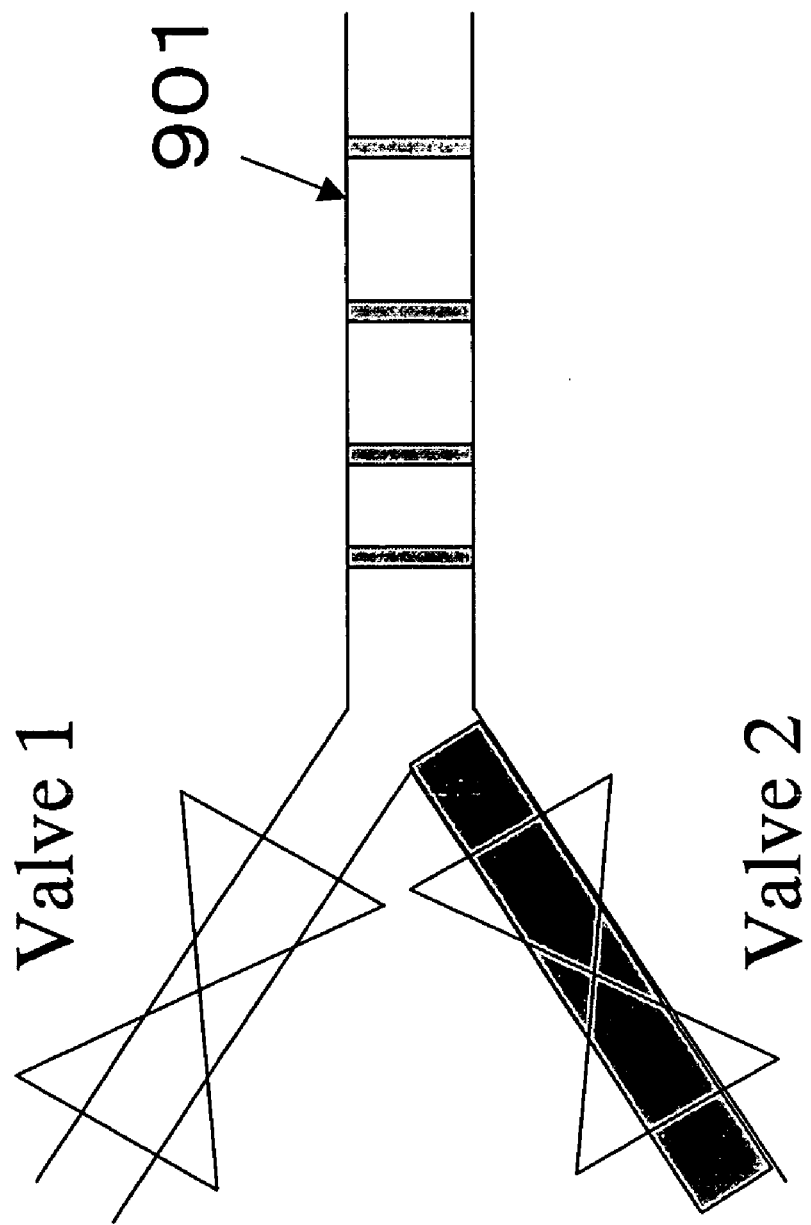

[FIG. 83] A view schematically showing an apparatus mounted with fast operating valves for formation of the buffer solution zone arrangement.

Figure 84:
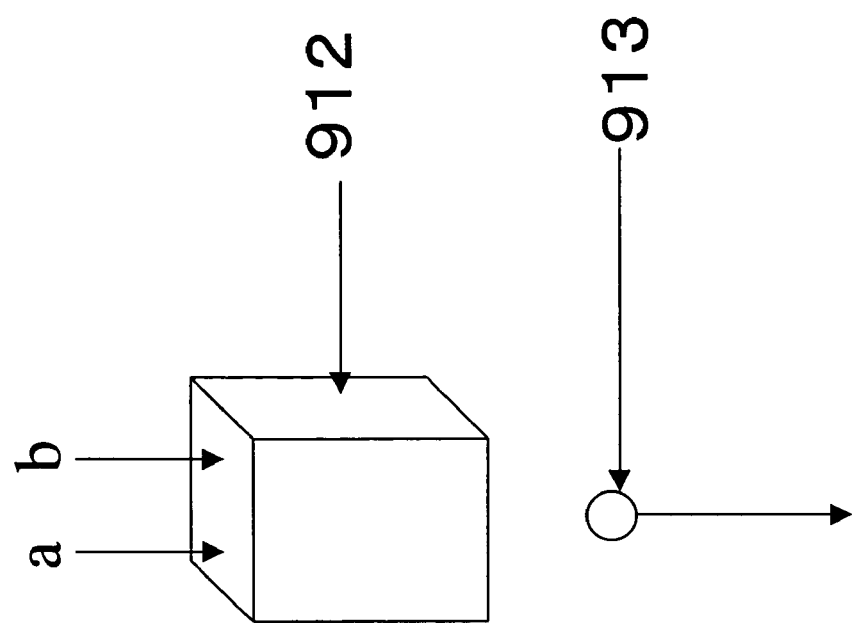

[FIG. 84] A view schematically showing an ejection means for formation of the buffer solution zone arrangement.

EMBODIMENT 1-1; FIGS. 1 TO 7

5; first reservoir, 6; second reservoir, 7; first liquid-introducing microchannel, 8; second liquid-introducing microchannel, 9; mixing microchannel, 10; third reservoir, 11; first electrode, 12; second electrode, 13; third power source, 14; first pump, 15; second pump.

EMBODIMENT 1-2; FIGS. 8 TO 29

130; liquid-introducing microchannel, 131; mixing microchannel, 132; fast operating valve.

EMBODIMENT 1-3; FIGS. 30 TO 35

205; first reservoir, 206; second reservoir, 207; first liquid-introducing microchannel, 208; second liquid-introducing microchannel, 230; mixing compartment, 233; mixing microchannel, 234; premixing microchannel, 235; connecting portion.

EMBODIMENT 1-4; FIGS. 36 TO 43

330; liquid-introducing microchannel, 330a; liquid inlet, 331; mixing microchannel, X; branching direction, Y; converging direction.

EMBODIMENT 2-1; FIGS. 44 TO 46

405; first reservoir, 406; second reservoir, 407; first liquid-introducing microchannel, 408; second liquid-introducing microchannel, 430; mixing section or converging portion, 431, 432, 451, 452; introducing microchannel, 433, 453; mixing microchannel, 435; heater, 440, 450; mixing section or converging portion, 441, 442; introducing microchannel, 443; mixing microchannel, 445, 455; heater.

EMBODIMENT 2-2; FIGS. 47 TO 50

505; first reservoir, 506; second reservoir, 507; first liquid-introducing microchannel, 508; second liquid-introducing microchannel, 509, 533; mixing microchannel, 535, 536; liquids to be mixed, 510, 537; vibrator, 538; valve, 511; lifting surface, 512; rotator, 513; oscillator.

EMBODIMENT 2-3; FIGS. 54 to 58

707; first liquid-introducing microchannel, 708; second liquid-introducing microchannel, 709; gradient region channel for liquid mixing (mixing microchannel), 709a; lower surface of gradient region channel, 709b; upper surface of gradient region channel, 730; mixing section or converging portion, 731; nano- to micron-structures.

EMBODIMENT A; FIGS. 59 to 68

801; microchip, 802; denaturing gradient forming portion, 803; sample introduction portion, 804; electrophoretic portion, 805; first reservoir, 806; second reservoir, 807; first channel (liquid-introducing microchannel), 808; second channel (liquid-introducing microchannel), 809; gradient region channel (mixing microchannel), 810; first electrode, 811; first power source, 812; second electrode, 813; second power source, 814; first pump, 815; second pump, 816; third reservoir, 817; fourth reservoir, 818; fourth channel, 819; fifth channel, 820; third electrode, 821; third power source, 822; fourth electrode, 823; fourth power source, 824; fifth reservoir, 825; fifth electrode, 826; fifth power source.

EMBODIMENT B; FIGS. 69 TO 84

901; nucleic acid analytic channel (microchannel), 902; nucleic acid sample introduction channel, 903; microchip substrate, 905; detecting portion, 906; denaturant-containing buffer solution introduction channel, 910; substrate, 911; stage means, 912; ejection means, 914; slab gel.

DETAILED DESCRIPTION OF THE INVENTION

[Liquid Mixing Apparatus and Method]

The liquid mixing apparatus of the present invention comprises at least two liquid-introducing microchannels for introducing liquids, and a mixing microchannel that connects to the at least two liquid-introducing microchannels, wherein the liquids introduced from the respective liquid-introducing microchannels converge in the mixing microchannel, the apparatus further comprising mixing enhancing means for enhancing the mixing of the liquids that converge in the mixing microchannel.

In the first embodiment according to the present invention, the mixing enhancing means is a means for increasing the area of the interface between the liquids to be mixed. Examples of the liquid mixing apparatus of the first embodiment include the embodiments 1-1, 1-2, 1-3 and 1-4 described below.

In the second embodiment according to the present invention, the mixing enhancing means is a means for rendering the interface between the liquids, which are to be mixed, unstable by thermal, mechanical and/or structural means. Examples of the liquid mixing apparatus of the second embodiment include the embodiments 2-1, 2-2 and 2-3 described below.

The respective embodiments of the present invention will be described sequentially.

EMBODIMENT 1-1 (FIGS. 4 TO 7)

The mixing enhancing means of the apparatus according to the present embodiment is at least one liquid-introducing means by which the flow rate of the liquid being introduced into one liquid-introducing microchannel can be controlled independently of the flow rate of the liquid being introduced into another liquid-introducing microchannel.

Figure 1:
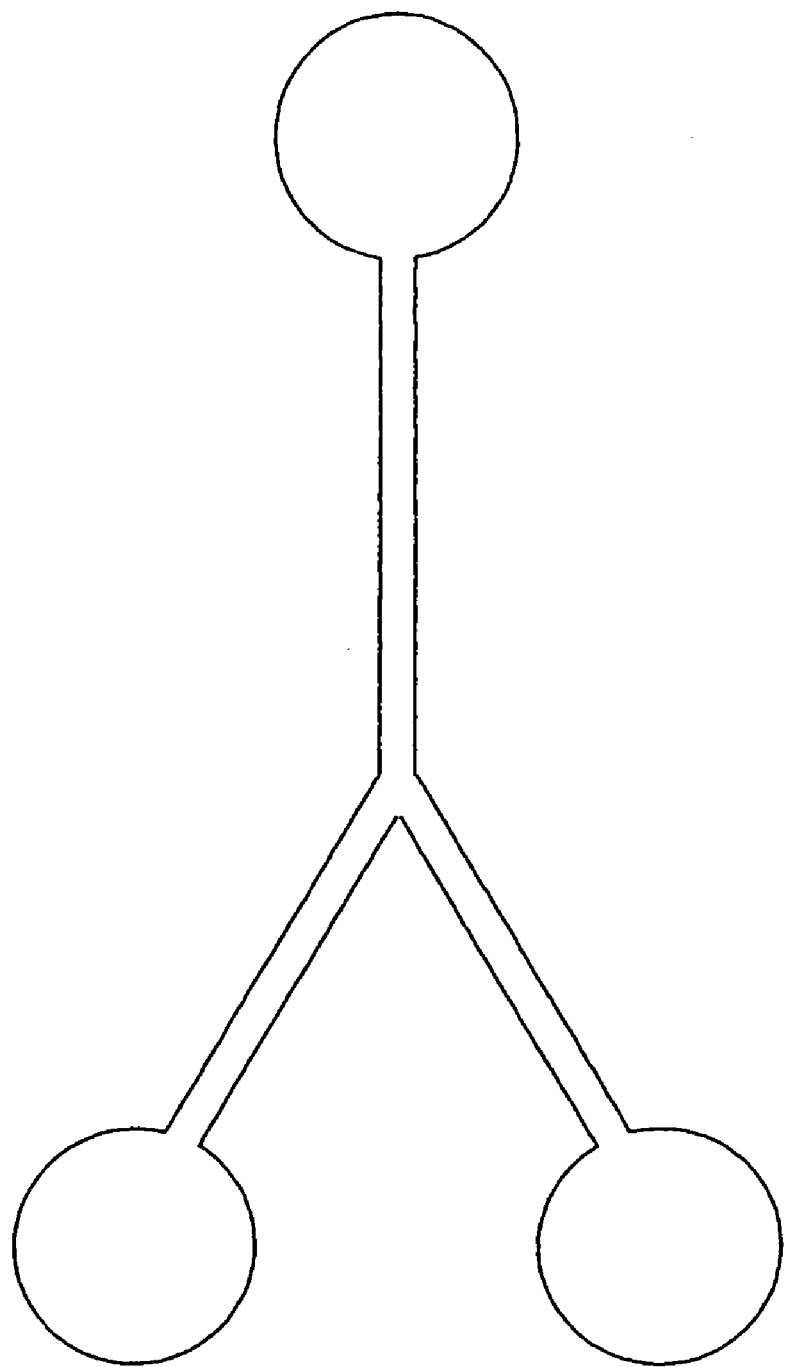
[FIG. 1] A schematic view showing a publicly known, standard micromixing microchannel.
Figure 2:
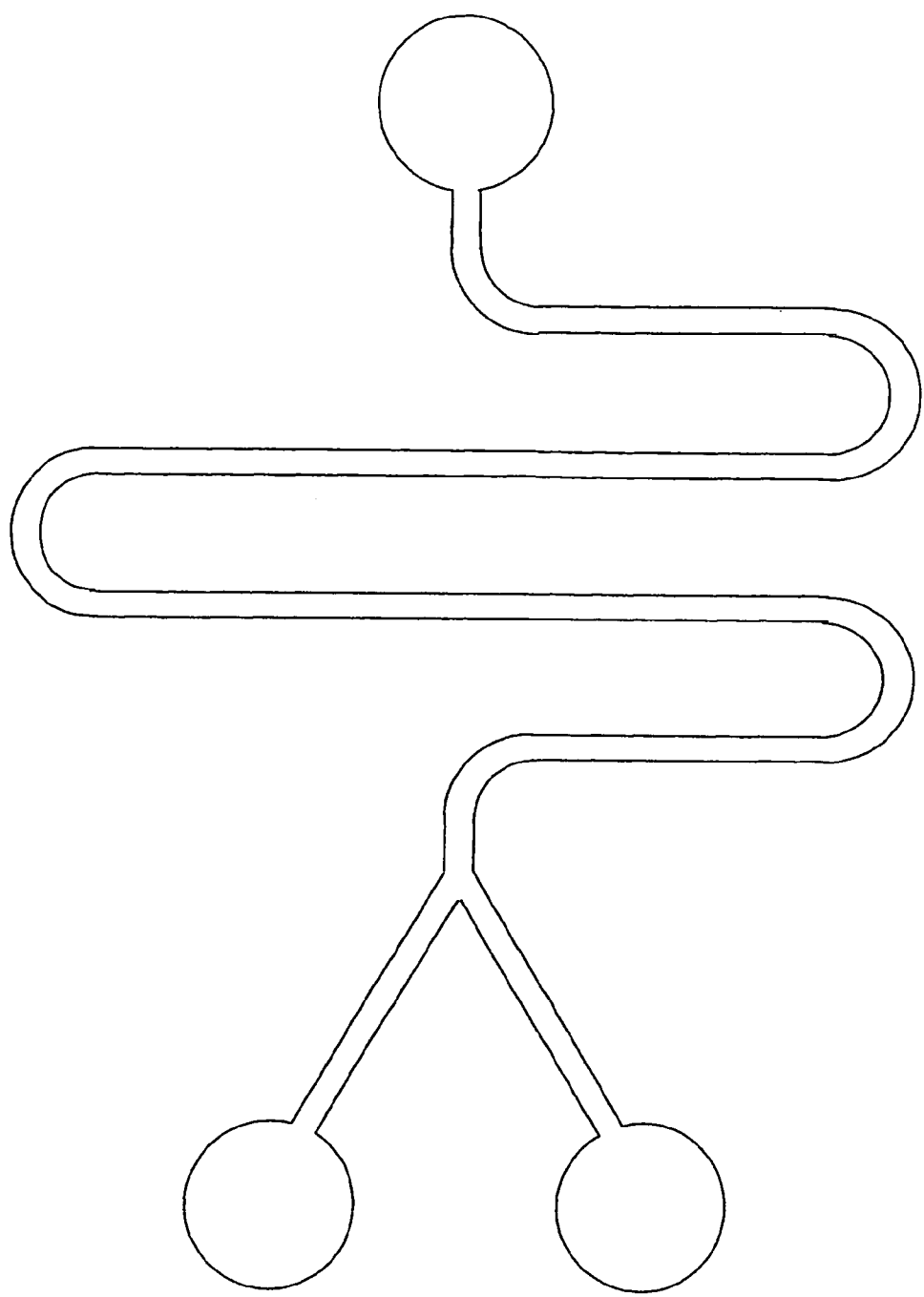
[FIG. 2] A schematic view illustrating a micromixing microchannel which is a mixing microchannel lengthened for ensuring an adequate diffusion distance.
Figure 3:
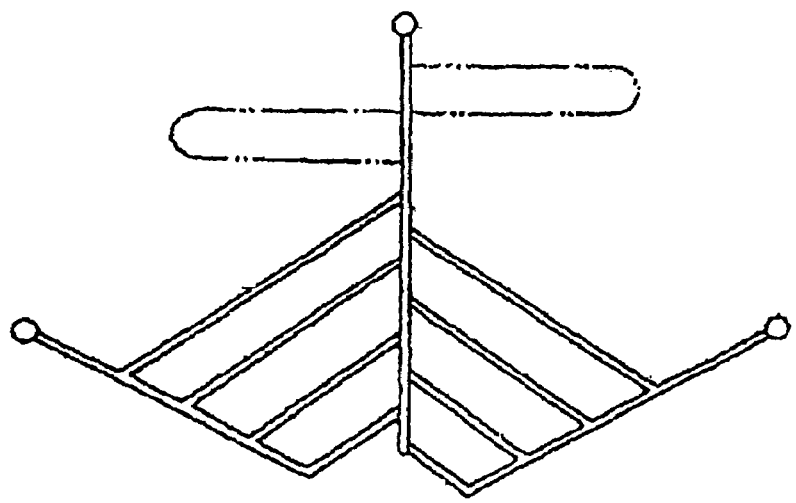
[FIG. 3] A view illustrating a microchannel having liquid dividing thin grooves for enhancing mixing. (Embodiment 1-1).
Figure 4:
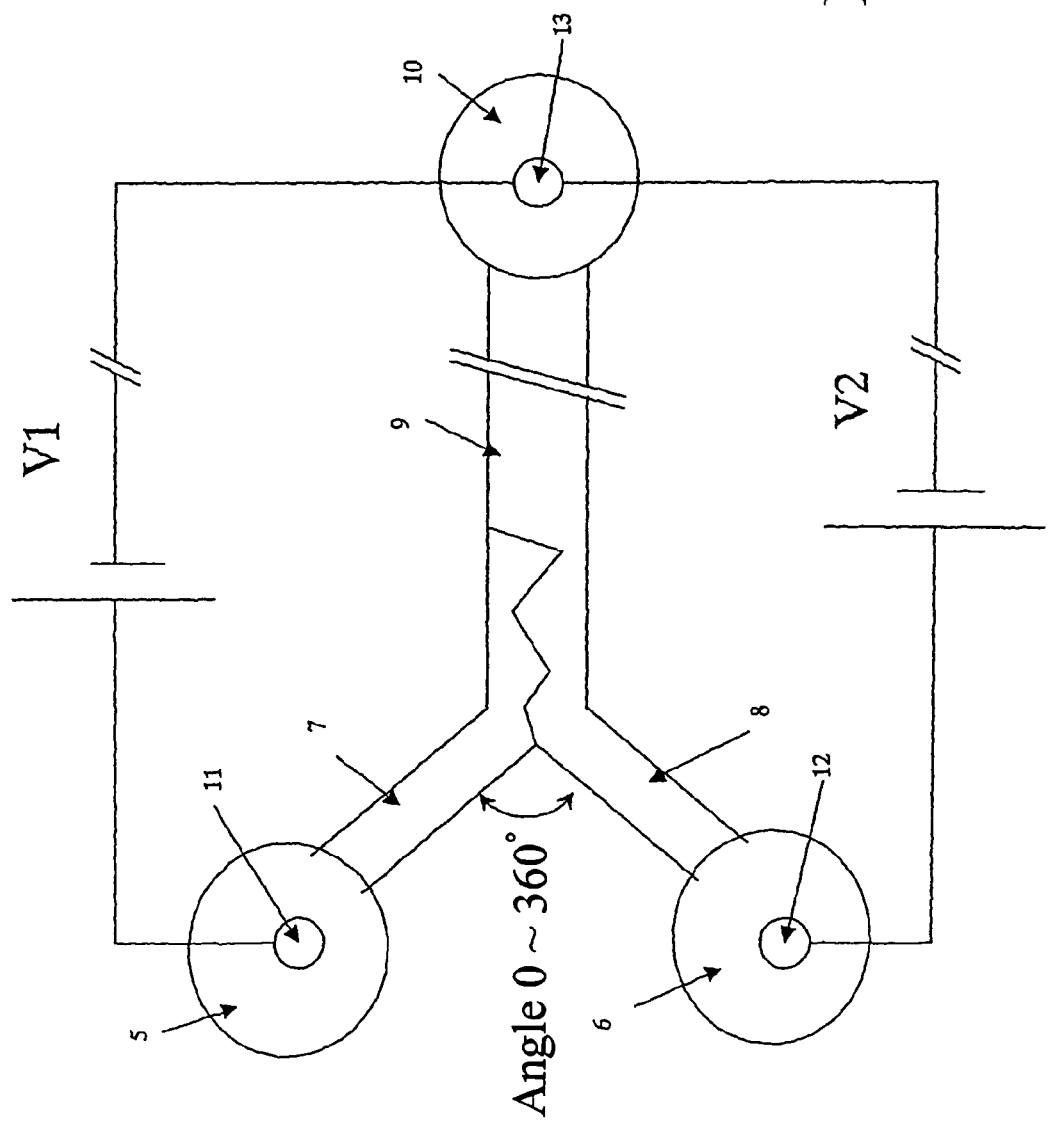
[FIG. 4] A schematic view showing an apparatus of the embodiment 1-1.

FIG. 4 shows the apparatus of the present embodiment. This apparatus includes a first reservoir 5 filled with a first reagent solution, a second reservoir 6 filled with a second reagent solution, a first channel (liquid-introducing microchannel) 7 leading from the first reservoir 5, a second channel (liquid-introducing microchannel) 8 leading from the second reservoir 6, a third channel (mixing microchannel) 9 which connects to the first channel 7 and the second channel 8, and a third reservoir 10. The first reservoir 5 further includes a first electrode 11, the second reservoir 6 further includes a second electrode 12, and the third reservoir 10 further includes a third electrode 13.

When a voltage V1 is applied between the first electrode 11 and the third electrode 13, the first reagent solution is introduced from the first reservoir 5 into the third channel 9 through the first channel 7 by an electroosmotic flow produced. Similarly, when a voltage V2 is applied between the second electrode 12 and the third electrode 13, the second reagent solution is introduced from the second reservoir 6 into the third channel 9 through the second channel 8.

Figure 5:
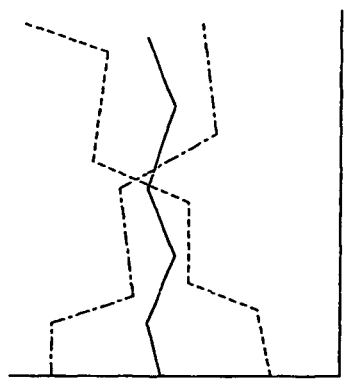
[FIGS. 5(a) and 5(b)] Conceptual views showing the voltage control of the present embodiment.
Figure 5:
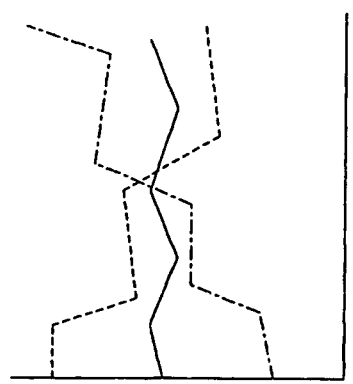
Figure 5:
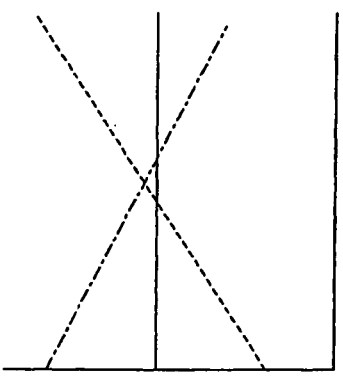
Figure 5:
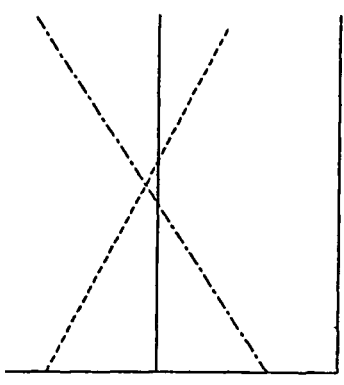

Generally, when two liquids converge in a microchannel, a laminar flow is formed, and an interface between the two liquids is stably maintained. In the case as such, it is known that mixing due to diffusion does not occur sufficiently in the solutions with a small amount diffusion coefficient, and these liquids flow in a mixing microchannel while being separated into two layers. If, on this occasion, suitable variances of voltage are given to the voltage V1 and the voltage V2, as shown by the solid lines in FIG. 5(b), instability is caused to the interface between two liquids, and the interfacial structure can be destroyed. Thus, the two liquids can be mixed at a high speed and uniformly. Accordingly, the first reagent solution and the second reagent solution can be promptly mixed at an arbitrary ratio on the third channel 9 by giving varying components, as appropriate, to the voltage V1 and the voltage V2. Furthermore, if the voltage V1 and the voltage V2 are continuously changed as indicated by dashed lines and dashed dotted lines in FIG. 5(a), the flow rate ratio between the first reagent solution and the second reagent solution can be continuously changed. If varying components are superimposed on a voltage as indicated by a dashed line and a dashed dotted line in FIG. 5(b), the first and second reagent solutions are thoroughly mixed, and a concentration gradient region of the reagent solutions can be promptly formed in the third channel 9. As the varying components, a sinusoidal wave, a sawtooth wave, a rectangular wave, and a combination of them can be conceived. Moreover, it is conceivable to shift the phases of the variance components for the respective channels in order to promote diffusion and maintain the flow rates.

Figure 6:
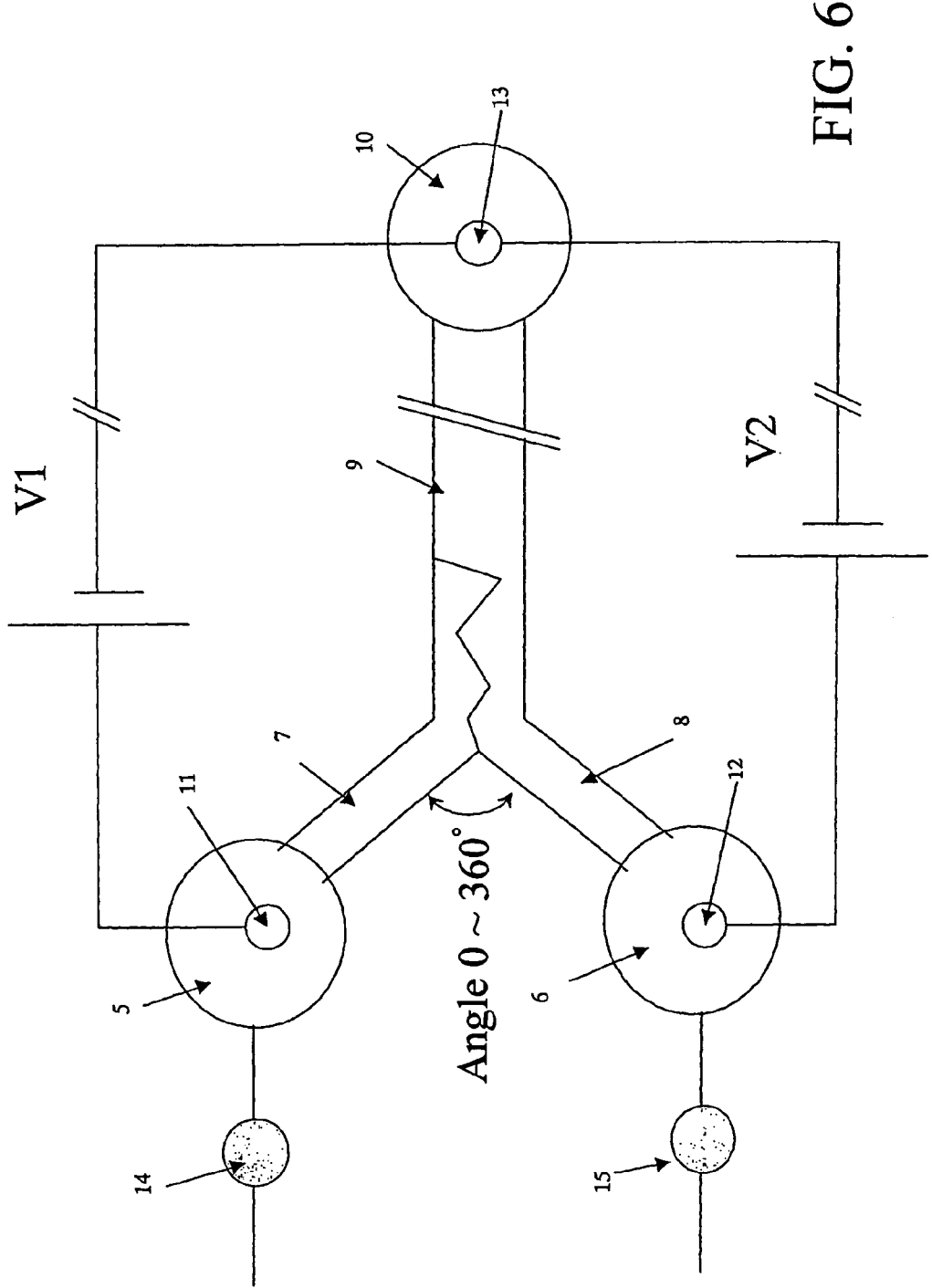
[FIG. 6] A schematic view showing the gradient forming apparatus of the present embodiment.

FIG. 6 shows an example of the present embodiment. This example includes a first reservoir 5 filled with a first reagent solution, a second reservoir 6 filled with a second reagent solution, a first channel (liquid-introducing microchannel) 7 leading from the first reservoir 5, a second channel (liquid-introducing microchannel) 8 leading from the second reservoir 6, a third channel (mixing microchannel) 9 which connects to the first channel 7 and the second channel 8, and a third reservoir 10. The first reservoir 5 further includes a first electrode 11, the second reservoir 6 further includes a second electrode 12, and the third reservoir 10 further includes a third electrode 13. The structure of this example has a first pump 14 and a second pump 15 further added to the first reservoir 5 and the second reservoir 6, respectively.

Figure 7:
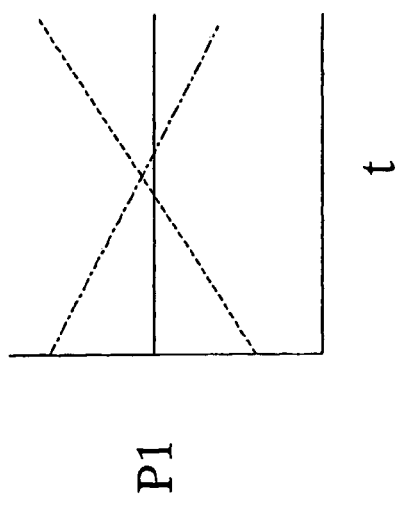
[FIGS. 7(a) and 7(b)] Conceptual views showing the pressure feed control of the present embodiment. (Embodiment 1-2)
Figure 7:
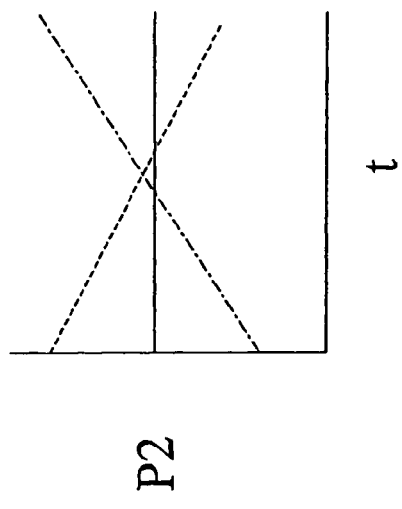
Figure 7:
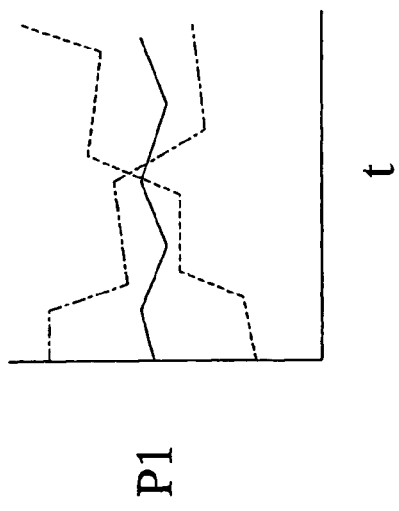
Figure 7:
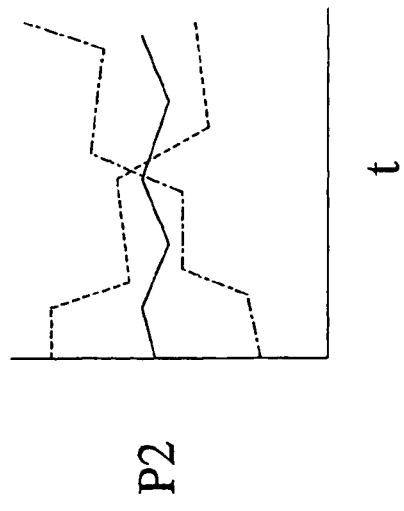

Liquid feeding by these pumps can assist in the liquid feeding by the electroosmotic flows in FIG. 4, and permits liquid feeding at a relatively high speed even if the viscosity of the reagent solutions is high. If, in this case, suitable varying components are given to the liquid feeding pressures of the first pump 14 and the second pump 15, as shown by the solid lines in FIG. 7(b), instability is caused to the interface formed by the two liquids, with the result that the area of the interface on which the two liquids contact can be increased, or the structure of the interface can be destroyed. Thus, the two liquids can be mixed at a high speed and uniformly. Accordingly, the first reagent solution and the second reagent solution can be promptly mixed at an arbitrary ratio on the third channel 9 by giving varying components, as appropriate, to the liquid feeding pressures of the first pump 14 and the second pump 15. Furthermore, if the liquid feeding pressures of the first pump 14 and the second pump 15 are continuously changed as indicated by dashed lines and dashed dotted lines in FIG. 7(a), the flow rate ratio between the first reagent solution and the second reagent solution can be continuously changed. If varying components are superimposed on the liquid feeding pressure as indicated by a dashed line and a dashed dotted line in FIG. 7(b), the first reagent solution and the second reagent solutions are thoroughly mixed, so that a concentration gradient region of the reagent solutions can be formed in the third channel 9. Furthermore, in FIG. 6, the liquid feeding pressures of the pump 14 and the pump 15 and the potentials applied to the electrode 11 and the electrode 12 are simultaneously controlled, whereby promotion of diffusion and control of the concentration gradient can be performed more effectively. As the varying components, a sinusoidal wave, a sawtooth wave, a rectangular wave, and a combination of them can be conceived. It is also conceivable to shift the phases of the varying components for the respective channels in order to promote diffusion and maintain the flow rates.

EMBODIMENT 1-2 (FIGS. 8 TO 22)

The mixing enhancing means of the apparatus according to the present embodiment is a fast operating valve provided on at least one of liquid-introducing microchannels.

Figure 8:
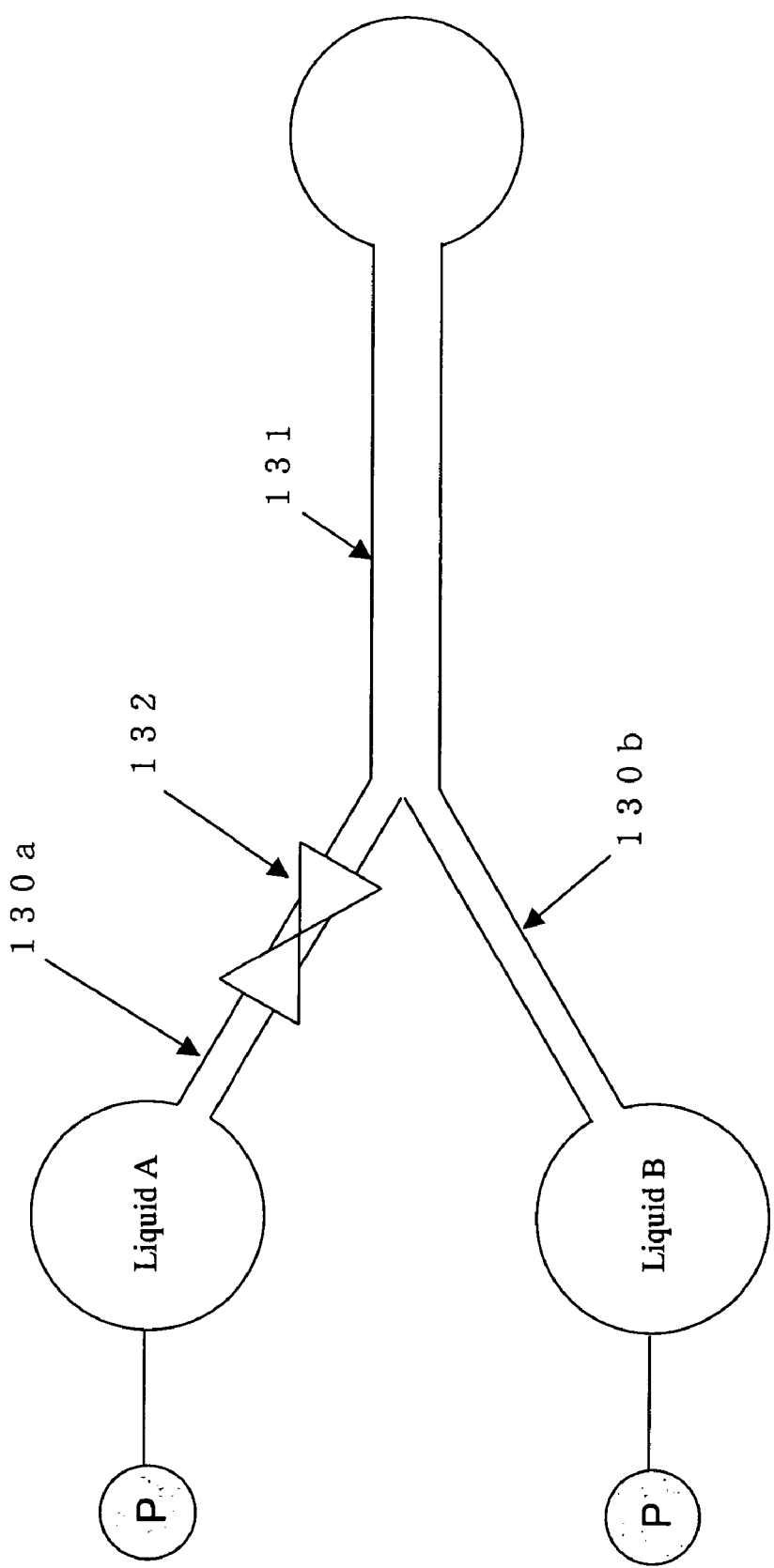
[FIG. 8] A schematic configurational drawing showing a liquid mixing apparatus of embodiment 1-2.
Figure 9:
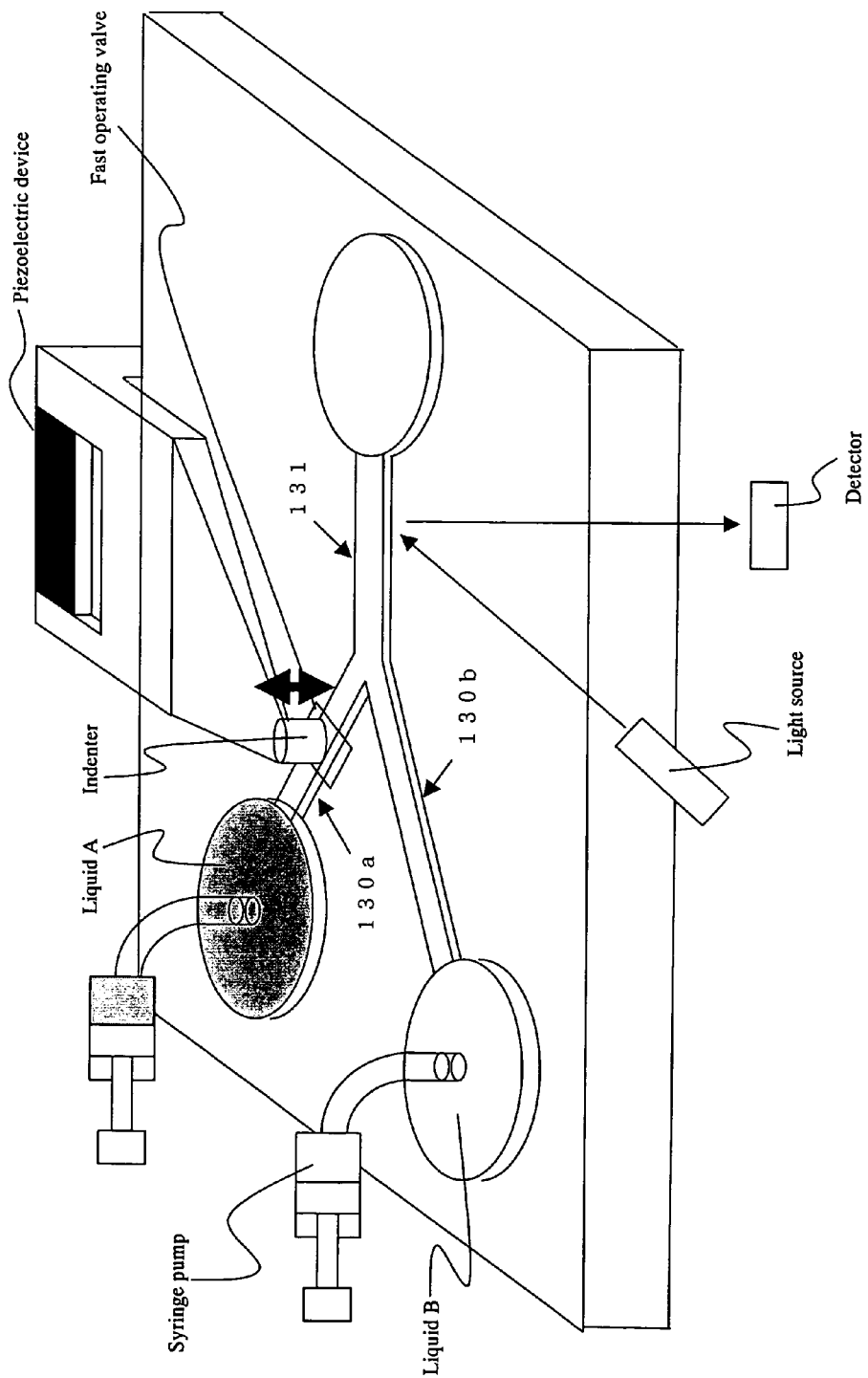
[FIG. 9] A perspective view showing the concrete configuration of the liquid mixing apparatus of FIG. 8.

FIG. 8 shows the schematic configuration of the channels of the microchip apparatus of the present embodiment, and FIG. 9 shows the concrete configuration of the microchip of the present embodiment. The microchannels of this microchip consist of two liquid-introducing microchannels 130a, 130b, and one mixing microchannel 131 into which the microchannels 130a and 130b converge. According to the present embodiment, a fast operating valve 132 is mounted on one of the liquid-introducing microchannels.

Figure 10:
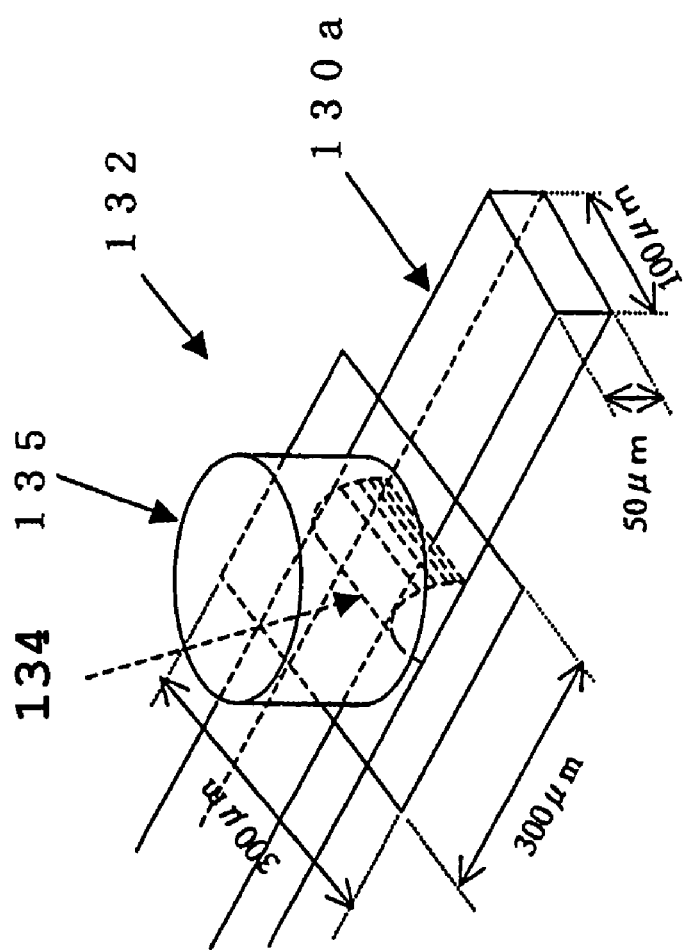
[FIG. 10] A perspective view showing, on an enlarged scale, a fast operating valve of the liquid mixing apparatus of FIG. 8.
Figure 11:
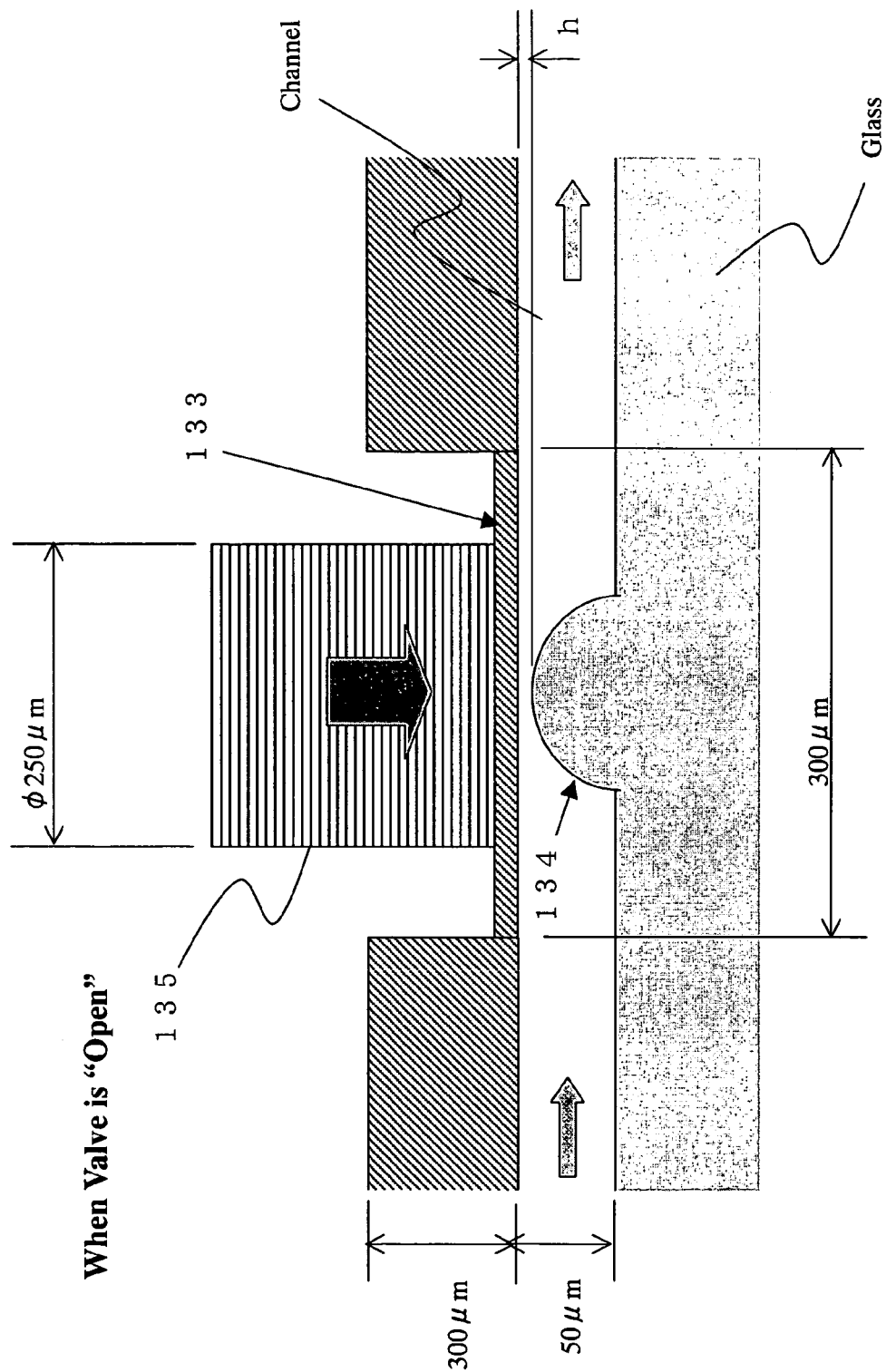
[FIG. 11] A sectional view showing the fast operating valve (when not in operation) of FIG. 10.

FIG. 9 shows the configuration of the entire microchip. FIG. 10 shows, on an enlarged scale, a fast operating valve mechanism, and FIG. 11 shows the cross section of the fast operating valve. As shown in FIG. 9, a liquid A and a liquid B are pressurized by syringe pumps P, introduced from reservoirs for the liquid-introducing microchannels 130a, 130b into these microchannels 130a, 130b, and converged in the single mixing microchannel 131. The fast operating valve 132, which is driven by a piezoelectric device, is provided halfway through the liquid-introducing microchannel 130a for introduction of the liquid A. The fast operating valve opens and closes to control the introduction of the liquid A from the liquid-introducing microchannel 130a into the mixing microchannel 131. Control by the fast operating valve 132 applies variations to the inflow amount of the liquid A, thus controlling, for example, the mixing ratio between the liquid A and the liquid B supplied into the mixing microchannel 131.

Figure 12:
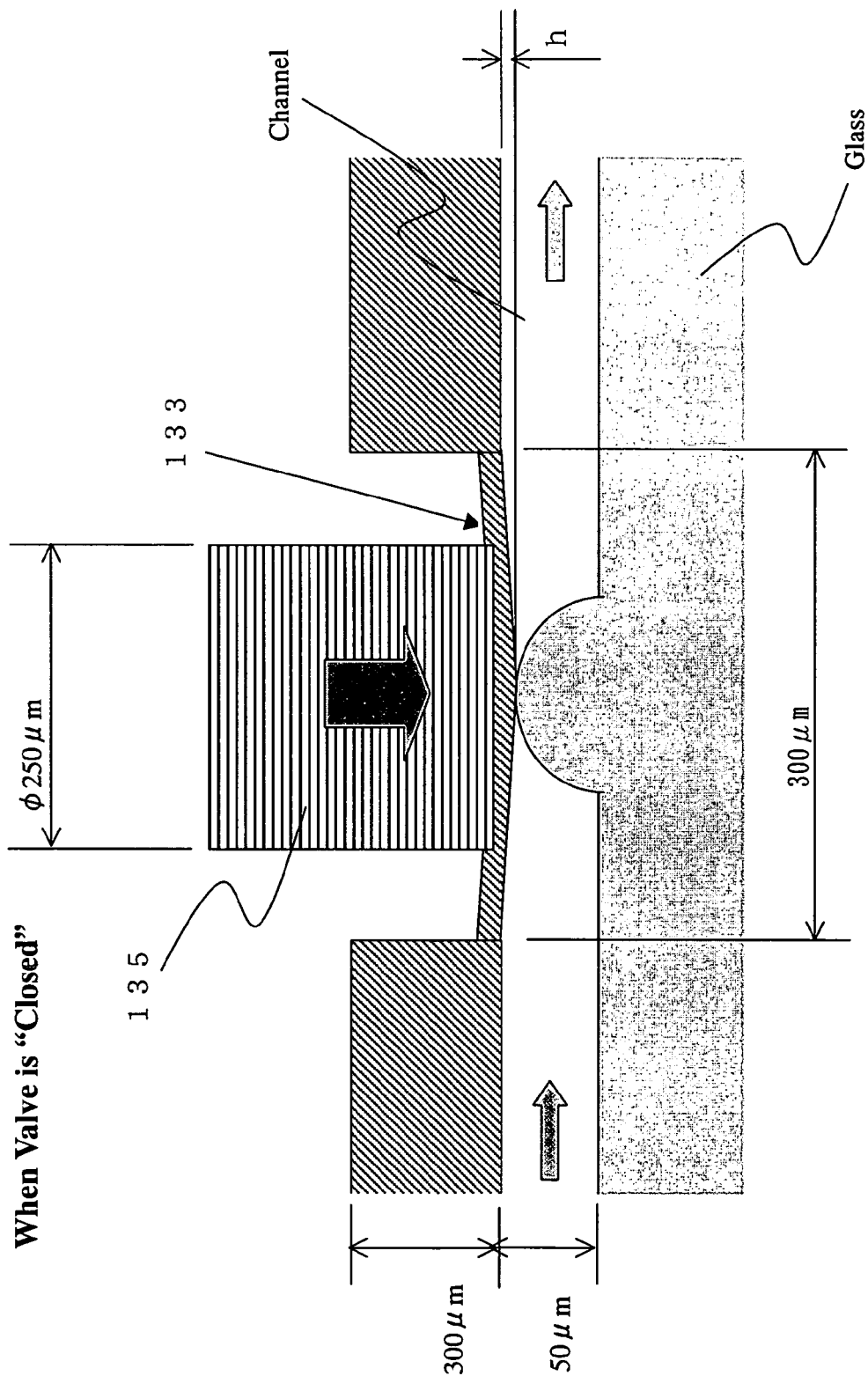
[FIG. 12] A sectional view showing the fast operating valve (when in operation) of FIG. 10.

The fast operating valve includes a part of the liquid-introducing microchannel 130a, as shown in FIG. 11 (a cross section in the axial direction of the liquid-introducing microchannel 130a) and FIG. 12. This part is a valve element 133 made of a PDMS (polydimethyl siloxane) film and having a thickness of 20 μm and a width of 300 μm. In the same channel, a protrusion 134 is provided in proximity to the valve element. An indenter 135 with a diameter of the order of 250 μm, which contacts the valve element 133 from the outside, is provided. This indenter 135 is adapted to be driven by the piezoelectric device. A space between the valve element 133 and the protrusion 134 is a micro-clearance h on the order of 10 μm. The valve element 133 is driven at a high speed upward and downward directly by the piezoelectric device acting with a response frequency of 10 Hz or more, whereby this micro-clearance h is unclosed and closed.

The advantageous functions of the fast operating valve used in the present embodiment are a high speed valve opening and closing action, and a small operating volume (corresponding to the volume of the liquid forced out of the channel when the channel is closed by the movement of the valve element) during opening and closing. In this connection, it is preferred, as in the present embodiment, that the protrusion within the channel be in a semicylindrical shape or the like so that the valve element makes a nearly linear contact with the protrusion, and that the stroke (h) over which the valve element moves up and down be as small as 10 μm.

Another fast operating valve usable in the present embodiment is a valve as used in an ink jet printer. For example, there may be used a valve which can locally heat a liquid-introducing microchannel by heat to vaporize a liquid flowing in the liquid-introducing channel and increase its volume, thereby controlling at a high speed the ejection of a constant minute flow rate from the liquid-introducing channel into a mixing microchannel.

Figure 14:
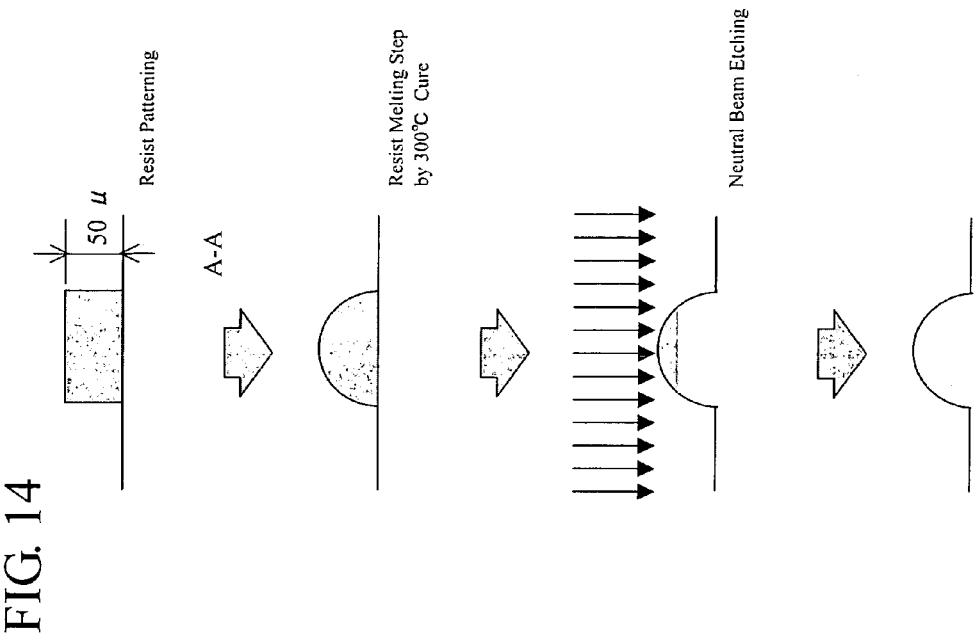
[FIG. 14] A view for explaining steps for producing the protrusion for use in the fast operating valve.
Figure 13:
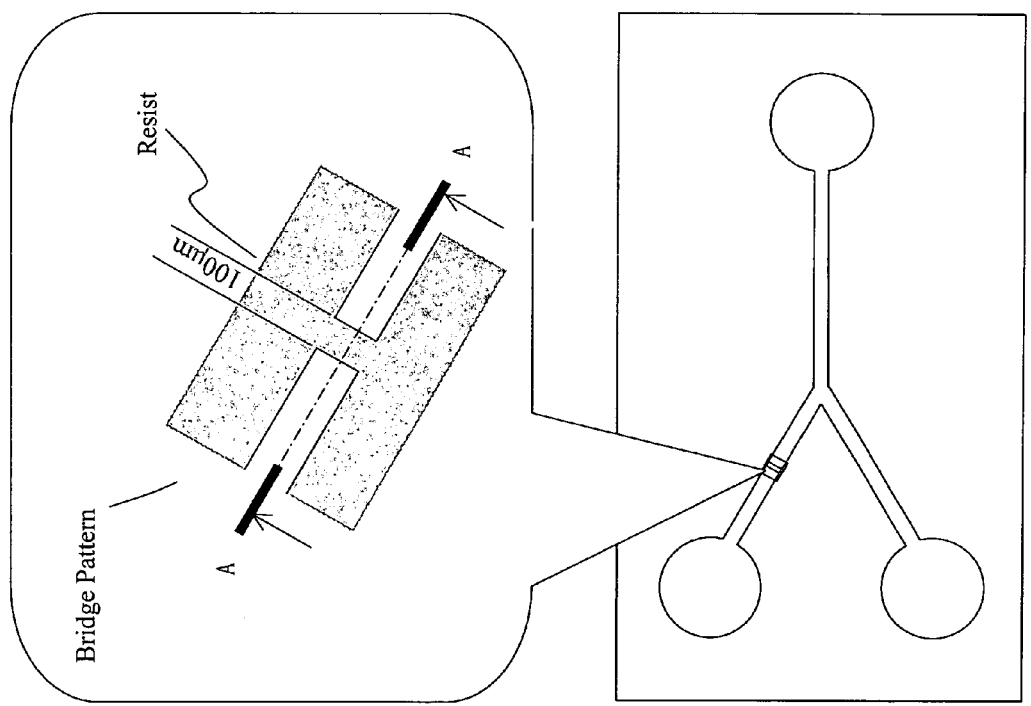
[FIG. 13] A view for explaining a method for producing a protrusion for use in the fast operating valve.

The method of producing the semicylindrical protrusion 134 used in the fast operating valve will be explained by reference to FIGS. 13 and 14. A 50 μm thick film resist is coated on a glass substrate, and a channel-forming pattern is exposed to g-line (ultraviolet light at a wavelength of 436 nm) in a photolithography step, followed by development. As shown in FIG. 13, the channel width of the liquid-introducing microchannel is, for example, 100 μm, and a line pattern with a channel width of 100 μm is applied to perpendicularly intersect the portion where the semicylindrical protrusion is formed. As shown in FIG. 14 (cross section taken on line A-A in FIG. 13), in order to deform the bridge pattern into the shape of a semicylindrical protrusion, the glass substrate which has undergone resist patterning is placed in a thermostatic furnace, where the glass substrate is heat-treated for 20 minutes at 300° C. Since the resist softens at 250° C. or higher, its edge deforms in a round shape under surface tension, eventually resulting in a semicylindrical shape. Then, this substrate is subjected to dry etching. When the glass substrate is etched, the resist is etched at the same time. As a result, the shape of the resist can be transferred, unchanged, to the glass substrate. This processing can be performed using RIE (reactive ion etching), but a neutral beam etching process is preferred for satisfactory transferability of the shape. In this manner, an appropriate protrusion structure can be formed in the liquid-introducing microchannel.

The "high speed opening and closing action" of the fast operating valve used in the present embodiment refers to an action with a cycle of about 10 Hz or more, preferably 10 Hz to 20 kHz, as the response frequency of the valve element.

Next, the liquid mixing method of the present embodiment will be described with reference to FIGS. 15 to 21.

When the liquid A and the liquid B are to be introduced in the above configured microchip, the fast operating valve mounted on the liquid-introducing microchannel for the liquid A is caused to perform a high speed opening and closing action on constant cycles. If variations are applied to the flow rate of the liquid at short time intervals, the interface between the liquid A and the liquid B, which is formed in the mixing microchannel, takes a "wavy" form as depicted in the mixing microchannel 31 of FIG. 15. The liquid A, which is introduced past the fast operating valve, can have a proportion in the width direction of the mixing microchannel continuously changed in a shot time. Thus, the liquid A increases in its area of contact with other liquid B converging in the mixing microchannel. In this manner, the interface between the two liquids widens, facilitating the diffusion and mixing of the two liquids.

Figure 28:
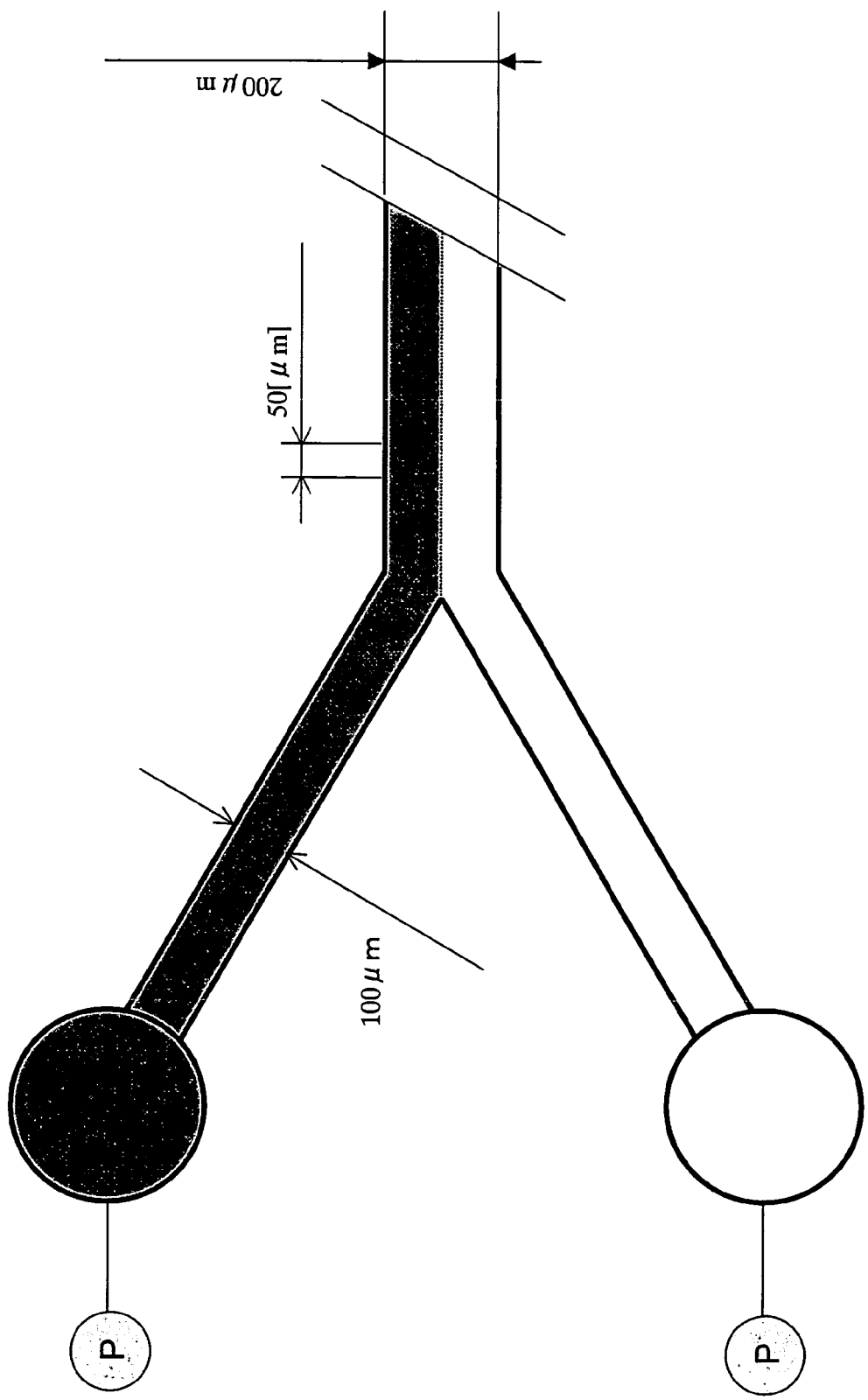
[FIG. 28] A view for explaining the problem of a conventional liquid mixing apparatus.
Figure 29:
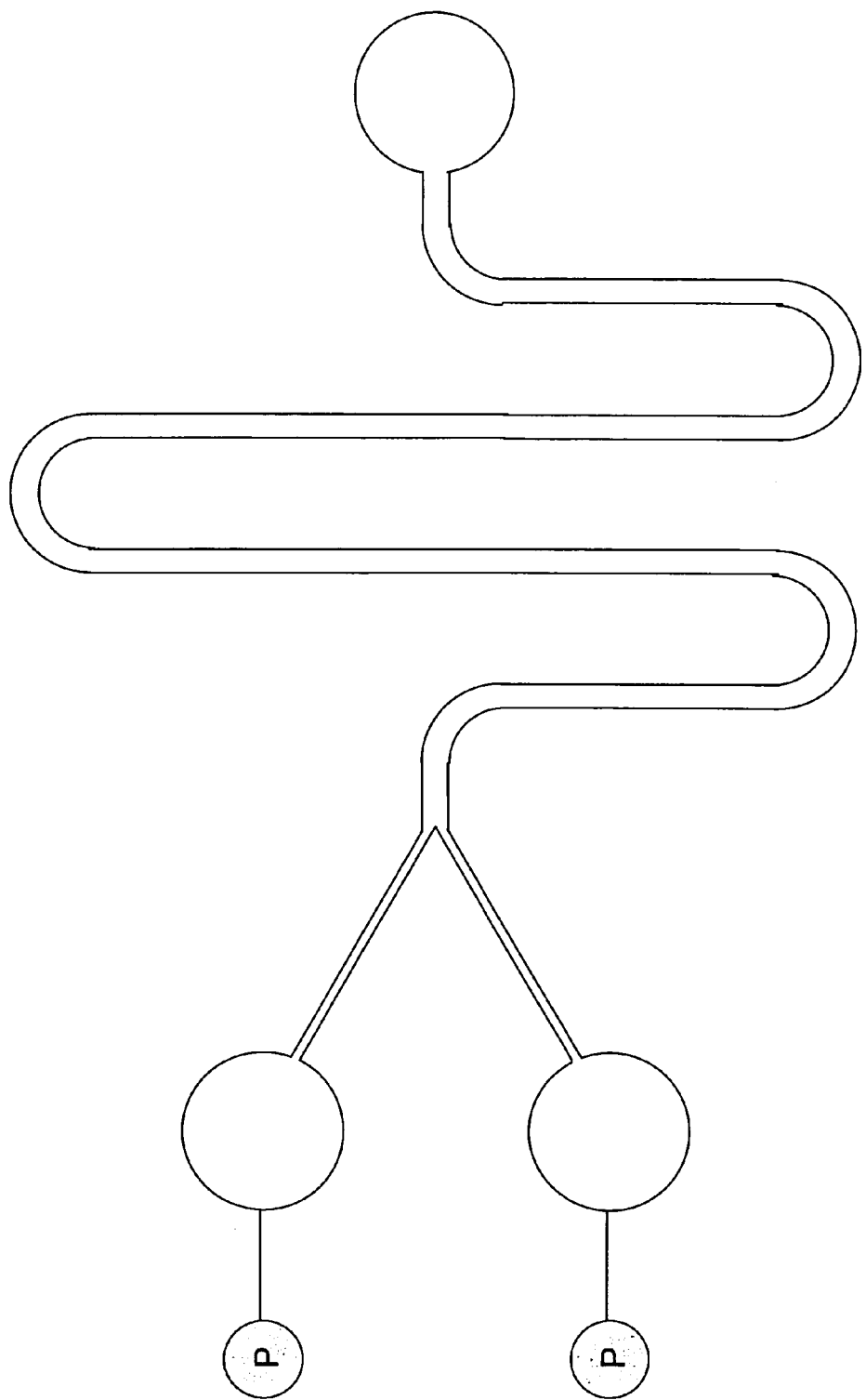
[FIG. 29] A view for explaining the problem of the conventional liquid mixing apparatus. (Embodiment 1-3)

In the customary manner without the use of a fast operating valve, the interface between two liquids is formed nearly rectilinearly in a mixing microchannel, as shown in FIG. 28. For example, assume that a unit length is taken in the flowing direction in a channel with a width of 200 µm, and a flat interface (see FIG. 28) is compared with a wavy interface (see FIG. 15) having cycles of 50 µm and a width of 100 µm which has been formed by using the fast operating valve. Provided that the wavy form is approximated by a sinusoidal wave, the surface area of the wavy interface is increased to 4 times that of the flat interface.

Figure 16:
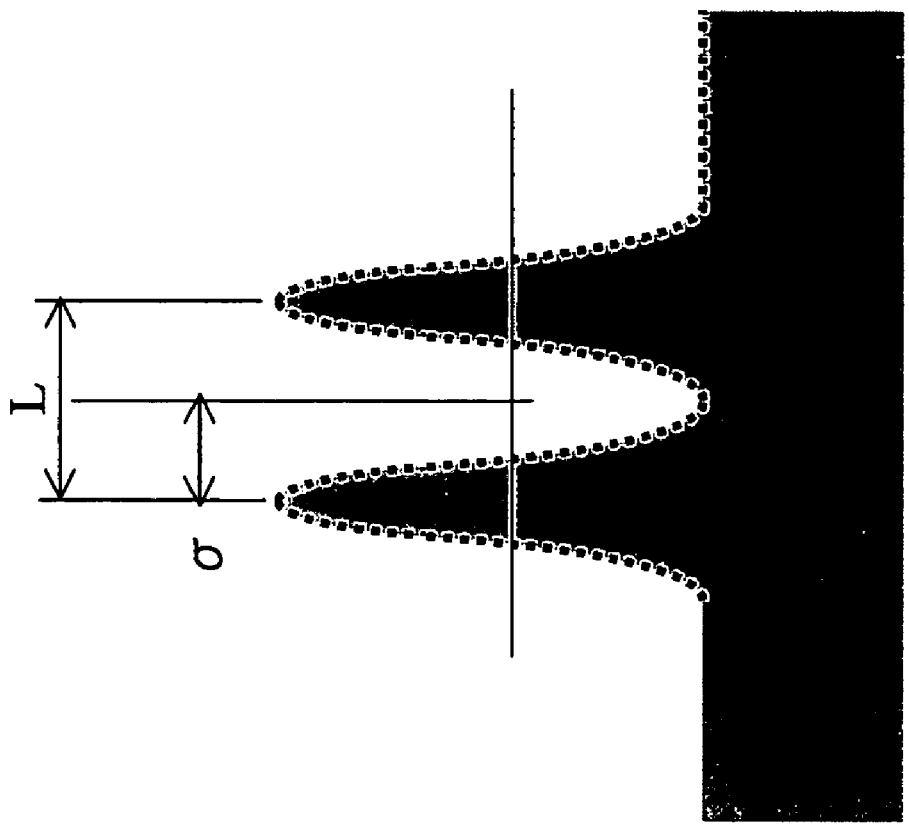
[FIG. 16] A view for explaining the effect of mixing according to the present embodiment.

How much the mixing time is shortened by the formation of the waves in the interface between the two liquids is shown by the calculation model given below. In the model of FIG. 16, let the period of the wave be L. If diffusion proceeds up to a half of it, i.e., L/2, mixing is assumed to have been completed, because diffusion actually proceeds, starting on both sides of the wave. A calculation model for simple diffusion concerning the diffusion of a liquid is described by the following equation ($D_0$=diffusion coefficient [m$^2$/sec] (denaturant; $10^{-10}$, water; $10^{-9}$), t=time [sec]):

$$\sigma[m]=\sqrt{2D_0 t} \qquad \text{Equation 1}$$

In the case of a denaturant (diffusion coefficient $D_0=10^{-11}$), for example, assume that the period L=2σ is designed such that mixing is completed in 5 minutes. A calculation for this purpose is represented by the following equation:

$$\begin{aligned}\sigma &= \sqrt{2\times 10^{-11}\times 300} \text{ [m]} \\ &= \sqrt{6000\times 10^{-12}} \text{ [m]} \\ &= 77\times 10^{-6} \text{[m]} \\ &= 77 [\mu m]\end{aligned} \qquad \text{Equation 2}$$

As noted above, the diffusion distance σ is 77 [µm]. This means that given the wave-to-wave interval of 50 µm, mixing can be completed in 5 minutes. This time is sufficiently short for DGGE analysis.

Figure 15:
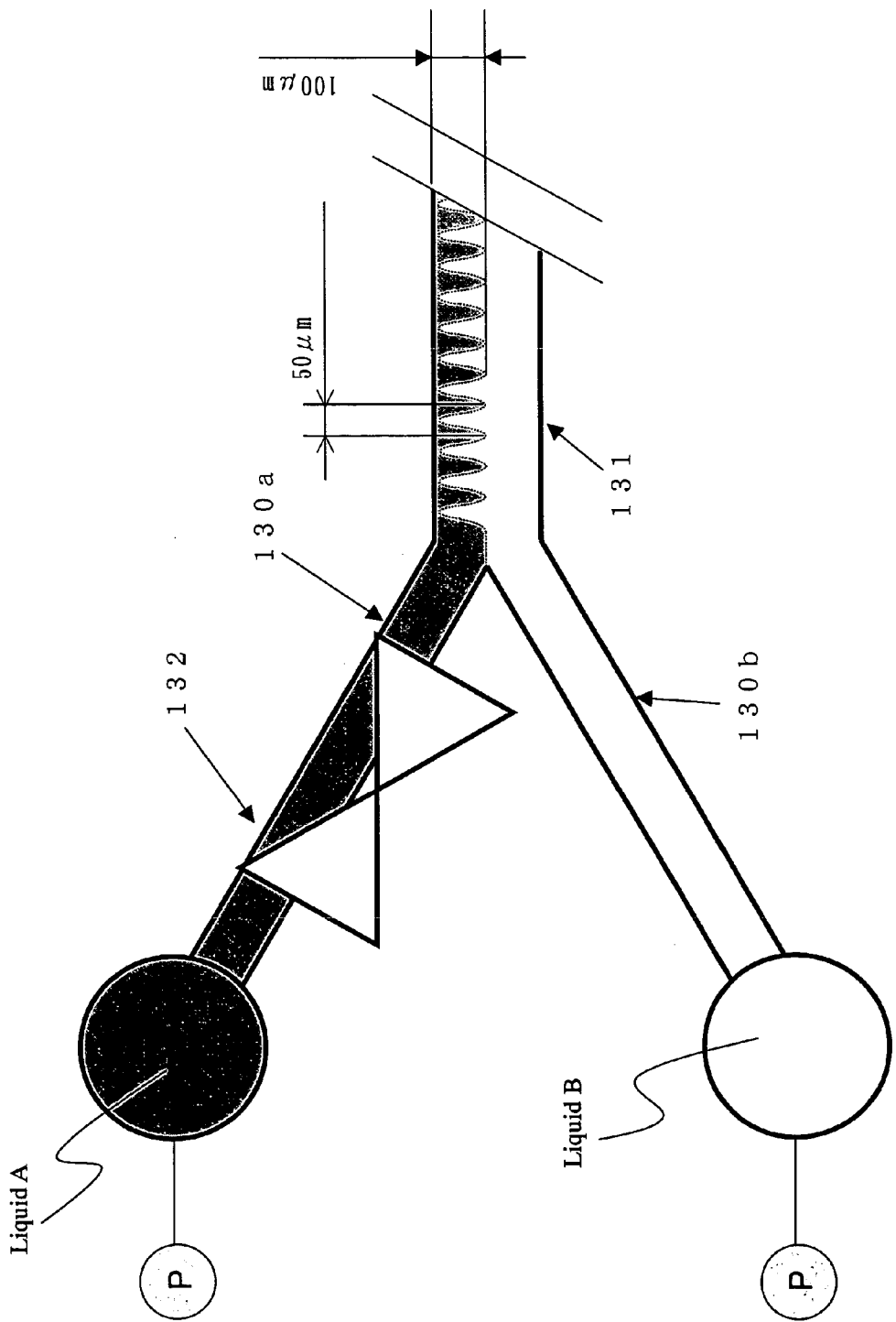
[FIG. 15] A configurational drawing showing another example of the liquid mixing apparatus of the present embodiment.
Figure 17:
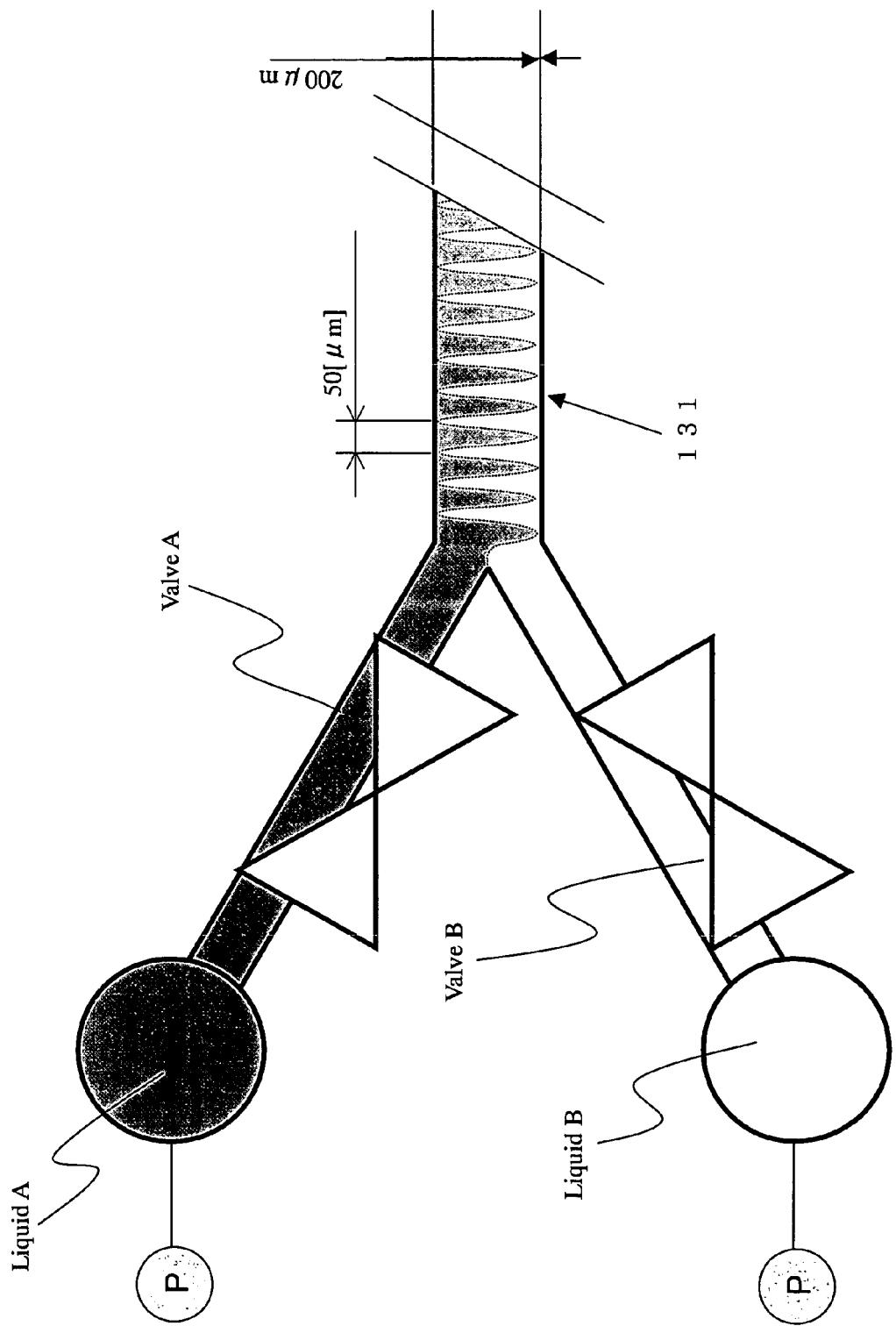
[FIG. 17] A configurational drawing showing still another example of the liquid mixing apparatus of the present embodiment.

The apparatus of FIG. 17 can increase the mixing efficiency further as compared with the mixing apparatus of FIG. 15. This apparatus has fast operating valves (valve A and valve B) mounted on two liquid-introducing microchannels for two liquids A and B. Examples of an operating time-chart for the fast operating valve, which are preferred for this embodiment, are shown in FIGS. 18 and 19.

Figure 18:
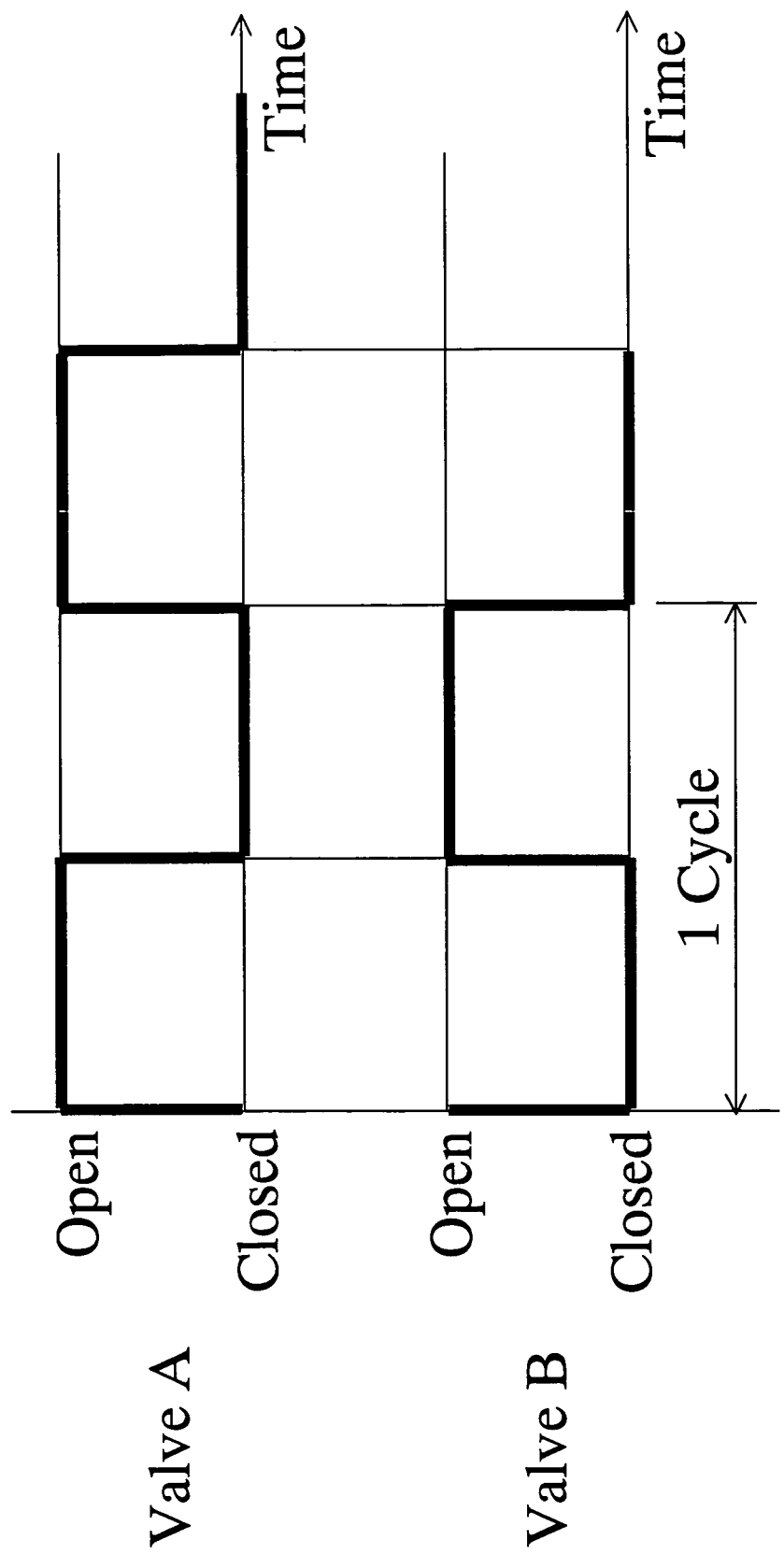
[FIG. 18] A time-chart concerned with the control of the liquid mixing apparatus of FIG. 16.
Figure 19:
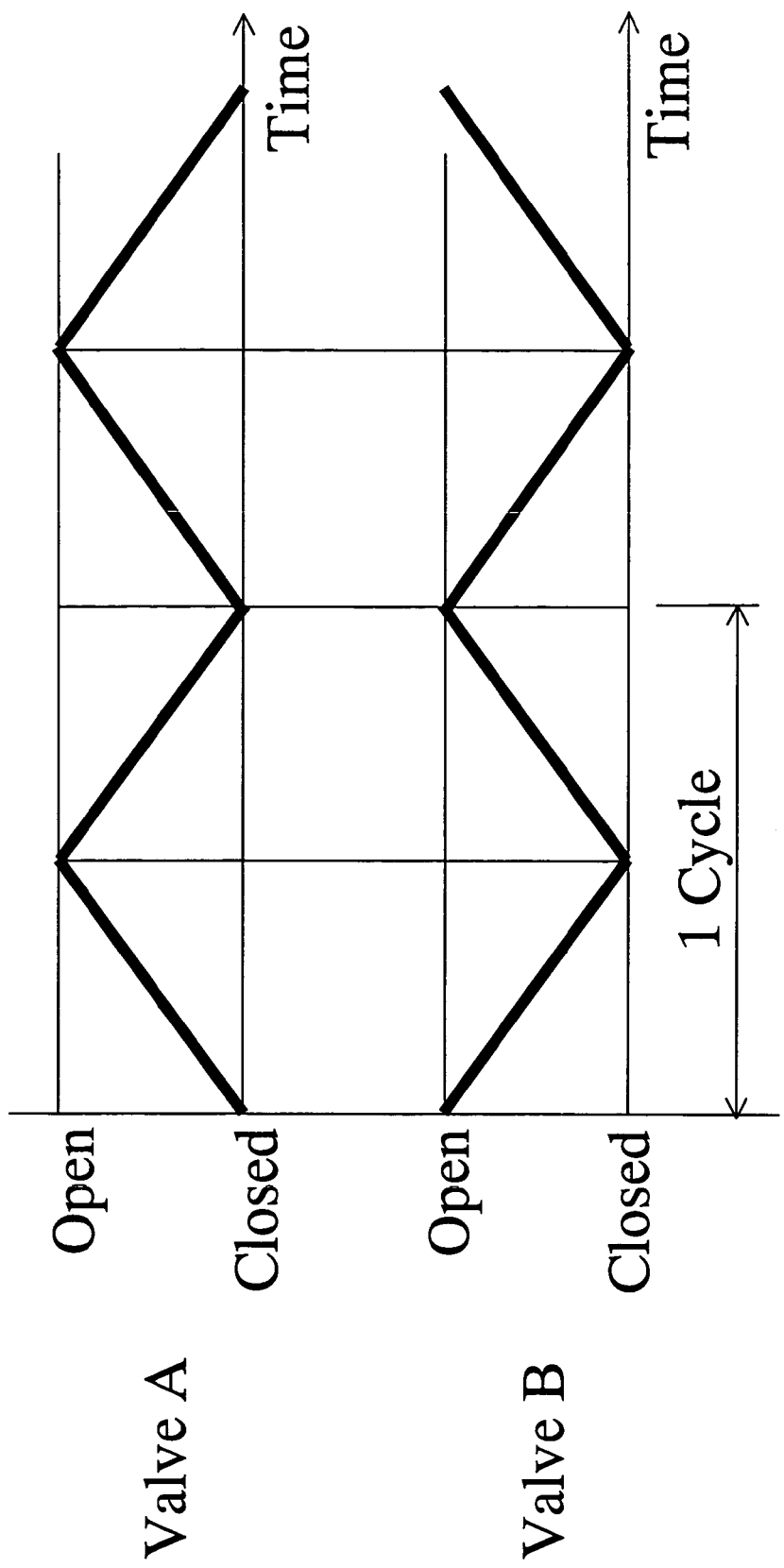
[FIG. 19] Another time-chart concerned with the control of the liquid mixing apparatus of FIG. 16.

In the apparatus of the aforementioned embodiment, as shown in FIG. 18, opening and closing actions for the valve A and the valve B are synchronized to render the valve B "closed" when the valve A is "open" and, conversely, render the valve B "open" when the valve A is "closed". By so doing, the width of the wavy form created by the liquid A within the mixing microchannel can be increased to the entire width of the channel. Moreover, the sum of the flow rates of the liquid A and the liquid B becomes always constant. Thus, the liquids flow within the mixing microchannel at a constant flow velocity. Hence, control characteristics preferred for forming a concentration gradient in the mixing microchannel can be obtained. The method of forming a concentration gradient with the use of the embodiment 1-2 will be described later on.

With the apparatus of FIG. 17, the surface area of the interface between the two liquids is twice that in FIG. 14, namely, 8 times that obtained when no wave is formed (FIG. 28). In FIG. 18, the opening and closing of the valves are controlled in a full-open/full-closed mode. However, valve opening need not be controlled so as to be either fully closed or fully open, but may be variably controlled by using a piezoelectric device and adjusting a potential given to the piezoelectric device. For example, the opening and closing of the valves may be performed according to an operating time-chart as shown in FIG. 19. Anyway, the operating time-chart is not limited to the above-mentioned modes, but the opening and closing of the valves can be controlled in other various modes.

Figure 20:
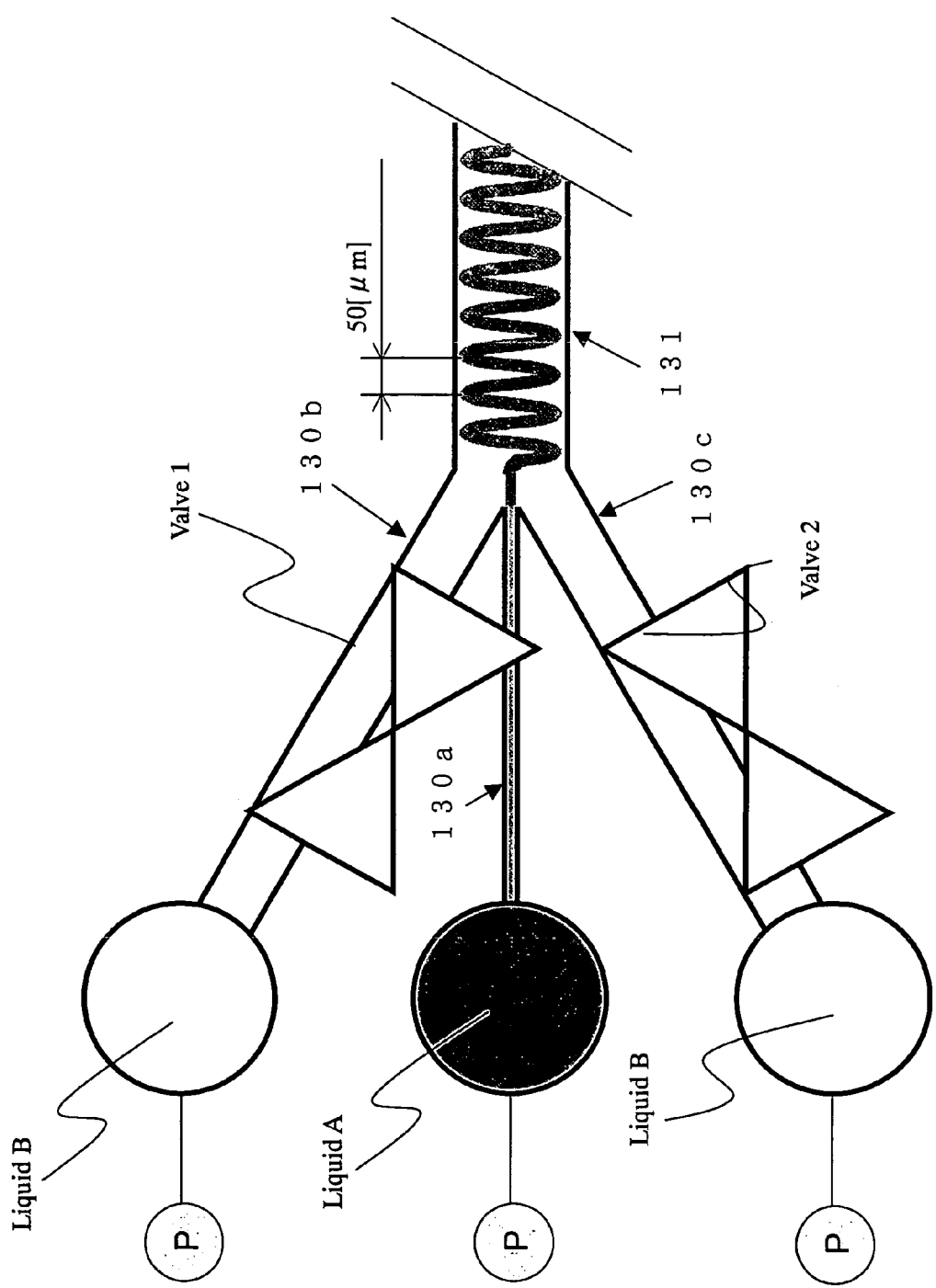
[FIG. 20] A configurational drawing showing still another example of the liquid mixing apparatus of the present embodiment.
Figure 21:
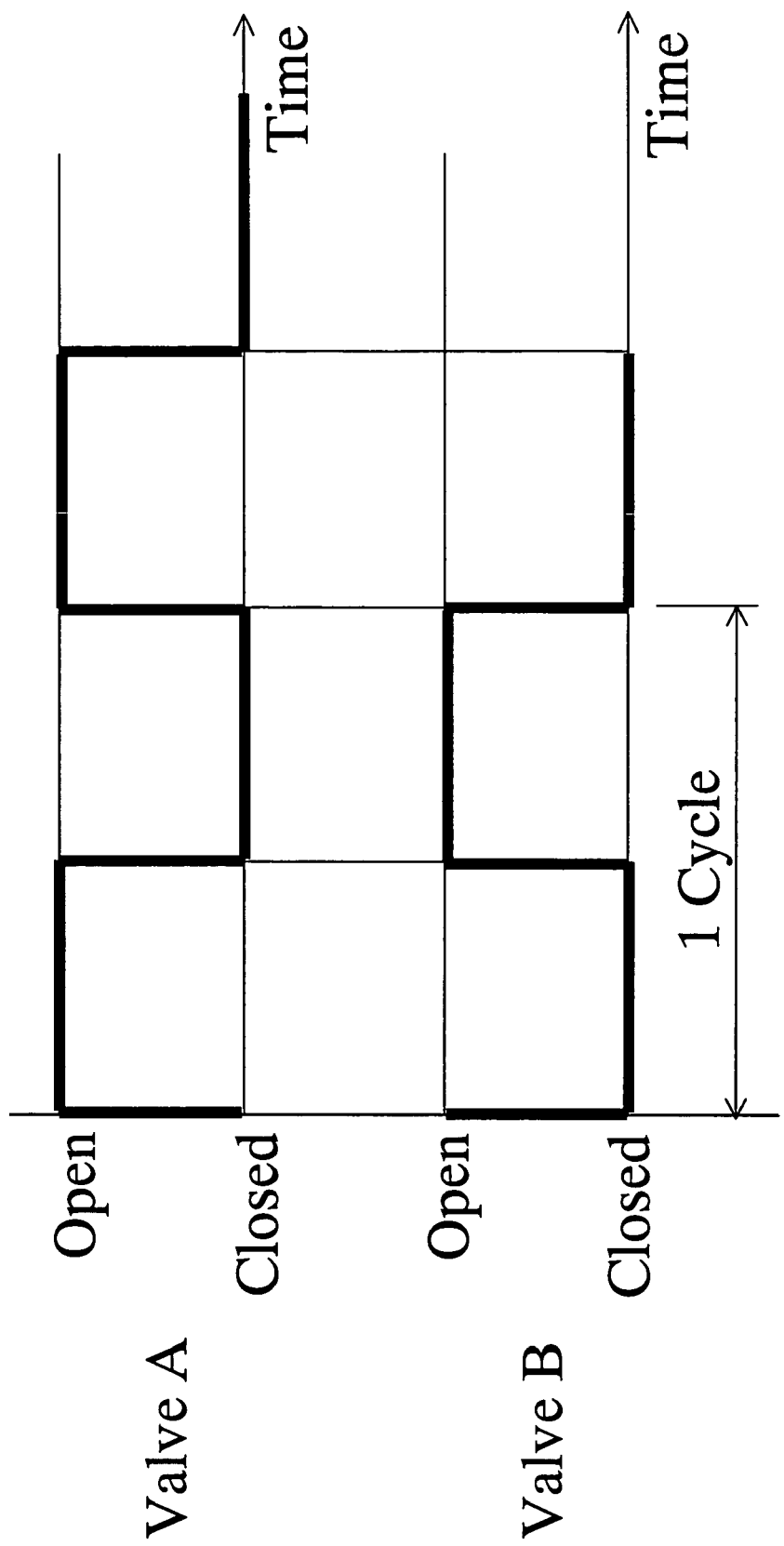
[FIG. 21] Another time-chart concerned with the control of the liquid mixing apparatus of FIG. 20.

The apparatus of FIG. 20 can raise the mixing efficiency still further. In this apparatus, three liquid-introducing microchannels 130*a*, 103*b* and 130*c* connect to a mixing microchannel 131. A liquid A is introduced from the liquid-introducing microchannel 130*a*, located at a central position, into the mixing microchannel 131. A liquid B is introduced from the two liquid-introducing microchannels 130*b* and 130*c* located on both sides of the liquid-introducing microchannel 130*a*. Fast operating valves (valve 1 and valve 2) are mounted on the two liquid-introducing microchannels 130*b* and 130*c*. These valves can be opened and closed as shown in the operating time-chart of FIG. 21, whereby a wavy interface, as depicted within the mixing microchannel 131 of FIG. 20, can be formed. The interface between the two liquids (i.e., the total surface area of the waves) is twice that in FIG. 15. That is, an interface surface area, which is 16 times that when no wave is formed (FIG. 28), can be obtained, so that a very high efficiency liquid mixing can be achieved. Here, the mixing of two liquids, liquid A and liquid B, is illustrated. However, if one of the two liquid-introducing microchannels 130*b* and 130*c* for feeding the liquid B is used for a liquid C, three liquids, i.e., A, B and C, can be preferably mixed in the mixing microchannel 131.

Next, the method of controlling liquid introduction by the present embodiment will be described with reference to FIGS. 22 to 25.

In a method for mixing a liquid A and a liquid B such that a concentration gradient is formed in a mixing microchannel, liquids containing a solute (for example, a nucleic acid denaturant) at different concentrations can be used as the liquid A and the liquid B. The gradient forming method can be suited for this case by changing the operating method for the valve opening and closing action in the apparatus described earlier. An example of the mixing method for forming a concentration gradient comprises fixing the frequency of a fast operating valve (i.e. rendering the opening and closing cycle of the valve constant), and variably controlling the ratio of time during which the valve remains open (namely, duty ratio) to one cycle.

Figure 22:
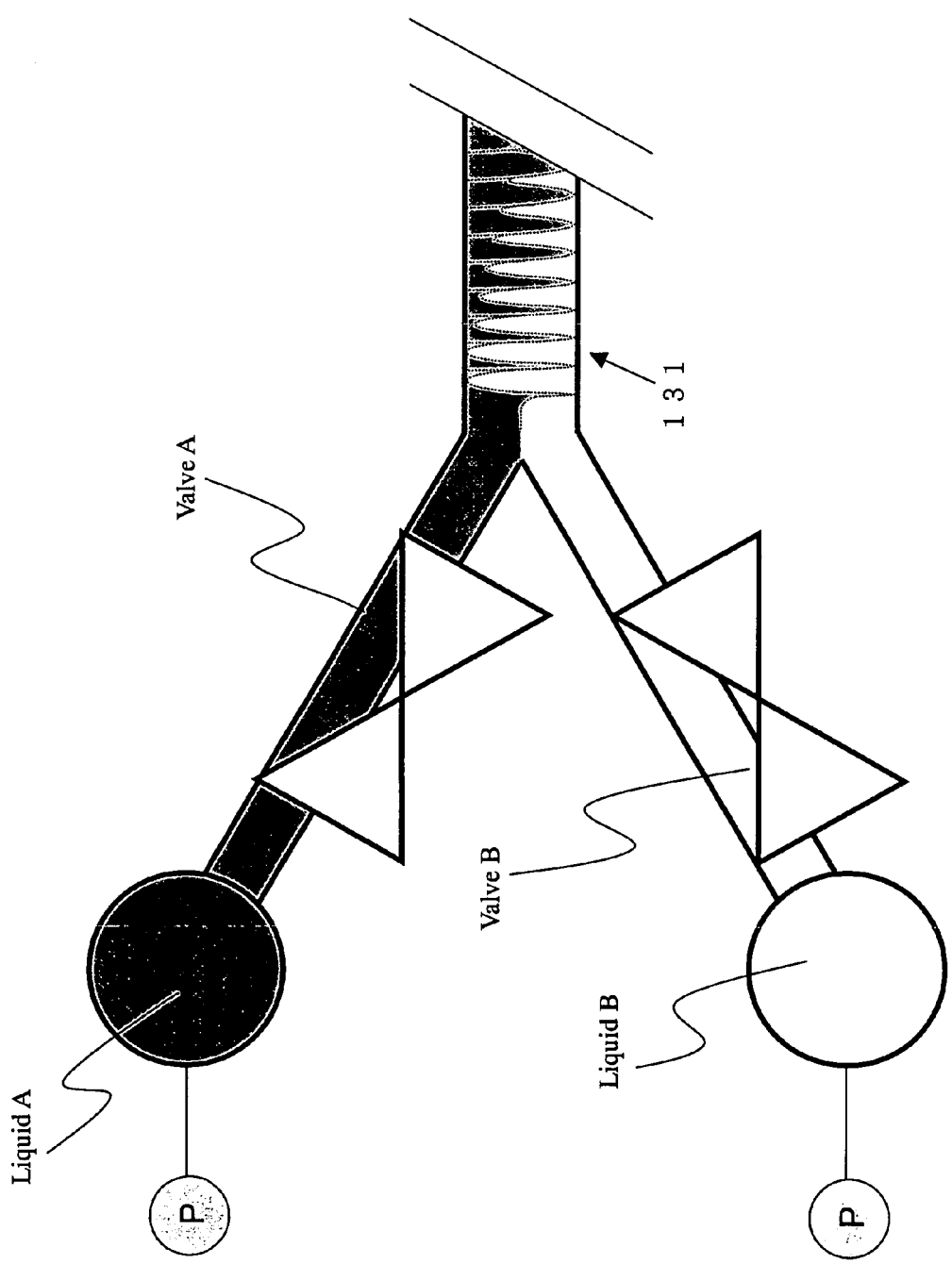
[FIG. 22] A configurational drawing showing still another example of the liquid mixing apparatus of the present embodiment.
Figure 23:
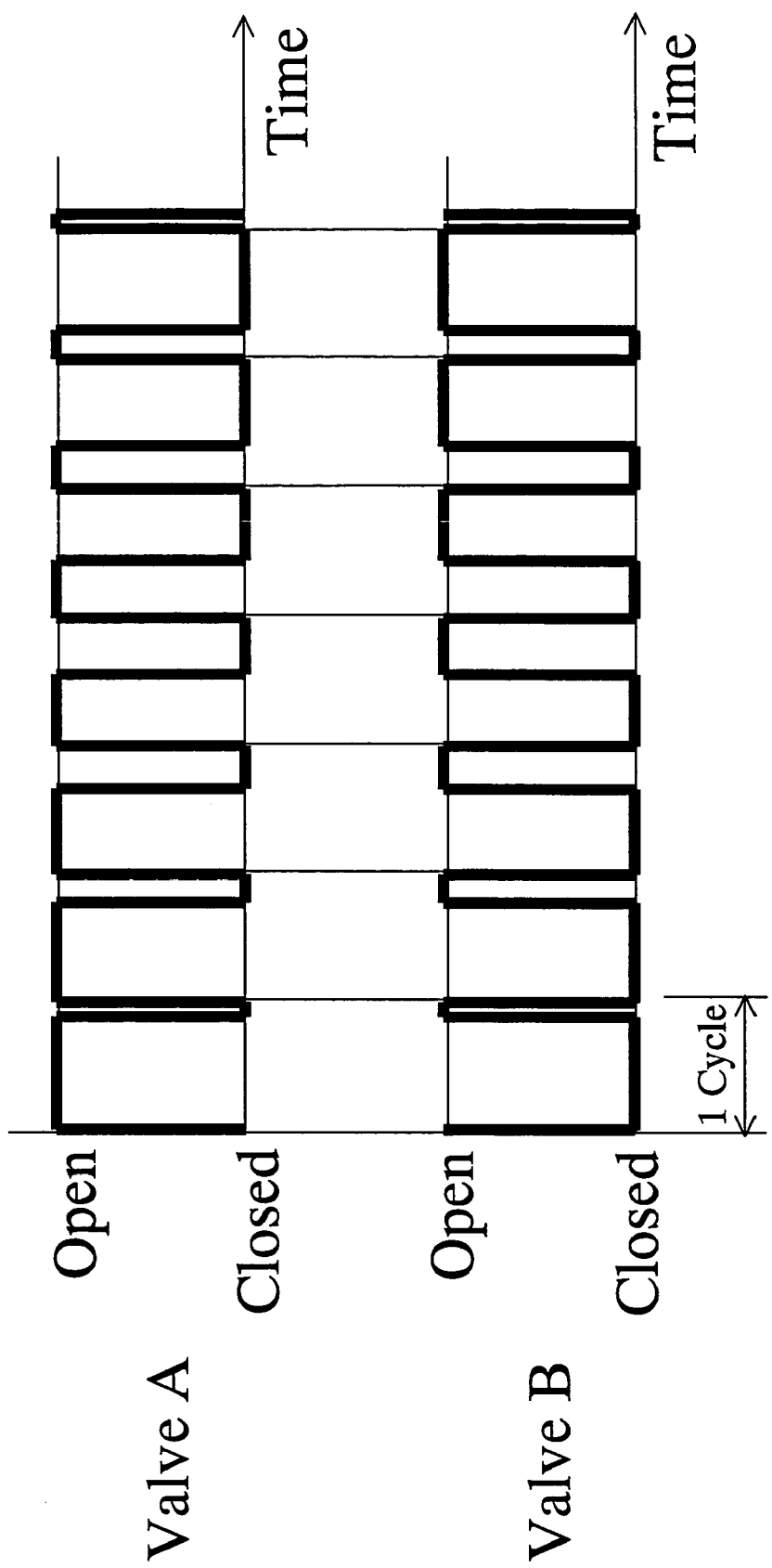
[FIG. 23] Another time-chart concerned with the control of the liquid mixing apparatus of FIG. 22.
Figure 24:
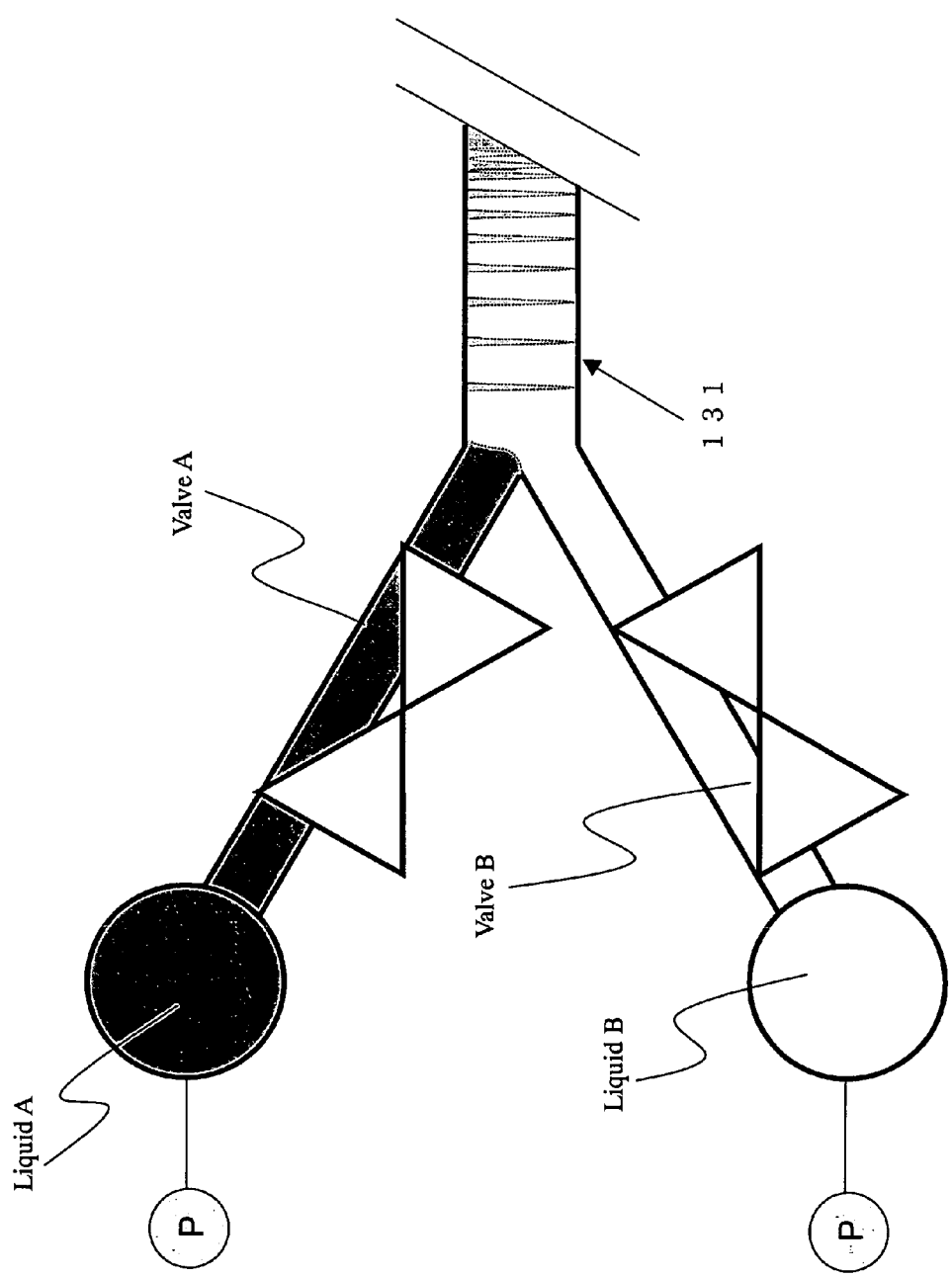
[FIG. 24] A configurational drawing showing still another example of the liquid mixing apparatus of the present embodiment.
Figure 25:
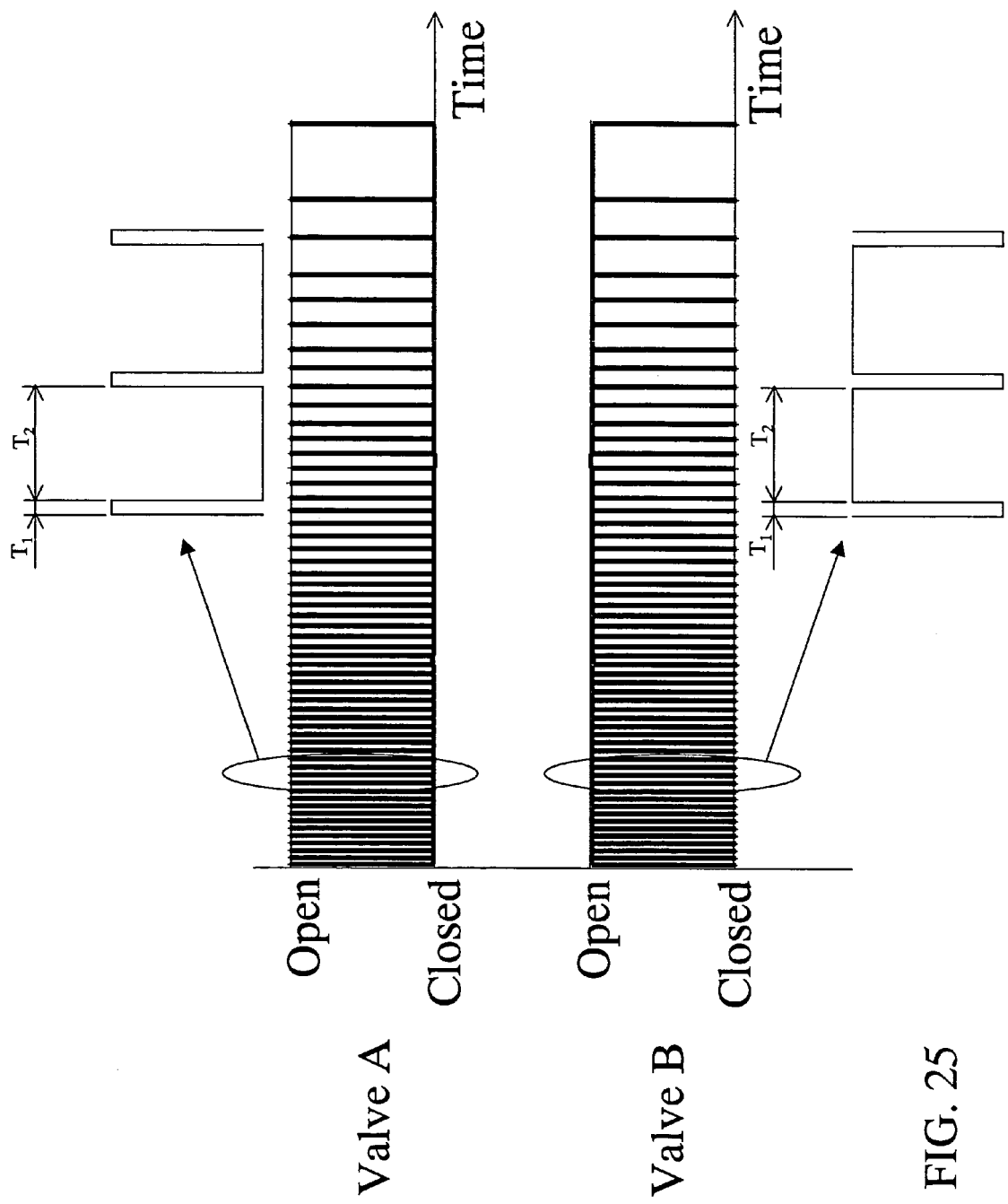
[FIG. 25] Another time-chart concerned with the control of the liquid mixing apparatus of FIG. 24.

For example, the actions of a valve A and a valve B are performed as in an operating time-chart of FIG. 23. In this case, the wavy form of the interface between the two liquids having different concentrations can be produced, with the size of the wavy form being progressively changed (as depicted in a mixing microchannel of FIG. 22). Then, the valves are allowed to stand for 5 minutes or so. By so doing, a prompt diffusive mixing of the two liquids takes place via the interface, so that a mixture having a certain concentration gradient can be formed in the mixing microchannel 31.

An example of an operating time-chart preferred for a mixing method for forming a concentration gradient will be described using FIG. 23. Basically, when the valve A is "open", the valve B is "closed", and when the valve A is "closed", the valve B is "open". In accordance with these basics, the duration of one cycle is set, for example, at 100 msec (milliseconds). In the first one cycle, the valve A is rendered "open" for 90 msec. In the next second cycle, the valve A is rendered "open" for 80 msec. In the following third cycle, the valve A is rendered "open" for 70 msec. In this manner, the time that the valve A remains open in one cycle is gradually shortened. As a result, a concentration gradient in which the concentration gradually increases in a primary linear form in a downstream direction (from the left side toward the right side in the drawing) is obtained in the mixing microchannel.

Diffusive mixing sufficiently proceeds even in the above-described mode. According to the apparatus and method shown in FIGS. 24 and 25, however, diffusive mixing is improved further. In this mode, a time T1 that the valve A is "open" is fixed, while a time T2 that the valve A is "closed" is varied. T1 is preferably set to be of the order of the shortest pulse time that the fast operating valve can act. For example, if the response frequency of the valve is 1 kHz, T1 is set at 5 msec, which is several times the minimum operating time of 1 msec. If a concentration gradient as in FIG. 22 is to be formed, T2 should be set to become gradually longer. By so doing, the interface between the liquid A and the liquid B is greater than that in FIG. 22. Thus, diffusive mixing proceeds faster, and mixing is completed in a short time.

Figure 26:
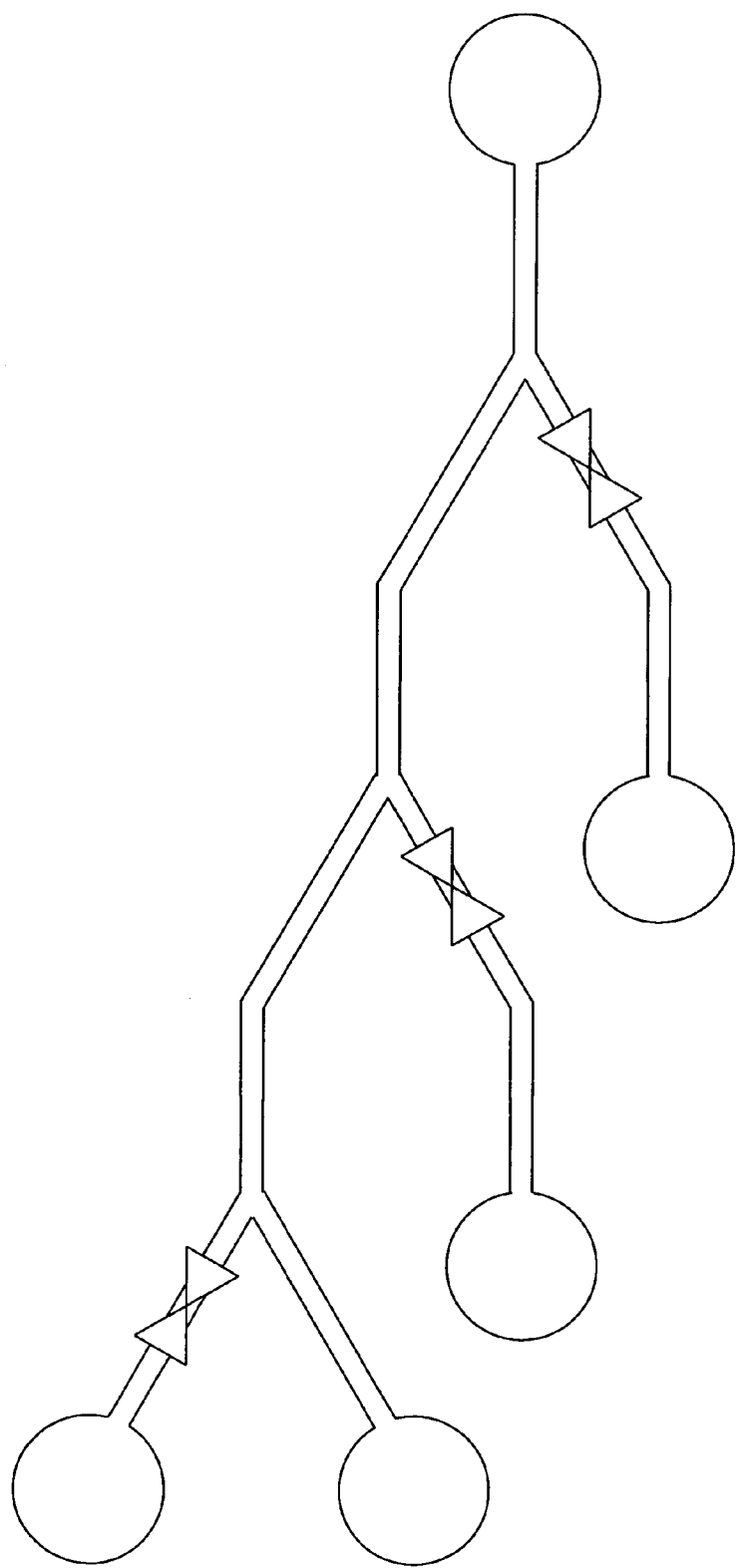
[FIG. 26] A conceptual view showing still another example of the liquid mixing apparatus of the present embodiment.
Figure 27:
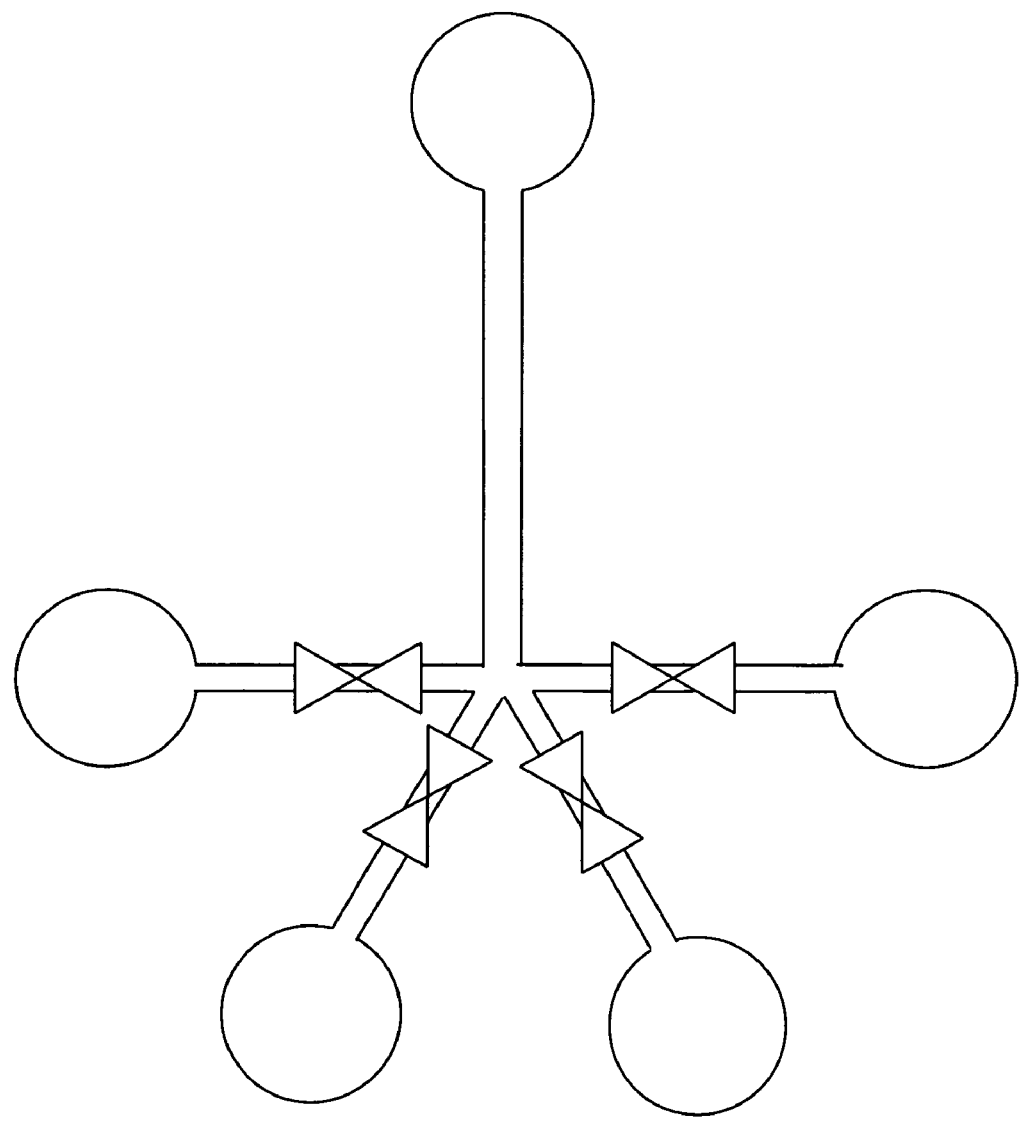
[FIG. 27] A conceptual view showing yet another example of the liquid mixing apparatus of the present embodiment.

The foregoing explanation shows an example in which the two liquid-introducing microchannels converge into one mixing microchannel for liquid feeding. However, it is possible to combine the mixing constituents in stages, thereby performing a multiplicity of mixings, as shown in FIG. 26. In this case, it goes without saying that liquids introduced into various sites may be of different types. As shown in FIG. 27, moreover, many (two or more) liquid-introducing microchannels (four liquid-introducing microchannels in the drawing) may be introduced, in a single step, into one mixing microchannel to perform mixing.

EMBODIMENT 1-3 (FIGS. 30 TO 35)

The mixing enhancing means of the apparatus according to the present embodiment concerns the shape of a mixing microchannel. The mixing enhancing means is a mixing compartment formed by rendering the channel height of the mixing microchannel smaller than its channel width.

Figure 30:
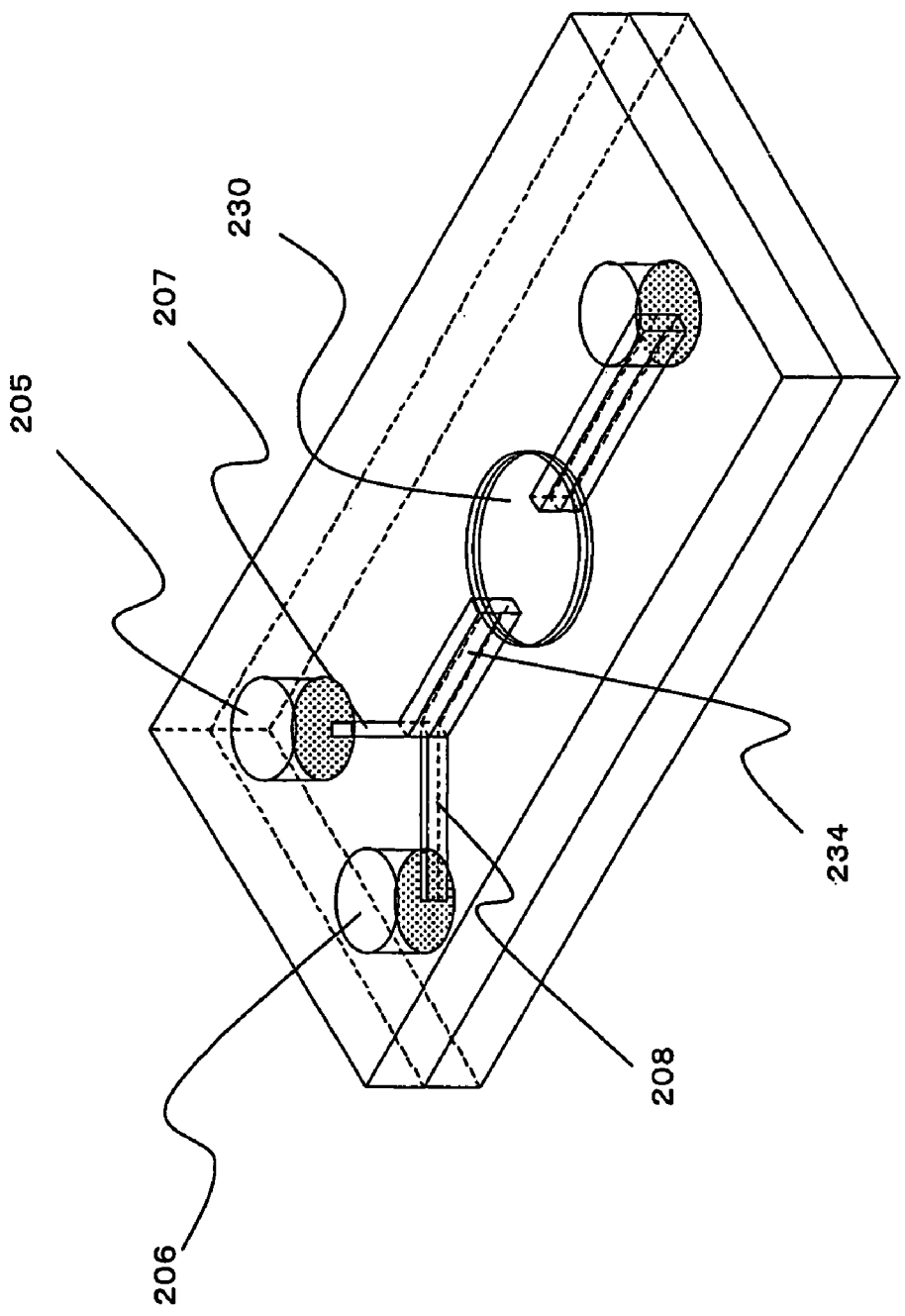
[FIG. 30] A view showing an example of the liquid mixing apparatus of the embodiment 1-3.

The apparatus of the present embodiment, shown in FIG. 30, includes two liquid-introducing microchannels 207 and 208 for introducing liquids to be mixed, a premixing microchannel 234 composed of the two liquid-introducing microchannels stacked in a vertical direction and combined together, and a mixing compartment 230 connected to the premixing microchannel. The premixing microchannel 234 and the mixing compartment 230 constitute a mixing microchannel.

In the apparatus of the present embodiment, the liquids to be mixed are introduced from the two liquid-introducing microchannels 207 and 208, converged as a stack in the vertical direction, and introduced into the premixing microchannel 234 connected to the liquid-introducing microchannels. The convergent liquids are introduced from there into the mixing compartment 230 connected to the premixing microchannel. In the present embodiment, the liquids having passed through the narrow channels, i.e., the liquid-introducing microchannels and the premixing microchannel, are introduced into the mixing compartment 230 of a flat shape. Thus, the area of the interface between the liquids is increased, whereby mixing of the plural liquids is enhanced.

In the apparatus of the present embodiment, reservoirs 205, 206 can be connected to the liquid-introducing microchannels 207, 208 upstream of the liquid-introducing microchannels 207, 208. In this case, two types of liquids are supplied to the reservoirs 205, 206. The supply of the liquids can be performed by any publicly known method and, for example, can be performed by a mechanical or electrical drive force. Concretely, the supply can be performed by adjusting the flow rates of the liquids with the use of a liquid feed pump or a valve. For example, the flow rates of the liquids can be adjusted by control of an electroosmotic flow by adjusting a voltage applied between the reservoirs or a potential applied to the reservoirs, or control of a liquid feed pump by adjusting the pressure of liquid feeding by use of a microsyringe or the like.

In the present embodiment, the liquids to be mixed are of two types. However, the two types are not limitative, and the liquids to be mixed are of two or more types. In the present embodiment, moreover, the number of the liquid-introducing microchannels is two, but it is not restrictive, and may be 2 or larger.

In the present embodiment, the channel height refers to a channel dimension in a direction normal to a liquid interface formed by contact of a plurality of liquids. The channel width refers to a channel dimension in a direction parallel to the liquid interface and perpendicular to the direction of flow. In the present embodiment, it is possible to design, for example, the premixing microchannel 234 such that its channel width is 500 μm and its channel height is 100 μm, and the mixing compartment 230 such that its channel width (at the site of maximum channel width) is 10 mm and its channel height is 5 μm.

The process of mixing the liquids according to the present embodiment will be described in greater detail. In the present embodiment, first of all, the flow of liquids in the liquid-introducing microchannel and the premixing microchannel is substantially a laminar flow, because the widths of the liquid-introducing microchannel and the premixing microchannel are small. This tendency is more remarkable if the flow rates of the liquids flowing through the liquid-introducing microchannels are low. As a result, in the premixing microchannel, mixing occurs only at the interface between the liquids, but the area of the interface between the liquids is so small that mixing of the liquids takes place minimally. When the convergent liquids flow out of the premixing microchannel into the mixing compartment, on the other hand, the area of the interface between the liquids in the mixing compartment is so large that the liquids to be mixed are mixed sufficiently promptly by diffusive mixing at the interface.

The liquid-introducing microchannels may be directly connected to the mixing compartment, or the premixing microchannel may be provided upstream of the mixing compartment, as in the embodiment of FIG. 30. However, it is preferred to provide the premixing microchannel upstream of the mixing compartment, as in the embodiment of FIG. 30. This is because if the liquid-introducing microchannels are directly connected to the mixing compartment without provision of the premixing microchannel, the channel width increases sharply, disturbing the flow. When a premixing chamber is provided upstream of the mixing compartment, as in the present embodiment, the flow of the inflowing liquids is not disturbed.

Figure 31:
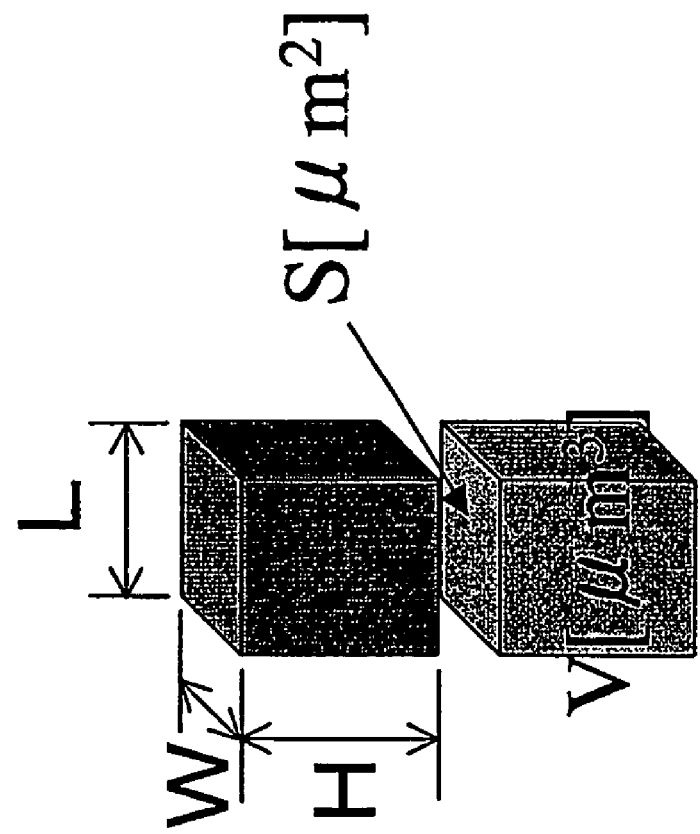
[FIG. 31] A view illustrating the ratio (S/V) of the area (S) of the interface to the channel volume (V) per unit channel length.

The miscibility of the liquids in the premixing microchannel and the mixing compartment will be investigated here. If diffusive mixing at the interface is thought of, the miscibility of the liquids depends on the ratio (S/V) of the area (S) of the interface to the channel volume (V) per unit channel length. This ratio (S/V) can be expressed as 1/H if the channel height H is used (see FIG. 31, L; channel length, W; channel width, H; channel height). Thus, one can see that the miscibility of the liquids depends solely on the channel height (H).

$$S/V = 1/H \qquad \text{Equation 3}$$

S: Area of interface [μm$^2$]
V: Channel volume [μm$^3$]
H: Channel height [μm]

Assume, for example, that the channel height of each liquid in the premixing microchannel is 50 μm, and the channel height of each liquid in the mixing compartment is 2.5 μm. In this case, the ratio (S/V) of the area (S) of the interface to the channel volume (V) is 1/50 (μm$^{-1}$) for the premixing microchannel, and 1/2.5 (μm$^{-1}$) for the mixing compartment. Hence, mixing is about 20 times as easy in the mixing compartment as in the premixing microchannel.

In the apparatus of the present embodiment, the liquid-introducing microchannels are caused to converge in the height direction of the channels. The reason is that the convergence in the height direction of the channels results in a sufficiently broad interface between the liquids in the mixing compartment, thus leading to prompt mixing of the liquids. If the liquid-introducing microchannels are caused to converge in the channel width direction (FIGS. 32(a), 32(b)), on the other hand, the area of the interface between the liquids is small with respect to the channel volume, making it difficult to mix the liquids promptly. The liquid mixing apparatus of the present embodiment has the liquid-introducing microchannels converging and stacked in the vertical direction and connected in this state to the premixing microchannel and the mixing compartment.

Next, the mixing time in the mixing compartment will be investigated. Generally, diffusion of liquids can be described by an equation of simple diffusion.

$$\sigma[m] = \sqrt{2D_0 t} \qquad \text{Equation 4}$$

D$_0$: Diffusion coefficient [m$^2$/sec]
t: Time [sec]
σ: Diffusion distance [m]

This equation means that when two liquids having a diffusion coefficient D$_0$ (m$^2$/sec) are brought into contact, they diffuse up to σ (m) in a time t (sec) and mix with each other.

If the diffusion coefficient D$_0$ of a denaturant is 10$^{-11}$, for example, the diffusion distance σ after 5 seconds is 10 μm. Thus, if the channel height is 20 μm or less, mixing can be completed, theoretically, in 5 seconds. Actually, diffusion of an upper liquid and a lower liquid proceeds from above and from below in the present embodiment. Thus, provided that the channel height of the mixing compartment is L, if diffusion proceeds up to a half thereof, i.e., L/2, mixing can be deemed to have been nearly completed. If mixing is to be completed in 5 seconds, the channel height can be actually designed to be 10 μm. In case microchip DGGE is to be performed, the mixing time of 5 seconds is sufficiently short, so that the liquid mixing apparatus of the present embodiment can be judged to be a liquid mixing apparatus preferred for microchip DGGE.

Based on the above investigations, it can be understood that a small channel height can result in a shortened mixing time. However, if the channel width is small similarly to the channel height, the flow rate is too low to be put to practical use in industry. To feed liquids at a high speed and shorten the mixing time, therefore, it is preferred to render the channel width larger than the channel height.

Figure 33:
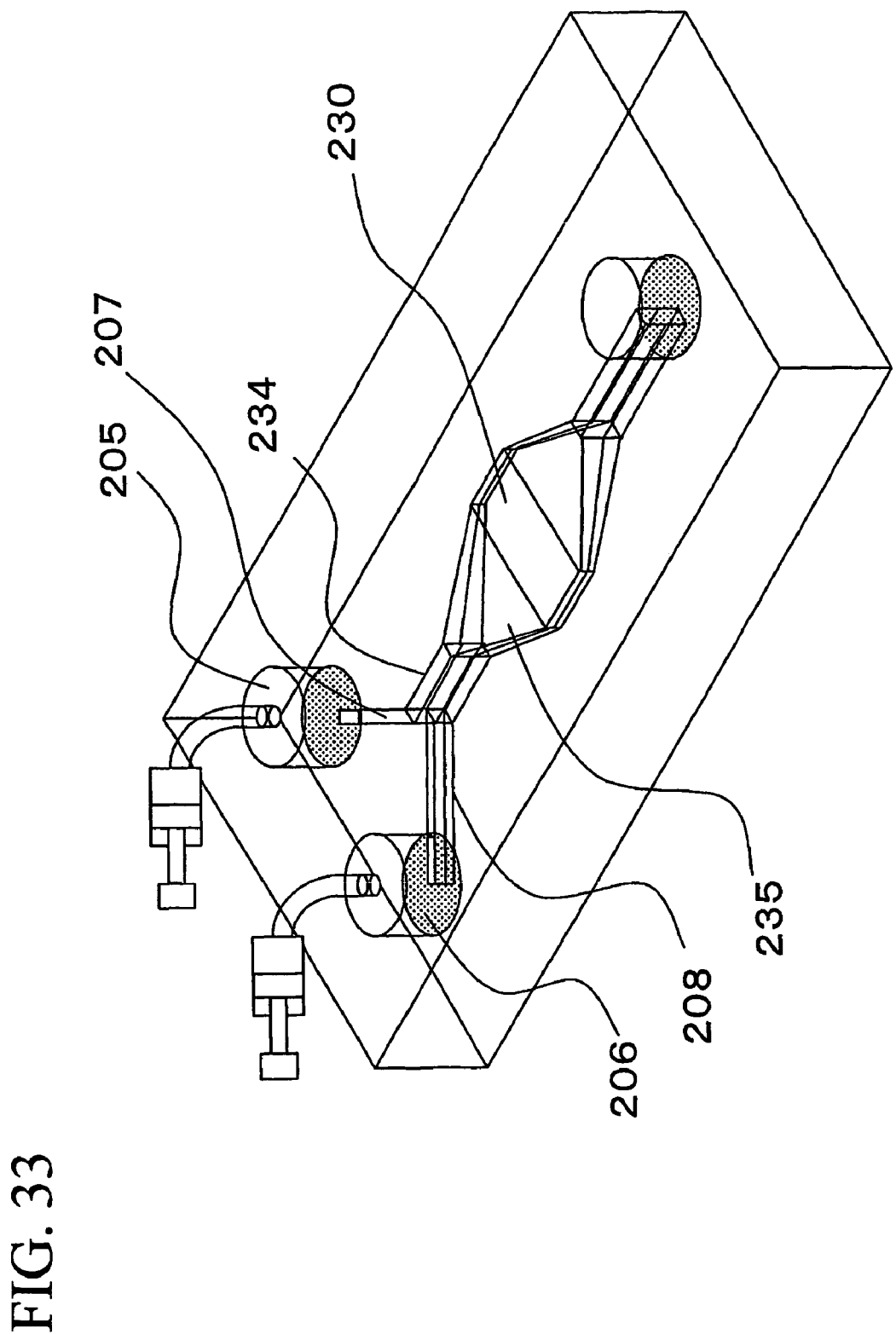
[FIG. 33] A view showing an example of the liquid mixing apparatus of the present embodiment.

FIG. 33 shows another embodiment. The apparatus of this embodiment includes two liquid-introducing microchannels 207 and 208 for introducing liquids to be mixed, a premixing microchannel 234 composed of the two channels stacked in a vertical direction and rendered convergent, a connecting portion 235 for connecting the premixing microchannel and a mixing compartment, and a mixing compartment 230 connected to the connecting portion. In the liquid mixing apparatus of the present embodiment, the premixing microchannel and the mixing compartment are connected together by a converging portion 235 having a smooth slope.

It is preferred that the premixing microchannel and the mixing compartment are connected with a smooth slope, as in the present embodiment. The reason is that if the premixing microchannel and the mixing compartment are connected with a gentle slope, no stagnation region occurs in the site of convergence of the premixing microchannel and the mixing compartment, and the liquids do not swirl midway through the channel. Thus, the interface between the liquids is not disturbed, and the liquids can be mixed in the sequence of flowing, and withdrawn from the mixing compartment (FIG. 34a). If the connecting portion does not gradually fan out, on the other hand, a stagnation region occurs, and a vortex occurs there. As a result, even when a plurality of liquids are simultaneously poured in from the liquid-introducing microchannels, the liquids dwell in the stagnation region. Thus, the liquids, which should be mixed with pinpoint accuracy, arrive at the mixing compartment, with one liquid arriving earlier than another liquid, and they are mixed with some delay. This poses difficulty in forming a precise concentration gradient (FIG. 34b). For microchip DGGE for which the formation of an accurate concentration gradient is desirable, in particular, the liquid mixing apparatus of the present embodiment is preferred.

In the embodiment of FIG. 33, it is possible to design, for example, the premixing microchannel 234 such that its channel width is 500 μm and its channel height is 100 μm, the connecting portion 235 such that its channel length in the flowing direction is 15 mm, and the mixing compartment 230 such that its channel width is 10 mm and its channel height is 5 μm.

Figure 35:
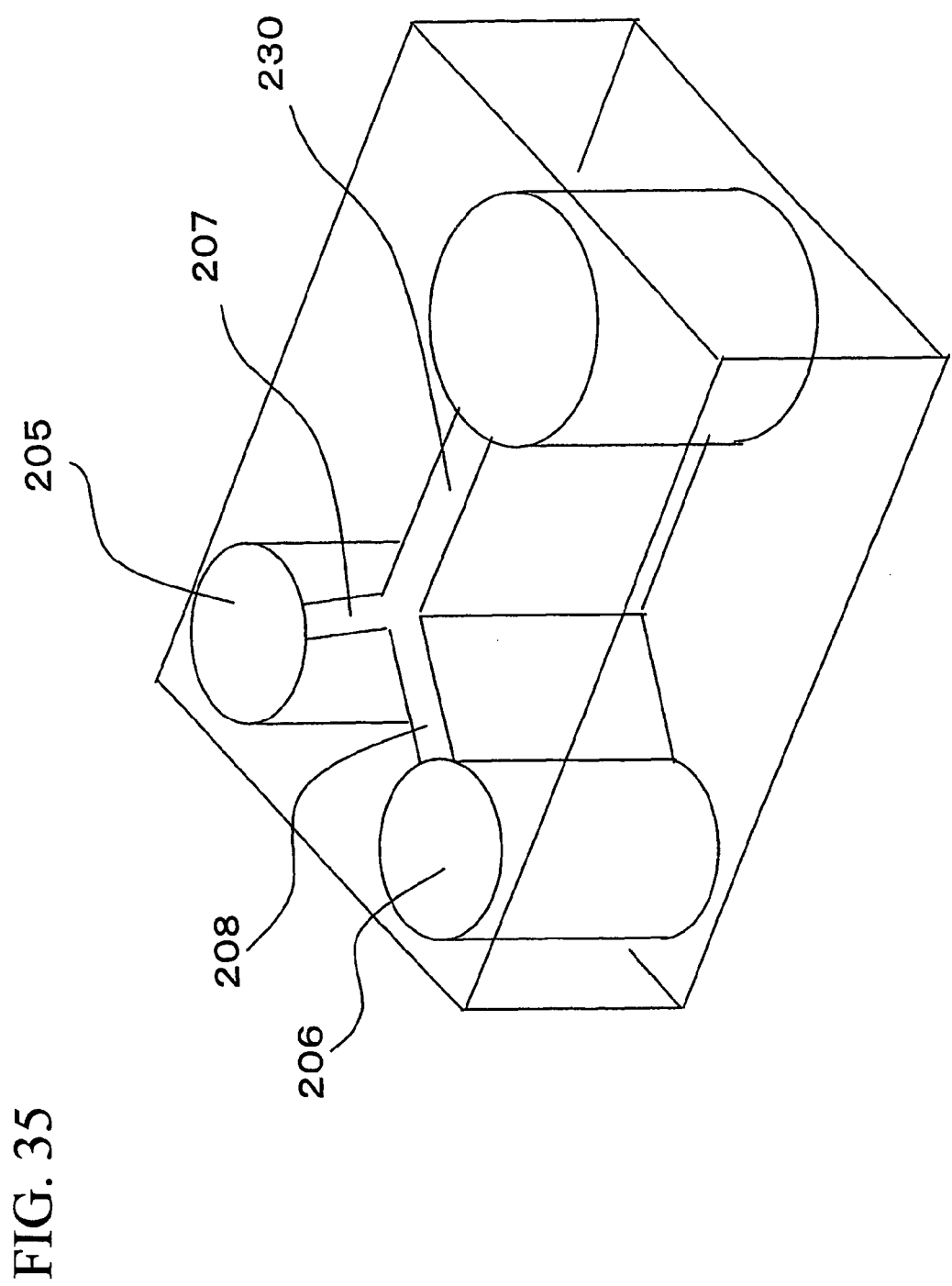
[FIG. 35] A view showing another example of the liquid mixing apparatus of the present embodiment. (Embodiment 1-4).

FIG. 35 shows still another embodiment. The apparatus of this embodiment includes two liquid-introducing microchannels 207 and 208 for introducing liquids to be mixed, and a mixing microchannel (mixing compartment 230) into which the liquid-introducing microchannels converge. In the present embodiment, the liquids to be mixed converge via the liquid-introducing microchannels 207 and 208, and the mixing compartment 230 is designed such that the area of the interface between the liquids after convergence increases.

In the embodiment of FIG. 35, the mixing compartment, for example, can be designed such that its channel height is 20 μm and its channel width is 100 μm. The apparatus of the present embodiment need not be produced by laminating two substrates, but can be processed from glass by dry etching. In detail, the apparatus can be processed by performing ICP etching with the use of a Ni sputtering film as a pattern mask.

EMBODIMENT 1-4 (FIGS. 36 TO 43)

The mixing enhancing means of the apparatus according to the present embodiment relates to the shape of a mixing section or converging portion where liquid-introducing microchannels connect to a mixing microchannel, the arrangement of the liquid-introducing microchannels, and so on. In detail, each of liquid-introducing microchannels has a plurality of branches, and the mixing enhancing means defines a mixing section where the branches converge into a mixing microchannel. At the mixing section, the plurality of branches are three-dimensionally connected with the mixing microchannel in such a way that the branches are alternately allocated to each other.

The technical background for this embodiment will be described.

The present embodiment is based on the following discovery: Channels are fractionalized for two or more liquids to be mixed, and the fractionalized channels are connected alternately due to the species of d convergent in a nested manner. By so doing, many types of liquids are arranged in layers and flowed within the channels. This procedure makes it easy to increase the area of contact between the liquids and enhance diffusion among the liquids. Further study has led to find the following problems:

(1) If the number of liquid inlets to liquid-introducing microchannels is one for each liquid, a structure in which the channel is branched for each liquid and the branches are converged again is necessary to achieve the present embodiment. Formation of this structure in a layer of a two-dimensional chip is not easy. This structure requires a geometrical arrangement, such as three-dimensional crossing. Production of such a three-dimensional structure by lithography and etching requires etching at the front and back of one chip or the formation of sacrificial layers, making the manufacturing process complicated.

(2) In the process of manufacturing microchannels by lithography and etching, which have the width of the order of 100 μm, square-corners of the mixing section result in increasing a pressure loss during liquid feeding.

(3) As a method for introducing liquids, it is possible to provide a plurality of inlets according to the number of branches, without adopting a structure in which branches are led from one liquid-introducing microchannel. According to this structure, a mixing microchannel can be formed in one layer of a two-dimensional chip. In this case, however, mechanisms or methods for liquid introduction upstream of the chip, or in a preparatory stage, become complicated.

(4) In connection with an apparatus having a plurality of inlets, as described above, a method for freely controlling the concentration ratio between mixed liquids in the mixing microchannel has not been established. With a microchip electrophoretic apparatus for performing DGGE, for example, the formation of a nucleic acid denaturing gradient with accuracy and high reproducibility requires the strict control of the concentration gradient.

The present embodiment relates to a liquid mixing apparatus solving the above-described problems. Further, the present embodiment provides a liquid mixing apparatus having liquid-introducing microchannels provided with a plurality of inlets, the apparatus being capable of promptly mixing reagent solutions in a microchannel and satisfactorily controlling a concentration gradient in a flowing direction.

Figure 36:
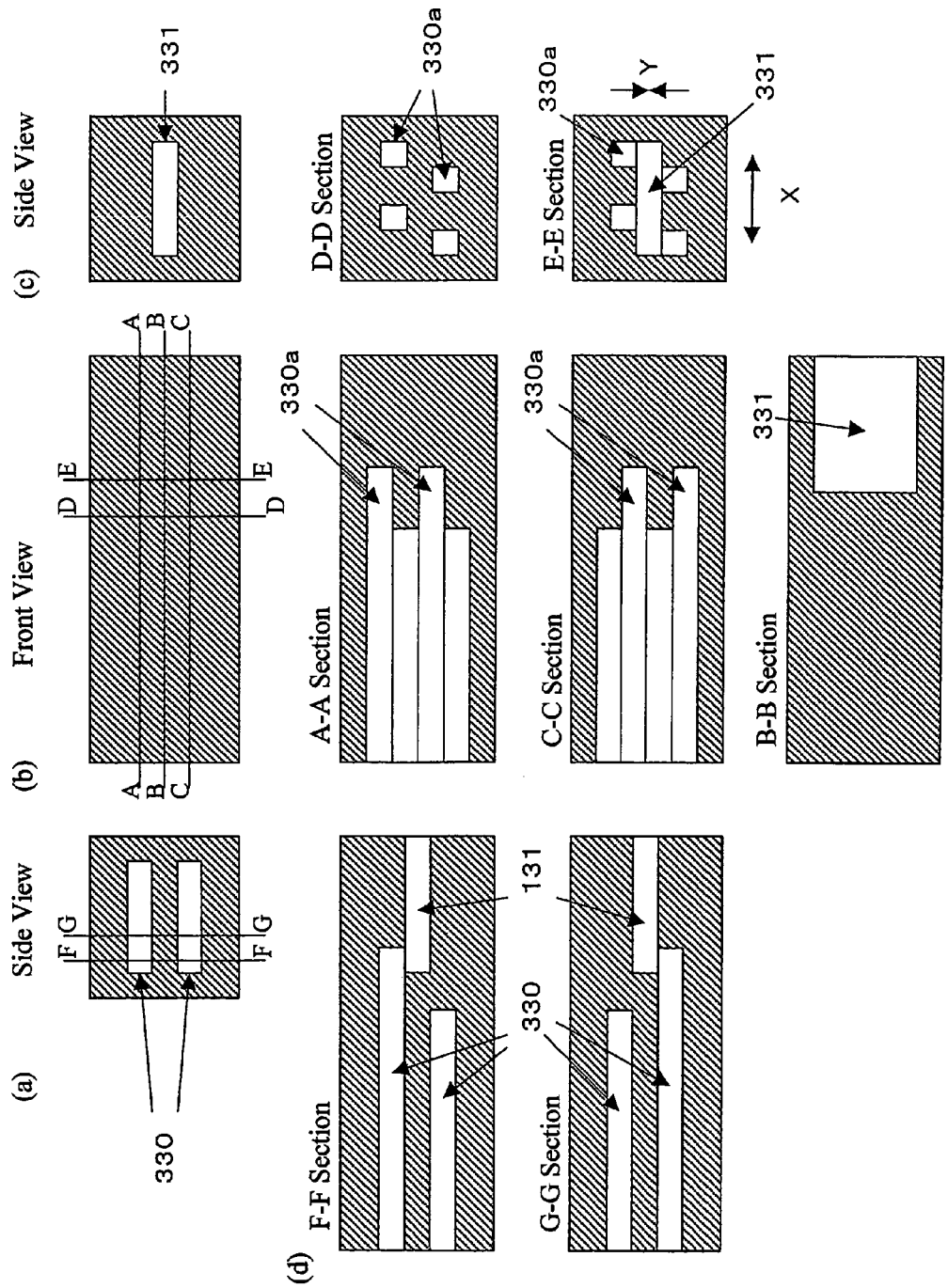
[FIGS. 36(a) to 36(d)] A left side view (FIG. 36(a)), a front view (FIG. 36(b)), a right side view (FIG. 36(a)), and sectional views (FIG. 36(d)) showing the schematic configuration of the liquid mixing apparatus of the embodiment 1-4.

FIGS. 36(a) to 36(d) show the schematic configuration of the apparatus of the present embodiment as side views (FIGS. 36(a), 36(c)), a front view (FIG. 36(b)), and sectional views (FIG. 36(d)). This apparatus is a microchip comprising two liquid-introducing microchannels 330 for introducing liquids, and a mixing microchannel 331 to which the liquid-introducing microchannels 330 connect. Liquids enter through the two liquid-introducing microchannels 330 (left side in FIG. 36), converge in the inside, and mix in one mixing microchannel 331. Each of the liquid-introducing microchannels 330 has two branches 330a fractionalized in a comb shape, and these two branches connect to the mixing microchannel 331 from above and from below (this connecting direction is called a converging direction Y). In a mixing section or converging portion where the branches connect to the mixing microchannel, as shown by a cross-section DD and a cross-section EE in FIG. 36(d), the branching direction X of the branches 330a is nearly normal to the converging direction Y, forming a comb-shaped arrangement. These branches 330a are integrated so as to engage each other three-dimensionally, converging into the single mixing microchannel. Liquids converging via the mixing section of this shape can be mixed promptly and uniformly even in the microchannel.

Figure 37:
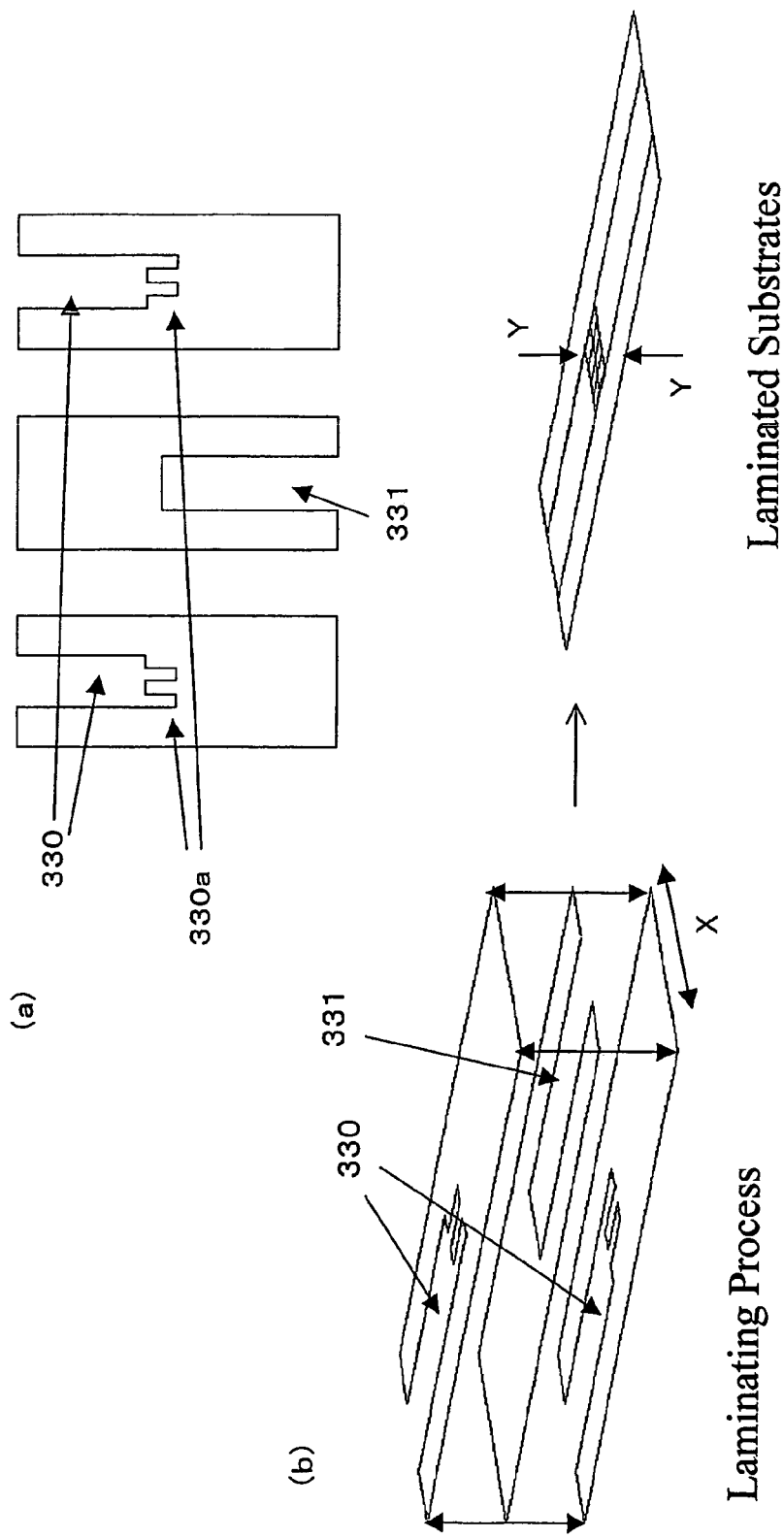
[FIGS. 37(a) and 37(b)] Views showing the layered structure of the liquid mixing apparatus, and the step of lamination.

FIGS. 37(a) and 37(b) show the schematic configuration of the apparatus of FIG. 36 by perspective views, etc. This apparatus can be produced by laminating substrates in which predetermined channels have been formed. This embodiment is of a structure having an intermediate substrate and two substrates laminated together. The liquid-introducing microchannels 330 and their branches 330a, as well as the mixing microchannel 331, are each formed on a substrate. The intermediate substrate has the mixing microchannel 331 formed thereon (a substrate of cross section BB in FIG. 36(d)). The two substrates (substrates of cross sections AA and CC in FIG. 36(d)) having the liquid-introducing microchannels formed thereon are laminated from above and from below, with the intermediate substrate in the middle, and a substrate serving as a cover is further laminated. This procedure forms a layered structure, the substrates stacked in the converging direction Y, namely, in a direction nearly perpendicular to the branching direction X. The plurality of branches 330a are provided on nearly the same plane as the one liquid-introducing microchannel. Such converged branches can be referred to as a comb-shaped structure.

Figure 38:
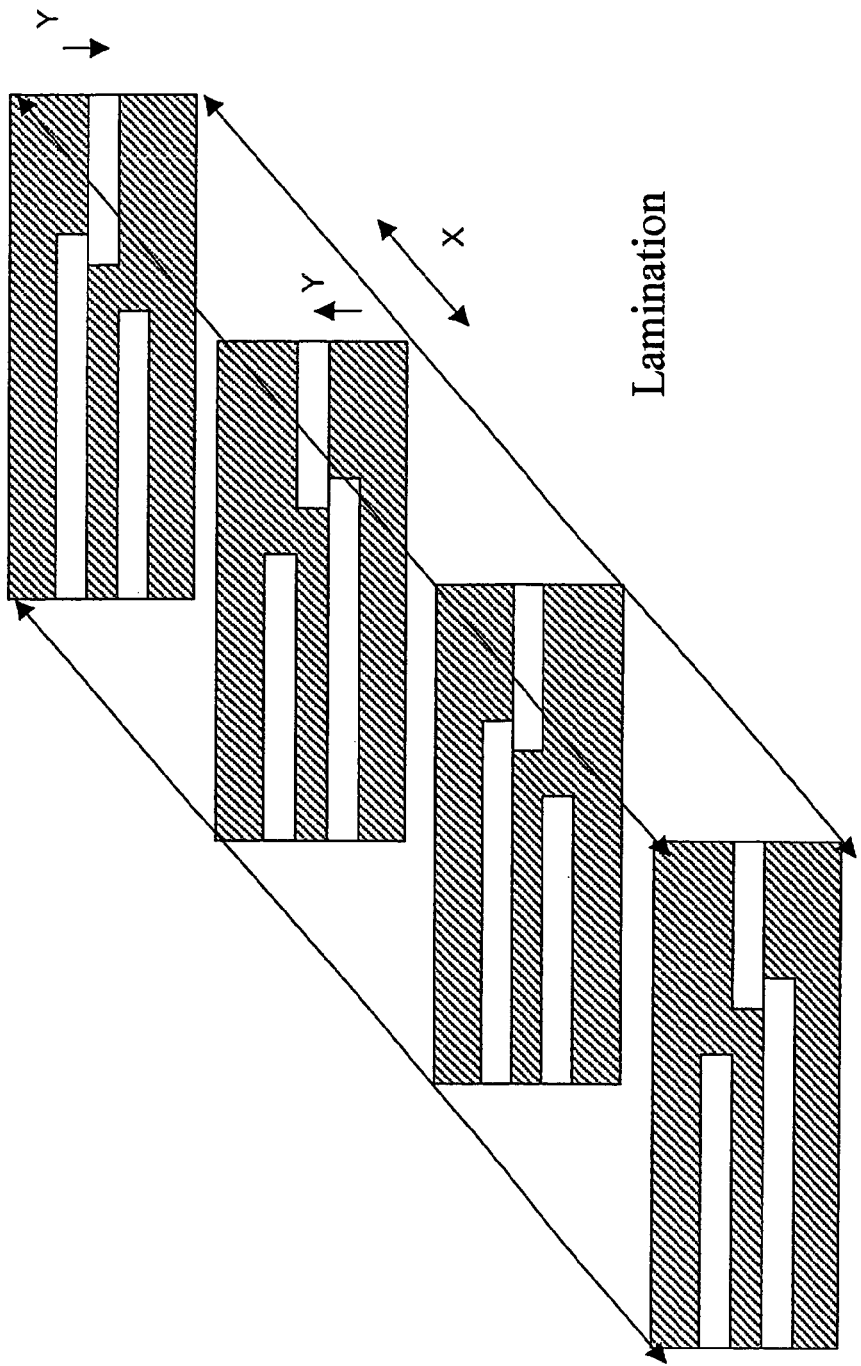
[FIG. 38] A sectional view showing another layered structure.

In FIG. 38, the same channel structures as in the apparatus of FIG. 36 are laminated in the branching direction X (a direction nearly perpendicular to the converging direction Y). In this embodiment, a layered structure having the substrates for the resulting branches is formed.

Figure 39:
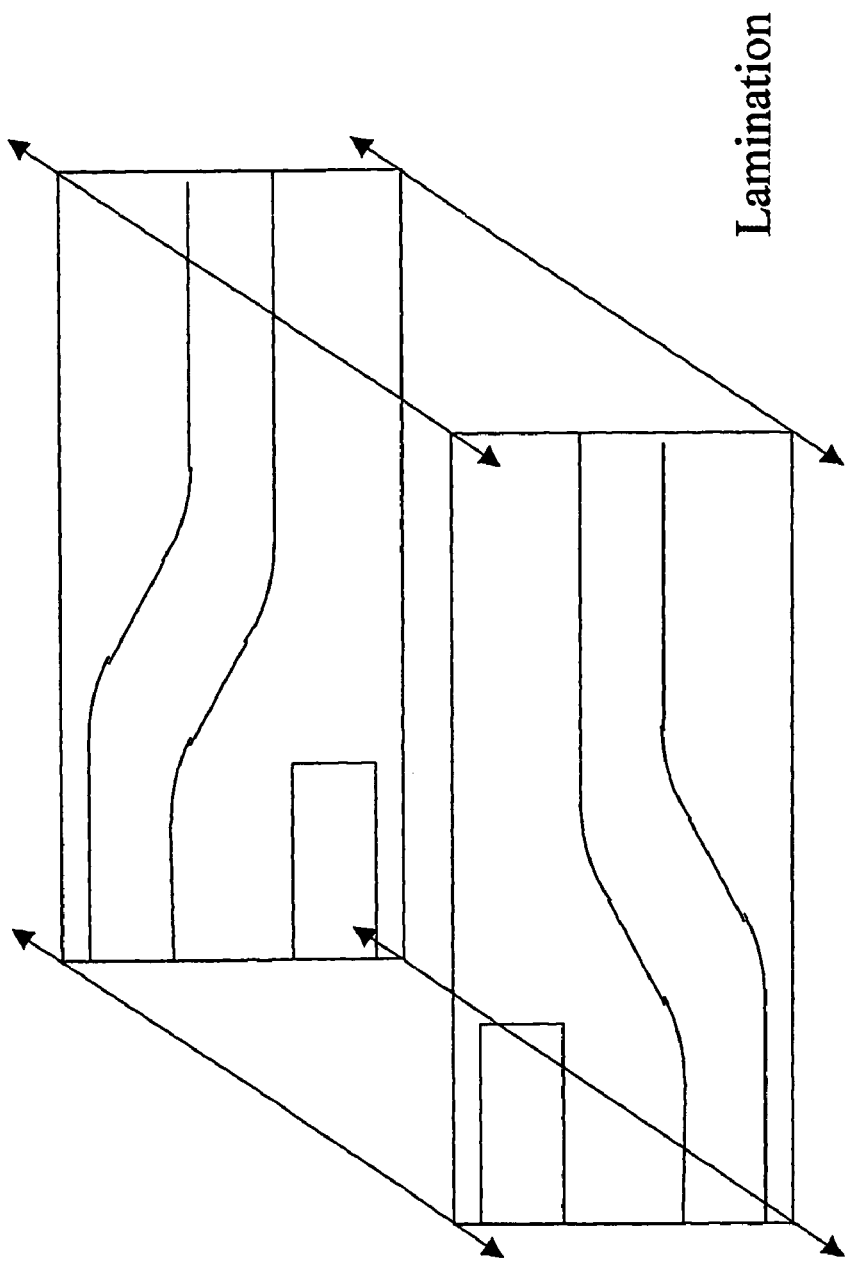
[FIG. 39] A sectional view showing another constitution of a mixing section or converging portion of the liquid mixing apparatus.

FIG. 39 illustrates a feature in which a curved shape is applied to the structure of the mixing section in the cross sections FF and GG of FIG. 36 and in FIG. 38. As seen here, the channels at the mixing section may be configured to be curved. By so doing, a liquid mixing apparatus with a pressure loss at the mixing section decreased can be produced.

The material for the substrate can be selected, as appropriate, from among glass, quartz, plastics, and silicone resins. The aforementioned laminate of many layers, and structures having the front and back processed in a plurality of stages can be manufactured by lithography and etching. However, the apparatus of the present embodiment can also be produced by a photolithography technology, and may be constructed such that a pressure loss is decreased by processing (making) the wall surface of each channel at the mixing section into a curved shape (generally, a streamlined shape).

Next, an embodiment for performing liquid introduction efficiently will be described. This embodiment relates to an apparatus comprising liquid-introducing microchannels having a plurality of inlets.

Figure 40:
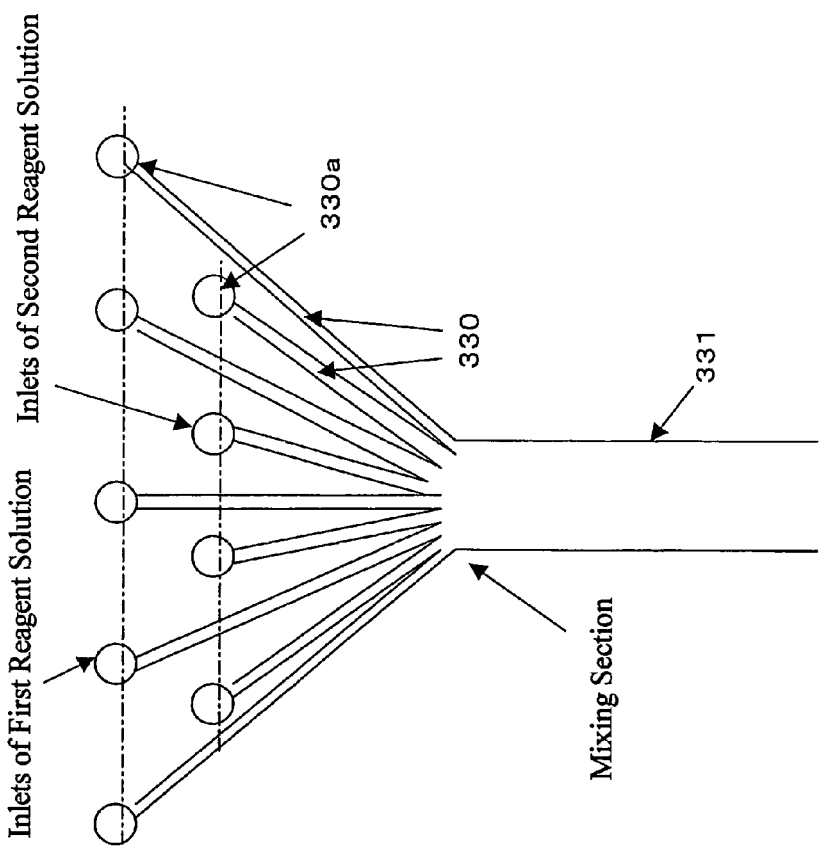
[FIGS. 40(a) and 40(b)] Views showing configuration examples of the embodiment 1-4 having a plurality of liquid inlets.
Figure 40:
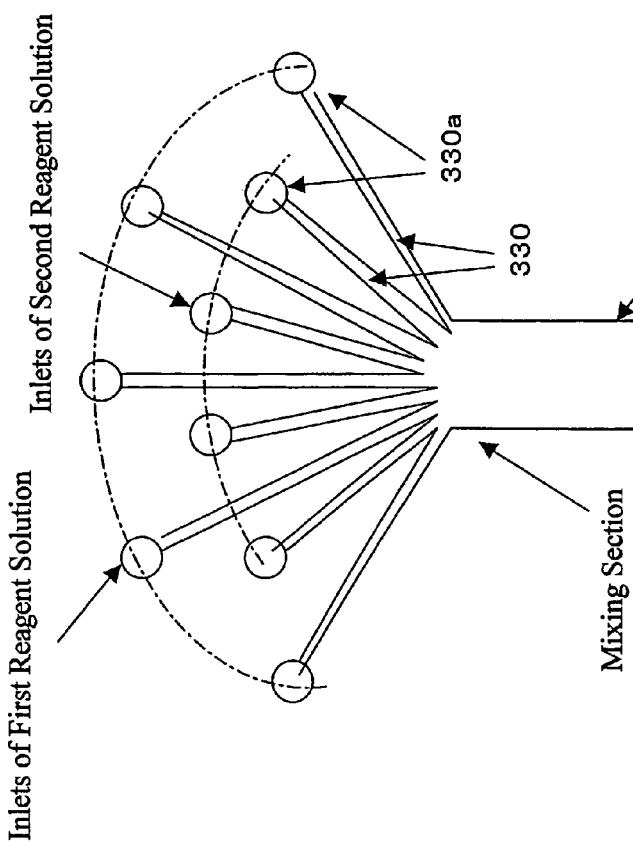

In the apparatus of FIGS. 40(*a*) and 40(*b*), liquid-introducing microchannels 330 having a plurality of liquid inlets 330*a* for introducing reagent solutions gather and connect to a mixing microchannel 331. In this gathering-type channel structure, the width of the resulting gather of the liquid-introducing microchannels 330 is the same as the channel width of the mixing microchannel 331. A group of a plurality of the liquid inlets 330*a* corresponds to a liquid-introducing microchannel group which feeds the same liquid (a buffer solution of the same concentration or a reagent solution of the same type; in FIGS. 40(*a*) and 40(*b*), a first reagent solution or a second reagent solution). They are provided in a regular geometrical arrangement on the substrate. Examples of the geometrical arrangement are two-dimensional arrangements, such as straight-line, arcuate arrangements as in FIG. 40(*a*) or 40(*b*). As in these apparatuses, the geometrical arrangements of the groups of liquid inlets 330*a* are preferably similar with respect to the converging point to each other.

Figure 41:
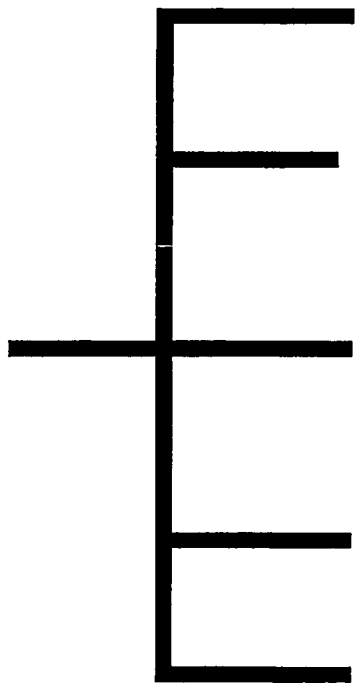
[FIGS. 41(a) and 41(b)] Views showing configuration examples of a branched electrode usable in the apparatus of FIGS. 40(a) and 40(b).
Figure 41:

In some apparatuses of the present embodiment, the liquid inlets 330*a* are each provided with an electrode, and the liquid is driven by an electroosmotic flow. In this embodiment, a branched drive electrode as shown in FIG. 41(*a*) or 41(*b*) may be prepared, and mounted in correspondence with a predetermined geometrical arrangement of each liquid inlet group. FIG. 41(*a*) or 41(*b*) schematically shows the configuration of the branched electrode corresponding to the straight-line geometrical arrangement. By providing such a branched electrode detachably, the reagent solution can be efficiently driven from a fixed liquid inlet group. For example, one branched electrode is used for a plurality of liquid inlets 330*a* for introducing the same reagent solution, and liquid feeding can be performed simultaneously from the plurality of liquid inlets 330*a*.

Figure 42:
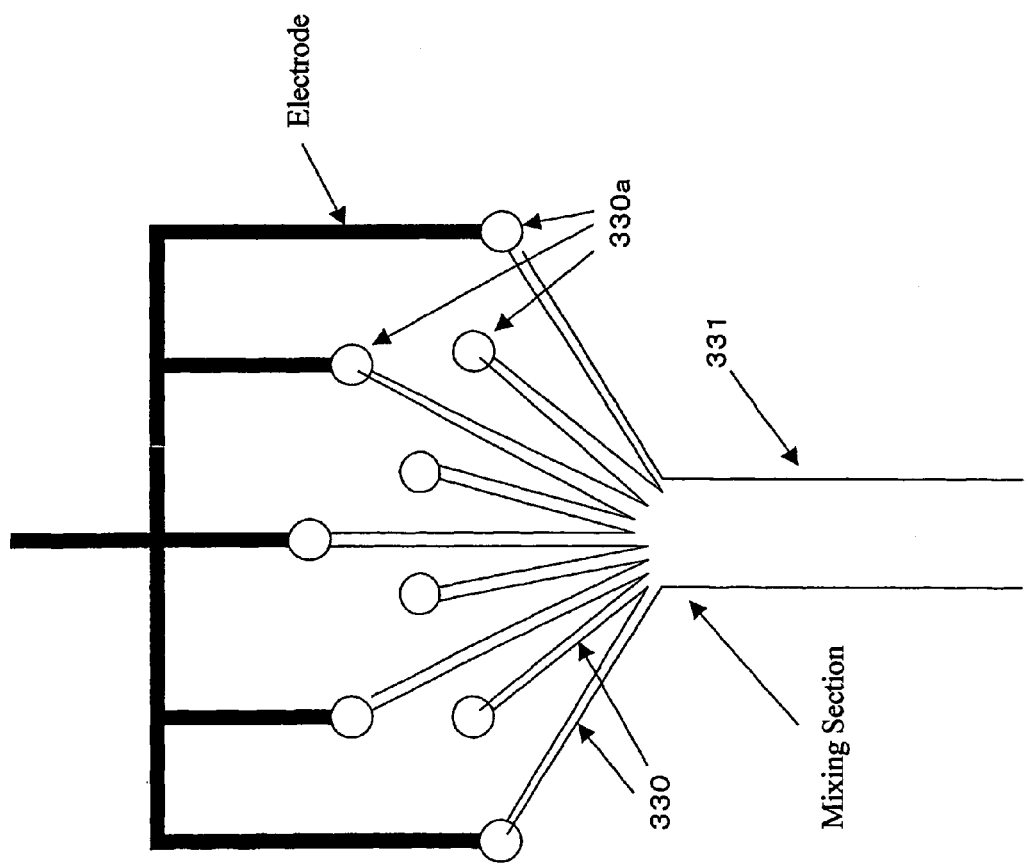
[FIG. 42] A view showing another configuration of the embodiment 1-4 having a plurality of liquid inlets.

In the apparatus designed to drive the liquid by a pump pressure, although not shown, a branched hydraulic introduction pipe corresponding to the geometrical arrangement of the liquid inlet group for the liquid is mounted so that pressure can be applied simultaneously and equally to all liquid inlets, and the efficient introduction of the reagent solution can be performed similarly. Moreover, the application of the mixing apparatus of the present embodiment to a microchip enables a microchip apparatus to be of a low profile. As shown in FIG. 42, a branched drive electrode corresponding to the positions of the plurality of liquid inlets 330*a* can be provided on nearly the same plane as the liquid inlets.

Next, liquid introduction control means and methods preferred for the apparatus of the present embodiment will be described. In the aforementioned embodiment in which the same liquid is introduced through the group of liquid inlets 330*a*, pumps or electroosmotic flow drive mechanisms can be provided upstream of the liquid-introducing microchannel group. In this case, if the number of the pumps or electroosmotic flow drive mechanisms used is smaller than the number of the liquid-introducing microchannels for introduction of the same type of liquid, liquid introduction can be controlled properly.

Figure 43:
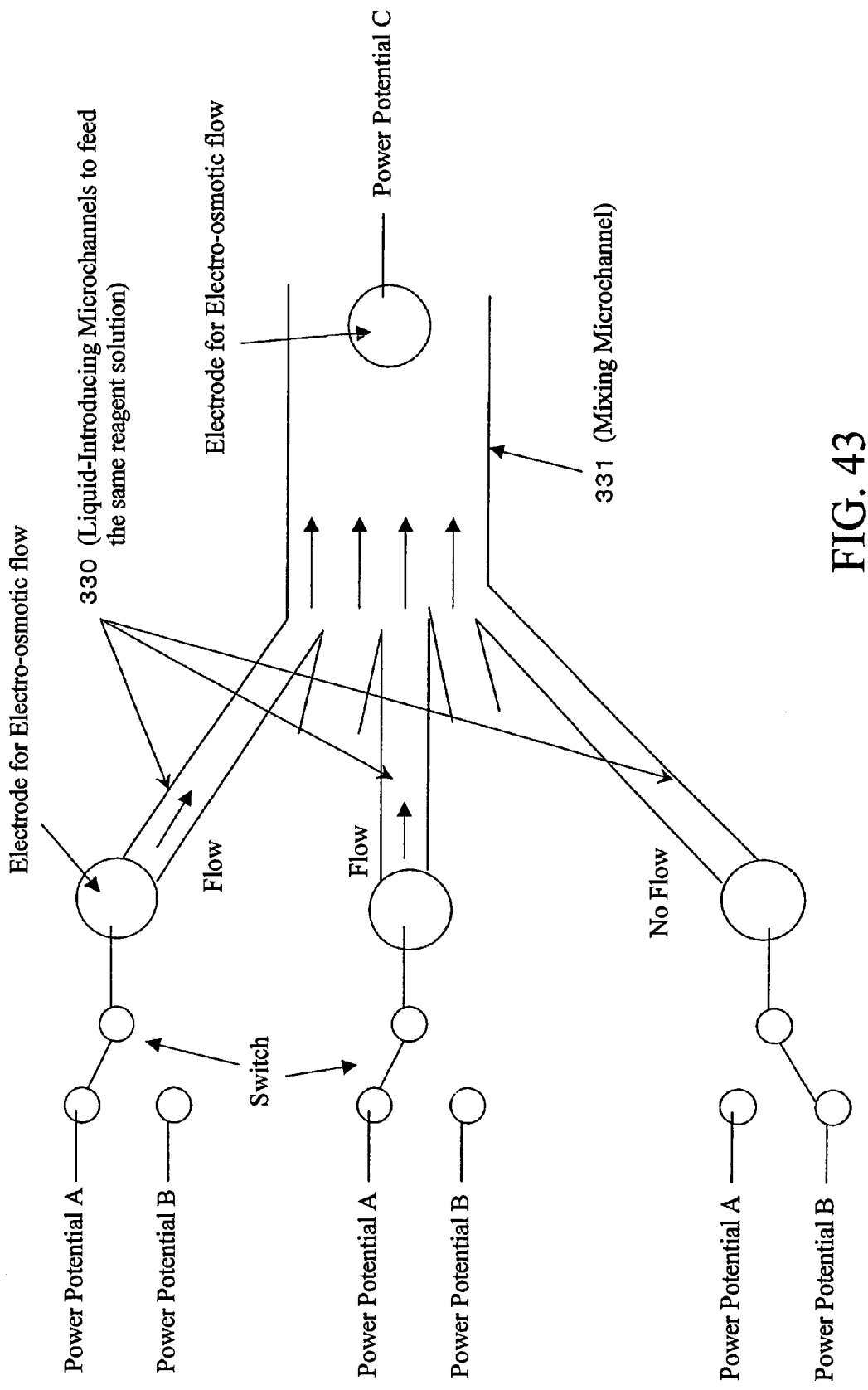
[FIG. 43] A view for explaining the control means and method of the liquid mixing apparatus of FIGS. 40(a) and 40(b) or FIG. 42. (Embodiment 2-1)

FIG. 43 shows an example of control means for driving an electroosmotic flow. The same reagent solution is fed from each liquid-introducing microchannel 330 toward a mixing microchannel 331 by an electroosmotic flow. In the channels to which a power supply potential difference A-C is applied by switches, the reagent solution is fed downstream, and converged in a layered state together with other reagent solution for mixing. In the channels for the same reagent solution, on the other hand, a power supply potential difference B-C is applied by switches. In these channels, the reagent solution can be arranged not to flow downstream, and not to flow backward, by setting an appropriate potential B.

By controlling the ON and OFF positions of these plural switches appropriately, the effective number of the introducing channels to feed the same reagent solution can be changed. As a result, the total amount of inflow of the same reagent solution into the mixing microchannel 331 can be changed successively and independently. Simply by controlling the group of switches, the amount of inflow of each reagent solution can be changed in multiple stages by a small number of power supplies, and the concentration of the reagent solution in the mixing microchannel can be controlled. Particularly, if its total inflow amount of the concerned reagent solution is successively controlled with the streamwise distribution of the concentration after mixing, can be controlled with high accuracy.

Relays may be used as the plural switches, or pressure pumps may be provided instead of or as assistance for the electrodes to control pressure driving for each reagent solution. If the pressure pumps are provided, control valves may be provided for respective liquid-introducing microchannels, and the drive of the control valves may be controlled to vary the flow rate of each reagent solution.

EMBODIMENT 2-1 (FIGS. 44 TO 46)

The mixing enhancing means of the apparatus of the present embodiment includes a heater mounted on a liquid-introducing microchannel and/or a mixing microchannel.

FIG. 44 shows the apparatus of the present embodiment. The apparatus of the present embodiment comprises liquid-introducing microchannels 431, 432 for introducing liquids to be mixed, a mixing microchannel 433 having a mixing section or converging portion 430 where the plural channels converge, and a heater 435 for heating the liquids in the mixing microchannel.

In the apparatus of the present embodiment, the liquids to be mixed are introduced from the liquid-introducing microchannels 431, 432, and converged by the mixing section 430. The convergent liquids are introduced into the mixing microchannel 433 connected to the mixing section 430, and the liquids in the mixing microchannel are heated by the heater 435 (for example, a chromium steel heater or a Peltier device), whereby the liquids in the mixing microchannel are mixed. According to the present embodiment, the liquids convergent in the mixing microchannel are heated by the heater 435. As a result, the temperature of the liquids in the mixing microchannel is raised, so that the Brownian movements of the solutes in the liquids are activated. Thus, molecular diffusion is promoted to enable prompt mixing of the plurality of liquids. Also, heat convection due to heating enhances the mixing of the convergent liquids.

The supply of the liquids can be carried out by any publicly known method, for example, by a mechanical or electrical drive force. Concretely, the supply of the liquids can be changed by adjusting the flow rates of the liquids with the use of a liquid feed pump or a valve. For example, the flow rates of the liquids can be adjusted by control of an electroosmotic flow by adjusting a voltage applied between the reservoirs or potentials applied to the reservoirs, or control of a liquid feed pump by adjusting the pressure of liquid feeding by use of a microsyringe or the like.

In the apparatus of the present embodiment, the liquids to be mixed are of two types. However, the two types are not limitative, and the liquids to be mixed may be of two or more types. Moreover, the number of the liquid-introducing microchannels in the present embodiment is two, but it is not restrictive, and may be 2 or larger.

FIG. 45 shows another embodiment. The apparatus of the present embodiment comprises liquid-introducing microchannels 441, 442, a mixing microchannel 443 having a mixing section or converging portion 40 where the liquid-introducing microchannels 441 and 442 converge, and a heater 445 mounted on the underside of the mixing microchannel 443 for heating the microchannel 443. According to the present embodiment, the liquids to be mixed are converged, in a vertically stacked state, by the mixing section 440. The convergent liquids are introduced into the mixing microchannel 443 connected to the mixing section 440, and the liquids in the mixing microchannel 443 are heated, from the underside of the mixing microchannel 443, by the heater 445 mounted on the underside of the mixing microchannel 443. In this manner, the mixing of the liquids in the mixing microchannel is enhanced. In the present embodiment, the convergent liquids are heated by the heater 445. As a result, the temperature of the liquid located in a lower portion of the mixing microchannel is raised, whereby thermal convection occurs in the channel 443. Thus, a diffusive effect by vertical convection is enhanced to promote the mixing of the convergent liquids. Also, the increase in molecular diffusion by heating enhances mixing of the convergent liquids.

Figure 46:
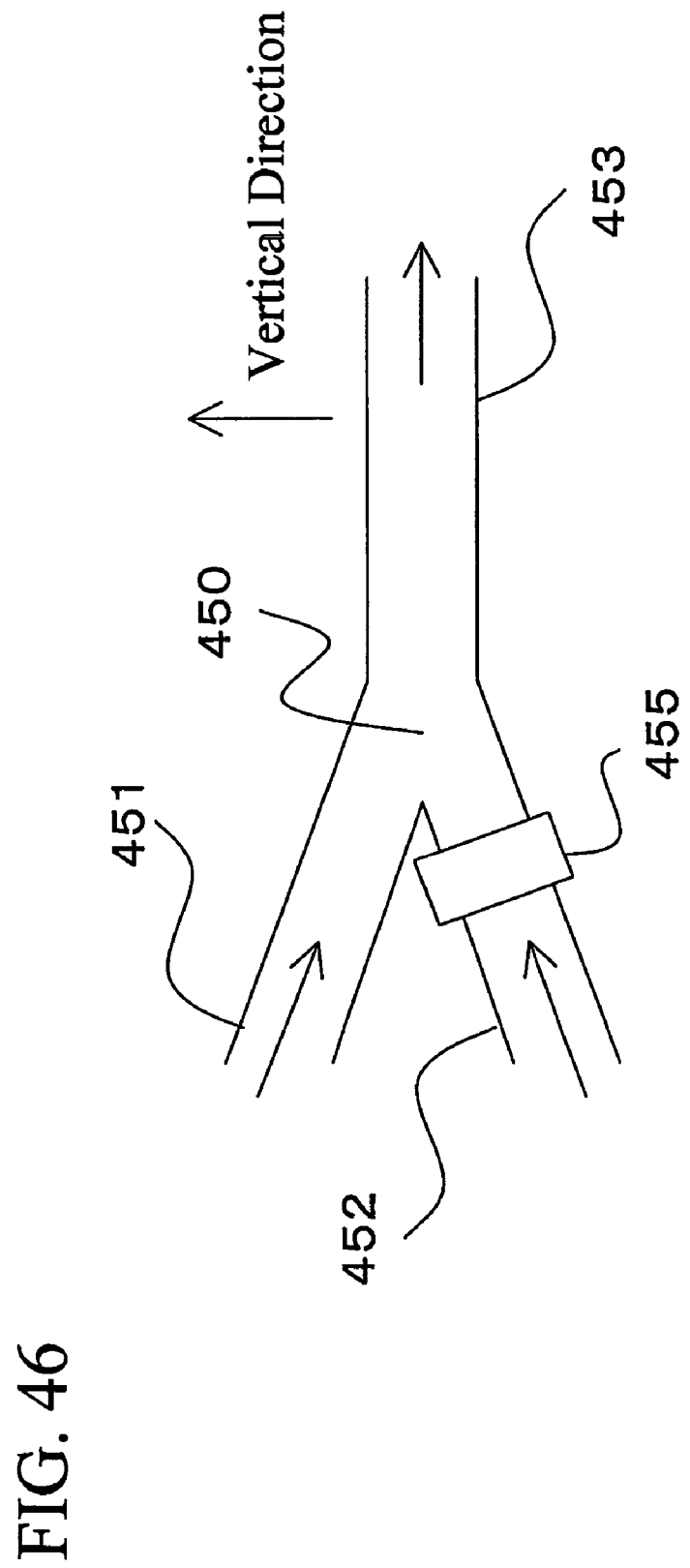
[FIG. 46] A view showing another example of the liquid mixing apparatus of the present embodiment. (Embodiment 2-2)

FIG. 46 shows still another embodiment. The apparatus of the present embodiment comprises liquid-introducing microchannels 451, 452, a mixing microchannel 453 having a mixing section or converging portion 450 where the liquid-introducing microchannels 451 and 452 converge, and a heater 455 for heating the liquid-introducing microchannel 452. According to the present embodiment, the solution in the liquid-introducing microchannel 452 is heated by the heater 455, and the unheated liquid in the channel 451 and the heated liquid in the channel 452 are converged at the mixing section 450 while being stacked in the vertical direction, with the heated and high-temperature liquid in the channel 452 being placed in the lower layer. The convergent liquids are introduced into the mixing microchannel 453 connected to the mixing section 450. In this manner, the mixing of the liquids in the mixing microchannel is enhanced. In the present embodiment, although the liquid in the channel 452 is heated by the heater 455, it is converged at the mixing section 450 while being placed below the unheated liquid in the channel 451. Thus, the liquid, which has been heated, tends to move upward, thereby causing heat convection in the channel 453. As a result, a diffusive effect by vertical convection is enhanced to promote the mixing of the convergent liquids. Also, the increase in molecular diffusion by heating enhances mixing of the convergent liquids.

In the case of heating the liquid-introducing microchannel by the heater as in the present embodiment, the liquids in the liquid-introducing microchannels are converged while being stacked vertically, with the high-temperature liquid being placed in the lower layer of the stack. The heater usable in the present embodiment can be selected from all publicly known heating equipment. For example, a chromium steel heater or a Peltier device can be used. The position of mounting of the heater may be any position which enables the liquid in the channel to be heated. For example, the heater can be mounted on the wall surface of the channel. Alternatively, the number of the heaters mounted need not be one, but may be plural.

EMBODIMENT 2-2 (FIGS. 47 TO 53)

The mixing enhancing means of the apparatus according to the present embodiment is a mechanical mixing and/or stirring means for disturbing the interface between the liquids which converge in the mixing microchannel. A first type of the mechanical mixing and/or stirring means is a vibrator, a lifting surface, a rotator or an oscillator mounted in or near the area where the liquids converge in the mixing microchannel. A second type of the mechanical mixing and/or stirring means is a vibrator mounted not only in the converging area in the mixing microchannel, but also on the inner wall surface or outer wall surface of the mixing microchannel downstream of the converging area.

Figure 47:
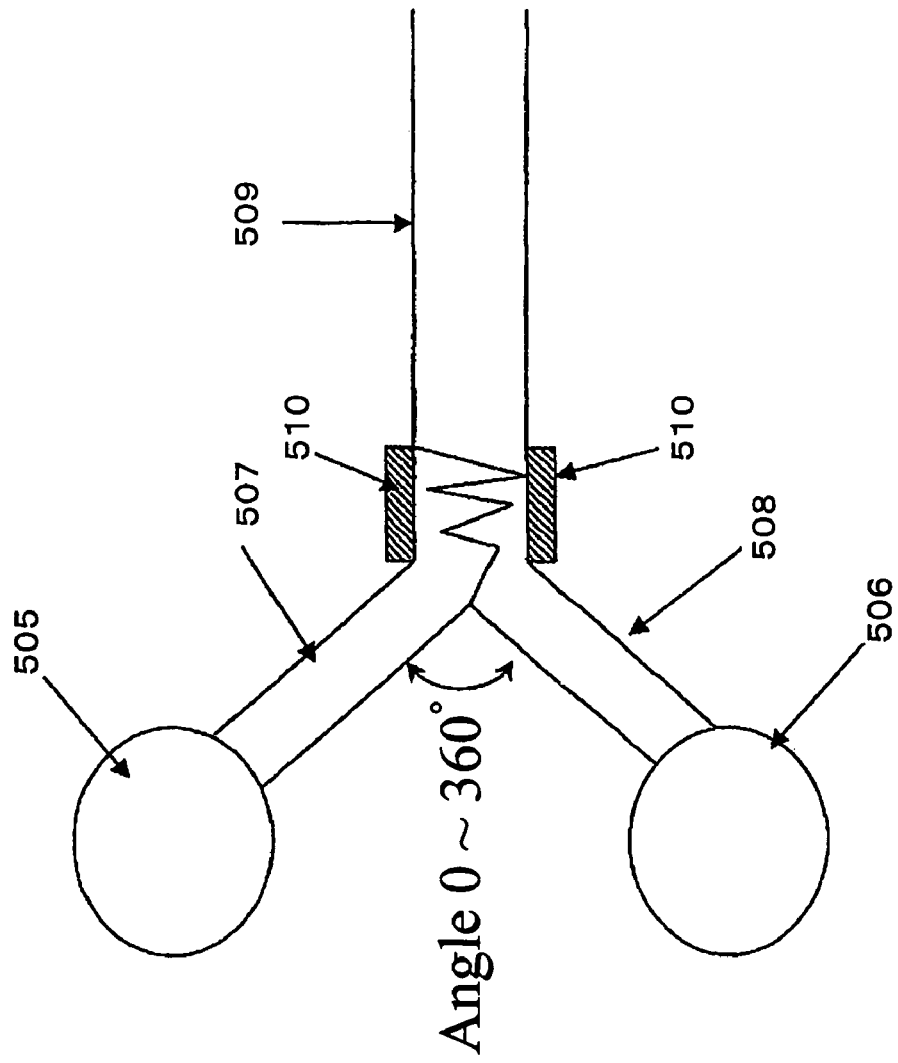
[FIG. 47] A schematic view showing an example of the liquid mixing apparatus of the embodiment 2-2.

FIGS. 47 to 50 show one embodiment having the first type of the mechanical mixing and/or stirring means. In the apparatus of FIG. 47, a vibrator 510 is mounted at the converging area. This apparatus includes a first reservoir 505 filled with a first liquid, a second reservoir 506 filled with a second liquid, a first channel 507 (liquid-introducing microchannel) leading from the first reservoir 505, a second channel 508 (liquid-introducing microchannel) leading from the second reservoir 506, a third channel 509 (mixing microchannel) which connects to the first channel 507 and the second channel 508, and a vibrator 510 mounted on the wall surface of the third channel 509. The vibrator 510 is connected to a power source and drive control means (not shown). The first liquid is introduced from the first reservoir 505 into the third channel 509 through the first channel 507, and the second liquid is introduced from the second reservoir 506 into the third channel 509 through the second channel 507.

Generally, when two liquids converge in a microchannel, a laminar flow is formed, and an interface in contact with the two liquids is stably maintained. In the case as such, it is known that mixing due to diffusion does not take place sufficiently, and these liquids flow while being separated into two layers. If, on this occasion, the flow in the mixing section is given suitable fluctuation by the vibrator 510 (or one or more vibrators) mounted on the wall surface of the channel or at a site very close to the outside of the wall surface, instability is caused to the interface formed by the two liquids, or the structure of the interface can be destroyed by a vortex (vorticity) generated by the aforementioned lifting surface, or cavitation generated within a negative pressure region. Thus, the two liquids can be mixed promptly and uniformly.

Figure 48:
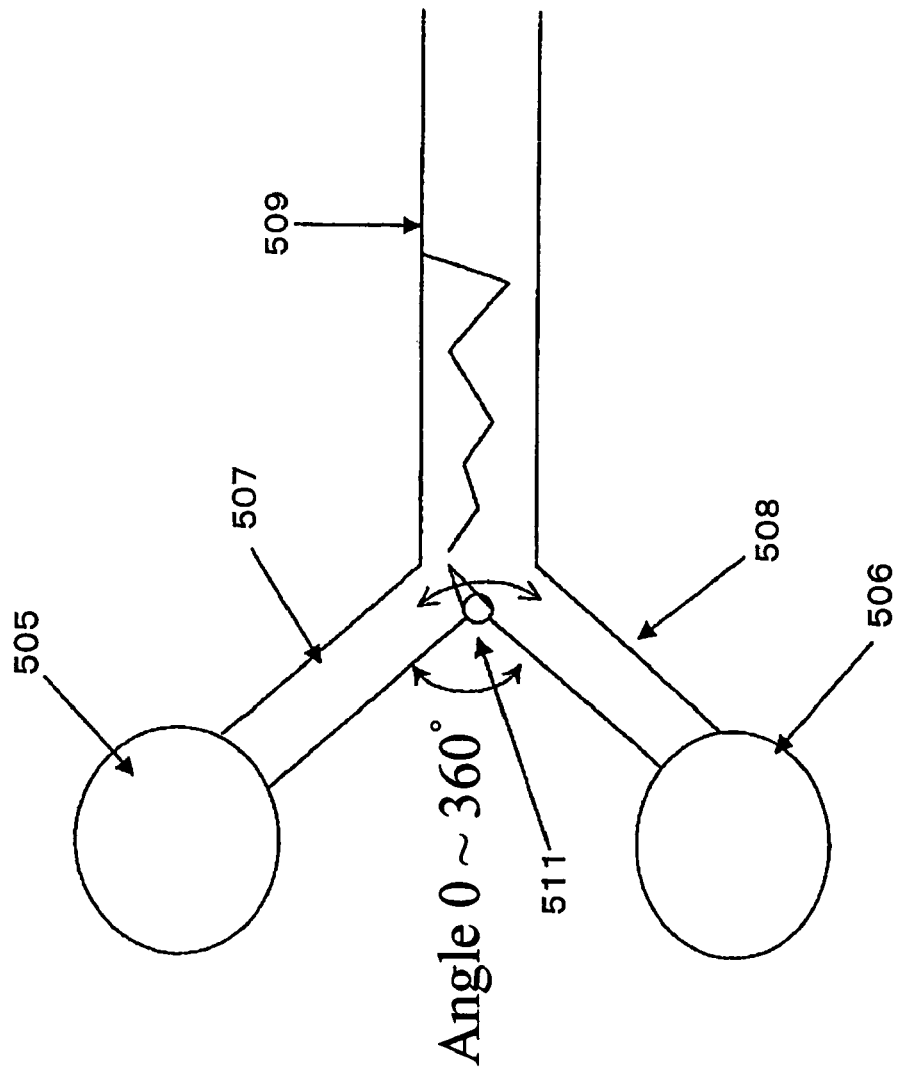
[FIG. 48] A schematic view showing another example of the liquid mixing apparatus of the present embodiment.

In the apparatus of another embodiment shown in FIG. 48, a lifting surface 511 is mounted at the site of convergence. This apparatus includes a first reservoir 505 filled with a first liquid, a second reservoir 506 filled with a second liquid, a first channel 507 leading from the first reservoir 505, a second channel 508 leading from the second reservoir 506, a third channel 509 which connects to the first channel 507 and the second channel 508, and the lifting surface 511 mounted on the converging area of the third channel 509. The lifting surface 511 is connected to a power source and drive control means (not shown). The first liquid is introduced from the first reservoir 505 into the third channel 509 through the first channel 507, and the second liquid is introduced from the second reservoir 506 into the third channel 509 through the second channel 507. If, on this occasion, varying components are given, as appropriate, by the lifting surface 511 mounted on the converging area with a frequency which induces instability of the interface, instability is caused to the interface formed by the two liquids, with the result that the area of the interface on which the two liquids contact can be increased, or the structure of the interface can be destroyed, or cavitation can be generated in the liquids. Thus, the two liquids can be mixed at a high speed and uniformly.

Figure 49:
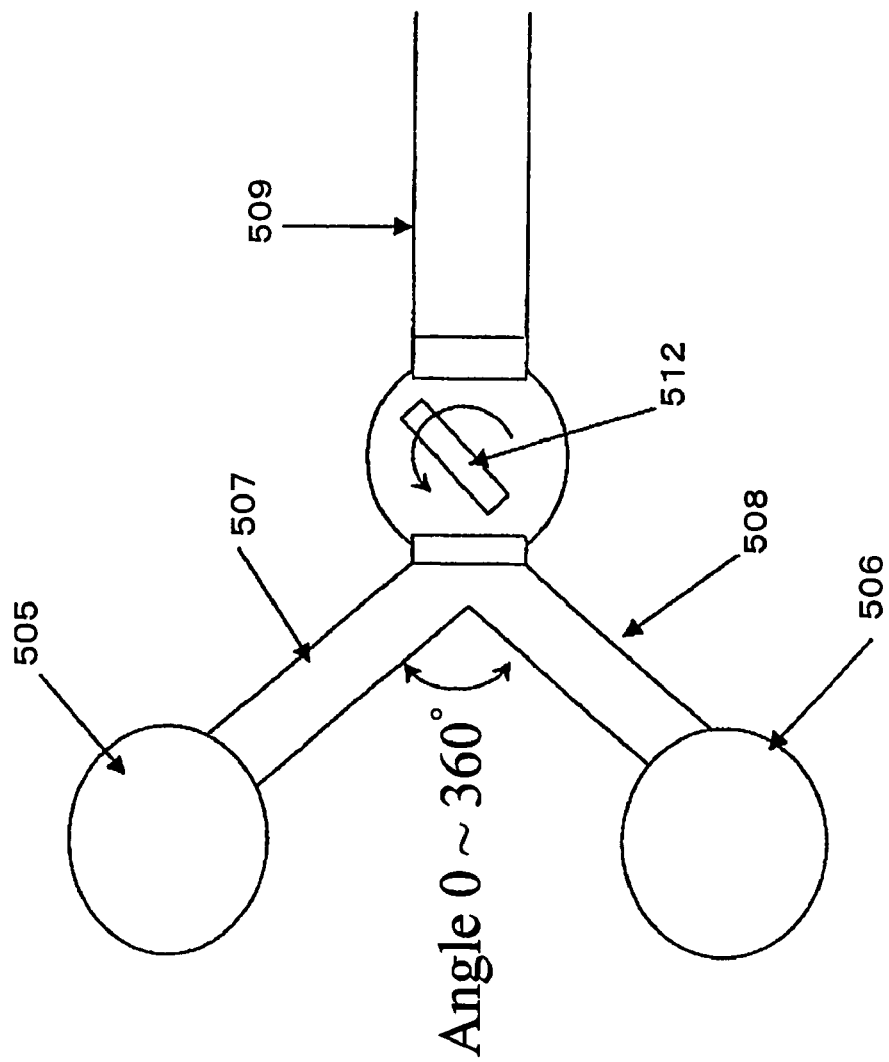
[FIG. 49] A schematic view showing still another example of the liquid mixing apparatus of the present embodiment.

In the apparatus of another embodiment shown in FIG. 49, a rotator 512 is mounted at the site of convergence. This apparatus includes a first reservoir 505 filled with a first liquid, a second reservoir 506 filled with a second liquid, a first channel 507 leading from the first reservoir 505, a second channel 508 leading from the second reservoir 506, a third channel 509 which connects to the first channel 507 and the second channel 508, and the rotator 512 mounted within the third channel 509. The rotator 512 is connected to a power source and drive control means (not shown). The first liquid is introduced from the first reservoir 505 into the third channel 509 through the first channel 507, and the second liquid is introduced from the second reservoir 506 into the third channel 509 through the second channel 507. If, on this occasion, varying components are given, as appropriate, by the rotator 512 (or a row of plural rotators) mounted within the channel 509, instability is caused to the interface formed by the two liquids. As a result, the area of the interface on which the two liquids contact can be increased, or the structure of the interface can be destroyed, or cavitation can be generated in the liquids. Thus, the two liquids can be mixed at a high speed and uniformly.

Figure 50:
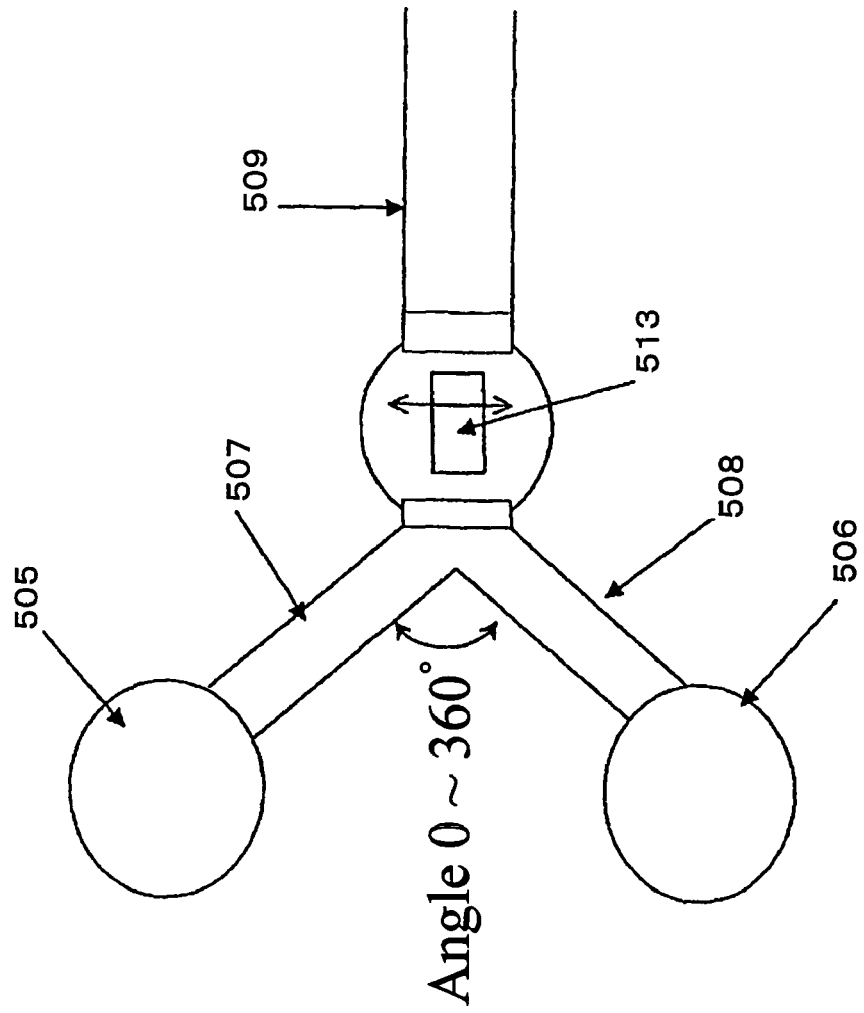
[FIG. 50] A schematic view showing yet another example of the liquid mixing apparatus of the present embodiment.

In the apparatus of still another embodiment shown in FIG. 50, an oscillator 513 is mounted at the site of convergence. This apparatus includes a first reservoir 505 filled with a first liquid, a second reservoir 506 filled with a second liquid, a first channel 507 leading from the first reservoir 505, a second channel 508 leading from the second reservoir 506, a third channel 509 which connects to the first channel 507 and the second channel 508, and the oscillator 513 mounted within the third channel 509. The oscillator 513 is connected to a power source and drive control means (not shown). The first liquid is introduced from the first reservoir 505 into the third channel 509 through the first channel 507, and the second liquid is introduced from the second reservoir 506 into the third channel 509 through the second channel 507. If, on this occasion, varying components are given, as appropriate, by the oscillator 513 (or a row of plural oscillators) mounted within the channel, instability is caused to the interface formed by the two liquids. As a result, the area of the interface on which the two liquids contact can be increased, or the structure of the interface can be destroyed, or cavitation can be generated in the liquids. Thus, the two liquids can be mixed at a high speed and uniformly.

According to each of the above embodiments, the first liquid and the second liquid can be mixed promptly at an arbitrary ratio on the third channel 509. If the first liquid and the second liquid of different concentrations are used, a concentration gradient region can be formed in the third channel 509 by continuously changing the mixing ratio.

FIGS. 51 to 53 show an embodiment of the apparatus having the second type of mechanical mixing and/or stirring means. This type of apparatus includes a plurality of liquid-introducing microchannels, a mixing microchannel where the plurality of liquid-introducing microchannels converge, and a vibrator for rendering instable the interface between the liquids in the mixing microchannel. This embodiment is characterized in that the vibrator (preferably, a plurality of the vibrators) is also provided on a downstream side of the mixing microchannel, and enhancement of mixing is carried out after introduction of the liquids into the mixing microchannel. Concretely, the liquids to be mixed are introduced such that the interface between the liquids is retained. Then, the introduction of the liquids is stopped, whereafter the interface between the liquids is rendered unstable by the above vibrator to mix the liquids. If a concentration gradient is to be formed, convergence of the liquids is completed such that the volume ratio of the two liquids is continuously changed in the flowing direction in the mixing microchannel. Then, the vibrator is driven, with the output and drive time of the vibrator being controlled.

The two liquids are introduced, with the ratio between the flow rates from the liquid-introducing microchannels being changed, whereby various geometrical patterns can be formed within the mixing microchannel (for example, flow rate control according to the embodiments 1-1 and 1-2 can be applied). FIGS. 51(a) to 51(d) show the forms of the two liquids created in the mixing microchannel. Liquids 635, 636 to be mixed are introduced from a plurality of liquid-introducing microchannels into a mixing microchannel 633 through a converging area. As explained in connection with the background art, mixing proceeds minimally in the microchannel. Thus, these liquids tend to be maintained in a state in which the interface is retained. When the liquids are introduced, with the ratio between the two liquids being changed, the liquids can be introduced such that the ratio between the two liquids continuously varies in the lengthwise direction of the channel (FIG. 51(a) and FIG. 51(b)). Alternatively, the liquids can be introduced such that the two liquids are alternately introduced and their ratio is changed in the lengthwise direction of the channel (FIG. 51(c)). Furthermore, the liquids can be introduced simply such that the channel is divided in two in the lengthwise direction by the two liquids (FIG. 51(d)). To form a continuous concentration gradient, it is desirable that the interfaces be stably retained such that the volume ratio of the liquids continuously changes in the lengthwise direction of the channel.

Figures 51A, 51B, 51C, 51D:
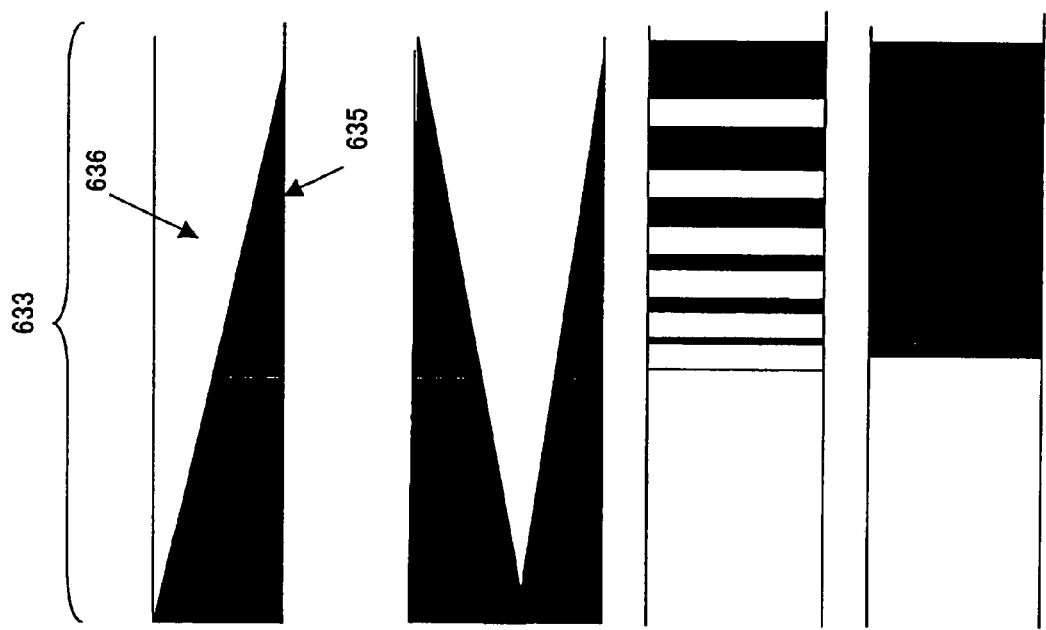
[FIGS. 51(a) to 51(d)] Schematic views showing the manner of introduction of liquids in the liquid mixing apparatus of the present embodiment.
Figures 52A, 52B:
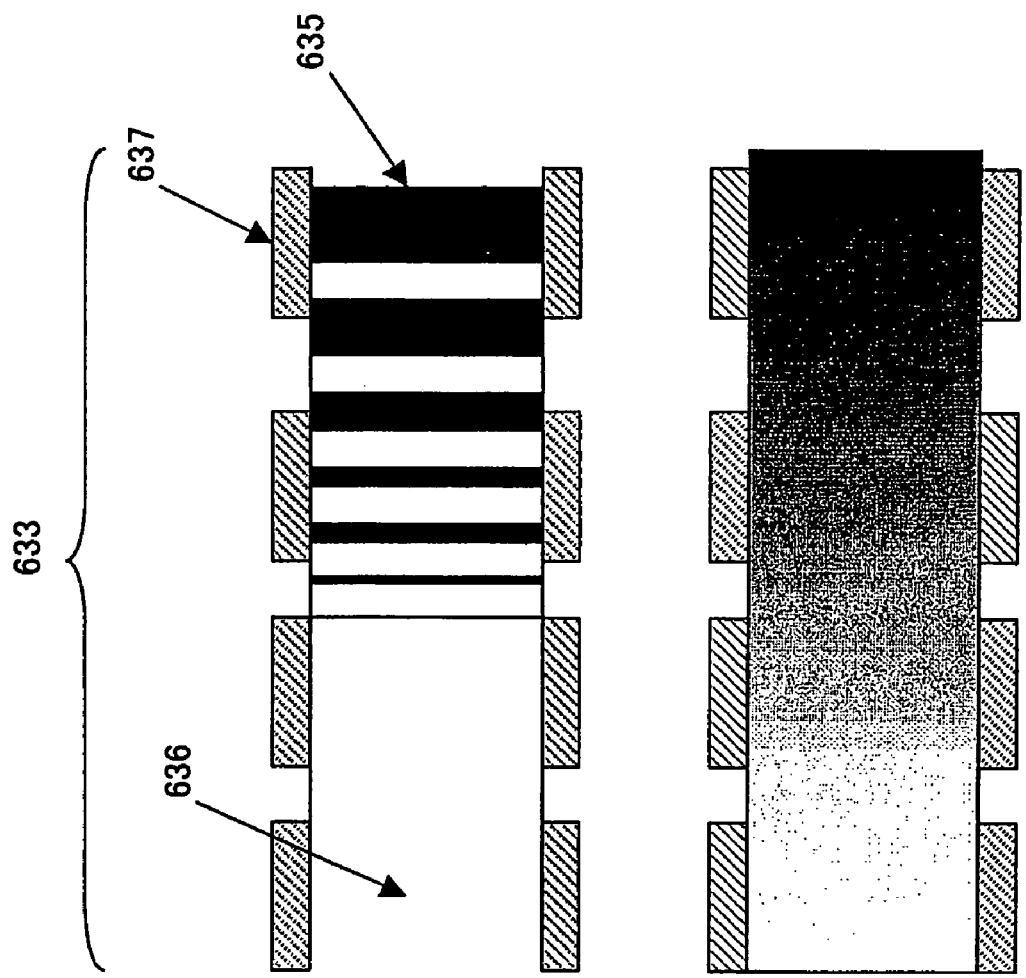
[FIGS. 52(a) and 52(b)] Schematic views showing other examples of the liquid mixing apparatus of the present embodiment.

FIGS. 52(a) and 52(b) show a process in which two liquids introduced into a mixing microchannel 633 in accordance with the form of FIGS. 51(a) to 51(d) are mixed with the use of a plurality of vibrators mounted on the wall surface of the mixing microchannel 633 to form a concentration gradient. The plurality of vibrators are mounted along the wall surface of the mixing microchannel 633. As described above, liquids 635, 636 are introduced into the mixing microchannel, with the interface being retained (FIGS. 51(c), 52(a)). Then, the vibrators 637 are driven to impart varying components, as appropriate, with a frequency inducing the instability of the interface between the liquids 635 and 636, whereby the interface between the liquids can be rendered unstable. Upon driving of the vibrators, the area of the interface between the liquids is increased, or the interface between the liquids is destroyed, or cavitation is generated within the liquids, whereby the liquids can be mixed promptly and uniformly. The two liquids introduced so as to maintain an appropriate volume ratio are mixed with each other in the lengthwise direction of the channel by driving of the vibrators. As a result, a concentration gradient uniform and continuous in the flowing direction of the channel can be formed (FIG. 52(b)).

FIGS. 53(a) and 53(b) show a manner in which two liquids introduced into the mixing microchannel of FIG. 51 are mixed. First, the liquids 635, 636 are introduced into the mixing microchannel, with the interface being retained (FIG. 51(a)). Then, the vibrator 637 mounted at the end of the mixing microchannel is driven to impart varying components, as appropriate, with a frequency inducing the instability of the interface, whereby the interface between the liquids is rendered unstable. As a result, the area of the interface between the liquids is increased, or the interface between the liquids is destroyed, or cavitation is generated within the liquids, whereby the liquids can be mixed promptly and uniformly (FIG. 53(b)). Concretely, the liquids 635, 636 are introduced, with their volume ratio being changed and such that the interface between the liquids is stably retained, in order that after mixing, the mixing ratio of the two liquids is continuously changed in the flowing direction within the channel. Also, the vibrator is driven, with its output and drive time being controlled, whereby a concentration gradient, as shown in FIG. 53(b), can be formed.

As the method and apparatus for introducing the liquids to be mixed, any publicly known methods and apparatuses can be used. Their examples are a method of controlling the flow rate from a pump to introduce two liquids at an arbitrary ratio, a method of controlling the opening and closing time of a valve to change the ratio of liquids to be mixed, a method of controlling an applied potential in an electroosmotic flow drive mode to introduce liquids, and the method of Seki et al. (see M. Yamada and M. Seki, Proc. IEEE the 16th International Symposium on Micro Electro Mechanical Systems (MEMS), 2003, pp. 347-350, 2003). The method and apparatus for introducing liquids to be mixed are desirably those which can introduce the liquids such that the volume ratio of the liquids is changed, and the interface between the liquids is stably retained so that after mixing of the liquids, the mixing ratio of the liquids becomes continuous in the length direction of the channel.

The vibrator used in the present embodiment, and the method for driving it can be any publicly known means and methods. Their examples are methods using a piezoelectric device, an electrostatic actuator, a shape memory effect moving element, an electromagnetic actuator, and a polymeric electrodynamic material. The liquids used in the present embodiment are of two types, but these are not restrictive, and they may be of two or more types. The number of the liquid-introducing microchannels of the present embodiment is two, but this is not limitative, and the number may be two or larger.

The position of mounting of the vibrator may be any position which makes it possible to vibrate the interface of the liquids in the mixing microchannel. For example, the vibrators can be mounted on the wall surface of the mixing microchannel (FIGS. 52(a) and 52(b)), or the vibrator can be mounted at the end of the mixing microchannel (FIGS. 53(a) and 53(b)). Alternatively, the vibrators can be mounted on both sides of the wall surface and both ends of the mixing microchannel. Furthermore, the vibrator may be provided at a position remote from the channel, if the vibration of vibrator can be transmitted to the objective liquids in the channel in such a way that ultrasonic wave vibrator can vibrate another body through a kind of fluid. Moreover, the number of the vibrators mounted is not limited to one, but may be plural.

EMBODIMENT 2-3 (FIGS. 54 TO 58)

The mixing enhancing means of the apparatus of the present embodiment is a number of nano- to micron-structures allocated in or near the area where the liquids converge in the mixing microchannel.

The basic configuration of the apparatus of the present embodiment comprises two or more liquid-introducing microchannels for introducing liquids, and a mixing microchannel formed by the connection of these liquid-introducing microchannels. Many nano- to micron-structures are arranged in the mixing microchannel. Liquids that are introduced from the liquid-introducing microchannels and converged are brought into contact with the group of nano-to micron-structures in the mixing microchannel, and their mixing is enhanced thereby. If a microchip electrophoretic apparatus is taken as an example, the liquid-introducing microchannels are microchannels for introducing buffer solutions and/or denaturant-containing buffer solutions, and the mixing microchannel is a channel as a concentration gradient forming region. An embodiment of the microchip electrophoretic apparatus will be described below.

Figure 54:
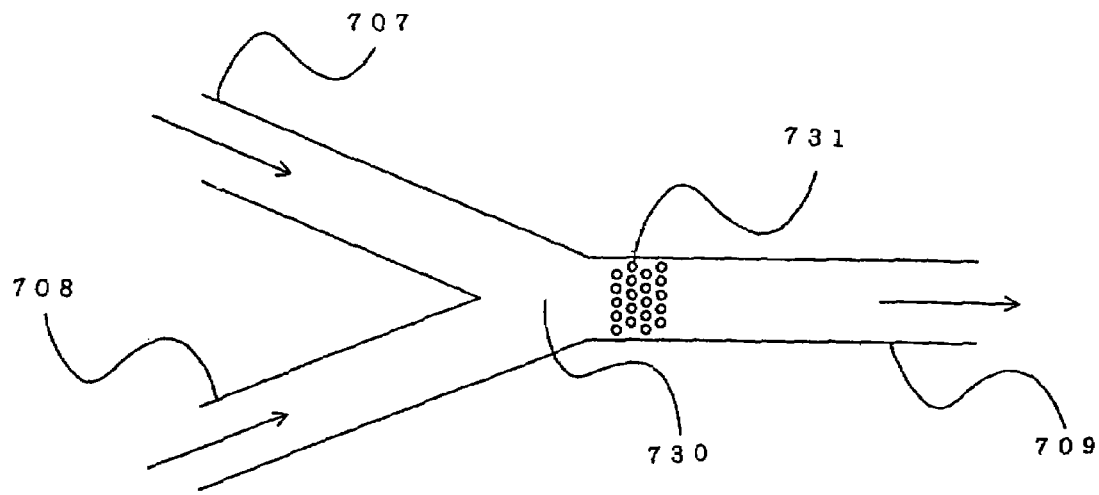
[FIG. 54] A schematic configurational drawing showing the liquid mixing apparatus of the present embodiment 2-3.
Figure 55:
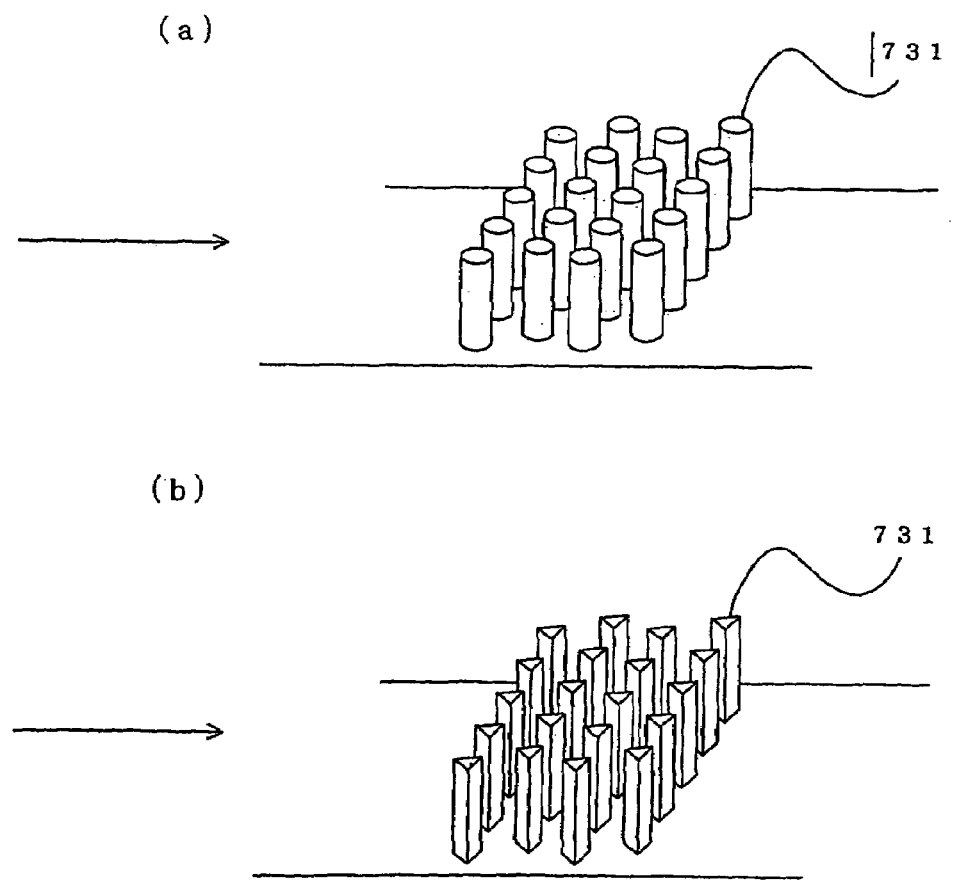
[FIGS. 55(a) and 55(b)] Views showing examples of columnar nano- to micron-structures of the apparatus of FIG. 54.

The apparatus of FIG. 54 has nano- to micron-structures provided as a mixing enhancing means in a gradient region channel 709 (mixing microchannel). As shown in this drawing, a first channel 707 (liquid-introducing microchannel) and a second channel 708 (liquid-introducing microchannel) for introducing liquids are connected at a common mixing section or converging portion 730, and connected to a microchannel 709 in a denaturing gradient forming portion 2. Nano- to micron-structures 731 smaller than the channel width of the microchannel 709 are provided downstream of and in the vicinity of the mixing section 730. These nano- to micron-structures 731 are provided such that tiny structures are allocated at equal spacing in a geometrical arrangement and, preferably, the structures of the respective rows are arranged at a staggered position such as to hinder the flow of the liquids. The liquids introduced from the first channel 707 and the second channel 708 converge together at the mixing section 730 and then flow in layers. However, when they pass through the nano- to micron-structures 731, their interface undergoes a diffusive action due to a vortex. Thus, these two liquids are satisfactorily mixed, and then flow downward (in the direction of an arrow) in the channel 709.

FIGS. 55(a) and 55(b) show an embodiment having an allocation of pillar structures as the nano- to micron-structures 731. These columnar structures can be constituted as having an axis parallel to the interface between the liquids to be mixed and perpendicular to the flowing direction. They may be cylinders as in FIG. 55(a) or triangular prisms as in FIG. 55(b). The shape of the nano- to micron-structures 731 is not limited, and any shape can be applied, if it can cause the separation of the flow from the side wall during their passage, and enables prompt mixing by the diffusive effect of the separated vortex. If a nucleic acid sample flows from the upstream side, its flow is entangled with the columnar structures, so that separation of nucleic acids based on molecular weight can be performed.

Figure 56:
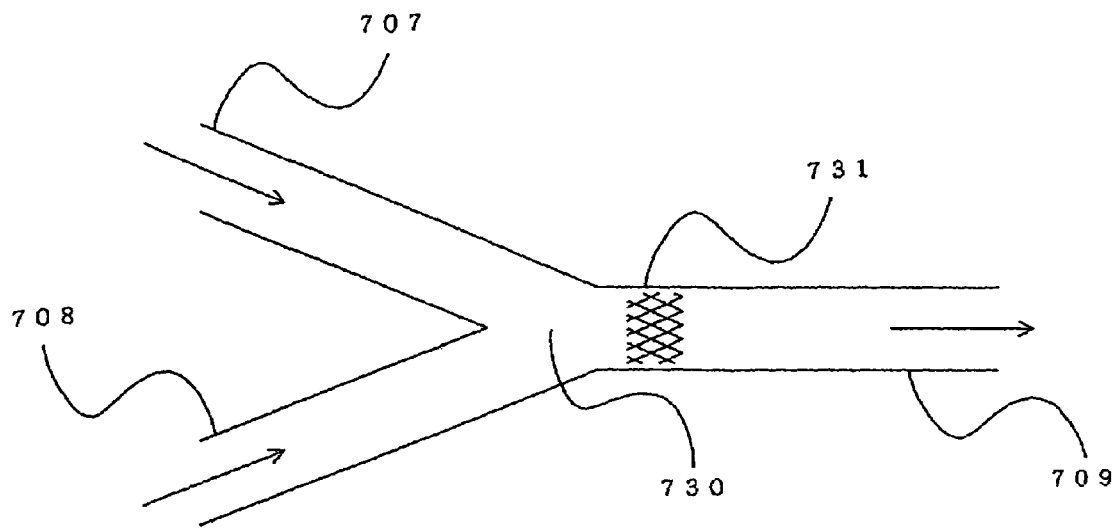
[FIG. 56] A schematic configurational drawing showing the present embodiment having groove-shaped nano- to micron-structures.

FIG. 56 shows an embodiment in which, as nano- to micron-structures 731, grooves or cavities arranged in a regular geometrical form are provided in the wall surface of the microchannel 709 downstream a mixing section or converging portion 730. The liquids which have converged at the mixing section 730, form the secondary flow in the width direction of the channel along each groove or cavity when passing through the nano- to micron-structures 731. Furthermore, a peeling vortex occurs from the edges of the grooves, producing a diffusive action, which permits prompt mixing.

Figure 57:
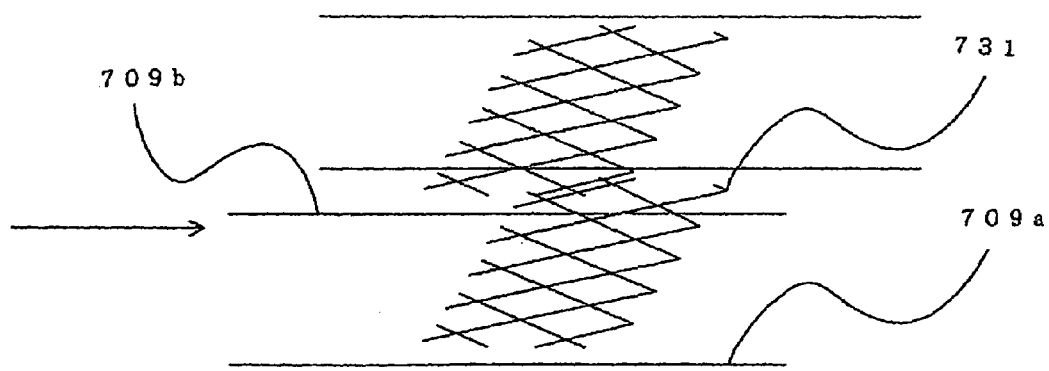
[FIG. 57] A schematic view showing an example of the groove-shaped nano- to micron-structures.
Figure 58:
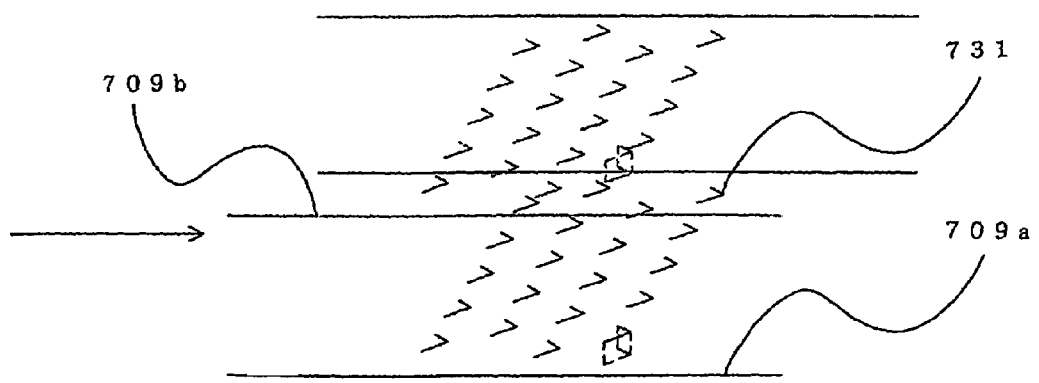
[FIG. 58] A schematic view showing another example of the groove-shaped nano- to micron-structures. (Embodiment A)

The nano- to micron-structures 731 may be a mesh-shaped groove which is not parallel to the flowing direction as in FIG. 57, or many un-connected groove or cavities as in FIG. 58. As shown in these drawings, the nano- to micron-structures 731 have the above-mentioned groove arrangement on each of a lower surface 709a and an upper surface 709b of the microchannel 709. Such nano- to micron-structures 731 can be produced using a publicly known microfabrication technology, such as a photolithography technology.

Method for Producing Liquid Mixing Apparatus

The liquid mixing apparatus of the present invention is produced by a customary method for microchip production which is well known in the technical field concerned.

The liquid mixing apparatus of the present invention is normally composed of two substrates, but can also be composed of a single substrate. If a microchip is to be constituted by two substrates, channels with a width and a depth of the order of 10 to 100 µm are formed in one substrate by use of a microfabrication technology, such as a photolithographic technique, and holes for reservoirs are created in another substrate by use of machining such as ultrasonic machining. When these two substrates are laminated by a bonding technique such as thermal bonding, a microchip having the channels and reservoirs at predetermined positions is obtained.

The dimensions (width and depth) of microchannels are determined based on specifications required and achievable processing accuracy. If they are larger than an analyte (for example, a double-stranded nucleic acid), a permissible size is up to 1 mm. The dimension of the "microchannel" applicable to the present invention is generally 1 nm to 1,000 µm, preferably 1 µm to 500 µm more preferably 10 µm to 100 µm, in the light of the current processing accuracy.

As the processing of the substrate, not only wet etching, but dry etching or sandblasting may be used in accordance with the pattern width and depth. Needless to say, a mask is not limited to a photoresist mask, and a metal mask of Ni or Cr may be used. For example, the microchannel can be formed by patterning the resist mask by a photolithographic technique, and then performing wet etching with a 10% dilution of HF. Portions different in depth in the channel can be formed by performing a patterning step and an etching step a plurality of times with the use of different masks.

The material for the substrate can be selected from glass, quartz, Pyrex (registered trademark), plastic, silicon, resin, and metal according to uses and the manufacturing method. For example, the lamination of glass substrates can be performed by dripping a HF solution diluted to 1% onto surfaces of glass to be bonded, superposing the two substrates in alignment, and allowing them to stand for 60 hours at a pressure of 70 kPa. As bonding, thermal bonding, or direct bonding using irradiation with a beam within a vacuum apparatus can be used.

In the case of plastic, injection molding, mold transfer, nanoimprinting, or nanostamping can be used for the preparation of a microchip. This material is low in cost, and is suitable for mass production and disposable products.

Uses of Liquid Mixing Apparatus

The liquid mixing apparatus of the present invention can be used in any apparatus requiring the mixing of a small amount of liquid. For example, the present invention can be applied for Micro-Total Analysis Systems (µTAS) for chemical analysis or biochemical analysis, such as analytical microchips, and can realize high speed mixing of minute amounts of liquids in these apparatuses. When applied to microreactors for chemical synthesis, the present invention enables applications to fine chemicals hitherto unachievable by an in-beaker reaction, such as suppression of an intermediate reaction by addition of an instantaneous heating and/or cooling mechanism.

An example of use as a microreactor is an apparatus which obtains only a mono-substituted product in a high yield by Friedel-Crafts reaction in mixing an aromatic compound and carbon cations with high reaction activity. With a conventional in-beaker reaction, when trimethoxybenzene and iminium cations are mixed, the substitution rate of trimethoxybenzene is 80% or less, the yield of the desired mono-substituted product is 40% or less, and the yield of a di-substituted product as a by-product is 30% or more. According to a microreactor to which the present invention is applied, on the other hand, highly efficient and prompt mixing of the reactants can be achieved. Thus, the trimethoxybenzene substitution rate is 90% or more, the yield of the mono-substituted product is 90% or more, and the yield of the di-substituted product is 5% or less, meaning that only the desirable reaction product can be selectively produced. As a result, the amounts of the starting materials and reaction reagents needed to obtained the same yield are decreased.

A microchip electrophoretic apparatus can be named as other use to which the present invention can be put. Electrophoresis on a microchip has various advantages, such that a sample and a reagent used may be in small amounts; the reaction time and the analysis time are shortened; the reaction and process handling times are shortened to increase the reaction efficiency and product yield; a waste liquid is in a small amount; and the invention is suitable for high throughput analysis. A microchip electrophoretic apparatus useful for DGGE can be provided, particularly, by using the liquid mixing apparatus and method of the present invention for mixing of buffer solutions for forming a denaturing gradient.

[Apparatus and Method for Separating Analyte]

An apparatus and method for separating an analyte by use of DGGE will be described.

Embodiment A Concerning DGGE

In embodiment A, a denaturing gradient is formed so as to be continuously changed in the direction of electrophoresis.

The microchip electrophoretic apparatus of the present embodiment comprises at least two liquid-introducing microchannels for introducing buffer solutions containing a denaturant at different concentrations; and a mixing microchannel to which the at least two liquid-introducing microchannels connect, and a concentration gradient region of the denaturant is formed by the convergence, in the mixing microchannel, of the buffer solutions introduced at varying ratios from the liquid-introducing microchannels.

A preferred embodiment has a mixing enhancing means for enhancing the mixing of the buffer solutions converging in the mixing microchannel. As this mixing enhancing means, each of the aforementioned embodiments 1-1 to 2-3, and any combination of these embodiments can be applied.

Microchip Electrophoretic Apparatus of the Embodiment A

FIGS. 59a, 59b, 59c and 59d schematically show the fundamental structure of a microchip electrophoretic apparatus. The basic concept of the present embodiment will be described by reference to these drawings.

Figure 59A:
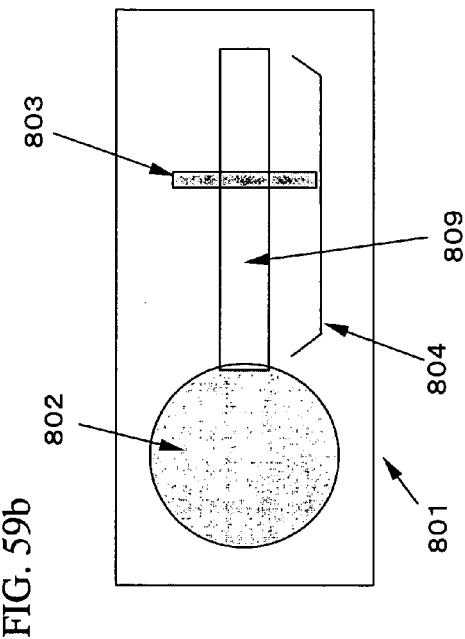
[FIG. 59a] A conceptual view schematically showing an example of the basic configuration of a microchip electrophoretic apparatus of the embodiment A.

FIG. 59a includes a denaturing gradient forming portion 802 and an electrophoretic portion 804 on a microchip 801. The denaturing gradient forming portion 802 is connected to a gradient region channel 809 of the electrophoretic portion 804, and an electrophoretic buffer solution containing a denaturant is supplied from the denaturing gradient forming portion 802 to the gradient region channel 809. The electrophoretic portion 804 includes the gradient region channel 809, and a sample introduction portion 803 connected to a downstream side of the gradient region channel 809. In the general manner, buffer solutions containing the denaturant at different concentrations are mixed at varying ratios in the gradient forming portion 802. A buffer zone having the so obtained denaturing gradient is sequentially introduced from the upstream side of the gradient region channel 809 to the electrophoretic portion 804 located on the downstream side of the gradient region channel 809.

The sample introduction portion 803 is provided in the electrophoretic portion 804. A nucleic acid sample such as purified DNA (hereinafter referred to as a DNA sample) is introduced from the sample introduction portion 803 into the gradient region channel 809 of the electrophoretic portion 804. When the DNA sample is introduced into the denaturing gradient region within the channel 809, double-stranded DNA's in the DNA sample are separated based on a difference in base sequence.

Figure 59B:
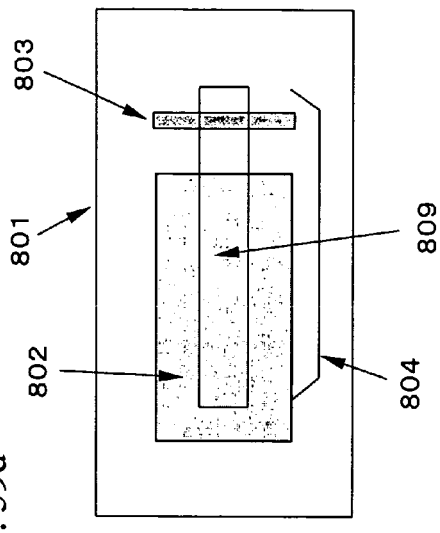
[FIG. 59b] A conceptual view showing another example of the basic configuration of the embodiment A.

The microchip electrophoretic apparatus of FIG. 59*b* includes a denaturing gradient forming portion 802, a sample introduction portion 803, and an electrophoretic portion 804 on a microchip 801. In the electrophoretic portion 804, the sample introduction portion 803 is connected to a gradient region channel 809 while crossing the gradient region channel 809. Since the sample introduction portion 803 is connected to the gradient region channel 809 in this form, a DNA sample can be introduced from outside the region of the electrophoretic portion 804 (i.e., from a sample introduction channel separate from the gradient region channel 809), facilitating the procedure for sample introduction.

Figure 59C:
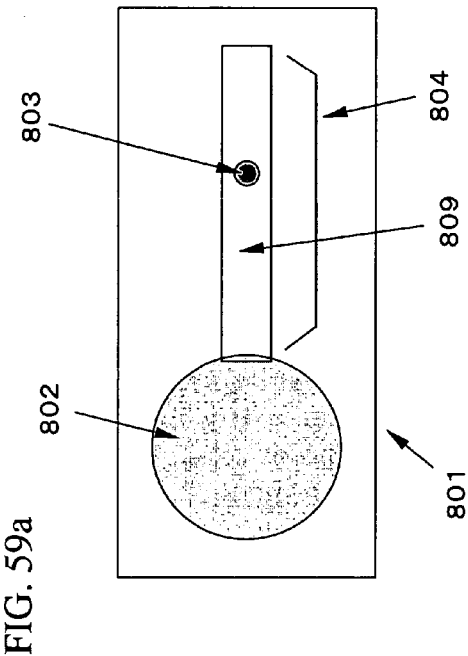
[FIG. 59c] A conceptual view showing still another example of the basic configuration of the embodiment A.
Figure 59D:
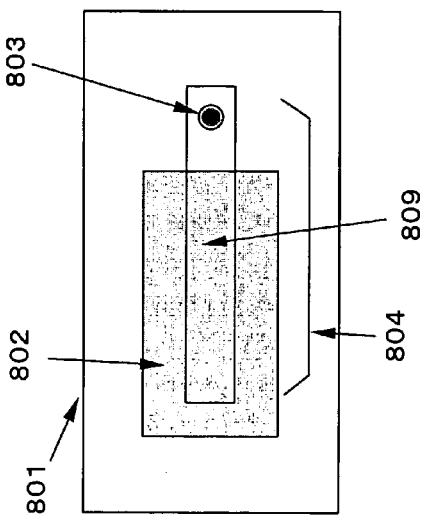
[FIG. 59d] A conceptual view showing yet another example of the basic configuration of the embodiment A.

The microchip electrophoretic apparatuses of FIG. 59*c* and FIG. 59*d* each include a denaturing gradient forming portion 802, a sample introduction portion 803, and an electrophoretic portion 804 on a microchip 801. The denaturing gradient forming portion 802 includes the electrophoretic portion 804, and thus the denaturing gradient forming portion 802 concurrently serves as the electrophoretic portion 804. Since the denaturing gradient forming portion 802 concurrently serves as the electrophoretic portion 804, the microchip can be downsized. Moreover, a denaturing gradient region formed by the denaturing gradient 802 need not be moved to the electrophoretic portion 804.

Next, each constituent portion of the above-described embodiment will be described.

For simplification of explanation, a description will be offered of an embodiment using a denaturant-containing buffer solution and a denaturant-free buffer solution (may herein be referred to simply as a buffer) as buffer solutions containing a denaturant at different concentrations.

In the present embodiment, it does not matter whether one of the buffer solutions contains the denaturant, or is free from the denaturant. What is important is a relative denaturant concentration difference between the buffer solutions. For example, the same effect is obtained, if "the denaturant-free buffer solution" contains a relatively low concentration of the denaturant, and "the denaturant-containing buffer solution" contains a significantly higher concentration of the denaturant than "the denaturant-free buffer solution". Such an embodiment is also within the scope of the present invention.

Figure 60:
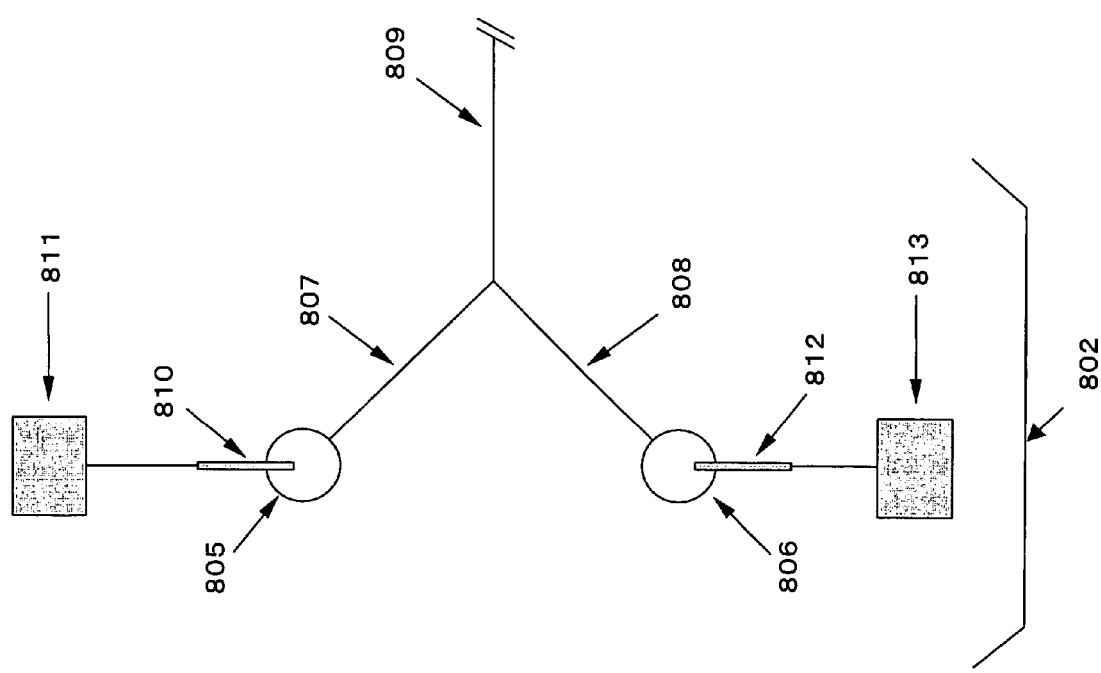
[FIG. 60] A schematic view showing a configuration example of a denaturing gradient forming portion for the embodiment A.

FIG. 60 shows the concrete configuration of the denaturing gradient forming portion 802 in the apparatuses of FIG. 59*a* to 59*d*. The denaturing gradient forming portion 802 of FIG. 60 includes a first reservoir 805 filled with a buffer solution containing a denaturant at a constant concentration, a second reservoir 806 filled with a buffer solution containing no denaturant, a first channel 807 (liquid-introducing microchannel) leading from the first reservoir 805, a second channel 808 (liquid-introducing microchannel) leading from the second reservoir 806, and a gradient region channel 809 (mixing microchannel) formed by the convergence of the first channel 807 and the second channel 808. The first reservoir 805 includes a first electrode 810 connected to a first power source 811. The second reservoir 806 includes a second electrode 812 connected to a second power source 813.

In the denaturing gradient forming portion 802, a potential is applied to the interior of each reservoir via the fist power source 811 and the first electrode 810 and the second power source 813 and the second electrode 812, whereby electroosmotic flows are generated in the channels. By virtue of the electroosmotic flows, the denaturant-containing buffer solution is introduced from the first reservoir 805 into the gradient region channel 809 through the first channel 807 and, similarly, the buffer solution is introduced from the second reservoir 806 into the channel 809 through the second channel 808.

By controlling the potential to each of the first power source 811 and the second power source 813, the ratio of the buffer solutions inflowing through the channels 807 and the channel 808 can be changed. In this manner, the denaturant-containing buffer solution and the buffer solution can be mixed at an arbitrary ratio at an upstream point of the gradient region channel 809 (the convergence point of the buffer solutions from the channel 807 and the channel 808). To form a continuous denaturing gradient region in the channel 809, the potentials to the first power source 811 and the second power source 813 are continuously changed or, preferably, the ratio between the flow rates of the convergent two buffer solutions is changed at a constant rate, whereby the mixing ratio between the denaturant-containing buffer solution and the buffer solution is continuously changed.

Figure 61:
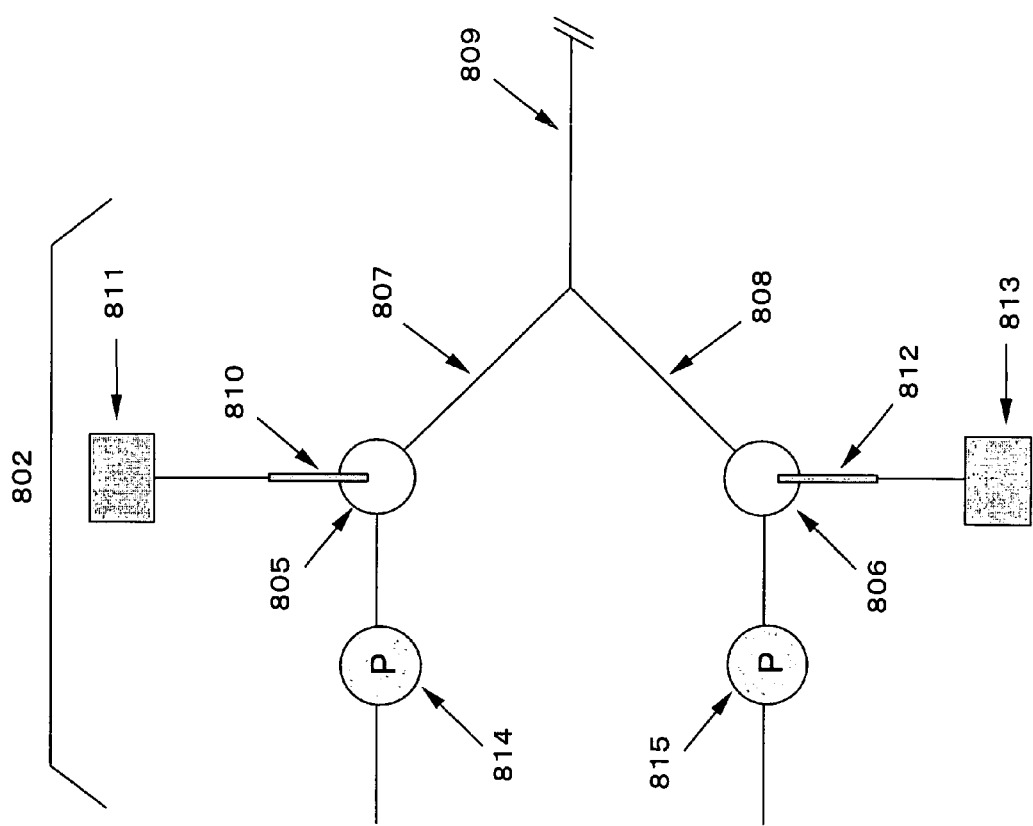
[FIG. 61] A schematic view showing another example of the denaturing gradient forming portion.

FIG. 61 shows another configuration of the denaturing gradient forming portion 802. The denaturing gradient forming portion 802 of FIG. 61 includes a first reservoir 805 filled with a denaturant-containing buffer solution, a second reservoir 806 filled with a buffer solution, a first channel 807 leading from the first reservoir 805, a second channel 808 leading from the second reservoir 806, and a gradient region channel 809 formed by the convergence of the first channel 807 and the second channel 808. The first reservoir 805 includes a first electrode 810 connected to a first power source 811, and a first pump 814 is connected to the upstream side of the first reservoir 805. The second reservoir 806 includes a second electrode 812 connected to a second power source 813, and a second pump 815 is connected to the upstream side of the second reservoir 806.

The denaturing gradient forming portion 802 of FIG. 61 has a structure in which the first pump 814 and the second pump 815 are added, respectively, to the first reservoir 805 and the second reservoir 806 shown in FIG. 60. This embodiment is advantageous in that liquid feeding via the first pump 814 and the second pump 815 can assist in the liquid feeding by electroosmotic flows and, even if the denaturant-containing buffer solution and the buffer solution have high viscosities, appropriate liquid introduction into the gradient region channel 809 can be achieved, and the formation of a denaturing gradient can be ensured.

Even in the denaturing gradient forming portion 802 of FIG. 61, the flow rates from the first pump 814 and the second pump 815 are controlled in addition to control of the potentials to the fist power source 811 and the second power source 813. By virtue of these controls, the denaturant-containing buffer solution is introduced from the first reservoir 805 into the channel 809 through the first channel 807 and, similarly, the buffer solution is introduced from the second reservoir 806 into the channel 809 through the second channel 808. In this manner, the denaturant-containing buffer solution and the buffer solution can be mixed at an arbitrary ratio at an upstream point of the gradient region channel 809 (the convergence point of the buffer solutions from the channel 807 and the channel 808). To form a continuous denaturing gradient region in the channel 809, the potentials to the first power source 811 and the second power source 813 are continuously changed or, preferably, the ratio between the flow rates of the convergent two buffer solutions is changed at a constant speed, whereby the mixing ratio between the denaturant-containing buffer solution and the buffer solution is continuously changed. The first pump 814 and the second pump 815 may be connected to the first reservoir and the second reservoir, respectively, as shown in FIG. 61, or may be provided on the first channel 807 and the second channel 808, respectively.

Figure 62:
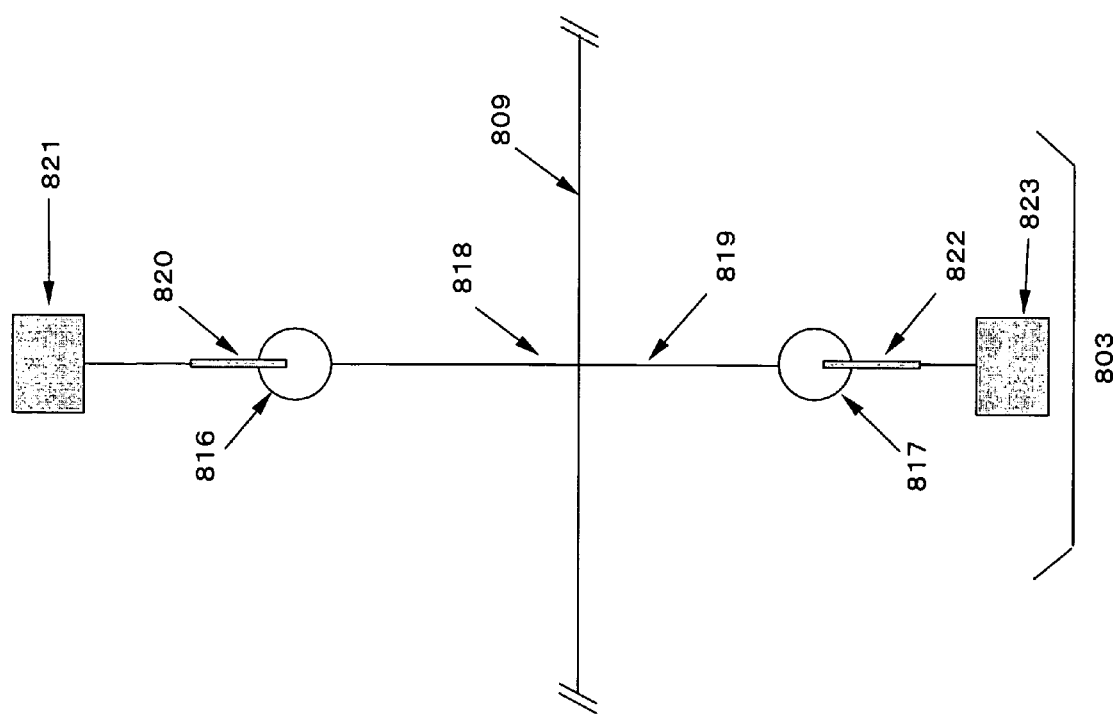
[FIG. 62] A schematic view showing an example of a sample introduction portion for the embodiment A.

FIG. 62 shows the concrete configuration of the sample introduction portion 803 in the apparatuses of FIGS. 59b and 59d. The sample introduction portion 803 shown in FIG. 62 includes a third reservoir 816 filled with a DNA sample, a fourth reservoir 817 for a DNA sample waste liquid to be discharged, a fourth channel 818 leading from the third reservoir 816, and a fifth channel 819 leading from the fourth reservoir 817. The fourth channel 818 and the fifth channel 819 are connected together while intersecting a channel 809, whereby the fourth channel 818 and the fifth channel 819 are brought into communication. A third electrode 820 is connected to the third reservoir 816, and a third power source 821 is connected to the third electrode 820. A fourth electrode 822 is connected to the fourth reservoir 817, and a fourth power source 823 is connected to the fourth electrode 822.

In the sample introduction portion 803, potentials to the third power source 821 and the fourth power source 823 are controlled to supply the DNA sample. The DNA sample is delivered from the third reservoir 816 toward the fourth reservoir 817 through the channels 818, 819 by an electroosmotic flow and an electrophoretic force generated by control of the potentials to the third power source 821 and the fourth power source 823. During this process, the DNA sample is introduced to the intersection of the fourth channel 818 and the fifth channel 819 on the channel 809. Then, a voltage is applied between both ends of the channel 809. Upon application of the voltage into the channel 809, only a DNA sample fragment introduced to the intersection of the channels 818 and 819 is introduced into the channel 809. Since a concentration gradient of a DNA denaturant is present in the channel 809, the DNA sample introduced there can be separated electrophoretically within the concentration gradient.

Figure 63:
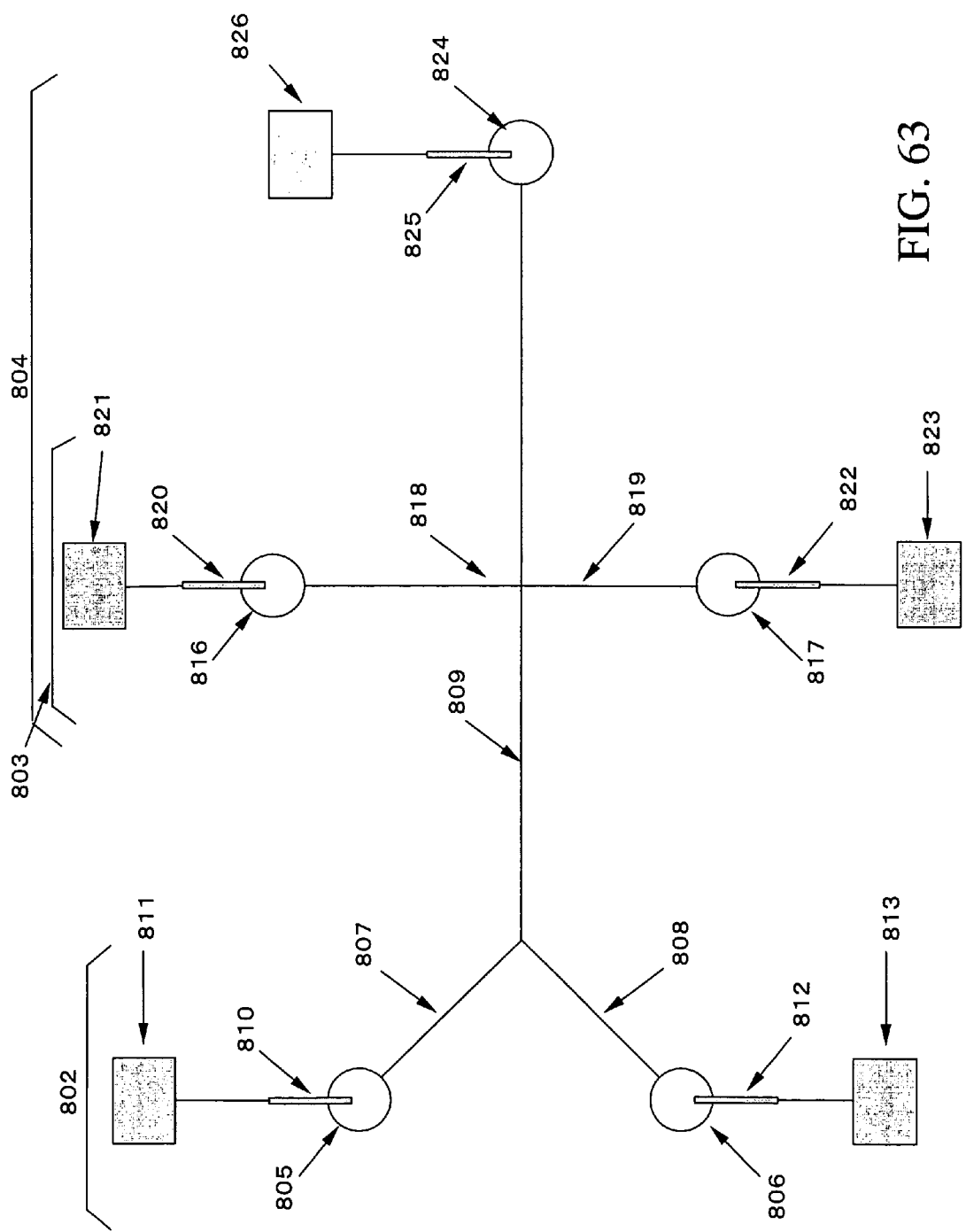
[FIG. 63] A schematic view showing an example of the embodiment A.

FIG. 63 shows an embodiment of the apparatus of FIG. 59b. In an electrophoretic portion 804, a fifth reservoir 824 for a waste liquid is provided downstream of the channel 809. The fifth reservoir 824 includes a fifth electrode 825 connected to a fifth power source 826. A denaturing gradient forming portion 802 as illustrated with reference to FIG. 60 is included upstream of the channel 809. On the upstream side of the channel 809, a sample introduction portion 803 as illustrated with reference to FIG. 62 is included. The first to fifth power sources may be shared, as appropriate.

In the embodiment of FIG. 63, a buffer flow having a denaturing gradient formed by the denaturing gradient forming portion 802 is introduced into the channel 809, whereby a flow (movement) of a denaturing gradient region is produced in the channel 809. A DNA sample is introduced from the sample introduction portion 803 onto the denaturing gradient region. The denaturing gradient region introduced into the channel 809 from its upstream side is moved downstream by an electroosmotic flow generated in the denaturing gradient forming portion 802 and the channel 809. On the other hand, the DNA sample introduced into the channel 809 is moved by the sum of the amount of downstream movement by the electroosmotic flow generated in the denaturing gradient forming portion 802 and the channel 809, and the amount of upstream movement by electrophoresis generated by the negative charge of the DNA sample itself. The net amount of movement of the DNA sample is smaller than the amount of downstream movement of the denaturing gradient region by the amount of upstream electrophoresis due to the negative charge of the DNA sample itself. In this case, after a lapse of ample time, the DNA sample can arrive at the denaturing gradient region located upstream. Thus, as a result of electrophoresis for a predetermined time, double-stranded DNA fragments with a GC clamp in the DNA sample are separated in the moving direction of the channel 809 by denaturing gradient gel electrophoresis (DGGE) according to differences in base sequence and the denaturing gradient.

The principle of DGGE in the present embodiment makes use of a phenomenon in which the charges of nucleic acid bases are neutralized by a DNA denaturant, such as urea and formamide, to break hydrogen bonds between nucleotides, thus dissociating a double-stranded DNA into single-stranded DNA's. The DNA sample includes double-stranded DNA which has been amplified with an artificial DNA sequence (GC clamp) being added at one end by PCR. The GC clamp is a sequence minimally dissociable into single-stranded DNA despite a high DNA denaturant concentration. When double-stranded DNA with the GC clamp is electrophoresed in a gel where the concentration gradient of the DNA denaturant has been formed, a region without the GC clamp is dissociated into single-stranded DNA at a certain denaturant level, and this double-stranded DNA has a low moving speed. The denaturant concentration which dissociates double-stranded DNA into single-stranded DNA depends on its base sequence. Thus, when double-stranded DNA's having different base sequences are electrophoresed on the same gradient region, a difference in migration distance occurs. Thus, double-stranded DNA's can be separated by a variety of base sequences.

Figure 64:
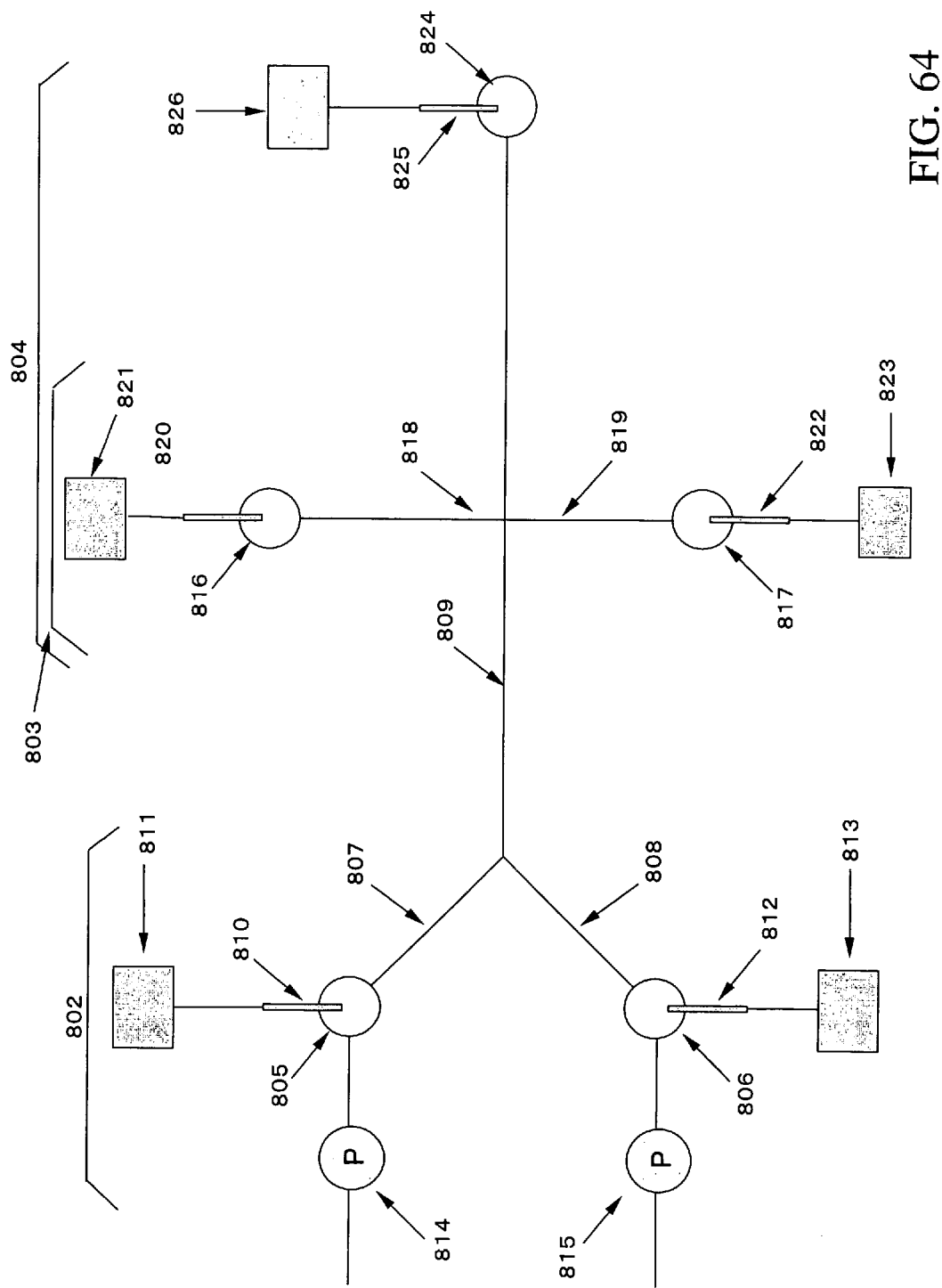
[FIG. 64] A schematic view showing another example of the embodiment A.
Figure 65:
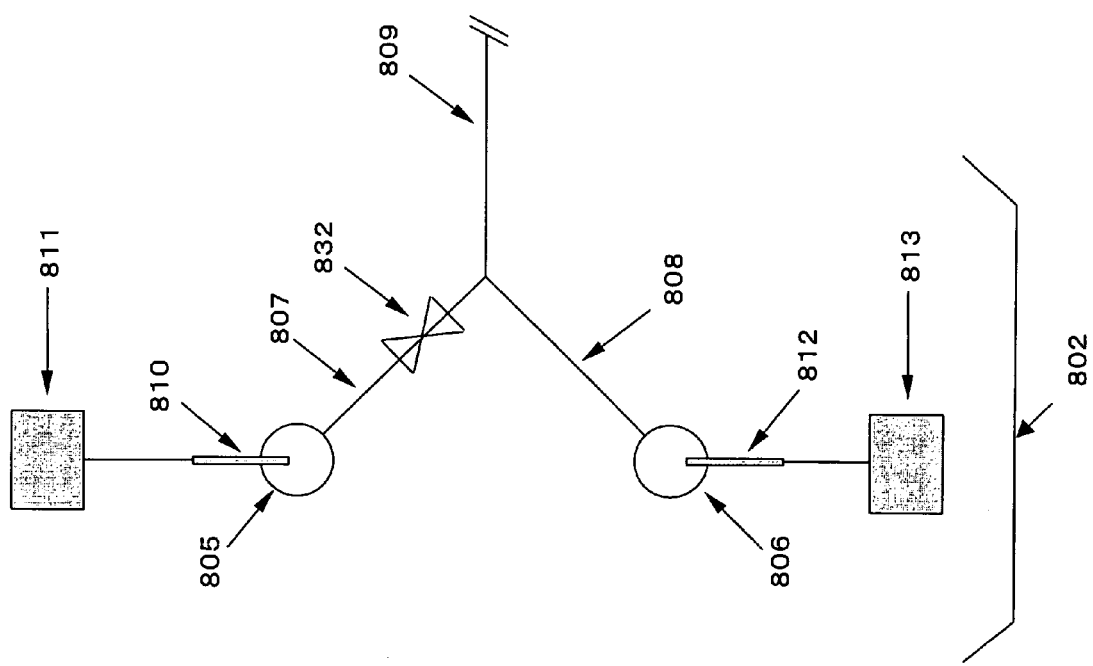
[FIG. 65] A schematic view showing the denaturing gradient forming portion of the embodiment A provided with a fast operating valve.
Figure 66:
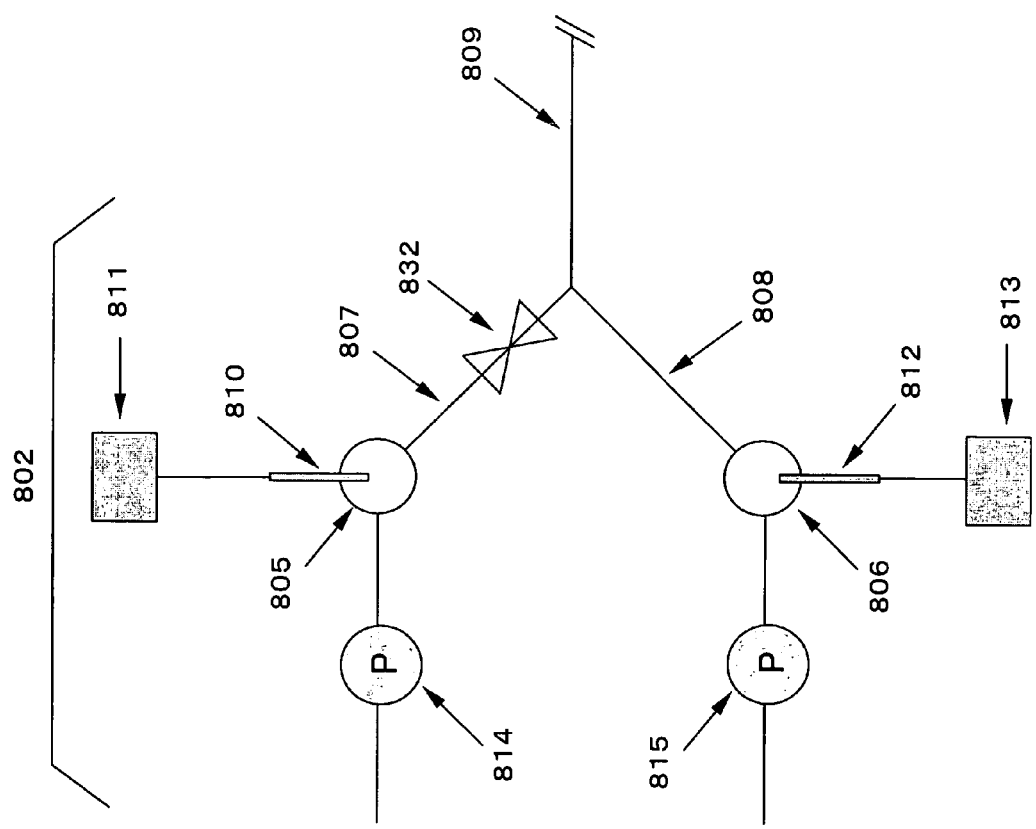
[FIG. 66] A schematic view showing another denaturing gradient forming portion provided with the fast operating valve.
Figure 67:
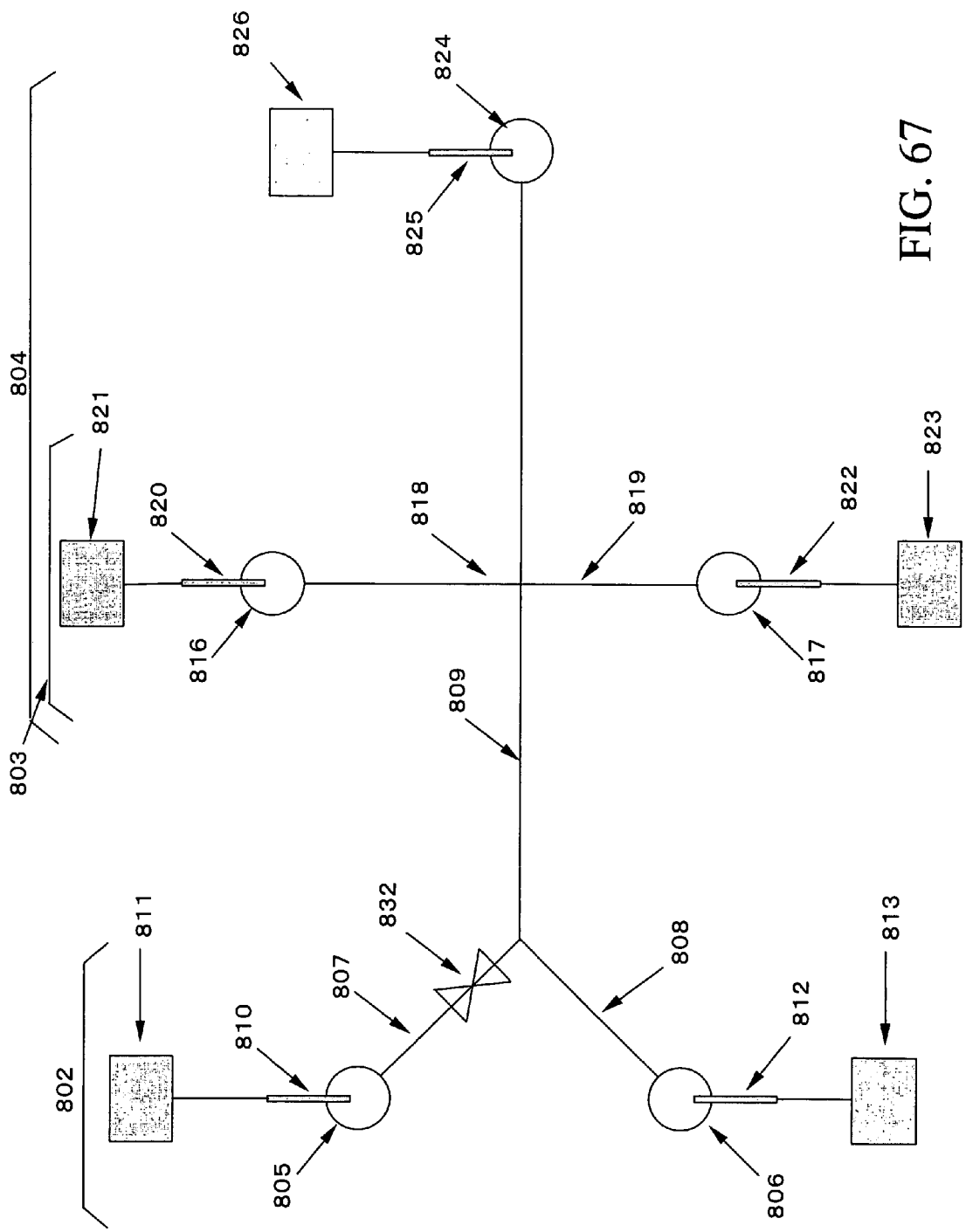
[FIG. 67] A schematic view showing an example of the embodiment A provided with the fast operating valve.
Figure 68:
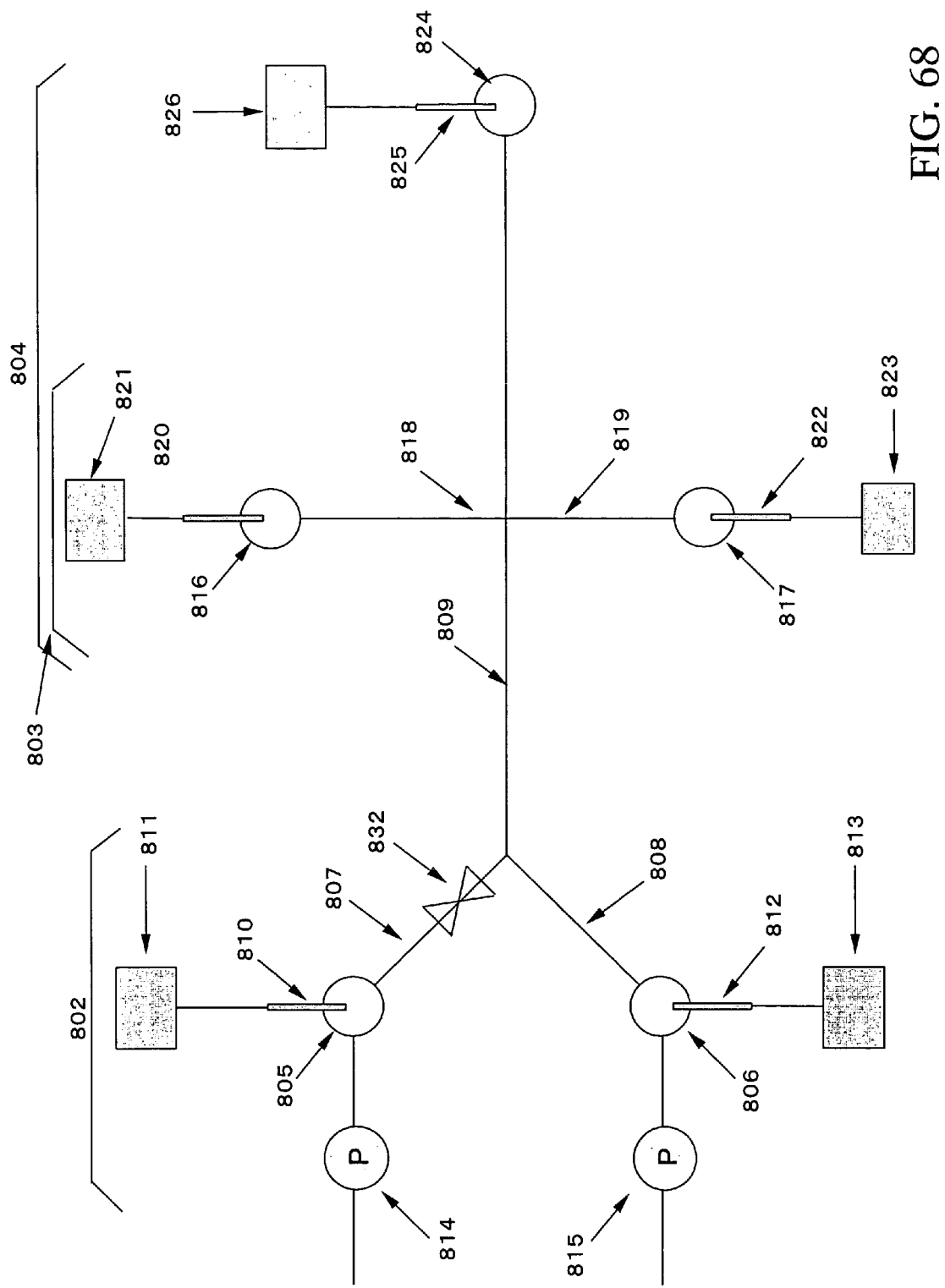
[FIG. 68] A schematic view showing another example of the embodiment A provided with the fast operating valve.

FIG. 64 shows an embodiment of the apparatus of FIG. 59b. An electrophoretic portion 804 of FIG. 64 includes a fifth reservoir 824 for a waste liquid, and a channel 809 leading to the fifth reservoir 824. The fifth reservoir 824 includes a fifth electrode 825 connected to a fifth power source 826. This embodiment includes, upstream of the fifth reservoir 824, a denaturing gradient forming portion 802 as illustrated with reference to FIG. 61, and a sample introduction portion 803 as illustrated with reference to FIG. 62.

In the embodiment of FIG. 64, a buffer flow (movement) having a denaturing gradient formed by the denaturing gradient forming portion 802 is introduced into the channel 809, whereby a flow of the denaturing gradient is produced in the channel 809. A DNA sample is introduced from the sample introduction portion 803 onto the denaturing gradient region. The denaturing gradient region is moved downstream in the channel 809 by driving of a first pump 810 and a second pump 815 in addition to electroosmotic flows by potentials to a fist power source 811 and a second power source 813. On the other hand, the DNA sample introduced into the channel 809 is moved by the sum of downstream movement by the action of the first pump 814 and the second pump 815 and the electroosmotic flows by the potentials to the fist power source 811 and the second power source 813, and upstream movement by electrophoresis generated by the negative charge of the DNA sample itself. The net amount of movement of the DNA sample is smaller than the amount of downstream movement of the denaturing gradient region by the amount of upstream electrophoresis due to the negative charge of the DNA sample itself. In this case, after a lapse of ample time, the DNA sample can arrive at the denaturing gradient region located upstream. Thus, as a result of electrophoresis for a predetermined time, double-stranded DNA fragments with a GC clamp in the DNA sample are moved in the moving direction of the channel 9 by denaturing gradient gel electrophoresis according to differences in base sequence and the denaturing gradient.

The channels and reservoirs of the microchip electrophoretic apparatus of the present embodiment are filled with a buffer solution containing a polymer matrix. This is because DNA can be separated by the mesh structure of the polymer matrix or the interaction between the polymer matrix and DNA. The polymer matrix usable in the present embodiment can be selected suitably from polyacrylamide, cellulose derivatives such as hydroxyethylcellulose, hydroxypropylmethylcellulose, hydroxycellulose, and methylcellulose, polyethylene oxide, polyols such as polymethylene glycol, polypropylene glycol, polyvinyl alcohol, and polyvinyl pyrrolidone, dextran, and pullulan. If the polymer matrix is hydroxyethylcellulose, its concentration is preferably in the range of 0.01% to 3.0%, depending on the length of double-stranded DNA. Examples of such buffer solution are Tris-acetate buffer solution, and Tris-borate buffer solution.

The DNA denaturant usable in the present embodiment is selected, as appropriate, from urea, formamide, formaldehyde, and strong alkalis such as sodium hydroxide. Preferred are urea and formamide. When formamide and urea are used as a denaturant, it is common practice to use a denaturant-containing buffer solution containing 7M urea and 40% formamide as a 100% denaturant-containing buffer solution, and use a buffer solution free from the denaturant as a 0% buffer solution. Generally, when electrophoresis is carried out at 60° C., a denaturing gradient is in the range of 0% to 100% or 20% to 70%. In the case of structural analysis of a microbial community using 16S rRNA gene, the range of 35% to 55% is preferred.

For a DNA sample analyzable in the present embodiment, there is used double-stranded DNA extracted from biological samples such as human blood and cells, foods, environmental samples such as soil, river water and seawater, or activated sludge or anaerobic digestion (methane fermentation) sludge. Use can be made of double-stranded DNA formed by amplifying a certain region of an extracted genomic DNA by a PCR reaction or the like, with this region having attached at one end an artificial DNA sequence (GC clamp) which is minimally dissociable into single-stranded DNA despite a high DNA denaturant concentration.

The means of detecting DNA by the present embodiment is selected from fluorescence detection, luminescence detection, absorbance detection, and electrochemical detection. Examples of fluorescence detection are previous fluorescence labeling of primers for PCR reaction, fluorescence labeling of a PCR product, previous staining of a PCR product with a DNA staining reagent, and addition of a DNA staining reagent into a polymer matrix-containing buffer solution for staining during electrophoresis. Fluorescence labeling substances are fluorescein, rhodamine, Cy3, Cy5, BODIPY FL, TexasRed, Alexa Fluor, etc. As the DNA staining reagent, SYBR Green, Vistra Green, ethidium bromide, YOYO-1, TOTO-1, and thiazole orange are available. As the detector, a photomultiplier, a UV detector, or a photodiode detector can be used in the case of fluorescence detection, luminescence detection or absorbance detection.

In connection with analysis using the microchip electrophoretic apparatus of the present embodiment, an example of an operating procedure will be described with reference to FIG. 63.

A buffer solution containing a polymer matrix is filled into the first channel 807, the second channel 808, the channel 809, the fourth channel 818, and the fifth channel 819 through the first reservoir 805, the second reservoir 806, the third reservoir 816, the fourth reservoir 817, or the fifth reservoir 824. If the buffer solution cannot be filled by capillarity, it is recommendable to fill the buffer solution under pressure by a syringe or the like.

After filling of the buffer solution, the first reservoir 805 is filled with a denaturant-containing buffer solution, the second reservoir 806, the fourth reservoir 817, and the fifth reservoir 824 are filled with a buffer solution, and the third reservoir 816 is filled with a DNA sample. The fourth reservoir 817 and the fifth reservoir 824 may be filled with a buffer solution containing no denaturant, according to circumstances. All of the buffer solutions and the DNA sample used preferably contain the polymer matrix. The DNA sample and the buffer solution filled into the fourth reservoir 817 and the fifth reservoir 824 may be free from the polymer matrix.

Then, the first electrode 810, the second electrode 812, the third electrode 820, the fourth electrode 822, and the fifth electrode 825 are plugged into the first reservoir 805, the second reservoir 806, the third reservoir 816, the fourth reservoir 817, and the fifth reservoir 824, respectively. However, these electrodes may be formed beforehand within the first reservoir 805, the second reservoir 806, the third reservoir 816, the fourth reservoir 817, and the fifth reservoir 824, respectively.

Then, the fifth electrode 825 is grounded, and predetermined potentials are applied to the first electrode 810 and the second electrode 811 to introduce the buffer solutions having predetermined denaturant concentrations into the channel 809. At this time, it is preferred to give predetermined-potentials to the third electrode 820 and the fourth electrode 822 so that the buffer solutions do not flow into the fourth channel 818 and the fifth channel 819.

Then, if the velocities of electroosmotic flows generated in the fourth channel 818 and the fifth channel 819 are greater than the electrophoretic speed of the double-stranded DNA, the fourth electrode 822 is grounded, and a predetermined voltage is applied to the third electrode 820 to introduce the DNA sample to the intersection of the channel 809, the fourth channel 818 and the fifth channel 819. If the velocities of electroosmotic flows generated in the fourth channel 818 and the fifth channel 819 are lower than the electrophoretic speed of the double-stranded DNA, the third electrode 820 is grounded, and a predetermined voltage is applied to the fourth electrode 822. In either case, predetermined potentials are preferably given to the first electrode 810, the second electrode 812 and the fifth electrode 825 so that the DNA sample does not flow into the third channel 809.

Then, the fifth electrode 825 is grounded, and voltages applied to the first electrode 810 and the second electrode 812 are continuously varied to introduce a region having a predetermined denaturing gradient into the channel 809. At the same time, at the intersection of this channel 809, the fourth channel 818 and the fifth channel 819, the DNA sample is introduced onto the channel 809 having the above-mentioned denaturing gradient region. At this time, it is preferred to give predetermined potentials to the third electrode 820 and the fourth electrode 822 so that the buffer solutions do not flow into the fourth channel 818 and the fifth channel 819. The procedure of varying the potentials applied to the first electrode 810 and the second electrode 812 is to render the potential to the second electrode 812 higher than the potential to the first electrode 810, and then progressively decrease the potential to the second electrode 812 and increase the potential to the first electrode 810. As a result, the denaturing gradient region introduced into the channel 809 is formed so as to have a denaturant concentration lower toward a downstream side and higher toward an upstream side.

By the above procedure, the double-stranded DNA's in the DNA sample are separated in the denaturing gradient region. During or after this separation, DNA's are detected by a DNA detector provided toward the channel 809 DNA detection may be performed anywhere on the channel 809 During analysis, the microchip needs to be kept at a constant temperature, preferably, 40° C. to 70° C.

Microchip Electrophoretic Apparatus of the Embodiment A having Mixing Enhancing Means The mixing enhancing means described in the embodiments 1-1 to 2-3 can be applied to the microchip electrophoretic apparatus of the embodiment A. In using the mixing enhancing means in the microchip electrophoretic apparatus, the microchannels 807, 808 for introducing the buffer solutions are the liquid-introducing microchannels, the channel 809 for the gradient forming region is the mixing microchannel, and the mixing enhancing means is used for the mixing of the buffer solutions in the channel 9. The reservoirs for feeding the buffer solutions are the liquid inlets or introduction portions for the liquid-introducing microchannels.

The mixing enhancing means is also useful for the formation of a concentration gradient. For example, the use of the flow rate independent control means according to the embodiments 1-1 and 1-2 (for example, control of an electroosmotic flow by adjusting an applied potential or an applied voltage, control of a liquid feed pump, such as a microsyringe, or secondary control by a valve for the liquid driven by these control methods) makes it possible to arbitrarily change the ratio of the buffer solutions introduced from the microchannels 807, 808 and, at the same time, increase the interface between the buffer solutions which converge. Since the mixing of the buffer solutions by molecular diffusion is enhanced by the increase in the interface, a concentration gradient uniform in the channel width direction can be quickly formed in the channel 809. This technique enables the provision of a microchip apparatus useful for DEEG, shortening of the DEEG analysis time, and high throughput realization.

FIGS. 65 to 68 show the apparatus of the embodiment A provided with a fast operating valve 832. As shown in these drawings, the fast operating valve 832 can be provided, for example, on the first channel 807. In the denaturing gradient forming portion 802, voltages are applied into the reservoirs via the first power source 811 and the first electrode 810 and the second power source 813 and the second electrode 812. The resulting electroosmotic flows introduce the denaturant-containing buffer solution from the first reservoir 805 into the gradient region channel 809 through the first channel 807 and, similarly, introduce the denaturant-free buffer solution from the second reservoir 806 into the channel 809 through the second channel 7. At this time, the opening and closing action of the fast operating valve 832 is controlled, whereby the mixing ratio of the denaturant-containing buffer solution from the first reservoir 805 to the constant flow rate of the buffer solution from the second reservoir 806 can be controlled. A continuous concentration gradient can be formed by continuously changing the opening and closing time of the fast operating valve 832.

Embodiment B Concerned with DGGE

The DGGE method of the embodiment B comprises arranging buffer solution zones (electrophoretic gel) containing a denaturant at different concentrations alternately in the direction of electrophoresis, and introducing an analyte into the resulting gradient region for electrophoresis.

In the microchip electrophoretic apparatus of the embodiment B, buffer solution zones containing a denaturant at different concentrations are arranged alternately in a microchannel in the direction of electrophoresis, and an analyte is introduced into the resulting gradient region for electrophoresis.

(1) Principle of the Present Embodiment

A method for separating double-stranded nucleic acids by the embodiment B is characterized by arranging at least two buffer solution zones containing a denaturant at different concentrations alternately in the direction of electrophoresis of the nucleic acids. The nucleic acids are electrophoretically moved in a discontinuous arrangement structure of such denaturant concentrations, and separated thereby. This principle will be explained by reference to the conventional DGGE method.

The principle of DGGE makes use of the following phenomenon: In a gel in which a concentration gradient of a nucleic acid denaturant, such as urea or formamide, is formed, such a nucleic acid denaturant neutralizes the charges of the nucleic acid bases of the double-stranded nucleic acids being electrophoresed, to cut the hydrogen bonds between nucleotides, thereby dissociating the double-stranded nucleic acid into single-stranded nucleic acids. Concretely, a nucleic acid fragment to be electrophoresed is PCR-amplified, under the conditions under which an artificial nucleic acid sequence (GC clamp) minimally dissociable into a single-stranded nucleic acid despite a high nucleic acid denaturant concentration has been attached to one end of the fragment. By this PCR amplification, the fragment is prepared into a double-stranded nucleic acid, and the resulting double-stranded nucleic acid is electrophoresed. At a certain denaturant concentration, a double-stranded nucleic acid without the GC clamp dissociates into single-stranded nucleic acids, and decreases in the migration speed. The denaturant concentration at which a double-stranded nucleic acid dissociates into single-stranded nucleic acids depends on the base sequence of the double-stranded nucleic acid. Thus, various double-stranded nucleic acids can be separated according to differences in base sequence. That is, DGGE ingeniously utilizes the base sequence dependence of the denaturant concentration required for the dissociation of a double-stranded nucleic acid. Double-stranded nucleic acids having different base sequences are different in the denaturant concentration at which they become dissociable according to the base sequence. Therefore, when these double-stranded nucleic acids are electrophoresed in a gel having a gradient of the denaturant concentration, differences gradually occur in the state of dissociation on the denaturing gradient, accomplishing their separation.

The inventor considered that the base sequence dependence of the dissociation denaturant concentration was caused by differences in a frequency with which denaturing molecules in the denaturant, such as urea and formamide, act on the hydrogen bonding sites of the double-stranded nucleic acid. This can be explained as follows: To partially break the hydrogen bond of a double-stranded nucleic acid having a certain base sequence, it is essential to cause the denaturing molecule to act on the hydrogen bonding site of the double-stranded nucleic acid at that part with a frequency which is a certain threshold or higher. A finite reaction time is necessary for the reaction that breaks the hydrogen bond at a certain part of the double-stranded nucleic acid. The denaturing molecule has to act on its hydrogen bonding site at least for a longer time than the required reaction time. This finite reaction time is also considered to depend on the base sequence.

Base on the above-described idea, the inventor examined the method of separating double-stranded nucleic acids, with particular attention paid to the threshold of the reaction time in addition to the threshold of the frequency of the reaction between the migratory nucleic acid and the denaturing molecule. As a result, the inventor found that the double-stranded nucleic acids could be separated by changing the reaction frequency, without continuously varying the concentration of the denaturant. The present method of separation relates to a method which makes use of the fact that the thresholds of the reaction frequency and the reaction time necessary for breaking the hydrogen bonds of the double-stranded nucleic acids differ according to the base sequence, and which comprises arranging buffer solution zones containing a denaturant at different concentrations in the direction of electrophoresis. Concretely, the "lengths (distances in the direction of electrophoresis)" of buffer solution zones containing a denaturant at a high concentration and/or buffer solution zones containing no denaturant or a denaturant at a low concentration are changed in the direction of electrophoresis, and these buffer solution zones are arranged such that the reaction frequency and/or the reaction time (the time of passage through the buffer solution zones containing the denaturant at a high concentration) for the reaction with the denaturing molecule will be progressively increased in the direction of electrophoresis. When the double-stranded nucleic acids are electrophoresed on the so arranged buffer solution zones, they can be separated according to the difference in base sequence.

In the embodiment B, a gradient, in which the denaturant concentration continuously varies, need not be formed in each buffer solution zone. The step to be taken is to form a gradient of a two-dimensional distribution of buffer solution zones containing a predetermined concentration of the denaturant such that the distribution of the denaturant becomes denser toward a downstream side in the direction of electrophoresis.

As described above, the present embodiment relates to the formation of a discontinuous arrangement structure of the denaturant concentration.

The wording used in the present embodiment, "discontinuous arrangement structure of the denaturant concentration" or "arrangement of buffer solution zones containing the denaturant at different concentrations", means a structure in which at least two buffer solution zones having different concentrations of the denaturant are alternately arranged.

The term "buffer solution zones" used in the present embodiment refers to an electrophoretic matrix, such as a gel, which contains a certain concentration of buffer solution.

In the following, an alternate arrangement of buffer solution zones containing a denaturant and buffer solution zones containing no denaturant (hereinafter referred to as "intermittent denaturant arrangement") will be described for simplified explanation. However, it does not matter whether each buffer solution zone contains the denaturant, or is free from the denaturant. What is important is a relative concentration difference in the denaturant. For example, the same effect is obtained, if "the denaturant-free zone" contains a relatively low concentration of the denaturant, and "the denaturant-containing zone" contains a significantly higher concentration of the denaturant than "the denaturant-free zone". This embodiment is also within the scope of the present invention.

A preferred embodiment is designed such that as a double-stranded nucleic acid moves over a longer distance, the frequency of its reaction with a denaturing molecule progressively increases, or the time of its reaction with the denaturing molecule progressively lengthens. This preferred embodiment uses an arrangement of denaturant-containing buffer solution zones and/or denaturant-free buffer solution zones of gradually changing length in the direction of electrophoresis.

The principle of separation by the above-described arrangement of buffer solution zones can be explained as follows: The embodiment of FIG. 69 (the first embodiment to be described later on) will be taken as an example for the purpose of explanation. As shown in FIG. 82, when the spacing between denaturant-containing buffer solution zones shortens in the direction of electrophoresis, each nucleic acid migrating across this arrangement pattern has a low ratio A of the time of its contact with the denaturant-containing buffer solution to the time t in a region of a small migration distance (an upstream region). In a region of a great migration distance (a downstream region), the nucleic acid has a high ratio B of the time of its contact with the denaturant-containing buffer solution to the same time t. That is, if there is no significant difference in the degree of nucleic acid migration between the upstream region and the downstream region, and if the time $\Delta t$ of passage through each region of the denaturant-containing buffer solution is the same, then the ratio of time of contact of the nucleic acid with the denaturant-containing buffer solution within the same length of time t depends on the number of the zones of the denaturant-containing buffer solution passed by the nucleic acid, so that the relation A<B holds. As noted here, depending on the migration distance (migration time), the ratio of time of contact of the nucleic acid with the denaturant-containing buffer solution to the same time t (i.e., the reaction frequency) increases gradually. As the ratio of the contact time gradually increases, double-stranded nucleic acids dissociate when different reaction thresholds are exceeded according to differences in base sequence. As a result, they have intrinsic migration degrees (migration distances). Thus, the use of an intermittent arrangement of denaturant-containing zones obtains the same separation effect as that obtained by the use of a continuously formed denaturing gradient.

FIG. 69 shows a first embodiment of the intermittent denaturant arrangement. This embodiment is an intermittent denaturant arrangement in which the lengths of respective zones of a denaturant-containing buffer solution are nearly constant in the direction of electrophoresis of nucleic acids, and respective zones of a denaturant-free buffer solution are progressively shortened. That is, the spacing between the denaturant-containing buffer solutions (the length of the buffer solution zone containing no denaturant) narrows in the direction of electrophoresis of the nucleic acids. When the nucleic acids migrate in the intermittent denaturant arrangement in this embodiment, they pass through the denaturant-containing buffer solution and the denaturant-free buffer solution alternately. The time required for the nucleic acids to pass through the denaturant-containing buffer solution zone is designed to be sufficiently shorter than the difference between the dissociation reaction times due to the difference in base sequence. As the nucleic acid migrates downstream, the frequency of its passage through the denaturant-containing buffer solutions during a certain period of time increases (namely, the reaction frequency increases), and thus the nucleic acid becomes dissociable. Hence, a nucleic acid having a base sequence, in which the coupling of double strand is relatively unstable, dissociates in a place where the density of denaturant-containing buffer solution zones on the intermittent denaturant arrangement is low (i.e., upstream region). On the other hand, a nucleic acid having a base sequence, in which the coupling of the double strand is relatively stable, dissociates in a place where the density of denaturant-containing buffer solution zones is higher (i.e., downstream region). This embodiment utilizes changes in the arrangement density (changes in the frequency of passage) of the denaturant-containing buffer solution zones.

FIG. 70 shows a second embodiment of the intermittent denaturant arrangement. This embodiment is an intermittent denaturant arrangement in which the lengths of respective zones of a denaturant-free buffer solution are nearly constant in the direction of electrophoresis of nucleic acids, and respective zones of a denaturant-containing buffer solution are progressively lengthened. In this embodiment as well, the time required for the nucleic acids to pass through an appropriate number of the denaturant-containing buffer solution zone is shorter than the difference between the dissociation reaction times due to the difference in base sequence. The nucleic acids to be electrophoresed have different degrees of dissociation, depending on whether the time of their passage through each denaturant-containing buffer solution zone has reached the reaction time required for the dissociation of the base sequence. As the nucleic acids migrate downstream, the time of their passage through the denaturant-containing buffer solution zone becomes longer, and thus the double strand becomes dissociable. Hence, if the double strand of the nucleic acid is unstable, it dissociates in the upstream region on the intermittent denaturant arrangement, but if the double strand is stable, it dissociates in the downstream region. This embodiment utilizes changes in the continual action (reaction time in a single arrangement) dependent on the length of each denaturant-containing buffer solution zone (length in the direction of electrophoresis).

The time required for a nucleic acid to pass through a denaturant-containing buffer solution is determined by the length of the denaturant-containing buffer solution and the migration speed of the nucleic acid. The frequency of the passage of a nucleic acid through a denaturant-containing buffer solution is determined by the length of the buffer solution and the migration speed of the nucleic acid. Thus, various double-stranded nucleic acids can be appropriately separated according to differences in base sequence by appropriately selecting the length of the denaturant-containing buffer solution zone, the length of the denaturant-free buffer solution zone, the migration speeds of the nucleic acids, the denaturant concentrations of the denaturant-containing buffer solutions, and the entire length of the intermittent denaturant arrangement. These parameters differ according to the types of the nucleic acids to be analyzed, and the accuracy of separation required. These may be determined by preliminary experiments conducted beforehand. For example, the length and concentration of the denaturant-containing buffer solution zone can be adjusted in order to control the separation of double-stranded nucleic acids. If the length of the denaturant-containing buffer solution zone is short, for example, the time that the nucleic acids pass through the denaturant-containing buffer solution zone is short, and thus detection with high accuracy is achieved. If the denaturant concentration of the denaturant-containing buffer solution zone is low, detection with high accuracy becomes possible. In order to control separation accuracy, as mentioned above, the length of the denaturant-containing buffer solution zone, the length of the denaturant-free buffer solution zone, the migration speeds of the nucleic acids, the denaturant concentrations of the denaturant-containing buffer solutions, and the entire length of the intermittent denaturant arrangement can be adjusted according to needs.

In the first embodiment of the intermittent denaturant arrangement, only the length of each zone of the denaturant-free buffer solution is changed. In the second embodiment, only the length of each zone of the denaturant-containing buffer solution is changed. These features are not limitative, and the length of each zone of the denaturant-free buffer solution and the length of each zone of the denaturant-containing buffer solution may both be changed.

The execution of the present embodiment on a microchip is advantageous in that there is no need for a mixing operation for buffer solutions at a point upstream of the gradient forming region (mixing on an analytic chip is required in the case of forming a continuous gradient of a denaturant as in the embodiment A). Another advantage is no need for means for enhancing mixing on such an analytic chip.

The buffer solution used in the present embodiment is a buffer solution containing, where necessary, a polymer matrix. This is because nucleic acids can be separated by the mesh structure of the polymer matrix or the interaction between the polymer matrix and the nucleic acids.

The polymer matrix usable in the present embodiment can be selected suitably from polyacrylamide, cellulose derivatives such as hydroxyethylcellulose, hydroxypropylmethylcellulose, hydroxycellulose, and methylcellulose, polyethylene oxide, polyols such as polymethylene glycol, polypropylene glycol, polyvinyl alcohol, and polyvinyl pyrrolidone, dextran, and pullulan. If the polymer matrix is hydroxyethylcellulose, its concentration depends on the length of double-stranded nucleic acid, and is preferably in the range of 0.01% to 3.0%. This polymer matrix is incorporated into tris-acetate buffer solution or tris-borate buffer solution, and is used as a buffer solution. However, the buffer solution can be driven into an existing slab gel to form an arrangement of buffer solution zones. For a gel having a mesh structure of the polymer matrix already formed, a buffer solution containing no polymer matrix can be used.

The denaturant usable in the present embodiment is selected from urea, formamide, formaldehyde, and strong alkalis such as sodium hydroxide. Preferred are urea and formamide. When formamide and urea are used as a denaturant, it is common practice to use a denaturant-containing buffer solution containing 7M urea and 40% formamide as a 100% denaturant-containing buffer solution, and use a buffer solution free from the denaturant as a 0% buffer solution. However, this practice is not restrictive. In the embodiment B, as described earlier, it suffices that an arrangement of buffer solution zones having a significant denaturant concentration difference can be formed.

A representative example of the analyte in the present embodiment is an isolated double-stranded nucleic acid (may be referred to simply as a nucleic acid or a nucleic acid molecule), and any type of nucleic acid molecule can be used, as long as it is dissociable by the denaturant. Typically, there is used a double-stranded nucleic acid formed by amplifying a certain region of a genomic nucleic acid (extracted from biological samples such as human blood and cells, foods, environmental samples such as soil, river water and seawater, or activated sludge or methane fermentation sludge) by a PCR reaction or the like, with this region having attached at one end an artificial nucleic acid sequence (GC clamp) which minimally dissociates into a single-stranded nucleic acid despite a high nucleic acid denaturant concentration. The analyte of the present embodiment is not necessarily restricted to a nucleic acid. Foe example, if such a biopolymer (e.g., protein) can be electrophoresed by selecting a buffer solution, a denaturant and separation conditions which are appropriate, the biopolymer can be included in the analyte of the present embodiment.

The nucleic acid separated on the intermittent denaturant arrangement of the present embodiment is detected by detection means. The detection means is selected from fluorescence detection, luminescence detection, absorbance detection, and electrochemical detection. As the detector, a photomultiplier, a UV detector, or a photodiode detector is used in the case of fluorescence detection, luminescence detection, and absorbance detection. Examples of fluorescence detection are previous fluorescence labeling of primers for PCR reaction, fluorescence labeling of a PCR product, previous staining of a PCR product with a DNA staining agent, and incorporation of a DNA staining agent into a polymer matrix-containing buffer solution for staining during electrophoresis. Fluorescence labeling substances are fluorescein, rhodamine, Cy3, Cy5, BODIPY FL, TexasRed, Alexa Fluor, etc. As the DNA staining agent, SYBR Green, Vistra Green, ethidium bromide, YOYO-1, TOTO-1, and thiazole orange are available.

(2) Separation Method and Apparatus of the Present Embodiment

As a support for performing the nucleic acid separation of the present embodiment, an analytic substrate such as a slab gel or an electrophoretic microchip is named.

The slab gel usable in the present embodiment includes, for example, a polyacrylamide gel containing a buffer solution, but this is not limitative. The polyacrylamide gel containing the buffer solution is formed, for example, by mixing an acrylamide solution comprising acrylamide, N,N-methylenebisacrylamide and distilled water, tris-acetate buffer solution, ammonium persulfate solution, N,N,N',N'-tetramethylethylenediamine, and distilled water, followed by polymerizing the mixture. Any type of slab gel can be prepared in accordance with the established method known in the technical field concerned.

On the slab gel, the intermittent denaturant arrangement is formed by the buffer solution zone forming method preferred for the present embodiment. If the slab gel is used, for example, it is immersed in an electrophoretic cell filled with other buffer solution, as shown in FIG. 71, and a cover is placed on the cell for preventing the evaporation of the buffer solution and the intermittent denaturant arrangement. As in the customary method of electrophoresis, sample holes are provided at equal spacing on an upstream side in the direction of electrophoresis on the slab gel, and an electrode and a power source are connected to the electrophoretic cell, although details are not shown.

The support includes not only the slab gel, but also any type of analytic substrate, as long as it can support the intermittent denaturant arrangement. The material for the substrate can be selected, for example, from glass, quartz, plastics, silicone resins, and paper. The substrate may also be prepared, for example, by laminating a substrate, which serves as a cover for preventing the evaporation of the intermittent denaturant arrangement, onto the substrate on which the intermittent denaturant arrangement has been formed. Moreover, a portion of the substrate, on which the intermittent denaturant arrangement has not been formed, may be bent to be used as a cover.

A typical analytical substrate is a microchip. As shown in FIG. 72, an intermittent denaturant arrangement can be formed in a microchannel which is a gradient forming region of the microchip. In this intermittent denaturant arrangement of the microchannel, denaturant-containing buffer solution zones and denaturant-free buffer solution zones are arranged alternately in the direction of electrophoresis, and the widths of the denaturant-free buffer solution zones are progressively decreased in the direction of electrophoresis.

The microchip usually consists of at least two substrates. Channels with a width and a depth of the order of 10 to 100 μm are formed in one substrate by use of a microfabrication technology, such as a photolithography technology, and holes for reservoirs are created in another substrate by use of machining such as ultrasonic machining. When these two substrates are laminated by a bonding technique such as melt bonding by heat, a microchip having the channels and reservoirs at predetermined positions is obtained. The material for the substrate can be selected, as appropriate, from glass, quartz, plastics, and silicone resins. With the microchip, the analytical channels have microstructures, so that high throughput analysis and downsizing of the entire apparatus can be realized.

Next, the microchip electrophoretic apparatus of the embodiment B will be described.

The microchip electrophoretic apparatus of FIG. 73 is provided as a plastic microchip 903 including a microchannel 901 being a gradient forming region (hereinafter referred to as "nucleic acid analytic channel 901"), and a microchannel 902 for introduction of a nucleic acid sample. An intermittent denaturant arrangement is formed in the nucleic acid analytic channel 901. The microchip 903 is produced by laminating a plastic substrate 903a having the above channels 901, 902 formed thereon, and a plastic substrate 903b provided with a nucleic acid inlet 902a for sample introduction, a nucleic acid outlet 902b, a first reservoir 901a and a second reservoir 901b.

An example of the procedure for the method of separating double-stranded nucleic acids by a difference in basic sequence with the use of the microchip of FIG. 73 will be shown below. A buffer solution is filled into the nucleic acid introduction channel 902. The method of introducing a sample into the nucleic acid analytic channel 901 is a method by which double-stranded nucleic acids as a sample are introduced into the nucleic acid analytic channel 901 by electrophoresis. A buffer solution containing double-stranded nucleic acids is placed into the nucleic acid inlet 902a, and electrodes (not shown) connected to direct current power sources are plugged into the nucleic acid inlet 902a and the nucleic acid outlet 902b. The nucleic acid sample includes a double-stranded nucleic acid which has been amplified, with an artificial nucleic acid sequence (GC clamp) being attached at one end of the nucleic acid, the artificial nucleic acid sequence minimally dissociating into a single-stranded nucleic acid despite a high nucleic acid denaturant concentration. Since the double-stranded nucleic acids have been negatively charged, the nucleic acid inlet side is rendered cathodic, and the nucleic acid outlet side is rendered anodic. The electrodes used may be formed beforehand at the nucleic acid inlet and the nucleic acid outlet, for example, by vacuum deposition or plating. When the double-stranded nucleic acids are introduced, the diffusion of the sample toward the nucleic acid analytic channel 1 should advisably be suppressed. For this purpose, it is recommendable to plug electrodes into the first reservoir 901a and the second reservoir 902a, and apply potentials which are higher than the potential of the nucleic acid inlet 902a and lower than the potential of the nucleic acid outlet 902b.

Then, electrodes (not shown) connected to direct current power sources are mounted at both ends of the nucleic acid analytic channel 901. Since the double-stranded nucleic acids have been negatively charged, the first reservoir side is rendered cathodic, and the second reservoir side is rendered anodic. The electrodes may be formed beforehand at the first reservoir and the second reservoir, for example, by vacuum deposition or plating. The double-stranded nucleic acids introduced as above are electrophoresed in the intermittent denaturant arrangement by applying predetermined potentials to the electrodes plugged into the first reservoir and the second reservoir, and applying a predetermined voltage between the electrodes mounted at both ends of the analytic substrate. The electrophoresed double-stranded nucleic acids are separated on the intermittent denaturant arrangement according to a difference in base sequence.

The nucleic acids separated by the above-described procedure are detected within the nucleic acid analytic channel 901 or a detection portion 905 located downstream of this channel. The detection method usable, as explained earlier, is selected from fluorescence detection, luminescence detection, absorbance detection, and electrochemical detection. The preferred method is fluorescence detection. Examples of the fluorescence detection are previous fluorescence labeling of primers for PCR reaction, fluorescence labeling of a PCR product, previous staining of a PCR product with a DNA staining agent, and incorporation of a DNA staining agent into a polymer matrix-containing buffer solution for staining during electrophoresis. Fluorescence labeling substances are as stated earlier, and the detector is also as described previously. During analysis, the analytic substrates 903a, 903b need to be kept at a constant temperature, preferably, 40° C. to 70° C.

The microchip used may be made of glass. Since the glass microchip increases the effect of an electroosmotic flow, the surface of the channel should desirably be modified by a publicly known technique to suppress the electroosmotic flow. By this treatment, double-stranded nucleic acids can be separated by electrophoresis on the glass microchip of the same configuration as that of a plastic microchip.

FIG. 74 shows an embodiment of a glass microchip electrophoretic apparatus. Even in the presence of an electroosmotic flow, analysis of double-stranded nucleic acids can be made by a configuration as shown in FIG. 74. The basic structure of this apparatus is the same as that of the microchip of FIG. 5, but is different in that the nucleic acid introduction channel 2 is provided on the downstream side.

First, double-stranded nucleic acids, which serve as a sample, are introduced from the nucleic acid introduction channel 2 into a nucleic acid analytic channel 901 having an intermittent denaturant arrangement by the action of an electroosmotic flow. A buffer solution containing double-stranded nucleic acids is placed into a nucleic acid inlet 902a, and electrodes connected to direct current power sources are inserted into the nucleic acid inlet 902a and a nucleic acid outlet 902b. A predetermined voltage is applied between the nucleic acid inlet and the nucleic acid outlet, whereby the buffer solution containing the double-stranded nucleic acids is moved through the nucleic acid introduction channel 902 by the electroosmotic flow, and introduced into the nucleic acid analytic channel 901. To utilize the electroosmotic flow, the nucleic acid inlet side is rendered anodic, and the nucleic acid outlet side is rendered cathodic. When the double-stranded nucleic acids are introduced, their diffusion toward the nucleic acid analytic channel 901 should advisably be suppressed. For this purpose, it is recommendable to plug electrodes into a first reservoir 901a and a second reservoir 901b, and apply potentials which are lower than the potential of the nucleic acid inlet 902a and higher than the potential of the nucleic acid outlet 902b. The electrodes may be formed beforehand, for example, by vacuum deposition or plating.

Then, the introduced double-stranded nucleic acids are electrophoresed for separation. A predetermined voltage is applied to the electrodes plugged into the first reservoir 901a and the second reservoir 902b, whereby buffer solution zones of the intermittent denaturant arrangement are transported within the nucleic acid analytic channel 901 by an electroosmotic flow. The double-stranded nucleic acids introduced into the buffer solution zones also migrate upon electrophoresis. Generally, the direction of movement of the intermittent denaturant arrangement by the electroosmotic flow and the direction of movement of the nucleic acids by electrophoresis are opposed to each other (directions opposite to each other). Thus, when the intermittent denaturant arrangement of FIG. 74 is to be used, the first reservoir 901a is rendered anodic, and the second reservoir 901b is rendered cathodic. By so doing, the intermittent denaturant arrangement moves toward the second reservoir 901b, while the double-stranded nucleic acids move toward the first reservoir 901a. Thus, the double-stranded nucleic acids are electrophoresed on the intermittent denaturant arrangement, and separated according to a difference in base sequence.

The double-stranded nucleic acids separated by the above-described procedure are detected within the intermittent denaturant arrangement or at a detection portion (not shown) located downstream of this arrangement.

FIG. 75 shows another embodiment of the glass microchip electrophoretic apparatus. This apparatus comprises a nucleic acid analytic channel 901 (first microchannel) where an intermittent denaturant arrangement is to be formed, a denaturant-containing buffer solution introduction portion intersecting the nucleic acid analytic channel 901 on one end side of this channel, and a nucleic acid introduction portion intersecting the nucleic acid analytic channel 901 on the other end side of this channel. A first reservoir 901a serves as a buffer solution inlet for a first buffer solution, and a second reservoir 901b serves as an outlet for this buffer solution.

The denaturant-containing buffer solution introduction portion has a denaturant-containing buffer solution introduction channel 906 (second microchannel) crossing the nucleic acid analytic channel 901. The denaturant-containing buffer solution introduction channel 906 has a denaturant-containing buffer solution inlet 906a for introducing a second buffer solution, and an outlet 906b for this buffer solution. The second buffer solution is introduced through the denaturant-containing buffer solution introduction channel 906.

The nucleic acid introduction portion has a nucleic acid sample introduction channel 902 crossing the nucleic acid analytic channel 901. The nucleic acid sample introduction channel 902 has a nucleic acid inlet 902a, and an outlet 902b for this sample.

The apparatus of FIG. 75 is a microchip produced, for example, by laminating a substrate 903a (see FIG. 76(a)) and a substrate 903b (see FIG. 76(b)) by a bonding technique such as melt bonding by heat, the substrate 903a having the nucleic acid analytic channel 901, the denaturant-containing buffer solution introduction channel 906, and the nucleic acid introduction channel 902 formed thereon, and the substrate 903b having the buffer solution inlet and the outlet therefor, the nucleic acid inlet and the outlet therefor, and the denaturant-containing buffer solution inlet and the outlet therefor formed therein at respective channel ends. Holes for the respective reservoirs are, for example, circular holes with a diameter of 2 to 10 mm, and they are formed, for example, by a well known machining technique such as ultrasonic machining.

In the apparatus of the above configuration, a desired intermittent denaturant arrangement as shown in FIG. 77 can be formed in the nucleic acid analytic channel 901 by the denaturant-containing buffer solution introduction portion. The method of forming it will be described in detail later in the paragraph "(3) Method and apparatus for forming arrangement of buffer solution zones for the embodiment B". Here, the microchip electrophoretic apparatus of FIG. 75 is used, and a separation step performed after formation of an intermittent denaturant arrangement in the nucleic acid analytic channel 1 will be shown.

After a desired intermittent denaturant arrangement is formed in the nucleic acid analytic channel 901, double-stranded nucleic acids are flowed from the nucleic acid inlet 902a toward the nucleic acid outlet 902b to introduce the double-stranded nucleic acids into the nucleic acid analytic channel 901. The method of flowing the double-stranded nucleic acids can be arbitrarily selected from methods capable of controlling the flowing direction and the flowing time (flowing distance). In the case of a glass microchip, it is preferred to perform a method in which a direct current voltage is applied between the nucleic acid inlet 902a and the nucleic acid outlet 902b to generate an electroosmotic flow. In order for a surplus sample not to outflow into the nucleic acid analytic channel 901 during a double-stranded nucleic acid introduction step, it is recommendable, for example, to apply a direct current voltage to or exert a pressure on the buffer solution inlet 901a, the outlet 901b therefor, the denaturant-containing buffer solution inlet 906a, and the outlet 906b therefor.

Then, the electrodes are inserted into the buffer solution inlet 901a and the outlet 901b, and a predetermined direct current voltage is applied therebetween. As a result, the introduced double-stranded nucleic acids are electrophoresed on the intermittent denaturant arrangement in the nucleic acid analytic channel 901, and separated according to a difference in base sequence. The electrodes may be formed beforehand on the chip, for example, by vacuum deposition or plating. If an electroosmotic flow simultaneously occurs in the case of a glass microchip or the like, the intermittent denaturant arrangement flows in a direction opposite to the direction of electrophoresis of the double-stranded nucleic acids, namely, flows toward the cathode, under the action of the electroosmotic flow. In this case, it is necessary to form the intermittent denaturant arrangement in the nucleic acid analytic channel 901 such that the lengths of the buffer solutions progressively shorten in the direction of electrophoresis of the nucleic acids, for example, as shown in FIG. 77.

After the double-stranded nucleic acids in the nucleic acid sample are separated by the above procedure, the double-stranded nucleic acids are detected at a predetermined location on the nucleic acid analytic channel 901, for example, at a detection portion (not shown) located downstream of the nucleic acid analytic channel 901. During analysis, the microchip needs to be kept at a constant temperature, preferably 40° C. to 70° C. The usable denaturant and buffer solution, the analyzable sample, and the detection method are also the same as those for the aforementioned apparatus.

(3) Method and Apparatus for Forming Arrangement of Buffer Solution Zones for the Embodiment B With the conventional DGGE, it has been necessary to provide the denaturant-containing buffer solution with a continuous concentration gradient. In the microchannel used in the microchip electrophoretic apparatus, however, there has been need for ample time for mixing the denaturant-containing buffer solution and the buffer solution, or there has been need for a mechanism for efficiently mixing the denaturant-containing buffer solution and the buffer solution.

According to the invention of the embodiment B, the nucleic acids are electrophoresed on the intermittent denaturant arrangement formed in the microchannel. Thus, nucleic acid separation can be achieved, even when the denaturant-containing buffer solution and the buffer solution are not mixed at all. There is no particular need for stirring means for mixing the denaturant-containing buffer solution and the buffer solution.

A desired method and apparatus for forming an arrangement of buffer solution zones which can be used in the separation method of the embodiment B will be provided.

FIG. 78 shows an embodiment of an apparatus for forming a buffer solution zone arrangement. This apparatus is an apparatus for forming an arrangement of buffer solution zones, which contain a denaturant for double-stranded nucleic acids at different concentrations, on an analytical substrate 910 for electrophoresis. This apparatus comprises stage means 911 for holding the analytic substrate 910, ejection means 912 for ejecting droplets 913 of buffer solutions containing a denaturant for double-stranded nucleic acids at different concentrations (for example, droplets of each of a denaturant-free buffer solution and a denaturant-containing buffer solution) toward the substrate 910, and control means (not shown) for positionally controlling the stage means 911 and/or the ejection means 912 and sequentially driving the ejection means. The stage means 911 and/or the ejection means 912 have or has a moving mechanism which enables these means to move rectilinearly relative to each other in a two-dimensional direction as shown by arrows in the drawing.

In the apparatus of FIG. 78, the substrate 910 having the above-mentioned nucleic acid analytic channel 1, such as a microchip, is held on the stage means 911. The ejection means 912 capable of ejecting at the substrate 910 the droplets 913 of the buffer solution containing no denaturant and/or the buffer solution containing the denaturant is used for the substrate 910. Also, the stage means 911 and/or the ejection means 912 can be positionally controlled, and the desired ejection means 912 can be sequentially driven. In this manner, the droplets 913 of the buffer solution of a predetermined denaturant concentration can be deposited from the ejection means 912 onto an arbitrary position in the nucleic acid analytic channel 901, whereby an intermittent denaturant arrangement can be formed there. If the thickness of the buffer solution coated by single ejection is too small, coatings of exactly the same distribution (the same denaturant region) may be stacked to a suitable thickness.

The above ejection means 912, more detailedly, can be constituted by an ejection mechanism having a droplet ejection head. For example, the buffer solution can be ejected at a target with an arbitrary timing by applying an electric signal via control means (not shown).

The simplest manner is to set a substrate in which a gel containing a buffer solution has been formed, and to use a droplet ejection head 912 for ejecting a buffer solution having a denaturant concentration different from the concentration of the buffer solution in the gel (i.e., a concentration at least higher than the buffer solution contained in the gel). This is a case, for example, where there is used a microchip already filled with a gel containing a buffer solution in the nucleic acid analytic channel, or a slab gel 914 containing a buffer solution (FIG. 79).

If a nucleic acid analytic channel or a glass substrate without a gel is used, on the other hand, a plurality of droplet ejection heads 912, 912' corresponding to buffer solutions of different concentrations may be provided as shown in FIG. 78, and desired droplets may be selectively ejected. In this case, a polymer matrix for forming a gel is usually incorporated into the buffer solution.

As the above-described droplet ejection mechanism, an ejection head for an ink jet printer, for example, can be used. By using an appropriate droplet ejection head, buffer solution droplets 913 at least having a smaller diameter than the width of the nucleic acid analytic channel 1 on the microchip substrate 910 can be easily coated.

As the above droplet ejection mechanism, a plurality of droplet ejection heads for ejecting a buffer solution of the same concentration may be connected together and used. By so doing, the formation time of an intermittent denaturant arrangement can be shortened. Also, droplet ejection heads for ejecting buffer solutions of different concentrations may be connected together. For example, droplet ejection heads for a denaturant-containing buffer solution, and droplet ejection heads for a buffer solution may be combined integrally to construct an ejection head module. The use of such an ejection head module can render the apparatus compact, and shorten the formation time of the intermittent denaturant arrangement. Furthermore, a plurality of such droplet ejection head modules are provided and used, whereby an intermittent denaturant arrangement can be formed with even higher efficiency.

Besides, as shown in FIG. 79, a slab gel 914 for electrophoresis can be held instead of the microchip substrate 910, and droplets 913 of a denaturant-containing buffer solution can be ejected at an arbitrary position on the slab gel 914. In this manner, the droplets 913 of the denaturant-containing buffer solution can be driven into an arbitrary place of the slab gel 914, whereby an intermittent denaturant arrangement can be efficiently formed in an arbitrary pattern in the place.

As described above, an intermittent denaturant arrangement having an arbitrary pattern can be easily formed by adopting positioning means (911) and droplet ejection means (912). Also, these means can be applied to any type of substrate, and their use makes it possible to form an intermittent denaturant arrangement of the same pattern with high efficiency, with satisfactory reproducibility, and in high volume.

Next, another method of forming an intermittent denaturant arrangement in a microchannel will be described with reference to FIG. 80 and FIG. 81.

First, a buffer solution (first buffer solution; a buffer solution containing no denaturant) is flowed from a buffer solution inlet toward an outlet by a buffer solution feeding step. The method of driving the buffer solution can be arbitrarily selected from methods capable of controlling the flowing direction and the flowing time (flowing distance), such as a method of applying a direct current voltage between the buffer solution inlet and the outlet to generate an electroosmotic flow, and a method of connecting a pump or pumps to the buffer solution inlet or/and the outlet to flow the buffer solution. During the buffer solution feeding step, care should be taken so that the buffer solution does not outflow from the nucleic acid analytic channel to the nucleic acid introduction channel or the denaturant-containing buffer solution introduction channel. For this purpose, it is preferred, for example, to apply a direct current voltage to, or exert a pressure on, the nucleic acid inlet, the nucleic acid outlet, the denaturant-containing buffer solution inlet, and the denaturant-containing buffer solution outlet. The method and procedure for driving the denaturant-containing buffer solution in the denaturant-containing buffer solution introduction channel are the same as the above-described method for driving the buffer solution, and so on.

In the buffer solution feeding step, a buffer solution zone is introduced into the nucleic acid analytic channel 901, and this buffer solution zone is introduced up to a point which is past the intersection of the nucleic acid analytic channel 901 and the channel 906. Then, as shown in FIG. 80, a denaturant-containing buffer solution (second buffer solution) is fed through the channel 906 by a denaturant-containing buffer solution feeding step. As a result, a denaturant-containing buffer solution zone from the channel 906 crosses the buffer solution zone of the channel 901 perpendicularly. In this manner, a denaturant-containing buffer solution zone dividing the buffer solution zone is formed. Then, in a buffer solution refeeding step, the denaturant-containing buffer solution zone portion located in the channel 901 is separated from the channel 906, and moved toward the outlet together with the buffer solution zone. Thus, an independent single denaturant-containing buffer solution zone 901c is formed in the buffer solution zone.

As described above, the buffer solution feeding step and the denaturant-containing buffer solution feeding step are alternately repeated, whereby an intermittent denaturant arrangement can be formed in the nucleic acid analytic channel 901. The spacing between the denaturant-containing buffer solution zone and the denaturant-containing buffer solution zone can be arbitrarily adjusted by adjusting the time of the buffer solution feeding step. For example, there can be formed an intermittent denaturant arrangement channel of a form in which the spacing between the denaturant-containing buffer solution zones becomes smaller toward the downstream side, as shown in FIG. 69.

The length of the nucleic acid analytic channel, the length of the denaturant-containing buffer solution, the concentration of the denaturant-containing buffer solution, and the spacing between the denaturant-containing buffer solution zones differ according to the types of double-stranded nucleic acids to be separated. Thus, they should be determined by preliminary experiments, etc. which are conducted beforehand.

FIG. 81 shows an example of a method which can decrease the length (width) in the direction of electrophoresis of a denaturant-containing buffer solution zone. By decreasing the length of the denaturant-containing buffer solution zone in the direction of electrophoresis, the accuracy of separating double-stranded nucleic acids can be increased. The length of the denaturant-containing buffer solution zone in the direction of electrophoresis, which is formed by the method of FIG. 80, is nearly equal to the width of the denaturant-containing buffer solution inlet. To decrease the length of such a denaturant-containing buffer solution zone, it suffices to narrow the denaturant-containing buffer solution inlet. However, narrowing the denaturant-containing buffer solution inlet causes a marked increase in a flow loss. Thus, a very great power may be needed to flow the denaturant-containing buffer solution.

To avoid the above problem, it is recommendable to provide auxiliary buffer solution channels 906' adjacent to the denaturant-containing buffer solution introduction channel 906 in the denaturant-containing buffer solution introduction portion, as shown in FIG. 81. By so increasing the amount of inflow of an auxiliary buffer solution from inlets 906c, 906d of the auxiliary buffer solution channels 906', the inflow width of the denaturant-containing buffer solution can be decreased, the length of the denaturant-containing buffer solution zone can be progressively shortened in the direction of electrophoresis, and simultaneously an increase in the flow loss can be prevented. A plurality of auxiliary buffer solution channels and inlets may be provided so as to sandwich the denaturant-containing buffer solution introduction channel 6, as shown in FIG. 81, or only one auxiliary buffer solution channel and only one inlet may be provided beside the denaturant-containing buffer solution introduction channel 6.

Apparatus for Forming Arrangement of Buffer Solution Zones of the Embodiment B Having Flow Rate Control Means In the apparatus of the embodiment B, the means for controlling the flow rates of buffer solutions from liquid-introducing microchannels as described in the embodiments 1-1 and 1-2 (for example, control of an electroosmotic flow by adjusting an applied voltage or an applied potential, control of a liquid feed pump by adjusting the pressure of liquid feeding by use of a microsyringe or the like, or control of a valve for secondarily adjusting liquid feeding by them) can be used as means for forming the above-described intermittent denaturant arrangement.

In the apparatus of the embodiment B, on the assumption that buffer solutions having a denaturant at different concentrations are minimally miscible by molecular diffusion (as explained earlier, mixing may not occur if the diffusion coefficient of the liquid is extremely low), the flow rate control means shown in the embodiments 1-1 and 1-2 can be used for alternate supply of buffers for forming an intermittent denaturant arrangement.

FIG. 83 shows an embodiment mounted with the fast operating valves described in the embodiment 1-2. In this embodiment, each of two buffer solution introduction channels (an introduction channel for a buffer solution containing no denaturant and an introduction channel for a buffer solution containing a denaturant) is provided with a fast operating valve (valve 1 and valve 2). By controlling the opening and closing time of the valve 1 and the valve 2, an intermittent denaturant arrangement can be formed in a nucleic acid analytic channel 1 as shown in FIG. 83.

Microchip Electrophoretic Apparatus of the Embodiment A Having Mixing Enhancing Means In the apparatuses for forming an intermittent denaturant arrangement shown in FIGS. 78 and 79, mixing enhancing means can be used.

FIG. 84 schematically shows an ejection means 912. An arrow a and an arrow b represent input paths for buffer solutions containing a denaturant at different concentrations. The ejection means 912 incorporate a mixing apparatus (not shown) which can mix two buffer solutions containing a denaturant at different concentrations, for example, a denaturant-containing buffer solution (arrow a) and a denaturant-free buffer solution (arrow b), at an arbitrary ratio.

As the mixing apparatus in the ejection means 912, a liquid mixing apparatus having the mixing enhancing means of the aforementioned embodiments 1-1 to 2-3 can be used. According to the mixing apparatus having an appropriate mixing enhancing means, the mixing of the two buffer solutions indicated by the arrow a and the arrow a is promptly performed. Thus, a buffer solution containing the denaturant at the desired concentration can be prepared continuously.

A denaturant-containing buffer solution prepared by mixing by means of the mixing apparatus is ejected from the ejection means 912 as droplets 913 of the desired concentration. According to this embodiment, it becomes possible to continuously supply denaturant-containing buffer solutions having different concentrations. Thus, it becomes unnecessary to replace a cartridge for supplying buffer solutions of different concentrations. Nor is there need to use a cartridge type ejection means. Nor is it necessary to mount a plurality of ejection means. According to an embodiment having this type of ejection means, an apparatus and method for formation of an intermittent denaturant arrangement, which are suitable for few-type mass production, can be provided.

If the liquid mixing apparatus of the embodiment 2-2 is used as the mixing enhancing means in the ejection means 912, for example, the mixing of buffer solutions can be performed at a high speed. Thus, the time from receipt of information on the mixing concentration until completion of mixing can be shortened. If the liquid mixing apparatus of the embodiment 2-3 is used as the ejection means, moreover, the apparatus can be rendered compact.

EXAMPLES

Example 1

Two double-stranded nucleic acids having different base sequences were separated by use of a microchip electrophoretic apparatus as described in each of the aforementioned embodiments. A nucleic acid sample containing a V3 region of 16S rRNA gene obtained from two microorganisms of the genus *Sphingomonas* was prepared as an analyte.

In experiments, the two microorganisms were cultured in liquid media, and then collected by centrifugation. The cells were mixed, and nucleic acids were extracted from the mixed cells by using benzyl chloride. The extracted nucleic acids were subjected to PCR using universal primers (forward; 5'-CGCCCGCCGC GCGCGGCGGG CGGGGCGGGG GCACGGGGGG CCTACGGGAG GCAGCAG-3' (sequence No. 1), reverse; 5'-ATTACCGCGG CTGCTGG-3' (sequence No. 2)) targeting the V3 region of the 16S rRNA gene. The resulting PCR product was used as a final nucleic acid sample. The universal primers used were FITC-labeled at the 5'-terminal. The forward primer was provided with a GC clamp region.

A microchip having channels with a width of 100 µm and a depth of 25 µm formed in Pyrex (registered trademark) glass (7 cm×3.5 cm) by a photolithography technology was used in experiments. This microchip was mounted on an inverted fluorescence microscope, and detected by a photomultiplier. Urea and formamide were used as a denaturant.

As a result of the experiments, two peaks corresponding to the two microorganisms were detected. Analysis was completed in a short time of 30 minutes, thus conforming that high speed analysis was possible.

Example 2

Two or more double-stranded nucleic acids having different base sequences were separated by use of the apparatus of Example 1. Enrichment culture from activated sludge with estradiol as a sole carbon source was used for a sample containing two or more double-stranded nucleic acids. The experimental method was the same as that in Example 1.

As a result of the experiments, a plurality of peaks corresponding to the plural microorganisms were detected. Thus, it was confirmed that the separation of two or more double-stranded nucleic acids different in base sequence was possible.

Comparative Example 1

As a control for Example 1, the same sample was analyzed using a conventional DGGE apparatus. Experiments were conducted based on the method of Muyzer et al. (Appl. Environ. Microbiol., March 1993, 695-700, Vol. 59, No. 3). The DGGE apparatus used was DCode Universal Mutation Detection System (BIORAD).

In the experiments, the same procedure as in Example 1 was performed. That is, two microorganisms were cultured in liquid media, and then collected by centrifugation. The cells obtained were mixed, and nucleic acids were extracted from the mixed cells by the benzyl chloride method. The extracted nucleic acids were subjected to PCR using the universal primers described in Example 1, the universal primers targeting the V3 region of the 16S rRNA gene. The resulting PCR product was used as a final nucleic acid sample. The universal primers used were not fluorescence-labeled, unlike those in Example 1. The double-stranded nucleic acids were detected by fluorescence staining with Vistra Green after electrophoresis. A GC clamp was present in the forward primer as in Example 1. The concentration gradient of a denaturing gradient gel was 35%-55%.

Upon electrophoresis of the nucleic acid sample, two bands corresponding to the two microorganisms were detected. However, the time of electrophoresis was 210 minutes, and analysis required a time of the order of 6 hours, including the time of preparation of the denaturing gradient gel and the gel staining time.

Comparative Example 2

As a control for Example 2, the same sample was analyzed using a conventional DGGE apparatus. The equipment and method for experiments were the same as in Comparative Example 2.

As a result of the experiments, a plurality of peaks corresponding to plural microorganisms were detected. However, as in Comparative Example 1, the time of electrophoresis was 210 minutes, and analysis required a time of the order of 6 hours, including the time of preparation of a denaturing gradient gel and the gel staining time. Furthermore, complicated manual operations, such as preparation of the denaturing gradient gel and staining of the gel, were necessary.

In the above examples, the use of the apparatuses of the embodiment A and the embodiment B enabled double-stranded nucleic acids to be separated and analyzed according to the difference in base sequence by DGGE on a microchip.

By applying a mixing enhancing method and apparatus, as described in the embodiments 1-1 to 2-3, to a microchip apparatus for DGGE, moreover, success was achieved in forming a concentration gradient promptly and performing separation and analysis in a short time.

What is claimed is:

1. A microchip electrophoretic apparatus for separating a double-stranded nucleic acid, the microchip electrophoretic apparatus comprising:
   a first reservoir filled with a first buffer solution;
   a first electrode connected to the first reservoir and being operable to provide power from a first power source;
   a first liquid-introducing microchannel connected to the first reservoir;
   a second reservoir filled with a second buffer solution;
   a second electrode connected to the second reservoir and being operable to provide power from a second power source;
   a second liquid-introducing microchannel connected to the second reservoir;
   a mixing microchannel to which the first liquid-introducing microchannel and the second liquid-introducing microchannel connect, wherein a denaturing gradient region is formed by introducing the first buffer solution and the second buffer solution from the respective liquid-introducing microchannels at varying ratios and mixing the first buffer solution and the second buffer solution in the mixing microchannel; and
   a sample-introducing microchannel connected to a sample reservoir, wherein the sample-introducing microchannel is connected to a downstream side of the mixing microchannel, wherein the double-stranded nucleic acid is introduced into the mixing microchannel from the sample reservoir through the sample-introducing channel;
   wherein the first buffer solution and the second buffer solution contain the denaturant at different concentrations,
   wherein the double-stranded nucleic acid is electrophoresed in the denaturing gradient region.

2. The microchip electrophoretic apparatus according to claim 1, further comprising means for enhancing the mixing of the buffer solutions that converge in the mixing microchannel.

SEQUENCE LISTING

<160> NUMBER OF SEQ ID NOS: 2

<210> SEQ ID NO 1
<211> LENGTH: 57
<212> TYPE: DNA
<213> ORGANISM: Artificial Sequence
<220> FEATURE:
<223> OTHER INFORMATION: Primer for PCR; forward

<400> SEQUENCE: 1
cgcccgccgc gcgcggcggg cggggcgggg gcacgggggg cctacgggag gcagcag      57

<210> SEQ ID NO 2
<211> LENGTH: 17
<212> TYPE: DNA
<213> ORGANISM: Artificial Sequence
<220> FEATURE:
<223> OTHER INFORMATION: Primer for PCR; reverse

<400> SEQUENCE: 2
attaccgcgg ctgctgg      17

3. The microchip electrophoretic apparatus according to claim 1, wherein the denaturing gradient reajon is formed as a plurality of buffer solution zones arranged alternately in a direction of electrophoresis, wherein the plurality of buffer solution zones contain the denaturant at zero or low concentration, wherein concentrations of the denaturant are different among the plurality of buffer solution zones, and wherein the plurality of buffer solution zones are arranged such that a length of each buffer solution zone decreases progressively in the direction of electrophoresis.

4. The microchip electrophoretic apparatus according to claim 1, wherein said denaturing gradient region is formed as a plurality of buffer solution zones containing the denaturant at different concentrations and being arranged alternately in a direction of electrophoresis.

5. The microchip electrophoretic apparatus according to claim 4, wherein the plurality of buffer solutions that contain the denaturant at high concentrations and are arranged such that their length increases progressively downstream of the direction of electrophoresis.

6. A method for separating an analyte, comprising:

introducing by electroosmotic flows a plurality of buffer solutions containing a denaturant for the analyte at different concentrations, at varying ratios, from at least two liquid-introducing microchannels into a mixing microchannel to form a denaturing gradient region in the mixing microchannel, introducing the analyte into the denaturing gradient region, and then, electrophoresing the analyte in the denaturing gradient region for separation, wherein said analyte is a double-stranded nucleic acid.

7. The method of claim 6, wherein the denaturing gradient region is formed in the mixing microchannel before the analyte is introduced into the denaturing gradient region.

8. A method for separating an analyte, comprising:

arranging by electroosmotic flows in a microchannel a plurality of buffer solutions containing a denaturant for an analyte at different concentrations alternately in a direction of electrophoresis to form a denaturing gradient region, introducing the analyte into the denaturing gradient region, and then, electrophoresing the analyte in the denaturing gradient region for separation, wherein the analyte is a double-stranded nucleic acid.

9. The method according to claim 8, wherein the plurality of buffer solution zones contain the denaturant at zero or low concentration and are arranged such that a length of each buffer solution decreases progressively downstream of the direction of electrophoresis.

10. The method according to claim 8, wherein the plurality of buffer solutions contain the denaturant at high concentrations and are arranged such that their length increases progressively downstream of the direction of electrophoresis.

11. The method of claim 8, wherein the denaturing gradient region is formed in the microchannel before the analyte is introduced into the denaturing gradient region.

* * * * *

UNITED STATES PATENT AND TRADEMARK OFFICE
CERTIFICATE OF CORRECTION

| | |
|---|---|
| PATENT NO. | : 7,588,671 B2 |
| APPLICATION NO. | : 10/992770 |
| DATED | : September 15, 2009 |
| INVENTOR(S) | : Morita et al. |

It is certified that error appears in the above-identified patent and that said Letters Patent is hereby corrected as shown below:

On title page Item (73) Assignee, please change "Ohtu-ku" to --Ohta-ku--.

Signed and Sealed this

Twenty-second Day of December, 2009

David J. Kappos
*Director of the United States Patent and Trademark Office*